US007396660B2

(12) United States Patent
Huang et al.

(10) Patent No.: US 7,396,660 B2
(45) Date of Patent: Jul. 8, 2008

(54) **CLONING GENES FROM *STREPTOMYCES CYANEOGRISEUS* SUBSP. *NONCYANOGENUS* FOR BIOSYNTHESIS OF ANTIBIOTICS AND METHODS OF USE**

(75) Inventors: Chengjin Huang, Fort Dodge, IA (US); Deborah T. Chaleff, Pennington, NJ (US); Mark E. Ruppen, Garnerville, NY (US); Jerome Stephens, Mentone, AL (US)

(73) Assignee: Wyeth, Madison, NJ (US)

(*) Notice: Subject to any disclaimer, the term of this patent is extended or adjusted under 35 U.S.C. 154(b) by 328 days.

(21) Appl. No.: 10/844,716

(22) Filed: May 13, 2004

(65) Prior Publication Data

US 2005/0003409 A1 Jan. 6, 2005

Related U.S. Application Data

(60) Provisional application No. 60/471,256, filed on May 16, 2003.

(51) Int. Cl.

| | |
|---|---|
| ***C12P 19/44*** | (2006.01) |
| ***C12N 15/52*** | (2006.01) |
| ***C12N 15/70*** | (2006.01) |
| ***C12N 15/76*** | (2006.01) |

(52) U.S. Cl. ...................... 435/41; 435/183; 435/252.3; 435/252.35; 435/320.1; 435/471; 536/23.2

(58) Field of Classification Search ....................... None
See application file for complete search history.

(56) References Cited

U.S. PATENT DOCUMENTS

| | | | | |
|---|---|---|---|---|
| 4,916,154 | A | 4/1990 | Asato et al. | 514/450 |
| 5,106,994 | A | 4/1992 | Carter et al. | 549/264 |
| 5,169,956 | A | 12/1992 | Carter et al. | 549/264 |
| 5,252,474 | A | 10/1993 | Gewain et al. | 435/172.3 |
| 5,418,168 | A | 5/1995 | Carter et al. | 435/253.5 |
| 6,004,787 | A | 12/1999 | Katz et al. | 435/183 |
| 6,143,526 | A * | 11/2000 | Baltz et al. | 435/76 |
| 6,864,073 | B1 * | 3/2005 | Omura et al. | 435/183 |
| 2003/0119018 | A1 * | 6/2003 | Omura et al. | 435/6 |
| 2005/0187167 | A1 * | 8/2005 | Bachmann et al. | 514/25 |

FOREIGN PATENT DOCUMENTS

| | | | |
|---|---|---|---|
| EP | 0463707 | A1 | 1/1992 |
| WO | 01/09155 | A1 | 2/2001 |
| WO | 01/68867 | A1 | 9/2001 |

OTHER PUBLICATIONS

D. J. MacNeil et al., "Correlation of the Avermectin Polyketide Synthase Genes to the Avermectin Structure," Annals of the New York Academy of Sciences 721:123-132 (1994).

D. J. MacNeil, "Characterization of a Unique Methyl-Specific Restriction System in *Streptomyces avermitilis*," Journal of Bacteriology 170(12):5607-5612 (Dec. 1988).

D. J. MacNeil et al., "A Comparison of the Genes Encoding the Polyketide Synthases for Avermectin, Erythromycin, and Nemadectin," Industrial Microorganisms: Basic and Applied Molecular Genetics, ed. Baltz et al., Chap. 30, pp. 245-256 (1993).

D. J. MacNeil et al., "Complex organization of the *Streptomyces avermitilis* genes encoding the avermectin polyketide synthase," Gene 115:119-125 (1992).

H. R. Tsou et al., "Biosynthetic Origin of the Carbon Skeleton and Oxygen Atoms of the LL-F28249α, A Potent Antiparasitic Macrolide," The Journal of Antibiotics (Tokyo) 42 (3):398-406 (Mar. 1989).

P. Caffrey et al., "Amphotericin biosynthesis in *Streptomyces nodosus*: deductions from analysis of polyketide synthase and late genes," Chemistry & Biology 8(7):713-723 (Jul. 2001).

H. Ikeda et al., "Organization of the biosynthetic gene cluster for the polyketide anthelmintic macrolide avermectin in *Streptomyces avermitilis*," Proc. Natl. Acad. Sci. USA 96(17):9509-9514 (Aug. 1999).

S. Omura et al., "Genome sequence of an industrial microorganism *Streptomyces avermitilis*: Deducing the ability of producing secondary metabolites," Proc. Natl. Acad. Sci. USA 98(21):12215-12220 (Oct. 2001).

* cited by examiner

*Primary Examiner*—Nashaat T. Nashed
*Assistant Examiner*—William W. Moore
(74) *Attorney, Agent, or Firm*—Barbara L. Renda; Anne M. Rosenblum

(57) ABSTRACT

The present invention relates to the complete biosynthetic pathway for the formation of the LL-F28249 compounds and, most importantly, the major component LL-F28249α. The purified and isolated nucleic acid molecule encoding the proteins of the biosynthetic pathway, which is isolated from a wild-type or mutant *Streptomyces*, is fully described in FIG. 6 to FIG. 6-39 and SEQ ID NO:1. The DNA gene cluster and its expression in a suitable host enable the efficient production of the highly active natural metabolites and semisynthetic derivatives. The invention further concerns plasmids, vectors and host cells that contain and express the novel nucleic acid molecule. Of particular interest, the entire biosynthetic pathway fits compactly in three plasmids, Cos11, Cos36 and Cos40. The invention also concerns the purified and isolated biosynthesis proteins that are encoded by the whole DNA gene cluster. Additionally, the invention involves a new efficient, biochemical method of preparing moxidectin.

8 Claims, 68 Drawing Sheets

GAGCTCTTCGCTCCCGCCGGACCGGTTGGTCGCGCCGGAGAGGACGAGCC
GGTAGCGGGTGTTGATCTCGTTGGTGCCGAGCCCGTTGGCCGGGCGGCCG
TGGAACCACCTCGGATCGGGCTCGGGGGTCTCCTGGCCCTTCTTCAGCGGC
AGATGGTACGGCTGGCCGATCAGCGAGGAGCCGACGGCCCTGCCGTCCGC
CGTGATCTCGGAGCCGTCGGCCCGGTCGCGGAAGAGTGCCTGGGCGACGC
CGGTGACGACCAGCGGGTAGCCGGCGCCCGTCACCAGGGTCAGCACGAG
GAGGGCCCGCAGGCCCGCCCCGAGCAGCCGGACGGTGTGGGTGGCGGAG
TTGTTCATGGCGGTCAGCACGCTTTCGTGACGTCACGGCCCGGGAACGAG
GGAGATGAACAGGTCGATGATCTTGATGCCTATGAAGGGCGCCACCAGGC
CGCCCAGGCCGTAGATCCCGAGGTTGCGCCGCAGCATCCGGTCCGCGCTC
ACCGGCCGGTACCGCACGCCCCTCAGGGACAGCGGCACCAGCGCCACGAT
GACCAGCGCGTTGAAGATCACCGCGGAGAGGATCGCGGAGTCGGGTGAG
GACAGGCCCATGACGTCGAGTCGCTCCAGGCCGGGATGGGCCGGCGCGA
ACAGCGCCGGGATGATCGCGAAGTACTTCGCGACGTCGTTGGCCAGGGAG
AAGGTCGTCAGTGCGCCGCGTGTGATCAGCAGTTGCTTGCCGATCTCCAC
GATCTCGATCAGTTTGGTGGGATCGGAGTCGAGGTCGACCATGTTGCCGG
CCTCCTTCGCGGCCGACGTACCGGTGTTCATCGCCACGCCGACGTCCGCCT
GGGCCAGAGCCGGGGCGTCGTTGGTGCCGTCCCCGGTCATGGCGACCAGC
CTGCCGCCTGCCTGCTCCCGCCTGATCAGCGCCATCTTGTCCTCGGGAGTC
GCCTCCGCGAGGTAGTCGTCGACGCCCGCCTCGCGCGCGACGGCCTGCGC
GGTCAGCGGGTTGTCACCCGTGATCATGACGGTCCTGATGCCCATGCGGC
GCAGTTCCTCGAACCGCGCGCGCATGCCGTCCTTGACGACGTCCTTGAGGT
GGACGGCTCCCAGCACCCGGGCGCCCCGCTCGTCCCGCGCGGCGACCAGC
AGGGGCGTGCCCCCCGATCCGGCGATGCGGTCGGCGATGGCCTTCGCGTC
CTGGGCGGCCTCACCGCCCTGCTCCTCGACCCAGGCGAGGATGGAACCGG
CCGCGCCCTTGCGGATCCTGCGGCCGCCGACGTCCACGCCCGACATGCGG
GTCCGGGCGGTGAACGCGATCCATTCGGCGCCGGCGAGTTCGCCCCGGTG
CCGCTCGCGCAGTCCGTACTGCTCCTTCGCCAGGACGACGACGGACCGGC
CCTCGGGCGTCTCGTCCGCGAGCGAGGAGAGCTGCGCGGCGTCCGCCACC
TCGGCCTCCGTGGTGCCGGACACCGGCACGAACCCGGCCGCCCGCCGGTT
GCCGAGCGTGATCGTGCCGGTCTTGTCCAGCAGCAGCGTGGAGACGTCGC
CCGCGGCCTCGACCGCCCGGCCCGACACGGCCAGCACATTGCGCTGCACC
AGGCGGTCCATGCCCGCGATGCCGATCGCCGAGAGCAGCGCGCCGATCGT
GGTCGGGATGAGGCAGACCAGCAGCGCCACCAGCACCGTCGGTGTCAGGT
GGGTGCCCGCGTGATCCGCGAAGGGCGGCAGCGTGGCGCAGACCAGCAG
GAAGACGATGGTCAGCGAGGCCAGCAGGATGTTCAGCGCGATTTCGTTAG
GCGTCTTCTGCCGGGCCGCGCCTTCGACGAGGTCGATCATCCGGTCGATG
AAGGTCTCACCGGGCTTGGTCGTGATCCGGATGACGACACGGTCGGACAG
GACCTTGGTGCCGCCGGTGACGGCGCTCCGGTCTCCCCCCGACTCGCGGA
TGACGGGTGCCGACTCGCCGGTGATGGCGGACTCGTCGACGGACGCGACG
CCCTCGACGACATCACCGTCGCCGGGGATGACGTCCCCGGCCTCGCAGAC
CACCAGATCGCCGATCCTCAGTCCGGTGCCCGGCACCCGCTCCTCCGAGC

FIG.6

CGTCCTCGCGCAGGCGGCGGGCGACGGTGCCGGTCCTGGTCTTGCGCAGG
GTGTCGGCCTGTGCCTTGCCGCGGCCTTCGGCGACCGCCTCCGCGAGGTTG
GCGAAGAGCACGGTCATCCAGAGCCAGGCGGAGACGGTCCAGCCGAACC
GGTCGCCGGGATCCATGAGGGCGAAGACGGTGGTGAGGACCGAGCCGAT
CCACACCACGAACATCACGGGCGTCTTGATCTGCACCCGCGGGTCCAGCT
TGCGGAAGGCGTCCGGCAACGACCTGACGAGCTGGCCCGGGTCGAACAG
ACCGCCGCCGACCCGCCTTTCGGACGGCTGGTGACCGGTGGGGGCGTCGC
GCTGCGGCGTCCGGGCGGGAGTGATCGTGGACATCGGGTTCCCTTGGTCG
TCCGGGTGTGCGCTCATGCCGCCAGCCCTTCGGCGAGCGGCCCCAGCGCC
AGGGCCGGGAAGTACGTCAAGCCGGCGAGGATCAGGATCGCGCCCACCA
TCAGGCCGCTGAACAGCGGCTTGTCGGTGCGCAGGGTGCCGGTGGTGACC
GGCACGGGCCGTTGCCCGGCGAGCGAGCCGGCCAGCGCCAGGACGAACA
CCATCGGCAGGAAGCGGCCGAGCAGCATCGCCAGTCCGATGGTGGTGTTG
AACCACTGCGTGTCCGCGTCGAGACCGGCGAAGGCCGAGCCGTTGTTGTT
GGCGCCGGAGGTGTAGGCGTAGAGGATCTCGGAGAACCCGTGCGCGCCG
CTGCCGGTCGTCGAGTTCACCGGCGTCGGCAGGGCCATCGCGCACGCGGT
GAGGATCAGGACCAGCGCCGGGGTGACCAGCAGGTGGCAAGCGGCCAGT
TTGATCTCGCGGGTGCCGATCTTCTTGCCCAGGTACTCGGGCGTGCGGCCG
ACCATCAGACCGGCGATGAACACCGCTGTGACGGCCATGACGAGCATGCC
GTAGAGGCCGGATCCCACCCCGCCCGGAGCGATCTCGCCCAGCATCATGC
CGAGCATCGCGATGCCTCCGCCAAGGCCGGTGAAGGAGGAGTGGAAGGA
GTCCACCGCGCCGGTCGAGGTGAGCGTGGTCGACACCGCGAAGATGGACG
AGGCGCCGACACCGAAGCGGACCTCCTTGCCCTCCATCGCGCCACCGGCG
ATCTCGAGCGCCGGGCCGCGGTGCGAGAACTCGGTCCACATCATCAGGGC
GACGAAGGCGATCCAGAAGGTGGCCATCGTCGCCAGGATCGCGTAGCCCT
GCCTGACCGAGCCGACCATGACGCCGAACGTCCGGGTGATCGAGAAGGG
GATCACCAGGATCAGGAAGATCTCGAAGAGGTTGGTGAAGGGCGTCGGG
TTCTCGAACGGGTGGGCGCTGTTGGCGTTGAAATAGCCGCCGCCGTTGGT
GCCCAGCAGTTTGATGGCCTCCTGGGAGGCGACCGCGCCCCCGTTCCACT
GCTGCGAGCCGCCCGTGAACCGGCCGACCTCGTGGATGCCGGAGAAGTTC
TGGATGACCCCGCAGGCGGCCAGCACCACGGCGCCGAGGGTGGCCAGCG
GCACCAGGACGCGGACCGTTCCGCGCACCAGATCGGCCCAGAGGTTTCCC
AGTTCACCGGTGCGGGAGCGCGCGAACCCGCGCACCAGCGCGACCGCGA
CGGCCATGCCCACGGCGGCCGAGGTGAAGTTCTGCACGGCCAGGCCGGCG
GTCTGCACGAGGTGTCCCATGGCCTGTTCGCCGGAGTACGACTGCCAGTT
GGTGTTGGTCACGAAGGACACGGCCGTGTTGAACGCCTGGTCCGGGTCGA
CGGCTCGAAAGCCGAGGGACAGCGGCAGGACGCCTTGCGCCCGCTGGAC
CAGGTACAGGAAGAGGACGCCGGCCACGGAGAAGGCCAGCACACCGCGG
AGGTACGCGGGCCAGCGCATCTGGGCGCCGGGGTCGACACCGATGCCCCG
GTAGATCCATCTCTCGACGCGCCAGTGCTCGTCGGAGGAGTAGACCTTGG
CCATGTGGTTGCCGAGGGGTTTGTGGACGAGTGCCAGAGCACTCGTCAGG
GCGAGCAGTTGGAGCACGCCGGCGAGTACGGGACCCATGGCTGCTCTCAG
AACCTCTCCGGGAAGATCAGGGCGAGGACGAGATAGCCCAGCAGGGAGA
CGGCCACGACCAGGCCGACGACGGTCTCGGCGGTCACAGCTTCGTCACCC
CCCTGGCGACAACAGCCACCAGCGCGAAGAGCGCGAGCGTGGTGACGAC

FIG.6-1

GAAGGCCGTATCGGCCATCGCGGACTCCTGGAATGAGGTGCGGTGGAAAC
GGACCCTTGCAGGTAAGCGCCTCACCGACCGAAACAGGACGTCCGTTGAC
GTTTCCCTTACGGCGTGACGTACGTCTTTGACGGAACTCTTACGCCTGAGG
TCCGTGTCCATGCCCCTCGGTCCGTTGCGGACCATGCCCCCGCGGCCACCG
GAGAGGGCGGCGTCCCCCTCAGCGGGCCCCGCCCGTCTCCCCCGGGGCCT
CCGTCTCCCCCACCTTCTCCACGACCGTCTCCTCCGGCCCGACCGGCCGTC
CGTCCGCGGCACGGATCCGCAAGGGGCGCAGCGGGCGGCCGGTGCGGCG
GTCGAGCAGGCGGGAGTGGTCCTCGCCGGGGGCGAAGCACTGCTCCTCGC
CCCACTGGCGCAGGGCGACGATCACCGGGAACAAGGCGCGGCCCTTGTCC
GTGAGGACGTACTCACGGTGGGAACCGCCGTCCGGCGCGGGCACGTTGCG
CAGTACCCCGGCCTCCTCCAGCGCGCGCAGCCGCGCCGTCAGGATGTTCTT
GGCGATGCCGAGGCTGCGCTGGAACTCGCCGAAGCGGCGACTGCCGTCGA
AGGCGTCCCGCACGATCAGCAGCGACCACCAGTCGCCGATGGCGTTCACC
GACCGGGCGACGGGACAGGGGTCGGCGTCGAAACGGGTGCGGGCGACCA
TCCGCGTCTCTCCTCTCCTCCGGCACCCCGGATCCCTCCAGGGATGGTTGC
AACATGCTACCTCGTACGGCTACCGTCCTCGCCGGTAGCAAGATGCAACC
GAGTGAGAGGTGTGACGGTATGGCGGTCCAGTGCTCCGGTGCGGACGGCG
GATGCGGCGAAGCCGGTGGTCGCGGAGCGGCCGGCACGGCGCCGCCCGC
GCGGCTCGTGCCCCTGCTCGCCCTGGCCTGTGGCAGCTCCGTCGCCACCGT
CTACTTCGCCCACCCCCTGCTGGTGACCCTCGGTGAGCGCTTCGCGCTCGG
CCCCGGGCTGCTCGGCGCGATCGTCACCGTGACGCAACTCGGTTACGCGG
TGGGCCTGCTGACACTCGTGCCGCTCGGCGACCTGCTCGGCCACCGGCGG
CTGGTCACCGCTCAGCTCGGACTGCTGGCACTGGCGCTGCTGGCCGCCGG
GCTGGCGCCGGGCGCGGCTGCGCTGCTCGGCGCGCTCGCCGCGGTCGGGC
TGCTCGCCGTCGTCGCCCAGACGATGGTCGCGGCTGCCGCCGCCCTGAGC
CCGCCCGACCGGCGAGGCCGCGCCGTGGGAACCGTCACCGGCGGCATCGT
CACCGGCATCCTGCTGGCGCGCGCCGCCGCGGGCGTCCTCGCCGACCTCG
CCGGCTGGCGGGCGGTCTACCTGGCGTCGGCGGGCGTCACCGCCGTCCTC
GCCGTGCTGCTGCGCCGTGCGCTGCCCCCGGGATCGCCGTCCGCAAAGGC
TCGCGAGACGTCGTACGTACGGCTGGTGGCCTCGACCGTCACCCTGTTCGC
CCGCCATCCGCTGCTGCGGATCCGGGGGGCCCTGGCCCTGCTGGTGTTCGC
GGCCTTCAGCACGCTGTGGAGCGGCGTGGCCCAGCCCTTGAGCGATCCGC
CGTGGTCGCTGTCGCACACCGCGATCGGCGCGTTCGGGCTCGCCGGGGCG
GCCGGAGCCGTCGCCGCACAGGTGGCCGGGCGCTGGAACGACCGGGGGC
TCGCCCGGCGCACGACCGGCGCCGGCCTCGCGCTGCTGGCGCTCTCCTGG
CTCCCGATCGCCCTGACCCGGCAATCGCTGTGGGCGCTGGCGATCGGCGC
CGTCCTGCTGGACTTCGCCGTGCAGGCCGTCCACGTCACCAACCAGACCCT
CATCCACGCCGTCCGGCCCGAGGCGGGCAGCAGGATCATCGGTGGTTACA
TGGTCTTCTACTCCGCGGGCAGCAGCCTCGGCGCCCTCGGTTCCTCCCTCG
CCTACGCCACGGCGGGCTGGCCGGCCGTGACGGCCCTGGGCGCGTCGTTC
AGCGTCGCCGCGCTGCTGCTGTGGACGGCGACCCGTCGTACGGGGCTGCC
CGGCGACGACCCGGCGGCCGAACGGACGGACCCTGGCCGTCCGTCCGGG
GACAGGGCTGCCGGGAGGCCCGCCCGCAGCCGCTCTTCCGGCCCCCGGTG
AACGTCTGGGGTGGCGCGGGGCGCGCGATAGGGGTCCGCCGAGAGTCAG
GGGTTGTCCCGCCTGTACAGCGGCATCGGCGGTCGGTCCAATGGAAGGCG

FIG.6-2

TGCCTCCGGATGCGGGGCGGGTCGTCGACGACCCTGTGCCGGCGGCGGAT
TCCCACCCTCCCCCGGAAGGCGAGGTCGTGATGACCGACGTCCGTCATGA
CAGCAGGCAGACGGGTCCGGCGCTGCGCGCTCAGCGCGGCCCGGCGG
GCGCGGGCCTTGGCGTCCGCGATGGCGGCGGCCGCCGCGGAGACGCGGC
AGGCCGTCGAGGCCGCGGACGGCACGGACCGCGCGGCCGCCGTAGCCGA
GATCGGCGCGGTACTGGAGGACGCCTCCCGGCACACGGACGCCGCCGCCG
AGGCCGCCGCCTCGGCTGCCGAGGCCGCCGCCCGGGCCGAGACGGCCGA
GGCCGCCCGCACGGTGGCCGCCGAGTCGGCCGAGGCCGTCGTCGCCGCCG
CCGAGACGGCGGTCCGGGCGGCCCGGGTCACCGAGGCCGCCACGAGCGC
CGCCGCCCAGGCCGCGGCCGGTACGGACGCGGCGGGCGTGATGGCGGAC
GCCGCGGCGCACACCCGGCAGGCCACCGCCGAGACCGCGGCGATCGCCG
AGGCCGCCGCCGCGGCGGCCAGCGCGGCCCGGGCCGCCGTCGGCGACGA
GGCGGCGGACGGCGCGGACCCGTGCCGACGGGCTGACGAGGCGGAGGCC
GCGGCCCTGCGGCTGTGCGAGGACACGCCGTGGCTGCGCAGGCACCTCCC
CGACGTGTGAGGCAGGGTGCCCGGCGGCGCCGGCGCGAGATGGAACCCG
GGCCGGGCGGCCCTCTTCCCTCCGGGTGCCGGCGACGAGACCGTCGCCCC
CACCTCGAACCGGGCCTTCCGGTCGCTGTACCGGCATCCGGAGATCGAGC
GGCGGCCGCACTCCGAGGGGGACCGGGTGCTCGGCGGCCGGGCCGCCAC
CTGGACGGATCCGCCGTCGCTGGAGCTGACGGGCCGGGTGGTCCACGACG
CGCTGCGCCTGTTCCCCGGACGGGCTGCTCACCGGGTCATCACCGAGGAC
ACGGGGCGCGCAGGGCGCGCGCCGCCGGCCGGCGGCGTCGTCGCCTGGGT
CGATCAGCAGCCCCCCGCGGCGGGTTGCTCACGTTCGGCGGCGGGCAGGC
GTCCGCCCGGTGCGCGTTCAGACCGGGCTTTCGATGTGCGCGCACAGCCG
GGCGGGCAGTTCCTGACGGCGGCTGATCTCCAGCTTGCGGTAGGCGCGCG
TCAGGTGCTGCTCCACGGTGCTGACGGTGATGCAGAGCCGGGCGGCGATC
TCCCGGTTGGTGTGCCCGTTGGCGGCGAGTTCCACGACCCTGAGCTCCGAT
CCGCTCAGCGCCGCCTCGGTCCGCCCCGTGCCGTCCCCGAACGACTGCCG
CCCAGGACCTCCCGGCAGGATCCGCTCGCACAGAGCCCGCGCCCCGCAGT
CGTTCGCCAGGTGCCAGGCGCGGCGGATCGTGGCGCCCGCCCGGGTCGAC
TCGCCGCGCTCCCGGTAGGCGGCGCCCAGATCGGCCAGGGCACCCGCCAG
GGCCAGCCGGTCGCCGCTGCTCTTCAGGTGGTTCACGGCCTCGGTCAGCA
GGTTCAGCCGATCCGGCGGTTCGGCGATCTGCGCGCGCAGCCGCAGCGAG
ACGCCGCGCACATGAGGATCGTCGTCCGGGGTCCGGGCCAGTTGTTCCCG
CAGGAGCCGATCGGCCCTCCTCGGCTCGCACAGCCGCAGGAACGCCTCCG
CCGCGTCCGAGCGCCACGGCATCAGCGTCGGCCGGTCGATCCCCCAGCGC
CGCAGCAGACGGCCGGCGCCGAGGAAGTCGCGGACGGCGGCGAGGGGCC
GGTCCAGGGCGAGGTAGTAGTGGCCCCGGGCGCGCAGGTAGGCGGGGCC
GTACACGCTGCGGAACAGGGCCTCCGGCACCGGGTGGTCGAGCTGCCGGG
TGGCCTCGTCGTAGCGCCCCATCGCGGTGGCCGCGAACACCCGGCTGGCC
AGCGGCCCGCCGATGAAGACGCTGCGGCTGCACCTCGGCACGCAGGCCAG
GGCCTGACGGGCGTACTCCTCGGTGTCGGCGAGCAGCCCCCGGCACAGCG
CGATCTCGGCCTGGAGGGCGAGGAACTGCGCCTTCCAGCCCGGCAGCCGG
CGACCGGCGGCCTCGCCGAGCAGACGTGTGCACCAGAGCGCCGCGGTCTC
GTACGAGCCGGTGCGGCACAGGACCCGGACCGCGTTGACGACGATCACCA
GGGTGGTGTCGGTGAGCGGCAGGCTCCTCAGGACGTGCTCCGCCGCGTCG

FIG.6-3

GAGGCCGAGGCGTTGGTGCCGTCGCCGGGGAGGTCCCAGATCCCGGTCAC
CGGCATCCGCGGGCGGGGGCTCTCCTCGTCCCCGGGCTCCGGGTCCGTCC
GGGGACGGATCAGCGGCTCCCAGAGCGCGGAGGCGTGGAAGCCCGTCTC
CAGCCGGGGAGTTCGCGGGTCGCCGTGGGGGCCCGGCCGTCCCATGACCT
CCGTGGCCTCCTCCAGCCGTCCGCAGCCGAGCAGCAGGTGACCCAGCCGT
TCGGTCTCGGCGCTCGTCAGTCGTCCGGCCCGCAGCTCGGTGACGAGTTCG
GCGAGGTGGTCCTCCGCCGCCGCCGGGTCGGTGCGCCGGGTGGCGACGGT
CAGGCGCAGCAGGATCTCGGCGCGCCGGGGCCCTCCCGCACAGGAGCGCC
GGGCCAGTTCGAGACAGGAGACGGCGGTCAGGACGTCGTCCCGCATCAGC
AGCTGCTCGGCGGCGTCCCGCAGCACGGACATCGCCCAGGGCCCGGCCGC
GTGCCGGGCGGCGAGCAGGTGCCGGGCCACCTCGTCCGGTTCCGCGCCGA
CGTCGTACAGCAGCGCGGCGGCGCGGCGGTGGAGGTGTGCGCGGTGGTCG
TGGTCCAGGGTGTCCAGGGCGGCCGCCTCGACCACGGGGTGCCGGAAGCG
GCCGGACGCCGTCAGGCCGGTCGCCTCCAGGGCGCGCAGCCCGCGGGCCG
CCATGGCGCGGCCGATGCCGAGCAGCCGGGCGATCACCTCGGCGCAGCCG
GAGTCACCGAGGACGGCGAGCGCGCCGGCGCTGTGCCTAACCAGGCTGTC
GGTGCGGGACAGTGAGGCGAGGACGGCCTGGTAGAACCGCCCGCCGATG
ACGGGCGACGCTGCTCTCCGGCGCCGGCCGGCACGCTCGTCGGTGTGCCC
TTGGGTGTGGCTTTCGACGAGTTCTTCGAGCAGGGCATGCACCAGCAGCG
GATTGCCGCCGGTGACGGCGAGGAGGTCGTCCGCGGGCAGGGCCTCGACG
GCCGGTCCGGGGCGGGCGGCGCGCAGTCCGGACACGGCGCGCAGGGAGA
GGCGGCCGAGCATGACGCGCTGGAGGGCCGGCTGGCACAGCAGCTCGGC
CTCCACGGCGGGGTCGGCCGCCAGGCCGGACGGCAGCGCGGTGCAGACC
AGCAGCAGTCGGGTGGCGCGGGGATGGTCGACGGCCTGGAGCAGGCAGT
GCAGGGACTGCGGGTCCGCGTGGTGCAGGTCGTCGATGCCGATGACGACC
GGCGCGGCGCCGGTGAGCTGGTGGAGCGCCGCCCGCACACGCTGCGCGGC
CGGGGTCTCCGTCCCGACGGCGTCCTGGAGCAGTGAGCGCTGGGCGTCCG
GGATGTCGGGGTCGACCGCCAGTTGCCGCAGGAGGTCGAAGGGGCGCCG
GCCCTCCGGCGGGCTTCCGGCGGACCGGAGGACCAGGAAGCCCGATGCCG
CCGCGTGCTTGAGCGCCTCCCCCAGGAACGCGCTTTTCCCGCAGCCGAGTC
CTCCTTCGACGACCAGCACCCGCACCCGGCCGGCGGCGCACGCCTCGAGC
GCCGTTCTCACGGCATGGGACTGCCTGCCCAGGCCGAGGAACGTGAGCCC
TTGCGGCTCCCGCACGGACACCGAAGGGGAAACGCCCCGCATAATCTCCC
TCTGACTCCCTCCCCCGAAGACCGGGGGCTTTACGGATTCGTACCAACAG
GAAAGCCCACAAGTCGACGAGATACTGCCCCTCTCCCGAAGCCGCCACAC
GCGCACCCCGATACGAGAATGAGCCAATGAGCAAGCGTGGTGGCCGAGTT
GATACGAACCCGTGAATTTACGTTATTTCGCTCACCCTTTCGAGCGTGTGG
AGAGTCCTCGGAATGGGCGGCCGGGAGGTTGGGCAGCCTCCGCGGGACG
GCGAGCCATTCGCGAGGTCACGCGGACACGCGTGTTGCGATAATCGCACT
TAAGGAGAGGACGAGCGATGCCCGACCTTTGCGAGACCGAATCCCTCTGG
CTCCGGCGGTTCCAGCCGGCTCCCGCGGCCCGGACGCGGCTCATGTGCTTC
CCGCACGCGGGCGGGTCCGCCAGCGCCTATCTGCGCCTGGCCCGGTCCCT
CGCCCCCGGCATCGAGGTCCTGGCGGTCCAGTACCCCGGACGACAGGACC
GGCGCGCCGAGCCCTGCCCGGACTCCGTCGAAGGCCTGGCGGACGATCTG
TTCGCGGCCGTCCGGCACCGCGTGGACGCGTCGACCGCGCTGTTCGGACA

FIG.6-4

CAGCATGGGCGCGGTCCTCGCCTTCGAGCTGGCCCGGCGGCTGGAGCGCG
ACGCGGGGGTCCGCTGCGCCCGGATCTTCGCCTCGGGGCGCCGGGCACCC
TCCCGGTTCCGTGACGACTCCGCCCCGGCCGCCAGCGACGCCTCGATGCTC
GCCGAGATGCGGACTCTCGGCGGAACCGACCTGCGGGTGCTCCAGGACGA
GGAACTGCTGATCGCCGCGCTGCCCGCGCTGCGCGCCGACTACCGCGCGA
TCGGGACCTACCGCGCCGCCGACGACGCCGTGGTCGGCTGCCCGGTCACC
GTGCTGGTCGGTGACGCCGATCCGAGGACCAGCCTCGACGACGCCCACGC
CTGGAGCGCCCACACCACGGCGGAGTCCGAGGTGCTCACCTTCTCCGGCG
GGCACTTCTTCCTCGACGCCCACCACGACGCGGTGGTGGAGGTCGTCACC
GCGCGCCTGCGGCAGGACCGCGCGCCCCGGCCGGACCGGGTGTGAGGGG
GCCCGGCCCGAAGGGCCGGGCCGCTCCGCGCGTCTGCCGGCACCGGGCCG
CACCGGACCCGGCGCCGGCAGACGCGCGGCGACCTCACATCATGGCGGGC
GCCAGGGCCATTCCCCCGCTGGCGTCCAGCAGTTGGCCGGTGATCCAGCG
GGCGTCGTCGGAGACCAGGAAGGCGACGATGCCGGCGATGTCGTTCGGCC
GGCCCAGCCGGCCGAGCGCGGTCAGGGCCGAGATGCCCGCCTCGGCCCCC
GGGGTCTCGCGCACCCAGCGGTTCATGTCGGTGTCCGTGATGCCGGGGGC
CACGGTGTTGACGGTGATGCCGCGCGAACCGAGTTCGTTGGCGAGCCGGG
GAGCCATCATCTCCAGCGCCCCCTTGGTCATGGCGTAGGGCAGCAGCGGC
CAGGCGATCCGGGTGACGGCCGAGGAGACATTGACGATGCGTCCGCCGTC
GGCCATCAGTGACAGGGCCCGCTGGGTCACGAAGAACGGTGCCCGGACGT
TGATGCGGTACACGCGGTCGAACTCCTCGGGCGTGGTGTCCGACAGGCCG
GGGACATAGCCGTCCTGTGCCGCGAGCGCCGGGTCGCCGGGGGCGGGGG
CGACGGCCGCGTTGTTCACCAGGATGTGCAGCGGACGCCCCTCCAGCTCC
CGCTCCAGTGCGGTGAAGAGCTCATCCACGGCGTCGTCCCGGAGGAGGTC
CGCCCGGACCGCGAAGGCCCGTCCCCCCGCGCGTTCGATCGTCTCCACCG
TCTCCTGGGCGCTCTTTTCCTGCGTTCCGTAGTGCACGGCGACCCGGACGC
CCTCGGCGGCGAGTCGCTGGGCGATGGCTTTTCCGATGCCGCGCGAGGCA
CCCGTGACCAAGGCCGTCCTGTCGTTCAATTCCGGCATCCCGAATCCCCTT
CTGCCGATTATCTTACTTTTCCTCTTGATGCATGGGGTCGGACCCGAGGCC
AGATCCGCACCCCGGCCACGCGTGAGGTCGCGACCTCACCGATTACTGTG
CCAGAGTCCAGGCGACACACGGGAGGGCGGGAATGCGATCGATTTCCGC
ACCCGGAACTCGTAGGGGGAGCAAGAAGATCGGCCGAATACCCCTGGGG
TGGATAGGGGGTACCAGGACCGTCGGGCGATCACTATTTTGAAACACGAC
TCCGGCGCGCGGCCGGCGGCGAAAGTCCTCTCCATGCCGGGCTGTCCCCT
GCCTCGAAATACCTGCGGCGACTTTCGCCCTGCGATGCGGCCGCCCATCCC
TGCCGAGCGGTGAGGAGACGACAAGTGCACGAGACACACGCGCACGGCG
AGGAAGGGTCGTCCGACGGGTCCGCGGACGCAGTGGTCTTCGTCTTCCCC
GGACAGGGGTCTCAGTGGCCGGGGATGGGTGCGGAACTGTGGGACACCTC
CCCGGTGTTCCGCGAGAGTGTGCGCGCCTGCGCCGACGCGCTCGCCCCGT
ACCTCGACTGGTCCGTCGAAGGCGTCCTGCGCGGCGCCCCGGACGCCCCG
GCCGGCCCGGCGCTCGATCGCGCCGACGTCGCGCAGCCGGCCCTGTTCAC
CCTCATGGTGTCGCTGGCCGAGCTCTGGCGCTCGCACGGAGTCGAACCCT
GCGCCGTCCTCGGGCACAGCCTCGGCGAGATCGCCGCCGCGCATGTGGCC
GGCGCCCTGACCCTGGCCGACGCCGCCCGGGTGGCGGCCCTGTGGAGCCG
GGCCCAGGCCACGCTGTCGGGCACCGGCACCCTTCTCGCGGCCAAGGCCG

FIG.6-5

CCCCCGAGGAACTGGCACCGCACCTTCAGCGGTGGAACGGCGACGACCGG
CACGGCACCCGGCTCGCGATCGCCGGCGTCAACGGGCCCGGCAGCACGGT
GGTGGCGGGGACCTCGACGCGATCGCCGCGCTGGCCGCCGACCTGGCCT
CGGCGGGGGTGCGGACCCGCCGGGTCGCCGTCGACGTGCCCACCCACTCC
CCCGCGATGCGGACCCTGCGGGAACGGATCCTCACCGACCTGGCCTCCGT
CGCCCCGTGCGTCTCCCGTCTCCCCTTCCACTCCTCGCTCACCGGCGGTCT
GGTGGACACCCGCGGGCTGGACGCCGACTACTGGTACCGCAACATCAGCG
AGACCGCGCGCTTCGACCTCGCCGCCCGCGGTCTCCTGGCCGACGGACAC
CGGACGTTCGTGGAGCTGAGCCCGCACCCGATACTCACCCTGGGCCTGCA
AGCGCTCGCCGACGACGTCCCCGGCGCCGCCGACGCGCTCGTGACGGGCA
CGCTGCGCCGCGGGCGCGGCGGAATGCGGCAGTTCCAGGACGCGCTCGGC
CGGCTCAGCGTCCCCGCGGGCGGGCGGCCCGGCCGCGAGGTGAGCGCCGC
GGCCCTGGCCGGCCGGCTGGCGCCGCTCTCCCCGGCGCAGCAGGAGCATC
TGCTGGTGGAATTGGTCTGCGCCCACTTCGCCGCACTCGTCGGCGGCGAC
GGCGGGGCGCCGCCGACGGTGCGGCCGTCGGCCGCCTTCACCGATCAGGG
CTGCGACTCCGCCACCGCCCTGGAGCTGCGCGACCGGCTCCGCGAGGCGA
CCGGGCTGCGCCTGCCCGCCACGCTGGTCTTCGACCACCCGACGCCGGCC
GCGGTCGCCGGCCGGTTGCGCCGACTCGCCCTCGGGATCGAGGAGACGGC
GGACACGGCACCGGTCGCCGTCCGCGGCCACCGGGAGGGCGAACCGATC
GCGATCGTCGGGATGGCCTGCCGCTTCCCGGGAGGTGTCCGGTCGCCGGA
GGACCTGTGGCGGCTGGTCACCGAAGGCGGTGACGCGCTCGGGCCGTTCC
CCACCGACCGCGGCTGGGACACCGGCCGCCACGCGGAGGACCCGGCCAC
ACCCGGCACCTACGTCCAGGGCGAGGGCGGATTCCTGTACGACGCGGGCG
AGTTCGACGCCGAGTTCTTCGGGATCTCCCCGCGTGAGGCGCTGGCCATG
GACCCGCAGCAGCGGTTGCTGCTGGAGATGGCGTGGGAGACCTTCGAACG
GGCGGGAATCGATCCCACCTCGGCCCGGGGATCGCGTACCGGCGTCTTCG
CCGGGGTCCTCCCGCTCGGCTACGGCCCCCGCATGGACGAGACGGACCAG
GGCACCGCCGACCTCCAGGGCCATCTCCTCACCGGCACACTGCCCAGCGT
CGCCTCGGGCCGCATCTCCTACACCCTCGGCCTGGAGGGCCCGGCGGTGT
CGGTGGAGACGGCCTGCTCGTCGTCGCTCGTCGCCCTCCACCTCGCCTGCC
GCTCGCTGCGGGCGGGCGAGTGCGACCTCGCCCTGACGGGGGGCGTCTCG
GTGCTGGCCACCCTCGGCCTGTTCGTCGAGTTCTCCCGGCAGCGTGGACTG
TCGGCGGACGGCCGGTGCAAGGCGTACGCGGCGGCGGCCGACGGGACCG
GATGGAGCGAGGGTGCCGGGCTGCTGCTGGTCGAACGGCTCTCCGACGCA
CGGCGGCTGGGGCACCGGGTGCTCGCGGTGGTCCGGGGCAGCGCGATCAA
CCAGGACGGCGCGTCGAACGGGCTGACCGCCCCCAGCGGGCCGTCCCAGC
AGCGGGTCATCCGCGAGGCCCTGGCCGACGCGGGCCTGACGGCGGCGGA
CGTCGACGCGGTGGAGGGGCACGGGACCGGCACACGACTGGGCGACCCG
ATCGAGATCGAGGCGCTGCTCGCCACCTACGGACAGGGACGCGCCCGGGA
ACGGCCGCTGTGGCTCGGATCGCTGAAGTCGAACATCGGTCACACCATGG
CCGCGGCGGGGGTGGGCGGGGTCATCAAGATGGTGATGGCGCTGCGGCA
CGGGGAGCTGCCCCGCACCCTGCACGTGGACGCGCCCTCGCCCCGGGCCG
ACTGGTCGGCGGGCGAGGTACGGCTGCTGACGGAGGCCGTCGCGTGGCCC
GCGGCGGCGGACGGTGAGCCGCGGCGGGCCGGGGTGTCGTCCTTCGGCGT
GAGCGGCACCAACGCGCACGCCATCCTGGAGGAGGCGCCCGCCCCGGAG

FIG.6-6

GACGAGGAACCGGCGCCGCCGGACGGTGAAGCACTACTGCCGTGGGCGG
TGTCCACGCGGTCGGAGGCCGCACTGCGGACGCAGGCACGGATGCTGGCG
GACGTCGTACGCGACGACCCCGGAGTCGGACTCGCCGATGTGGGTGCGGA
GCTGGCCCGGGGGCGGGCGGCTCTCGAGCACCGGGCCGTCGTCATCGCCT
CCGGGCGCGCGGAGTTCGCGCGGGCGCTGGAGGCGGTGGCGTCCGGCGA
GCCGCACCCGGCCGTGGTCCGGGGCCACGCGGGGAGCGAGCGCGGCGGA
GTGGTGTTCGTCTTCCCGGGCCAGGGCGGTCAGTGGGCCGGCATGGGACT
CGACCTCCTGCGAAGCTCACCGGTGTTCGCGGAGCACATCGCGGCCTGCG
GCAAAGCTCTGGCCCCGTGGGTGAAGTGGTCGCTCACGGAGGTGCTGCAC
CGGGACGCCGAGGATCCGGTCTGGGACCGGGCCGACGTCGTCCAGCCGGT
GCTGTTCTCGGTCATGACGTCGCTGGCGGCGCTGTGGCGCTCGTACGGCGT
CGAGCCGGACGCCGTGACCGGGCACTCGCAGGGGGAGATCGCCGCCGCG
TACGTCTGCGGAGCGCTCGGTCTGGAGGACGCCGCACGGACGGTGGCGCT
GCGCAGCCGCGCCCTGGTGGCGCTGCGCGGGCGGGGCGGCATGGCGTCCG
TCGCCTCCGCCGCCCCGGACGTCGAGGAGCTCATCGCGCGGCGCTGGCCC
GGCCGGCTGTGGGTCGCGGCGTTCAACGGCCCCGGCGCGGTGACCGTTTC
CGGGGACGGTGATGCGCTGGAGGAGTTCCTGGGCCACTGCGCGGACACGG
AGGTGAGGGCTCGGCGCGTCCCGGTGGACTACGCCTCCCACTGCCCGCAC
ACGGAGGCGATCGAGCGGGAACTGCTCGACGCCCTGGAGGACATCACCCC
CCGGCCGGCGGCGGTCCCGTTCTATTCGACGGTCGACGACGCGTGGCTGG
ACACCACACGGCTGGACGCCTCCTACTGGTACCGCAACCTGCGCCGGCCC
GTCCGTTTCAGCCAGGCCGTGCGCGCCCTCACGGACGGCGGCCACCGCGT
CTTCATCGAGGCGAGCCCGCATCCCACCCTCGTCCCCGCCATCGAGGACC
ACGGCGACGTCACCGCCCTCGGCACCCTGCGCCGCCACGGCGACGACACC
GAGCGGTTCCTCACCGCCCTCGCCCACCTCCATGTCACCGGAGCCGCCGG
CCAGGACCTCTGGCGCCACCACTACGCCCGGCTCAGGCCCGCCCCCCGCC
ACGTCGACCTGCCCACCTACGCCTTCCAGCGCGACCGGTACTGGTGGAGC
GGCGGCGCCGGGCGCGGGGACGTCACCACCGCCGGTCTGCACCCCGGCGG
CCATCCCCTCCTCGGCGCCGCGCTGGACCTCGCCGACGGCGGCGGCCGCC
TCCACACCGGCCGTGTCTCCCTGCGCACCCACCCCTGGATCGCCGACCACG
GCGTCGCGGGCATCACCCTCCTGCCCGGCACCGCCTTCCTCGAACTCGCCC
TGCACACGGGCGAGTCGGGGAACGTGCGGGAACTCACCCTGCACGCGCCC
CTGGTCGTTCCCGACGAGGAGGGCGTCGACCTGCAAGTGCACCTCGCCCG
GCCCGACGAAGCGGGCCTGCGCGCCCTGACCCGTCTTCTCCCGGGCCGCg
GGGTGCCGACCCCGAGAGCCCCCTGGCAGCCCCACGCCACCGGCCTTCTC
GGGCCGGCCGACCGAGCACCCGGCTCCTCCGGCCTCGAGCCGCACGACCT
GGGCGGCGCCTGGCCTCCGCCGGGGGCGGTCCCCCTCGTCCCCGGCGAAC
TCGGCGACGTGCCCGGCTGCTACGCCCGCCTGGCCGACGAGGGGTTCGAG
TACGGGCCGGCCTTCCGGGGGCTGCGTGCGGTGTGGCGCCGCGGCACGGA
GATCTTCGCCGAGGTCGCCCTCCCGGCCGGCGACGGCTCCGTGTTCCGGCT
GCATCCGGCGCTGCTGGACGCCGTGCTGCACCCCGTCGTACTCGGGCTGG
TGGACGGCGTGCCGGCCCGTCCGCTGCCCTTCTCCTGGAACGGCGTGGCG
CTGCACGCCCCCGCGAGCGGCGCGCTGCGGGTGCGCCTCGCGCCGGCCGA
CGACGGCGCTGTCGGCATCACGGCCGCGACGGCCGCCGGTGAGCCGGTGC
TCTCGGTCGCCGCGCTGGCCCTGCGGTCCGCCTCGGCGGAGCAGTTGCGC

FIG.6-7

GCGGCGATCCGCTCCGCGGCGGGCTCGCGCGACGCCCTCTACGAGCTGGA
CTGGCTGCCGCTCCCGGCGGACCGGGCCGCTTCGCCCGGTGGGGCCGACA
TCGCGGCCCTGGGCACATCGGAGCTGCCCTGCCGTACGTACGAGACCATC
GCGGAGCTGTCGCAGGCCCTCGCCGACGGTGCTCCCGCCCCCGACGCCGT
CGTCTCCGACGTCGGCGCCGTCGGCGGGCCGCTGGACACCGTGAGCCTGC
ACGGCCTCTGCCGGCGCGGGCTGGAACTCGTGCAAGCCTGGCTGGGCGAG
CCCCGGACGGCCGACACGCGGCTGGTGCTCGTGACGCGTGGGGCGGTCGG
CTGTGCCCCGGCCGAGCCGGTCGCCGATCCGGCCGCGGCCGCGCTGTGGG
GGCTGGTGCGGTCCGCGCAGGCGGAGCACCCCGGACGGCTGCTCCTGCTG
GACCTCGACCCCGCCGGGTCGCGGCCCGTCTCCGGCCGCCTGGTGGAACA
GGCGGTGGCCTGCGGTGAGCCGCACATCGCCGTACGGGGCGACGGCCTGC
GCGTCCCCCGGTTGTCCCGCGCGACGGCCGCCCCCGCACACCCTCCCGCC
GGTGGCCGGGAAGCGCAGTGGGACCCGGAAGGGACCGTCCTCATCACCG
GCGGCACCGGAAGTCTCGGCGCGCTGTTCGCCCGGCATCTGGTGACCGCG
CACGGGGTACGGCGGCTGCTCCTCGCCAGCCGCAGTGGCCCCGGCGCCCC
CGGCGCCGCCGGGCTGCGGACGAACTGACCGCTCACGGAGCCACCGTCA
CCGTCGCCGCCTGTGATGTGGCCGACCGGGAGGCCGTCGCCGCCCTCCTG
GCGTCCGTGCCGTCCGAGCACCCGCTGACCGCCGTAGTGCACACCGCCGG
CGTGCTGGACGACGGCGTACTCGCCTCGCTCACCGCCGACCGGCTGGCCC
GCGTCCTGCGTGCCAAGGCCGACGCCGCGCTCCACCTGCACGATCTCACC
CGCGATCTGCCGCTCGCCGCCTTCGTCCTCTTCTCCTCCGTCACGGCGACG
CTCGGCACACCCGGCCAGGCCAACTACACCGCCGCCAACGCGTTCCTCGA
CGCGCTCGCCCGGCATCGGCGCGCCGCGGGCCTGCCCGCCGTCTCACTCG
CCTGGGGGCTGTGGGAGCAGACCGGCGGGCTGACCGATCACCTCGGATCG
GTCGACCTGCGGCGGATGGCCCGCAACGGCCTGGTCGCGCTGCCCGCCGA
CGCCGGCCTGGCGCTCTTCGACACCGCGCTGGCCCTGGACCGCGCCAACC
TGGTCCCGGCGCGGCTCGACCTGCCCGCGCTGCGCCGCGCCACACACGTG
CCGCCCGTTCTGCGGCGGCTGGTCGAGGTGCCGGGGGCGCCGAGCGCGGA
CCGGTCCGCCGGGTCCGGCGGCGAGGTGAGGCCGCTGCGTGAGACGCTGG
CCGGGCTGGACGACCGGAAACGCCCCGCTGCCGTCTCCCGCCTGGTCCGC
AGGCACGTCGCGTGGGTGCTCGGCGCCGACGGTCCGGAGTCGGTGGACGA
GGACCGCAGCTTCCGCGACCTCGGCTTCGACTCGCTGATGGCCGTCGAAC
TGCGCAACCAGCTCAACACCGCCGCCGGCATCCGGCTCGCGGCCACCCTC
GTCTTCGACCACCCGACACCGTCGGCCGTGGCGCGGCACCTCCTCGACCG
GTGCTCGCCGGACCCGGCCGCCCCGGCCGCTCCCTCGGGTACGGCGGTCG
CGTCGGCGCTCGCCACTCTGGCCGAGCTGGAGACGGCTTTGAACGGCATC
CCGGCCGAGGAGTGGACGGCCGCCGGGGGCCCGGCCCGGCTGATGACGC
TGGCGTCCTCGCTGCCCGCGCCCGCGTCCGTCCCTCGGACACCGGCGGCC
GGCGAAGCCGCCGAGAAGCTCGCCCACGCCTCGCGCGACGAGATCTTCGC
GTTCATCGATCGGGAGCTGGGGCGTGACTCCGGGCCAGCCTCACCCTCTC
GCCTCGGTCCGCAGACCCCCGACTCGACAGACAAGGCGCCCTTTCATGGA
GAATGAGGAAAAGCTCCTGGACTACCTCAAGTGGGTCACCGCCGATCTGC
ACCGCTCGCGGGAACGCGTCACCGAGCTGGAGGAGGCCGGCCGGGAGCC
GATCGCCATCGTCGGGATGGCCTGCCGGTTCCCGGGCGAGGTGCGGTCGC
CGGAGGAGCTGTGGGGGCTGGTCGCCTCGGGCGGCGACGCGATCGGGGC

FIG.6-8

GTTCCCGGACGACCGCGGGTGGGATCTGGACGGGCTGTTCGACCCCGACC
CGGAGCGTGCGGGCACCTCGTACACCCGGCGCGGCGGTTTCCTGTACGAC
GCGGCGGAGTTCGACGCGGGCTTCTTCGGGATCTCCCCGCGTGAGGCGAT
GGCGATGGACCCGCAGCAGCGGCTGCTGCTGGAGACCTCGTGGGAGGCTT
TCGAGCGGGCCGGCATCGACCCGTCCTCGGTACGCGGGTCCCGGGTCGGT
GTCTTCGCCGGCCTCATGTACCACGACTACGCGGCGGCCCAGGGCAGCAC
CGGGGACGGAGACGGGGAGCCGGACTTCGAGGGCTACCTCGGCGACGGC
AGCGTCAGCAGCATCGCCTCGGGCCGTATCGCCTACACCCTCGGGCTCGC
GGGCGCGGCGATCACCGTCGACACGGCCTGCTCCTCTTCCCTGGTCGCCCT
GCACCTCGCCTGCCAGGCGCTGCGCACCGGCGACTCCGAGCTGGCCCTGG
CCGGCGGGGTCAGCGTCATGTCCACCCCCCGCACCTTCGTCCAGTTCTCGC
GGCAGCGGGGCCTGTCGGCGGACGGCCGGTGCAAGGCGTACGCGGCGGC
GGCCGACGGGACGGGGTTCTCCGAGGGCGTCGGCATGGTGCTGGTCGAAC
GGCTCTCCGACGCCCGGCGGCTGGGGCATCCGGTACTGGCGGTCGTGCGG
GGCAGCGCGGTCAACCAGGACGGCGCGTCGAACGGTCTGACGGCGCCCA
ACGGACCGTCGCAGGAGAGGGTGATCCGCGAGGCGCTGGCCAACGCGGG
CCTGACGGCGGCGGACGTCGACGCGGTGGAGGGGCACGGGACCGGGACA
CGGCTGGGTGACCCGATCGAGTTGCAGGCGCTGCTCGCCACCTACGGACA
GGGACGCGCCCGGGAGCGGCCGCTGTGGCTCGGATCGGTGAAGTCCAACA
TCGGTCACGCGCAGGCGGCGGCGGGGGTGGGCGGCGTCATCAAGATGGT
GATGGCGCTGCGGCACGGGGAGCTGCCGCGCACCCTGCACGTGGACGCGC
CCTCGCCCCGGGTCGACTGGTCGGCGGGCGAGGTACGGCTGCTGACGGAG
GCCGTCGCGTGGCCCGCGGCGGCGGACGGTGAGCCGCGGCGGGCCGGGG
TGTCGTCCTTCGGGGTGAGCGGCACCAACGCCCATGTGATCCTGGAGGAG
GCGCCCGCGTCGGAGGGCGAGGAAGCTCCGCCGCCGGAGCCCGGGTCGC
CGTTGCCGTGGGTGGTGTCCGGTCACTCGGAGGCGGGCTTGCGCGCCCAG
GCGCAGGCTCTGGCGGAGTTCGCACGGACCGCGCCCGGGGCCGAACTCGT
GGACGTGGGAGCGGCGTTGGCCCGGGGGCGGGCGGCGCTGGGGCATCGG
GCGGTCGTCGTCGCCTCGGAGCGTGAGGAGTTCGAGCGGGCGCTGGCCGC
GCTGGCCTGTGGCGAACCGCACCCGTGTGTGGTCGACGGGTCGGCGGACG
GCCGGCGCGAGGACGGTGTGGTGTTCGTCTTCCCGGGCCAGGGCGGTCAG
TGGGCCGGCATGGGACTCGATCTGCTGACGACCTCGGGGGTGTTCGCCGA
ACATATCGGTGCGTGTGAACGCGCGCTGGCGCCGTGGGTGGAGTGGTCGC
TGACGGAGATGCTCCACCGCGAGGCGGAGGACCCGGTGTGGGAGCGGGC
GGACATCGTCCAGCCGGTGCTGTTCTCGGTCATGGTGTCCCTGGCCGCGCT
GTGGCGGTCCTACGGCATCGAACCCGACGCGGTGGTCGGCCACTCCCAGG
GCGAGATCGCCGCCGCCCACGTCTGCGGCGCCCTCACCCTCGAAGACGCC
GCGAAAGTCGTGGCACTGCGCAGCCGGGCCCTGGCCGCACTGCGGGGCCG
CGGCGGCATGGTCTCCCTCTCGCTGTCGACCGCGGATGCCGGGGAGCTGG
TGGAGCGGCGGTGGGCCGGGCGGCTGTGGGTCGCGGCGCTCAACGGGCC
GGAGGCGACGACGGTCTCGGGGGACGTCGACGCGCTGGAGGAGCTCCTG
GCCCACTGCGCGAAAAGCGAGGTGCGAGCGCGGCGCGTCCCGGTGGACT
ACGCCTCCCACTGCCCGCACACGGAAGCGATCGCGGAAGAGATCGTCGAT
TCACTCGGGGACATCACGCCCCGGGCCGCCACCGTTCCGTTCTACTCGACG
GTCGACGACATGTGGTTGGACACCACACGGCTGGACGCCTCCTACTGGTA

FIG.6-9

CCGCAACCTGCGCCTCCCGGTCCGCTTCAGCCAGGCCGTGCGCGCCCTCAC
GGAAGAAGGCCACCGCCTCTTCATCGAGACGAGCCCGCATCCCACCCTCG
TCCCCGCCATCGAGGACCACGGCGACGTCACCGCCCTCGGGACCCTGCGC
CGCCACGGCGACGACACCGAGCGGTTCCTCACCGCCCTCGCCCACCTCCA
TGTCACCGGAGCCGCCGGCCAGGACCTCTGGCGCCACCACTACGCCAGGC
TCAGGCCCGCCCCCCGCCACGTCGACCTGCCCACCTACCCCTTCCAACGCC
GGCGCTACTGGCTGGAGAAACCCGACCCGCAGACCAGGCCCCAGCGGTCC
CGCTCCACCGCCCCGGACCTCGACAGGCTGGAGGCGGAGTTCTGGCAGGC
CGTCGAGGAAACCGACACCGACACCCTCGCCCACACCCTCCACCTCGACA
CCCAGACCCTCGAACCCGTCCTCCCCGCCCTCGCCACCTGGCACCAACAA
CAACGCGACCACGCCCGCATCAACACCTGGACCTACCAGGAAACCTGGAA
ACCACTCCACCTCCCCACCACCCGACCCACCACCCCCACCAGCTGGCTCAT
CGCCATCCCCGAAACCCACCGCAACCACCCCCACACCACCAACCTCCTCA
CCAACCTCCCCCACCACAACATCACCCCCATCCCCCTCACCATCAACCACA
CCACCGACCTCCACCACGCCTACCACCACGCCCACCACCACACCACCCCA
CCCATCACCGCCGTCCTCTCCCTCCTCGCCCTCGACGAAACACCCCACCCC
CACCACCCCCACACCCCCACCGGCACCCTCCTCAACCTCACCCTCACCCAA
ACCCACACCCAAACCCACCCACCAACCCCCCTCTGGTACCTCACCACCCA
AGCCACCACCACCCACCCCAACGACCCCCTCACCCACCCCACCCAAGCCC
AAACCATCGGACTCGCCCGCACCACCCACCTCGAACACCCCCACCACACC
GGCGGACACATCGACCTCCCCACCACACCCCACCCCAACACCCTCACCCA
ACTCATCACCGCCCTCACCCACCCCCACCACCAACACAACCTCACCATCCG
CACCCACACCACCCACACCCGACGACTCACCCCCACCACCCTCCAACCCA
CCACCCCCACACCACCCACCAACCCCCACGGCACCACCCTCATCACCGGC
GGCACCGGCGCCCTCGCCACCACCCTCGCCCACCACCTCGCCACCACCGG
CACCCAACACCTCCTCCTCACCAGCCGACGCGGCCCCCACACCCCCGGCG
CCCGACAACTCCACACCCAACTCACCCAACTCGGCACCAACACCACCATC
ACCGCCTGCGACCTCTCCGACCCCGACCAACTCACCCACCTCCTCACCCAC
ATCCCCCCCGAACACCCCCTCACCACCGTCATCCACACCGCCGGCATCCTC
GACGACGCCACCCTCACCAACCTCACCCCCACCCAACTCGACAACGTCCT
GCGCGCCAAAGCCCACACCGCCCACCTCCTCCACCACGCCACCCTCCACA
CCCCCCTCGACCACTTCGTCCTCTACTCCTCCGCCGCCGCCACCCTCGGCG
CCCCCGGCCAAGCCAACTACGCAGCCGCCAACGCCTACCTCGACGCCCTC
GCCCACCACCGCCACACCCACAACCTCCCCGCCACCACCATCGCCTGGGG
AACCTGGCAAGGAAACGGCCTCGCCGACTCGGACAAGGCCCGCGCCAAC
CTCGACCGCCGGGGCTTCCTGCCCATGCCCGAGACGCTGGCCGCAGCCGC
GGCCGTGCGGGCGATCGAGAGCAGGCGGCCGTCCGTGGTCATCGCCGCCA
TCGACTGGGCCAGAGCCGAGCGCACCCCCGACGTCGAGGATCTCCTCCCC
GCGGCCGACGAGGGGTCGTCGAGTGGCAAGCCGGAGGCCGCGCCGGTGG
ACCTGCGCGGTACCTTGAGCCGGCAGTCCGCCGCCGACCAACAGGCCACA
CTGCTCGGCCTGGTGCGGACCCAGGCAGCCGTCGTACTGCGCCACACGGA
GCCCGAGGCGCTCGCCCCGGGCCAGGCCTTCCGGGCGCTCGGCTTCGACT
CCCTCACCGCCGTCGAACTCCGCAACCGACTGGCCAAGGCCACGGACCTC
GCGCTGCCCGCCTCACTGGTCTTCGATCACCCGACTCCGGTGAAGCTCGCG
GAGTTCCTGCGCACCGAGCTGCTCGGCACCGCACCAGCTACCACCGCCGC

FIG.6-10

CGTCCCGGCCCTCCAGGCACACACCGACGAACCCATCGCCATCATCGGCA
TGGCCTGCCGCTTCCCCGGCGCCGTCACCACACCCGAACACCTGTGGAAC
CTCATCGCCACCGAACAAGACGCCATCGGCGAGTTCCCCACCGACCGCGG
CTGGGACCTGGACAACCTCTACCACCCCGACCCCGACCACCCCGGCACCA
CCTACACCCGCCACGGCGGATTCCTCCACGACGCCGGCGACTTCGACGCC
GACTTCTTCGGCATCAACCCACGCGAAGCCCTCGCCATGGACCCCCAACA
ACGACTCCTCCTCGAAACCGCCTGGGAAGCCATCGAACACGCCGGCATCC
TCCCCGACGCCCTGCACGGCACCCCCACCGGCGTCTTCACCGGCGTCAAC
GCCCAGGACTACGCCGCACACACCCACACCTCCCCCCACACCACCGAGGG
CTACACCCTCACCGGAACCGCCGGCAGCATCGCCTCCGGCCGCATCGCCT
ACGTCCTCGGACTCGAAGGCCCCGCCGTCACCATCGACACCGCCTGCTCCT
CCTCCCTCGTCGCCCTCCACCTCGCCTGCCAGGCCCTGCGAGCAGGCGAAT
GCACCACAGCCCTCGCCAGCGGCATCAGCATCATGACCACACCGCTGGCC
TTCACCGAGTTCTCCCGGCAGCGGGGTCTGGCGGCGGACGGCCGGTGCAA
GGCGTTCGCGGCGGCCGCCGACGGTACCGGCTGGTCGGAGGGGGTGGGG
ACGCTGCTGTTGGAGCGGTTGTCGGACGCCGAGCGGAACGGGCACCGGGT
TCTGGCGGTGGTGCGGGGCAGCGCGGTCAACCAGGACGGCGCCTCCAACG
GGCTGACGGCGCCGAACGGTCCGTCCCAGCAGCGTGTGATCCGCCAGGCC
CTGGTCAACGCGAACCTCTCCGCAGTTGATGTCGACGCCGTCGAAGCCCA
CGGCACGGGGACCAAGCTGGGCGACCCGATCGAAGCCCAGGCCCTGCTCG
CCACCTACGGCCAGGGACGTGCGCAGGAACAGCCACTGTGGCTCGGTTCG
GTCAAATCCAACCTGGGTCACACCCAGGCGGCGGCAGGCATGGCCGGCCT
GATCAAGATGGTGATGGCGCTGCGGCACGAGTCGTTGCCGCGGACGTTGC
ATGTGGATGAGCCGTCGCCGGAGGTGGACTGGTCGTCGGGGGCGGTGAGT
CTGCTGACCGAGGCGCGGCCCTGGCCGCGGGTCGAGGACCGGCCCCGGCG
GGCCGGGGTGTCCTCGTTCGGGGTGAGCGGGACGAACGCCCACGTCATCG
TGGAGGAGGCGCCCGCGCCGACGGGAGTGGAGGCGGTGGAAGCCGCGCC
GGCGGGGGTGGAGACTGCGGCGGCTGCGGCGGTGGTGGTGGAGACGGAC
GGTGCGGGCCGGGTGTCGGCGGATCTGCCGTTGGTGTGGGTGGCGTCGGG
CAAGTCGCAGGCCGCGATACGCGCCCAAGCCGCCGCCCTGCACGCCCACG
TCCTGGACCACCCCGAACAGGACGCGGACGACATCGGCTACAGCCTGGCC
ACCACCCGCGCCCTGTTCGACCACCGCGCCACCCTCATCGCCCCCGACCGC
CACACCGTCCCGGAGCCCCTCACCGGGCTGGGCGACGGACGCACGCACCC
CCACCTCATCCCCACACCCCCCACCGAACCCGGCCACACCCACAAAATCG
CCTTCCTCTGCTCCGGACAAGGCACCCAACGCCCCGGCATGGCCACCGGC
CTCTACCACACCTACCCCGCCTTCGCCGCCGCCCTCGACGAAACCTGCGCC
CACTTCGACCCCCACCTCGACCACCCCCTGCACGACCTCCTCCTCAACCAC
GACCCCACCGACCTCCTCACCCACACCCTCTACGCCCAGCCCGCCCTCTTC
ACCCTCCAAAAAGCCCTCCACCACCTCATCACCGAAACCTACGGCATCAC
CCCCCACTACCTCGCCGGACACTCCCTCGGCGAAATCACCGCCGCCCACCT
CGCCGGCATCCTCACCCTCCCCGACGCCACCCACCTCATCACCACCCGCGC
CCGCCTCATGCAAACCATGCCCCCCGGCACCATGACCACCCTCCACACCA
CCCCCGAACACATCCAACCCCTCCTCGACCAACACCCCGGCAAAGCCGCC
ATCGCCGCCGTCAACAGCCCCCACTCCCTCGTCATCAGCGGCGACCCCGA
CACCATCCACCACATCACCACCACCTGCCACAACCAAGGCATCACCACCA

FIG.6-11

```
AACCCCTCGCCACCAACCACGCCTTCCACTCCCCCCACACCGACACCATCC
TCGAACAACTCGACACCACCACCCACACCCTCACCTACCACCAACCCCAC
ACCCCCCTCATCACCAGCACCCCCGGCGACCCCCTCACCCCCCACTACTGG
ACCCACCAGACCCGCCAACCCGTCCACTGGACCGACACCATCCACACCCT
CCACACCCACGGCGTGACCACGTACATCGCACTCGGACCAGAGCACACCC
TCACCACCCTCACCCACCACAACGTCCCCCACCACCAACCCACCGCCATC
ACCCTCACCCACCCCCACCACAACCCCACCCACCACCTCCTCACCGCACTC
GCCCACCTCCACACAACCCAACCCACCGGCCCCAACATCTGGCACCACCA
CTACACCCCAGTCGCACCCGCCCCCCGCCACGTCGACCTGCCCACCTACCC
CTTCCCACGCCGGCGCTACTGGGTGCAGGCGTCCGCCGGTACGGGTGACG
TGTCGGCTGCCGGGCTCCAGCGACCGGACCACCCACTGCTCGGCGCGGTG
ATGGAGCTCGCGGACGGGGACGGAATCGTCCTCACCGGGCGCTTGTCCCT
GCACACCCACCCCTGGCTCGCCGACCACAGCGTCGGCGGCGTCGCCCTCC
TTCCCGGTACCGCTCTGCTGGAGCTGGCTTTTCAGGCTGGTCTGCGTGCGG
GTTGTCCTGGTGTCGATGAGCTGACTCTCCATGCTCCTCTGGTGGTTCCGG
AGTCGGGGCATGTGGTGGTGCAGGTGTCGGTTTCGGTGCCGGGCGAGGCG
GGTCGTCGTGGTGTGAGTGTGTACGGGCGGCTGGTGGAGGACGGGGGGCT
GGAGGGTGAGTGGACGCGGCATGCCGAGGGTGTGGTGTGTCCGTCTGTTC
CTGGGGAGTCGGTGGTTGTGGAGCCGGTGGCGGACGGGGTGTGGCCGCCG
TCCGGTGCGCAGCCGGTGGATCTTGAGGAGTTCTACGGTCGTCTGGCGGG
TGGGGGTTTTGTCTACGGTCCGGTGTTCCAGGGTTTGTGTGCGGCCTGGCG
GGACGGGGACGACGTGGTGGCCGAGGTGCGTCTGCCGGACGAGGGGCTG
GCCGATGTCGCGGGCTTCGGGGTGCATCCGGCGCTCCTGGACGCGGCCGT
GCAGGCAGTCACCCTCCTGTTCCCGGACCAGCAGCAAGCCGGTCTCGCGG
CCCACACATGGAACGGTGTCTCGCTCCACGCCCGGGGCGCCACCGTCCTG
CGCCTGCGCATGACTCCCACCGACGCGACCTCGACCGCCGTTCGCCTGCA
CGCCACCGACGAGACCGGAGCACCCGTTCTCACCCTCGACTCGCTCCTGA
TGCGTCCGGTGCCGTTGGAGGGGCTGGGGGCGGGGGTGCGGCGTGGCTCG
TTGTTCGAGCTGGGGTGGGTGCCGGTGGAGGGGATGCCGGCCTCGGTGGC
CGGTGGGGGCGGGGAGTTGGTGGCGTGGGAGTGCCCGGGTGGTGGGGTG
GCCGAGGTCACGGCCGCGGCGTTGGGAGTGGTGCAGGAGTGGCTCGCCGA
TGAGCGGGAGGGGGACGCGCGGCTGGTCGTGGTGACGCGTGGTGCGGTC
GCGGTGGATGCGGGGGAGCCGGTGCGGGACGTGGCGGGGGCCGCTGTGT
GGGGGCTGGTCCGCTCGGCCCAGTCCGAGCATCCCGACCGGTTCGCCCTG
CTCGACCTCGACCCCGACACCAAGACCGACCCCGGCATCGACACCGACGG
GGACACCGACGTGTCCGCCGACGCGAAGGTCGGCACCGGTGATGGTCTCG
ACGATGCCGCCGTCGCGTCCGCTCTGGCCCGCGGTGAGAGCCAACTCGCC
GTACGCGACGGGGTGGTTCGCGTAGCGCGGTTGGGGGGTTTGGTTGGGGG
GTTGTCGTTGCCTGGTGGGGTGGGGTGGCGGCTGGATGGTGGTGGGTCGG
GGTTGTTGGAGGGGGTGGGTGTGGTTGCTTCGGATGCGGCTGGGGTGGTG
CTGGGTCGGGGGCAGGTGCGGGTGGCGGTGCGGGCTGCCGGGGTGAACTT
CCGGGATGTTCTGGTGGCGTTGGGGATGGTGCCGGGTCAGGTGGGGGTGG
GCAGTGAGGGTGCGGGGGTGGTGGTGGAGGTGGGGCCCGGGGTGGAGGG
CCTGGTGGTGGGGGACCGGGTGTTCGGGGTGTTCGGGGACGCGTTCGCGC
CGGTGGTGGTGGCGCAGGAGGTGTTGCTGGCCCGTATCCCGGAGGGCTGG
```

FIG.6-12

TCGTTCGCGCAGGCGGCTTCGGTGCCGGTGGTGTTCGCTACCGCTTACCTG
GGACTGGTCGATCTGGCGGGGTGCGGCGGGGGAGAGTGTGCTGGTCCA
TGCGGCGGCCGGCGGGTCGGTACCGCCGCGGTGCAGCTCGCCCGTCATC
TGGGGGCGGAGGTGTATGCGACGGCCAGTGAGGCGAAGTGGGCGCGTCT
GCGGGCGGCGGGTGTCGCGCCGCAGCGGATCGCGTCCTCGCGGAGTGTGG
AGTTCGAGTCCCGTTTCCGCCGGGCCAGTGGCGGCCGGGGTGTGGATGTG
GTGCTGAACTGTCTGGCGGGTGAGTACACCGATGCCTCGTTGCGGCTGTGT
TCGCCGCAGGGGGGCCGGTTCCTGGAGCTGGGCAAGACCGACATCCGTGA
TGCCGGTGAGGTCGCCGCTCGGTTCCCGGGGGTGTCCTACCGGGCGTATG
ACCTGATGGACGCGGGTGCGCAGCGGGTGGGGGAGATCCTGCACACGGT
GGTGGATCTGTTCCGGCGCGGGGTGCTGGAGCCGTTGCCGGTCACCGCGT
GGGACGTGCGCCAGGCCCATCAGGCACTGCGGTCGATGCGGTCGGGCCTG
CACGTCGGCAAGAACGTGCTCACCCTGCCCGTGCCCCTGGATGCGGAGGG
GACGGTGCTGGTGACGGGCGGGACCGGCACTCTGGGGGCGGCGGTCGCG
CGCCATCTGGCCGCCGGGCACGGGGTGCGGCATCTGCTGCTGGTGAGCCG
GCGCGGCATGGCCGCCGCCGGTGCCGAAAAACTGTGTGCGGAACTGGGTC
AGGCAGGGGTTTCGGTGTCGGTGGCCGGGTGTGATGTCGCCGACCGCGCC
CAGGTCGCCGCCCTGCTGGAGCAGGTGCCCGCGGAGCATCCGCTGACCGC
TGTGGTGCACACGGCCGGTGTCCTGGACGACGCCACCGTGACCTGCCTGG
ACCGGAACAAGATCGATGCGGTGCTCGGGGCGAAGGTGGACGGTGCCCT
GCACCTGCACGAGCTGACCGCGGGGATGGACCTGTCGGCGTTCGTGCTGT
TCTCCTCCGCCGCCGGGGTCCTGGGCTCGCCGGGGCAGGGCAACTACGCC
GCCGCCAACGCCGCCCTGGACGCCCTGGCCCACCAGCGCCGCGCCGCCGG
TCTGCCCGCCCTCTCCCTGGCCTGGGGACTGTGGGAAGAGGCCAGCGGGA
TGACCGGCCATCTGGATGCCGCTGACCGTCACCGCATCACCCGCTCGGGG
CTGCATCCCCTGACCACCCCCGACGCCCTCGCCCTCCTCGACACCGCCCTG
GCCGCCGGACGCCCCGCACTCCTGCCCGCCGACCTACGCCCCACCCACCC
CGCACCGCCCCTCCTGGAACACCTCGCGCCCGCCCGCACCAGCCACCGCA
CCGCACACACCAGCACCGCAACCGGCGTGGGCCAGGACGTCTCCCTCACC
GACCGCCTCGCCACCCTGACCCCCGAACAGCGGCACGACACCCTGCTGGC
GCTGGCCCGTACCCACATCGCCGCCGTCCTGGGCCACCCCAGCCCCGACA
CCATCGACCCCGAACGCACCTTCCGCGACCTCGGCTTCGACTCCCTCACCG
CCGTCGAACTCCGCAACCGGCTCACCCGCGCCACCGGCCTGCGCCTGCCC
GCCACCCTCGCCTTCGACCACCCCACCCCCACCGCACTCACCCACCACCTC
ACCACCCTCCTCAACCCCAACGACAACGACAACGTCGGTCCGGTACTGAT
GGAGCTCGAAAGACTGGAATCCGCTCTCGCCGCGCTGGACAGGGACGACA
GCGCCTGCGAGCGGGTCACTCTGCGACTGCAATCGCTGATGCTCAGGTGG
AGCGGCTCCGAGCGGCAGTCAGCCGAAAACACGGACGACTCCAGCAGGT
TCGCGTCGGCGACCGCGGAGGAGCTACTCGAATTCATCGACCGAGACCTG
GGTCTTTCCTGAACCAGCTCGGTCTTCCCTGAACCAGCTCGACGACGCGGT
TTTCCCGTGCGCGACGGACTCCAAGGACGTGAACCAGACGTGGCGAATGA
CGAGAAGGTGCTCGAATACCTCAAGCGAGTCACCGCGGATTTGGACCGGA
CCAGGCGGCGCCTGTACGAAGTCGTCGAGCGGGAGCAGGAGCCGATCGC
CATCGTGGGGATGGCTTGCCGTTATCCGGGCGGGGCCGGGTCGCCCGCAG
GTCTCTGGGACCTCGTCAGCTCCGGTACGGACGCCATCGGGGAGTTCCCC

FIG.6-13

ACCGATCGTGGCTGGGATCTGGAACGTCTCTACGACCCCGACCCCGATCA
CCCGGGCACCACGTACACCCGCCACGGCGGATTCCTCGACGGCGTAGGTG
AGTTCGACGCGGAGTTCTTCGGCGTCAGCCCGCGTGAGGCCCTGGCGATG
GACCCCCAGCAGCGGCTCCTCCTCGAAACCGCCTGGGAAGCCATCGAACA
CGCCGGCATCGTCCCCGAGTCGCTGCGCGGCACGTCCACCGGCGTCTTCG
CCGGTATCAACCCGCAGGACTACACCATCAGTCAGTACGGACGGGATTCG
GAGATCGAGGGCTATCTGCTGACCGGGGCAGCCGCCAGTATCGCCTCCGG
CCGTATCTCCTACACCCTCGGCCTCGAAGGCCCAGCCGTCACCATCGACAC
CGCCTGCTCCTCCTCCCTCGTCGCCCTCCACCTGGCTTGCCAAGCGCTGCG
CGCAGGGGAGTGCACCATGGCCCTGGCGGGCGGCGCCTCGGTCCTGTCCA
CACCGCTGATCTTCGTCGAGTTCGCTCGCCATCACGGCCTGTCGGTCGACG
GCCGGTGCAAGGCGTTCTCCGCTTCGGCCGACGGCACGGGCTGGGGCGAG
GGCGCCGGCCTGCTCCTCCTCGAACGGCTCTCCGACGCCAAGCGCAACGG
CCGCCGCATCCTCGCTCTCGTACGGGGGAGCGCGGTCAACCAGGACGGCG
CCTCGAACGGGCTGACGGCGCCGAACGGACCCTCCCAGTGCAGGGTCATC
CGCCGGGCCTTGGCCAACGCCCATCTCGCCCCGGCCGACATCGATGCCGT
GGAAGCTCACGGCACCGGCACCACCCTGGGCGACCCCATCGAAGCCCAGG
CCCTCCAGGAAGCGTACGGCGCGGACCGACCCGACGATCGGCCGCTCTGG
GTCGGCACGCTCAAGTCGAACATCGGCCACTCGATCGCCGCGGCGGGTGT
GGGCGGGGTCATCAAGATGGTGATGGCGCTGCGGCACGAGTCGTTGCCGC
GGACCTTGCATGTGGATGAGCCGTCGCCGCAGGTGGACTGGTCGTCGGGT
GCGGTGAGTCTGCTGACCGAAGCGCGGCCCTGGCCGCGGGACGAGGACC
GGCCCCGGCGGGCCGGGGTGTCCTCGTTCGGGGTGAGCGGGACCAACGCG
CACGTGATCCTGGAGGAAGCGCCCGCGCCGGCGGAGGTGCAGGCGGTAG
AAACTGCGCCGGTGGTGCGGGTGGATGGTGGGGAGCGTTCCGCACCGGCG
GATGTGCCGTTGGTGTGGGTCGTGTCGGGCAAGTCGCAGGCCGCGCTACG
CGCCCAGGCCGCCGCCCTGCACGCCCACGTCCTGGACCACCCCGAACAGG
ACGCGGCCGACATCGGCTACAGCCTGGCCACCACCCGCGCCCTGTTCGAC
CACCGCGCCACCCTCATCGCCCCCGACCGCGACACCCTCCTGGACGCCCTC
ACCGCCCTGGCCGACGGCCGCACCCACCCCCACCTCGTCCCCGCACCCCC
CACCGAACCCGGCCACGCCCACAAAATCGCCTTCCTCTGCTCCGGACAGG
GCACCCAACGCCCCGGCATGGCCACCGGCCTCTACCACACCTACCCCGCC
TTCGCCGCCGCCCTCGACGAAACCTGCGCCCACTTCGACCCCCACCTCGAC
CACCCCCTGCGCGACCTCCTCCTCAACCACGACCCCACCGGCCTCCTCACC
CACACCCTCTACGCCCAGCCCGCCCTCTTCACCCTCCAAAAAGCCCTCCAC
CACCTCATCACCGAAACCTACGGCATCACCCCCCACTACCTCGCCGGACA
CTCCCTCGGCGAAATCACCGCCGCCCACCTCGCCGGCATCCTCACCCTCCC
CGACGCCACCCACCTCATCACCACCCGCGCCCGCCTCATGCAAACCATGC
CCCCCGGCACCATGACCACCCTCCACACCACCCCCGAACACATCCAACCC
CTCCTCGACCAACACCCCGGCAAAGCCACCATCGCCGCCGTCAACAGCCC
CCACTCCCTCGTCATCAGCGGCGACCCCGACACCATCCACCACATCACCA
CCACCTGCCACACCCAAGGCATCACCACCAAACCCCTCACCACCAACCAC
GCCTTCCACTCCCCCCACACCGACACCATCCTCGAACAACTCGACACCACC
ACCCACACCCTCACCTACCACCCACCCCACACCCCCCTCATCACCAGCACC
CCCGGCGACCCCCTCACCCCCCACTACTGGACCCACCAGACCCGCCAACC

FIG.6-14

CGTCCACTGGACCGACACCATCCACACCCTCCACACCAACGGCGTCACCA
CCTACATCGAACTCGGACCCGACCACACCCTCACCACCCTCACCCACCAC
AACCTCCCCCACCACCAACCCACCGCCATCACCCTCACCCACCCCCACCAC
AACCCCACCCACCACCTCCTCACCGCACTCGCCCACACCCCCACCACCTGG
CACACCCACCACCACACCCACACCAACCCCCACCCCCACACCATCCCCGA
CCTCCCCACCTACCCCTTCCAACGCCGGCACTACTGGCTCCAGGCGCCCAC
CACCAGCACCGATCAGCCGGTGGCCCCGACGAACGACGACGCCCCCGCGC
CTCGAGCGACATCGCTCCGGGACACTCTTGCCGGACGAAGCCCTCAAGAG
CGCGAAGAAGTGCTCCTGGATCTCGTACTGACCCAGGTCGCCGCCGTGCT
CGGCCACACCGCGCCTGAGGTGGTGGATCCCCAAAGGGCGTTCAAGGACC
TCGGCTTCGACTCACTGGCCGCCATCAAACTCCGCAACAGGCTCGCCGCA
GCCACCGGACTCGAGCTGCCGACCACCCTTGTCTTCGACCACCCCACGCC
GGTGGCACTCCGCCAGTACTTCCAGTCGCAGATCCTCGGAGCGGAGGCGG
ACGCCCCCAACCGTCTGCCCCTCCGGGCGGCGACCACCGACGAACCCATC
GCGATCGTCGGCATGGCGTGCCGCTTCCCGGGCGGCGTTCGGACGGCCGA
CGACCTGTGGCAGCTCCTGAGCGACGAACACGATGCGGTCGGCGGCTTCC
CCACCAACCGGGGTTGGGACGTGGCGAACCTCTACGACCCGGACCCGGAT
CGCCACGGCACCACGTACACCCAGCAGGGCGGCTTCCTCTACGAAGCGGG
GGAGTTCGACGCCGAGTTCTTCGGCATCAGCCCGCGTGAGGCCCTGGCGA
TGGACCCCCAGCAGCGGCTCCTCCTCGAAACCGCCTGGGAAGCCATCGAA
CACGCCGGCATCAACCCCGATGCCCTGCGCAACACGTCCACCGGTGTTTTC
GCCGGGGTCATCTACCACGACTACGCGAGCCGGTTCCTCACCGCGCCGGC
CGGTTACGAGGGCTACCTCGGCCACGGGAGTGCCGGCAGCATCGCGTCGG
GCCGTGTCGCGTACGTGCTGGGTCTCGAGGGTCCCGCGGTCACGGTCGAC
ACCGCGTGTTCGTCGTCGCTCGTCGCGCTGCATCTGGCCTGTCAGGCACTG
CGGTCGGGCGAGTGCACGATGGCTCTGGCGGGCGGCGCGACGGTGATGTC
GACCCCGCAGGCGTTCGTGGAGTTCTCCCGGCAGCGGGGTCTGGCGGCGG
ACGGCCGGTGCAAGGCGTTCTCCGCTGCGGCCGACGGCACGGGCTGGGGC
GAGGGCGCCGGCCTGCTTCTCCTCGAACGGCTCTCCGAGGCCGAGCGGAA
CGGACACCGGGTTCTGGCGGTGGTGCGGGGCAGCGCGGTCAACCAGGAC
GGCGCCTCGAACGGGCTGACGGCGCCGAACGGTCCGTCCCAGCAGCGCGT
GATCCGCCAAGCTTTGGCCAACTCGGGCCTGACCGGCGCCGATGTCGACG
CCGTCGAAGCCCACGGCACGGGGACCAAGCTGGGCGACCCGATCGAAGC
CCAGGCCCTGCTCGCCACCTACGGCCAGGAACACCACCCCGACCAGCCGC
TCTGGCTCGGCTCCCTGAAGTCCAACATCGGCCACGCCCAAGCGGCAGCA
GGCGTGGGCAGCATCATCAAGATGATCATGGCTATGCGCAACGAGTCGCT
GCCGCGGACGTTGCACGTGGATGAGCCGTCACCCCATGTGGACTGGTCGT
CGGGGGCGGTGAGTCTGCTGACCGAGCCACGCCCCTGGCCACGCCGGGAA
GACCGGCCCCGGCGAGCGGGAATCTCCTCCTTCGGAGTCAGCGGGACGAA
CGCCCACGTCATCGTGGAGGAGCCGCCTGCGCGGGCGGAGGTGGAGGCG
GTGGAAGCCGCGCCGGCGGGGGTGGAGACTGCGGCGGCTGCCGCGGTGG
TGGTGGAGACAGACGGTGCGGGCCGGGTGTCCTCCGATGTGCCGTTGGTG
TGGGTGGTGTCCGGCAAGTCGCAGGCCGCGCTACGCGCCCAGGCCGCCGC
CCTGCACGCCCACGTCCTGGACCACCCCGAACAGGACGCGGCCGACATCG
GCTACAGCCTGGCCACCACCCGCGCCCTGTTCGACCACCGCGCCACCCTC

FIG.6-15

ATCGCCCCCGACCGCGACACCCTCCTGGACGCCCTCACCGCCCTGGCCGA
CGGCCGCACCCACCCCCACCTCATCCCCACACCCCCCACCGAACCCGGCC
ACACCCACAAAATCGCCTTCCTCTGCTCCGGACAAGGCACCCAACGCCCC
GGCATGGCCACCGGCCTCTACCACACCTACCCCGCCTTCGCCGCCGCCCTC
GACGAAACCTGCGCCCACTTCGACCCCCACCTCGACCACCCCCTGCGCGA
CCTCCTCCTCAACCACGACCCCACCGACCTCCTCACCCACACCCTCTACGC
CCAGCCCGCCCTCTTCACCCTCCAAAAAGCCCTCCACCACCTCATCACCGA
AACCTACGGCATCACCCCCCACTACCTCGCCGGACACTCCCTCGGCGAAA
TCACCGCCGCCCACCTCGCCGGCATCCTCACCCTCCCCGACGCCACCCACC
TCATCACCACCCGCGCCCGCCTCATGCAAACCATGCCCCCCGGCACCATG
ACCACCCTCCACACCACCCCCGAACACATCCAACCCCTCCTCGACCAACA
CCCCGGCAAAGCCACCATCGCCGCCGTCAACAGCCCCCACTCCCTCGTCA
TCAGCGGCGACCCCGACACCATCCACCACATCACCACCACCTGCCACAAC
CAAGGCATCACCACCAAACCCCTCACCACCAACCACGCCTTCCACTCCCC
CCACACCAACACCATCCTCGAACAACTCGACACCACCACCCACACCCTCA
CCTACCACCCACCCCACACCCCCCTCATCACCAGCACCCCCGGCAACCCCC
TCACCCCCCACTACTGGACCCACCAGACCCGCCAACCCGTCCACTGGGCG
GACACCATCCACACCCTCCACACCAACGGCGTCACCACCTACATCGGACT
CGGACCCGACCACACCCTCTCCACCCTCACCCACCACAACCTCCCCCAAC
ACCAACCCACCGCCATCACCCTCACCCACCCCCACCACAACCCCACCCAC
CACCTCCTCACCGCACTCGCCCACACCCCCACCACCTGGCACACCCACCAC
CACACCCACACCAACCCCCACCCCCACACCATCCCCGACCTCCCCACCTAC
CCCTTCCAACGCCGGCACTACTGGCTGGAGGTCCCGAAGCCGACTGCCGA
AGCATCCGCCTCAGCCAGTGGCCCGGGGCGGAACCGGGCCGCCAAACTCT
CAGCGCTCGAGGCGGAGTTCTGGCAGGCCGTCGAGGAAACCGACACCGA
CACCCTCGCCCACACCCTCGACCTCGACACCCAGACCCTCGAACCCGTCCT
CCCCGCCCTCGCCACCTGGCACCAACAACAACGCGACCACGCCCGCATCA
ACACCTGGACCTACCAGGAAACCTGGAAACCACTCCACCTCCCCACCACC
CGACCCACCACCCCCACCAGCTGGCTCATCGCCATCCCCGAAACCCACCG
CAACCACCCCCACACCACCAACCTCCTCACCAACCTCCCCCACCACAACA
TCACCCCCATCCCCCTCACCATCAACCACACCACCGACCTCCACCACGCCT
ACCACCACGCCCACCACCACACCACCCCACCCATCACCGCCGTCCTCTCCC
TCCTCGCCCTCGACGAAACACCCCACCCCCACCACCCCCACACCCCCACC
GGCACCCTCCTCAACCTCACCCTCACCCAAACCCACACCCAAACCCACCC
ACCAACCCCCCTCTGGTACCTCACCACCCAAGCCACCACCACCCACCCCA
ACGACCCCCTCACCCACCCCACCCAAGCCCAAACCATCGGACTCGCCCGC
ACCACCCACCTCGAACACCCCCACCACACCGGCGGACACATCGACCTCCC
CACCACACCCCACCCCAACACCCTCACCCAACTCATCACCGCCCTCACCCA
CCCCCACCACCAACACAACCTCACCATCCGCACCCACACCACCCACACCC
GACGACTCACCCCCACCACCCTCCAACCCACCACCCCCACACCACCCACC
AACCCCCACGGCACCACCCTCATCACCGGCGGCACCGGCGCCCTCGCCAC
CACCCTCGCCCACCACCTCGCCACCACCGGCACCCAACACCTCCTCCTCAC
CAGCCGACGCGGCCCCCACACCCCCGGCGCCCGACAACTCCACACCCAAC
TCACCCAACTCGGCACCAACACCACCATCACCGCCTGCGACCTCTCCGAC
CCCGACCAACTCACCCACCTCCTCACCCACATCCCCCCCGAACACCCCCTC

FIG.6-16

ACCACCGTCATCCACACCGCCGGCATCCTCGACGACGCCACCCTCACCAA
CCTCACCCCCACCCAACTCGACAACGTCCTGCGCGCCAAAGCCCACACCG
CCCACCTCCTCCACCACGCCACCCTCCACACCCCCCTCGACCACTTCGTCC
TCTACTCCTCCGCCGCCGCCACCCTCGGCGCCCCCGGCCAAGCCAACTACG
CAGCCGCCAACGCCTACCTCGACGCCCTCGCCCACCACCGCCACACCCAC
AACCTCCCCGCCACCACCATCGCCTGGGGAACCTGGCAAGGAAACGGCCT
CGCGAGCGGTGACATCGGCGAGCATCTGCGCCGCCGCGGGATGATCCCGC
TGGATCCCGAGTCCGCTGTCGGTGCCTTCGACCGGGCGGTCGCGAGCGAT
CGGCCCAGCGTCTTCGTCGCGGACATCGACTGGCCCACCTTCGGCCGCAA
CACCTCCAGCGGTCTTCGCGCCCTCTTCGAGGACATTCCGGAGGCCACAC
AGCCTGAGCCGACCGCCCGGAGCGCGGACCAGCCGAACGGGCACGGTAG
CCTCCAGGAACTTCTCGCCCGCCAGTCCCCGGCCGAGCAGGCCGAAACGC
TCCTGGCATTGGTCCGGACGCATTCCGCGACCGTCCTCGGGCGTGACGGG
GCCGATGCCGTCGCCGCCGAACGTCCCTTCAGGGACCTGGGATTCGACTC
ACTGTCCGCCGTCGAGCTCCGCAATCATCTGACGGCCGACACGGAGCTCG
CTCTGCCGACAACGCTGGTCTTCGATCACCCGACTCCGGTGAAGCTCGCG
GAGTTCCTGCGCACCGAGCTGCTCGGCACCGCACCAGCCACCACCGCCGC
CGTCCCGGCCCTCCAGTCCCACACCGACGAACCCATCGCCATCATCGGCA
TGGCCTGCCGCTTCCCCGGCGCCGTCACCACACCCGAACACCTGTGGAAC
CTCATCGCCACCGAACAAGACGCCATCGGCGAGTTCCCCACCGACCGCGG
CTGGGACCTGGACAACCTCTACCACCCCGACCCCGACCACCCCGGCACCA
CCTACACCCGCCACGGTGGTTTCCTCTACGACGCCGGCGACTTCGACGCCG
AGTTCTTCGGCATCAACCCACGCGAAGCCCTCGCCATGGACCCCCAGCAA
CGACTCCTCCTGGAAACCGCCTGGGAAGCCATCGAACACGCCGGCATCCT
CCCCGACGCCCTGCACGGCACCCCCACCGGCGTCTTCACCGGCGTCAACG
CCCAGGACTACGCCGCACACACCCACGCCTCCCCCCACACCACCGAGGGC
TACACCCTCACCGGAACCGCCGGCAGCATCGCCTCCGGCCGCATCGCCTA
CACCCTCGGACTCGAAGGCCCCGCCGTCACCATCGACACCGCCTGCTCCTC
CTCCCTCGTCGCCCTCCACCTCGCCTGCCAGGCCCTGCGAGCAGGCGAATG
CACCACAGCCCTCGCCAGCGGCATCACCGTCATGACCAGCCCGGTCACGT
TCACCGAGTTCTCCCGGCAGCGAGGGCTCGCCCCCGACGGACACTGCAAG
GCGTTCTCCGCCTCGGCCGACGGCACCGGCTGGAGCGAGGGCGTGGGCAC
CATCCTCGTCGAACGGCTCTCCGACGCCGAGCGGAACGGGCACCGGATTC
TGGCGGTGGTGCGGGGCAGCGCGGTCAACCAGGACGGCGCCTCCAACGG
CCTGACGGCGCCGAACGGCCCCTCCCAGCAACGCGTCATCCGCCAGGCCC
TGGCCAACTCCGGCCTGACCGGCGCCGATGTCGACGCCGTCGAAGCCCAC
GGCACGGGAACCAAACTCGGCGACCCCATCGAAGCCCAGGCCCTGCTCGC
CACCTACGGCCAGGGACGTGCGCAGGAACAGCCACTGTGGCTCGGCTCGG
TCAAATCCAACCTCGGCCACACCCAGGCAGCGGCAGGCATGGCCGGCCTG
ATCAAGATGGTGATGGCGCTGCGGCACGAGTCGTTGCCGCGGACGTTGCA
TGTGGATGAGCCGTCGCCGCAGGTGGACTGGTCGTCGGGTGCGGTCAGCC
TGCTGACCGAGGCGCGGCCCTGGCCACGCCGGGAGGACCGGCCCCGGCG
AGCGGGAATCTCGTCCTTCGGGGTGAGCGGGACGAACGCGCACGTGATCC
TGGAGGAGGCGCCCGCGCCGGCGGAGGCGGTGGAGACGGAACAGGGTGT
GGTGCCGCAGGGCGACCAGGAGTGTTCCGCGCCGGTGGGTGTGCCGTTGG

FIG.6-17

TGTGGGTGGTGTCCGGCAAGTCGCAGGCCGCGCTACGCGCCCAGGCCGCC
GCCCTGCACGCCCACGTCCTGGACCACCCCGAACAGGACGCGGCCGACAT
CGGCTACAGCCTGGCCACCACCCGCGCCCTGTTCGACCACCGCGCCACCC
TCATCGCCCCCGACCGCGACACCCTCCTGGACGCCCTCACCGCCCTGGCCG
ACGGCCGCACCCACCCCCACCTCATCCCCACACCCCCCACCGAACCCGGC
CACACCCACAAAATCGCCTTCCTCTGCTCCGGACAAGGCACCCAACGCCC
CGGCATGGCCACCGGCCTCTACCACACCTACCCCGCCTTCGCCGCCGCCCT
CGACGAAACCTGCGCCCACTTCGACCCCCACCTCGACCACCCCCTGCGCG
ACCTCCTCCTCAACCACGACCCCACCGACCTCCTCACCCACACCCTCTACG
CCCAACCCGCCCTCTTCACCCTCCAAAAAGCCCTCCACCACCTCATCACCG
AAACCTACGGCATCACCCCCCACTACCTCGCCGGACACTCCCTCGGCGAA
ATCACCGCCGCCCACCTCGCCGGCATCCTCACCCTCCCCGACGCCACCCAC
CTCATCACCACCCGCGCCCGCCTCATGCAAACCATGCCCCCCGGCACCAT
GACCACCCTCCACACCACCCCCGAACACATCCAACCCCTCCTCGACCAAC
ACCCCGGCAAAGCCACCATCGCCGCCGTCAACAGCCCCCACTCCCTCGTC
ATCAGCGGCGACCCCGACACCATCCACCACATCACCACCACCTGCCACAC
CCAAGGCATCACCACCAAACCCCTCACCACCAACCACGCCTTCCACTCCC
CCCACACCGACACCATCCTCGAACAACTCGACACCACCACCCACACCCTC
ACCTACCACCAACCCCACACCCCCCTCATCACCAGCACCCCCGGCGACCC
CCTCACCCCCCACTACTGGACCCACCAGACCCGCCAACCCGTCCACTGGG
CGGACACCATCCACACCCTCCACACCAACGGCGTCACCACCTACATCGGA
CTCGGACCCGACCACACCCTCTCCACCCTCACCCACCACAACCTCCCCCAA
CACCAACCCACCGCCATCACCCTCACCCACCCCCACCACAACCCCACCCA
CCACCTCCTCACCGCACTCGCCCACACCCCCACCACCTGGCACACCCACCA
CCACACCCACACCAACCCCCACCCCCACACCATCCCCGACCTCCCCACCTA
CCCCTTCCAACGCCGGCACTACTGGCTGGAGGTCCCGAAGCCGACTGCCG
AAGCATCCGCCTCAGCCAGTGGCCCGGGGCGGAACCGGGCCGCCAAACTC
TCAGCGCTCGAGGCGGAGTTCTGGCAGGCCGTCGAGGAAACCGACACCGA
CACCCTCGCCCACACCCTCGACCTCGACACCCAGACCCTCGAACCCGTCCT
CCCCGCCCTCGCCACCTGGCACCAACAACAACGCGACCACGCCCGCATCA
ACACCTGGACCTACCAGGAAACCTGGAAACCACTCCACCTCCCCACCACC
CGACCCACCACCCCCACCAGCTGGCTCATCGCCATCCCCGAAACCCACCG
CAACCACCCCCACACCACCAACCTCCTCACCAACCTCCCCCACCACAACA
TCACCCCCATCCCCCTCACCATCAACCACACCACCGACCTCCACCACGCCT
ACCACCACGCCCACCACCACACCACCCCACCCATCACCGCCGTCCTCTCCC
TCCTCGCCCTCGACGAAACACCCCACCCCCACCACCCCCACACCCCCACC
GGCACCCTCCTCAACCTCACCCTCACCCAAACCCACACCCAAACCCACCC
ACCAACCCCCCTCTGGTACCTCACCACCCAAGCCACCACCACCCACCCCA
ACGACCCCCTCACCCACCCCACCCAAGCCCAAACCATCGGACTCGCCCGC
ACCACCCACCTCGAACACCCCCACCACACCGGCGGACACATCGACCTCCC
CACCACACCCCACCCCAACACCCTCACCCAACTCATCACCGCCCTCACCCA
CCCCCACCACCAACACAACCTCACCATCCGCACCCACACCACCCACACCC
GACGACTCACCCCCACCACCCTCCAACCCACCACCCCCACACCACCCACC
AACCCCCACGGCACCACCCTCATCACCGGCGGCACCGGCGCCCTCGCCAC
CACCCTCGCCCACCACCTCGCCACCACCGGCACCCAACACCTCCTCCTCAC

FIG.6-18

CAGCCGACGCGGCCCCCACACCCCCGGCGCCCGACAACTCCACACCCAAC
TCACCCAACTCGGCACCAACACCACCATCACCGCCTGCGACCTCTCCGAC
CCCGACCAACTCACCCACATCCTCACCCACATCCCCCCCGAACACCCCCTC
ACCACCGTCATCCACACCGCCGGCGTCAACCATTACGCTCCCGTGGCGGC
GACCGACCCGTCCACGTTCGCGTCCGTCCTCGCCGCGAAGGCGGCCGGCG
CGGCACACCTGCATGAACTCCTGCTGGAGCTGGACACGGTCGAGCAGTTC
ATCCTCTTCTCCTCCGGTTCGGGGGCCTGGGGCAGCGGCAACCAGTGCGC
GTACGCGGCTGCCAACGCCTACCTCGATGCGCTGGCGGCGCACCGCCAGG
CCCGCGGCCTGCCTGGCATGTCGCTCGCCTGGGGGCCTTGGGACGGTGAC
GGGATGTCGGCCGGAGAGGACGCCCAGCGGTACCTCCGTGAGCGGGGCG
TACTGCCCATGGATCCGCGGCTCGCCGTCGCGGCCTTCGACGAGGCGGTC
CGGGCGCGGCCGAACTCCAACCTCGTCGTCGCGGACATCGACTGGGAGCG
TTTCGTCCCGACGTTCACCGCGCGGGGCCACAACCCCCTGATCGAGGACA
TCCCCGAAGTCCGCCGGCTGGCCGCGGAGGCCGAGGCCGCCCAGACCACG
ACCGCCGCCACGGACGCCCCCGCCCTTCTCAACCGACTCTCAGGTCTGTCG
GCCACTCAGCAGAAGCAGCATCTTCTCCGGCTGGTGCGGTCACACATGGG
CGAGGTCCTCGGCCGCGAGGACGTCGACACGCTCGACGAGCGCCACACCT
TCCGGGACCTGGGCTTCGACTCGCTCACCTCGGCCCGATTCAGCCAGCGG
CTCGCCAAGGACACGGGGCTGCACCTTCCTGCCACCCTCGTCTTCGACCAC
CCGACGCCCGCCGACTGCGTGGCTCATCTGCGGGATCAACTTCTGGGTGA
AACGGACGACATGACTCCGAGGAAGCGAGATCACCTCGGGGAGGACCGG
CGGGCGGCCACCGCGGACGACCCGATCGCGATCGTCGGGATGGCGTGCCG
GTTCCCGGGCGGCGTGCGGTCCGCCGATGATCTGTGGGACCTGCTGTCGTC
GGGCACCGACGCCATCAGCGGCTTCCCCACCGATCGCGGCTGGGACATCG
AGAGCCTCTACGACCCCGACCCCGACCGCTCCGGCACCACGTACACCCGC
CACGGTGGTTTCCTCTACGACGCCGGGCAGTTCGACGCCGAGTTCTTCGGC
ATCAGCCCGCGTGAGGCCCTGGCCATGGATCCCCAGCAGCGGCTCCTTCT
CGAAACCGCCTGGGAGGCCGTCGAACACGCAGGCATCAACCCGCAGACA
CTCCACGGCACCCCCACCGGCGTCTTCACGGGCGTCAACGCCCAGGACTA
CGCAGCCCACCTGCGCCAGGCGTCGGGCAACGTCGAGGGGTACGCCCTGA
CCGGAAGCTCGGGCAGTGTCGTGTCGGGTCGGGTGGCTTACACCTTCGGT
TTCGAGGGGCCGGCCGTCTCGGTCGACACCGCGTGCTCGTCGTCGCTCGTC
GCACTGCACCTCGCAGGCCAAGCCCTGCGGTCCGGCGAGTGCACGATGGC
CCTCGCCGGCGGCGTCATGGTGATGTCCTCCCCTGAGACGTTCGTGGAGTT
CTCGCGGCAGCGGGGTTTGTCGGTGGACGGGCGGTGCAAGTCCTTCGCGG
CCGCGGCCGACGGTACCGGCTGGGGCGAGGGCGTGGGCATGCTGCTCGTG
GAGCGGTTGTCGGACGCCGAGCGCAACGGGCACCGGGTTCTGGCGGTGGT
GCGGGGCAGCGCGGTCAACCAGGACGGCGCCTCCAACGGCCTGACCGCA
CCGAACGGCCCCTCCCAGCAGCGCGTGATCCGCCAGGCCCTGGCCAACTC
CGGCCTGACCGGCGCCGATGTCGACGCCGTCGAAGCCCACGGCACAGGAA
CCAAACTCGGCGACCCCATCGAAGCCCAGGCCCTGCTCGCCACCTACGGC
CAGGAACACCACCCCGACCAGCCGCTCTGGCTCGGCTCCCTGAAGTCCAA
CATCGGCCACGCCCAAGCAGCGGCAGGTGTCGGCGGGATCATCAAAATGG
TGATGGCACTGCGCCACGAGACGCTGCCGCGCACGCTGCACATCGACGAG
CCGACCCCCCAGGTCGACTGGTCGTCCGGCGCGGTCAGCCTGCTGACCGA

FIG.6-19

GCCCCGCCCCTGGCCACGCCAGGGGGACCGGCCCCGACGCGCCGGCATCT
CCTCCTTCGGAGTCAGCGGAACCAACGCCCACGTCATCCTGGAAGAGGCA
CCCGCCCAGCCGGCCGGGGACCCCGCCCCAGAAGACGGCGCCCCGGTGCC
CTGGGCGATGTCGGCGCGTTCAAACGCCGCGCTGCGGGCACAGGCCGCAC
TCCTGCGTGACTTCCTCCAAGGCCCCGGCACCGACACCGCACTACGGGCG
GTCGGAGCCGAACTCGCCCATGGCAGGGCCGTCCTGGAACACCGCGCCGT
GATCGTGGCACGGGAACGGACAGAGTTCGAAGACGCGCTGGAAGCACTG
GCCTCGGGTGAACCGCACCCCGCACTCATCGAAGACACGACCGGCAGCCA
GACCAACAGCCACTCCGGTGGCGGGGTGGTGTTCGTCTTCCCCGGCCAGG
GCGGTCAGTGGGCCGGCATGGGACTCGACCTGCTGCGCGACTCCCAGGTG
TTCGCCGACCATGTCGGTGCGTGTGAACGCGCGCTGGCGCCGTGGGTGGA
GTGGTCGCTCACCGAAATGCTCCACCGGGACGCGGAGGATCCGGTGTGGG
AGCGGGCGGATGTGGTCCAGCCGGTGCTGTTCTCGGTCATGGTGTCCCTG
GCGGCGCTGTGGCGGTCCTACGGCATCGAACCCGAAGCGGTGGTCGGCCA
CTCCCAGGGCGAGATCGCCGCCGCCCACGTCTGCGGCGCACTCACCCTGG
AGGACGCCGCGAAGATCGTGGCACTGCGCAGCCGGGCCCTGGCCGCGCTG
CGGGGCCACGGCGGCATGGCCTCACTCGCCCTGACCGGAACCGAGGCCGA
GGACCTCATCACCACCCACTGGCCAGGACGGCTGTGGACGGCCGCGTTCA
ACGGGCCACGGGCCACCACCGTCTCCGGCGACACCGACGCCCTGGACGAA
CTCCTCACCCACTGCACCGAAACCGGGGTACGGGCCCGCCGCATCCCCGT
GGACTACGCATCCCACTGCCCCCACACCGAAACCATCGAACACGACCTGC
TCCACATGCTCCACGGCATCACCCCCCAGCCCGGCAGCATCCCGTTCTACT
CCACCGTCGAGGACGCCTGGACCGACACCACCACCCTGGACGCCGCCTAC
TGGTACCGCAACCTGCGCCGGCCCGTCCGCTTCACCCACGCCGTCCGCACC
CTCACCGCCCAGGGCCACCGCCTCTTCATCGAGACCAGCCCCCACCCCAC
CCTGACCCCCGCCATCGAAGACCACGACCACACCACCGCCCTGGGCACCC
TGCGCCGCCACGACAACGACACCCACCGCTTCCTCACCGCCCTCGCCCAC
GCCCACACCACCGGCCACACCGTCACCTGGACCACCCACTACCCCACCAC
CCCCCACACCCCCGCCATCGACCTGCCCACCTACCCCTTCCAACACCACCA
CTACTGGCTCCACACACCCACCACCAGCACCGGCGACGTCTCCGCCGCCG
GACTGCACCCCACCGAGCACCCTCTCCTCGGCGCCACCGTGGAACTCGCC
GACGGAGACGGAACCTTGCTCACCGGGCGCCTGTCCCTGCACACCCACCC
CTGGCTCGCCGACCACAGCGTCGGCGGCATCGTCCTCCTCCCCGGCACCG
CCCTCCTCGAACTCGCCCTCGAAGCCGGGACGCGCACCGGTTGCCCCCAC
GTCCAGGAACTCACCCTGCACACGCCCCTGGTGATTCCCGAGACCGGACA
CGTCGTCTTCCAGCTGACGGTCTCGGCACCGGACGAGACCGGGCAGCGCC
CGTTCACCGTCCATTTCCGTTCCGAGGCCGTCACCGGCGCGGACGATCCGG
CGGACCGGACCTGGACGCGGTGCGCCACCGGTGCGCTCTCGACCGCGGCC
GCCCCCGATCACTCCGAAGCCGCCACCTGGCCGCCGCCGTCCGCTCAGCC
GCTGGACCTCGACGGTCTGTACGACCGCATGGCGGAGGCGGGTCTGGTCT
ACGGTCCGGTGTTCCAGGGGCTCCGCGAGGCTTGGCTCGATGGCGAGGAC
ATCGTCGCCGAGGTGCGCCTGCCGCAGGAGGCGGCCGCCGACACGCAGG
GCTTCGGCCTGCATCCCGCCCTGCTCGACGCCGCTCTGCATGTGACGGCGC
TGACCTCACAGGCCGGTACAGCGGACGAAGACGCGCAGGAACGGCGTCG
GTTGCCGTTCGCGTGGGCCGGTGTCTCCCTGTTCGCCAGGGAGTGCGCGGC

FIG.6-20

GCTGCGTGTGCGGGTGGCGCCGTGTGCGCCGCACCCGGGGGACGCCGTGG
CGATCACAGCCACCGACGAGGACGGCCGTCCGGTGCTGGCGGTGGAATCG
CTCACCCTCCGGCCCGTCTCCCCCGACCAGTTGCGGGCGGCGGCCCCGGC
CGCCGGGCGGGATTCGCTGTTCCGCCTGGAGTGGGTACCGGTCACGGCCT
CCGCCTCCGCCTCCGCCCGGCCGACCGGGCCCTGGGCCGCCATCGGCACC
GGTCCGGCGGTGGCCGGCCTGGCCGGCCACGCAGACCTGACGGTGTACGC
GGAGGCCGGCGATCTGCTCCGGGATCTGGACGGAGGGGCCCCCGCGCCCG
CTGTGGTCGTGCTCAGCGTCACGCCCGATGCCGACGAATTCGCCACTCCCC
GTGCGGCGACCGGCCGGGCCCTCTCCGTCCTTCAGGCCTGGCTGGCGGAC
GAGCGCCTGGCCGACAGCCGGCTCGTGGCCGTCACTTCTGGGGCGGTCGT
CGCCGCGCCCGGGGACGACACGGTCGACGTCCCGGGTGCCGCCGTGTGGG
GCTTGGTGCGTTCCGGGCAGTCCGAGCACCCGGACCGCATCACGCTGCTC
GACTGTGCGAGCGGCGCCCGGCCCGGGCCGGACCTCGTCGCCGCCGCCCT
CGCCTCGGGCGAGCCGCAGCTCGCCGCCCGCGCCGGGGTCCTCTACACGC
CCCGGCTGGCCAGGCCGCACCGCGACGCCTCGGCCGTACCGCGGTCGCTG
CCGTCCCACGGCACCGTGCTCATCACCGGCGGCACCGGTCTGCTGGGCGG
GTTGGTCGCCCGGCGCCTGGTGGAGGCGCACGGTGTCCGCCGCCTTCTCCT
GGCCGGCCGCAGGGGTCCGGCGGCGGAGGGGCTGGACTCGCTGACGTCC
GAGTTGCGTGAGCGCGGGGCGACCGTCGAGGTCGCCGCGTGCGACGCGGC
CGACCGCACACAGTTGGAGGCGCTGCTGGCCGGGGTGCCCGAGGAGCATC
CCCTGTCCGCGGTCGTGCACGCCGCGGGTGTGCTCGACGACGGGGTTCTC
ACGTCCCTGACGAACGAGCGGCTGGGAGCTGTCCTGCGGGCGAAGGCGG
ATTCGGCGCTGCTTCTGCACGAGCTCACTCAGGACCTCGACCTGTCCGCCT
TCGTCCTGTTCTCCTCCGCCGCCGGCGTCCTCGGCTCTCCCGGCCAGGGCA
GCTACGCCGCCGCCAACGCCGTGCTCGACGCACTCGCCCACCAGCGCAGC
GCCGCCGGTCTGCCCGCTCTCTCCCTGGCCTGGGGGCTGTGGGCGGAGGG
CAGCGGGATGACCGGGCACCTCGACGCCGACGACCGCTCCCGGATCAACC
GGGCCGGTATGGCGCCGCTCCCGACGCCCGATGCCCTGGATCTGTTCGAC
GCCGCGCTGTCGTCGGACGAACCCTTCCTGGTACCGGCTCGCTTCGACCTT
TCCGCCGTACGCACCAGGACCGCGTACGGCCCGCTCCCGCCGCTGCTGCG
CGGCCTGGTCCGGACCTCGGGCGCGCACCGGGTCCGGGGCGCAGTCGGCG
AAGCCCGGGCGGCCGGCGTGGACGAGGCCGGACGGCTGCGGGAACGGCT
GGCCCGCCAGAGTGACGCCGAACGCCGGAACACCTTGCTGCGGCTCGTGC
AGTCGAACGTCGCGGCGGTGCTCGGTCACCGCGGCACGGGGACCGTCGCC
GAGACACGCGCCTTCCGTGAGCTGGGCTTCGACTCGCTCACGGCGGTGGA
GCTGCGGAACCGGCTGAAGGTCGCCACAGGGCTGGCGCTGCGGGCCACG
GTCGCCTTCGACTTCCCGACTCCGGCGGCGCTGGCCGAGCATCTGGGTGCC
CGCCTGCTTCCGCCGGACGGCGCCGTGTCCGAGGCGGTGGGCGAGAAGGA
GCTGCGCGGGCTCTTGACGTCGATCCCGATCGGCCGGCTGCGGGAGGCGG
GGCTGATCGACCGCCTCCTGGCGCTCGCCGCTGCGGCGCCAGACTCCGCC
GATCAGACGGCGGAGCAGCCCTCCCGGTCCGTGTCGGTCGAGGACATCGA
CGCCATGGACGTCGACAGCCTCATCGGCCTGGCCCACGACACCGGCACCG
ACTCCGGTCACGCCCCCTGCGAGGGCTGACCTCCACTTCACGGATGCGAG
AGACGACATGACGCAGATTCCGCCAACCGGTCACGACGCCGTGGCAGCCG
GGCCCGCCCCCGGCGCCGCGGAACAGAAACGAGGACGGAAACGGAAACC

FIG.6-21

AGGACGGGAGCCCCGGCCAGAGCATCGACGGGAACAGGAACGAGGGCAG
GGAGCAGGGCTGGGGCAGGGGCAGGAACGCGCGCGGCCCGCGGACGGTG
GTCGGCGGCTCGTGCTTGGCTGGGCGGCGCTCGGCGCGGTGTGCCTGGCC
CTGCAGGCGTACGTGCTCGTCCGCTGGGCGGCCGACGGTGGGTATCGCCT
GGTGGACGTACCCGGTGAGGGCGGCGCGGAGCGTGGCCACCGAAGGGTC
CTCGACATCGTGTTCCCGGCGCTGTCGGCGGCAGGTGTCGTGGGGCTGGC
GCTGTGGCTCTACCGCAGGTGCCGCGCGGAGCGGCGGGTGTCGTTCGACG
CCCTGCTGTTCGCCGGAGTGCTGTTCGCGGGCTGGCTGAGCCCGCTGATGA
ACTGGTTCCATCCCGTCCTGGTCTCCAACACGCACGTGTGGGGCGCGGTCG
GCTCCTGGGGGCCGTACACGCCGGGATGGCAGGGGTCCGCCCCCGGGATG
GAGGCCGAGCTGCCGCTGGTGACGTTCAGCGTGTGCTCGACAGCGCTCCT
GGGTGTGCTGGCCTGCTGTCACGTGCTGTCCCGCGTCCGGGACCGGTGGC
CCGGGGTCCGCCCGTGGCAACTGATCGGGGTGGCCGTCGCCACCGCGGTG
GCCCTGGACCTGTCGGAGCCGGCGATCTCCTTGATCGGTCTAGTCCGTCTG
GTCGAAGGCGCTGCCGGAGGTGTCGCTGTGGAGCGGTGCCTGGTACCAGT
TCCCTCTGTACCAGCTCCTGACCGCGGCCCTGGCCAGCGGGTTGCTGAGCG
CGCTCCGGTTCTTCCGCGACGAGCGGGACGAGACGCTGGTGGAGCGCGGT
GCCTGGCGCCTGCCGGGCCGTGTCCGCCTCTGGGCGCGGTTCCTGGCCGTC
GTCGGCGGCGTCCATGTCGTGATGGGCGGCTATACGGCCCTTCATGTGCTG
CTCTCGTTGGTCGGCGGCCAACCGCCGGACGCGTTGCCGGGGTTCTTCCGT
CCGCCGGCCGTCTACTGAGGGCGGGGCGGACGGCACGCAACGAGGGGAG
GGGCCGGCGTCTCATGCTCTGCTGTCCGGTCAGACCTCAGCGCGCTGGCA
CGGCGCGGTCAGGACGACGTACCCGATGTCCTCCGTGTACCACTGGCTGC
ACTTGCCCACGAACGTCTCCAGGTCGTCCGCCGTCATCTCCAGGGCTTCGG
CGTAGGCGTGGGCGTTGGCGCGTACGTCGTCACCCATCGCGCTGTACGAC
GGGGCGATGACGTGCTCACCGATGTCGGTGAGCTCGGTCAGCCGGAGTCC
GGCGTCGCTGATCATCCCGGCATAGGCGGTGATGGGGATCAGCGAGGGGA
CGGCGAGTTCGCTGGACGACCAGTCCGCCCCCGTCGGCTGTGATGCGCGG
AGTGTGACGTCCATGGCCGCCAGCCGCCCACCGGGGCGCAGCACACGGGC
CATCTCCTGGAACACCCGGGCCGGGTCGGGCATGTGCAGCAGGCACTCGA
GGGCCCAGACGGCGTCGAAGGAGGCGTCGGGGAAGGGCAGGTCCATGGC
GTCGGCGCACTCGAAGCGGACCCGGTTCGCGAGTCCGGACCGCTCGGCGA
GCGCGGTGGCCAGCTCGACCTGCCGGGGGCTGATGGTGATGCCGACGATG
TCCACCGGCTCGCTGTGCGCCAGGCGCAGGGCCGGCCGGCCGGAACCGCA
GCCGACGTCCAGCACACGTCTGACCGGGCGCCCGGTGTGTTCCCGAAGCT
TGCCGATCATATGGTCGGTGAGGCGGTCGGAGGCCTGGCCGAGTGTGCTG
CCGTCGTCCGGGTGCGGCCAGTATCCGAGGTGCGTGTTGCCGCCCAGGGC
CCGGTTCAACAGGCTGGTCATGCGGTCGTAGTAGTCACCGACGTCCGCGG
GGGTCGGTGATCCCTGGTGAGGCGCCTTGGTCATGGTTCCGGCAGCTCCTT
CGGTCGTGCGGCGGCCTCAAGGGAGGCGTCCGCGGGGGCGTGGCCGCGA
GGGATGGCGGGGGTCCTGGGCTCGGCTATCATCCGCAGGCGGTCGGGGAA
GACGTGGGTCGCCTTGGCGACCGGGCGGACGCGGTCGCCCTTGAGGGGAC
GCAGACGCCAGCGCGAGGCGATGACCGCGACGGCGACGGCCGTCTCCAT
GAGGGCGAAGTTGTCGCCGATGCACTTGTAGGTGCCGAGCGCGAAGGGA
ACCCAGGCGCCCTTCGGAACGTCGCGCGTGGTCTCTTTCGACTCCCAGCGG

FIG.6-22

TCGGGGTCGAGCTTCTCCGGATCACGGTACCAGCGGGGGTCACGCTGGAG
CGCGTACGAGCTGTACATGATTTCCACGTCGGCCGGCAGCTCGTGTTCCCC
GAGCCGGACGGGGCGCACCGTGCGCCGCGAGCCCACCCAGCCGGGGTAC
TTGCGCAGCGCCTCCTTGACCAGGCGCTGGGTGTACGGAGGCGCGGGAG
GTCCGCGCTGGTGGGAGCCGGCCTCCGAGGACGGTGTCGATTTCGGCGT
GCAGCCTCTGTTCGATGAGGTGGTCGTGAGCGAGTTCGTGGAAGATCCAC
GCGGTGAGAGCGGCCGGCCCACCGATTCCGGCGACCGCGAGCCCCATGAT
CTCGTTGTGCACCTCGTCGTCCGTCATGGTGTTGCCCTCGGCGTCCCGCGC
GCGCAGCATCGTCGAGAGCAGGTCGCCGTGGTCGCGGCCGTCGGCGCGGT
AGGCGGTGACCGCCTCCCGGATGGCGGCGCTGGTGCGGCCCATGTGGCGC
TTGGCGGCAGTGGGCAGGGAGGTGTAGAGCTGCGGGGCGAGCGCGCTCA
GCCTGGCCACCTTCAGGATGTCGTGCCCCGTGGTGCGCAGTTCCGCCTCGG
CCGCCGCACCCAGGTCGGACTGGAACAACGCCTTCGTGATCATGGCCAGT
GAGAGGTCGCTCGCCATCTTCGGGACATCCACGACCTGGCCCGGCCGCCA
GGAATCGGCGGTCTCCTCGGCGGCGGCGGACATGCTGATGACGTAGTGGT
CGAGCTTGCCCCGGTGGAATCCGGGTTGCATCATCCGCCGCTGGCGGCGG
TGCGAGTCCCCGGAGACGGCCACGAGGATGGGGCCGATGAACCGGCTGG
CGCCCGCCGCGCCCTTGCTGCGGGTGAAGTCCGCCGCGCCGGACACCAGC
ATGGTCCGCACGATTTCGGGGTGGGTGGCGAGGTAGACGGTGTTGTGGCC
GAGGCGGATGCGGAAGAGGTCCCCGCGTTCCGTGACGGCGGACAGGAAG
CCCAGGGGGTCGCGGAGGAGGGCCGGCAGGTGGCCGAGGACCGGCCAGG
CACCGGGGGCCTCGGGGATGGTCGACGGAGGTGAGGACACTGTTGCTCCT
GAGGGGAGGGCCGGGCGAGTCGGCGTGGGGTGGGGTGAGGTGTGCGGTC
GGGCAGGTGGTCGCGTCGCCGGTGGTCGGCGACGGGTGGTGGGTCAGGG
GGATCCGGTTTCCTGGTCGATGAGCGCGAACATCTCCTCGTCCGTCGCCTC
CCCGAGGTCGGGACGCGGCGCCTCCTCCCCGCCGAGCACCTGGGCGAGTG
AGCGAAGCCGCGACGCCAGCCGGGACCGGGCTTCCTCTCCCAGGCCCTGC
GCCCCGGGGAGCGGCGACGCGACGGAGGAGAGCACCGCTTCCAGCCGGC
CGATCTCCGCGAAGAGGGACTGCTCGGGCGGCGCCGTGGCCGCGTCGTCG
GGGAGGAGCCGGGTCAGCAGGTGCCGGGTGAGCGCGGTGGCGGTGGGGT
GGTCGAAGGCGAGGGTGGCGGGCAGGCGCAGGCCGGTGGCGCGGGAGAG
CCGGTTGCGGAGTTCGACGGCGGTGAGAGAGTCGAAGCCGAGGTCCCGG
AAGGCCGAGTCCGCAGGGACCGCCTCCGGCGTCTGATGGCCGAGGACCGT
GGCGATCTGGGTGCGCACCACGGTGAACAGGGTGTCGTGTTGTTGCTCGG
GGGTCAGGGTGGCGAGGCGGTCGGCGAGGGAGACGTCCTGGCCTGCGCCT
GCACTGGTGCCGGTGTGTGCGGTGCGGGGGCTGGTGCGGGCGGGCGCGAG
GTGTTCCAGAAGGGGCGGTGCGGGGTGGGTGGGGCGTAGGTCGGCGGGC
AGGAGTGCGGGACGTCCGGTGACCAGGGCGGTGTCGAGGAGGGCGAGGG
CGTCGGGGGTGGTCAGGGGGTGCAGCCCCGAGCGGGTGATGCGGTGACG
GTCACCGGCGTCCAGATGCCCGGTCATCCCGCTGGCCTCTTCCCACAGTCC
CCAGGCCAGGGAGAGGGCGGGCAGGCCGGCGGCGCGGCGCTGGTGGGCC
AGGGCGTCCAGGGCGGCGTTGGCGGCGGCGTAGTTGCCCTGCCCCGGCGA
GCCCAGGACACCGGCCGCGGAGGAGAACAGCACGAACGCCGACAGGTCC
ATCCCCGCGGTCAGCTCGTGCAGATGCAGGGCACCGTCCACCTTCGCCCC
GACCACCGCATCGATCTTCTCCCGGTTCAGACAGGCCACGGTGGCGTCGT

FIG.6-23

CCAGGACACCGGCCGTGTGCACCACAGCCGTCAGCGGATGCTCCGCGGGC
ACCTGCTCCAGCAGGGCGGCGACCTGGGCGCGGTCGGCGACATCGCACGC
CGCCACCGACACCGACACCCCTGCCTGACCCAGTTCCGCACACAGTTCTTC
GGCACCGGTGGCGGCCATGCCGCGCCGGCTCACCAGCAGCAGATGCCGCA
CCCCGTGCCCGGCGGCCAGATGGCGCGCGACCGCCGCTCCCAGAGTGCCG
GTCCCACCCGTCACCAGCACCGTCCCCTCCGCATCGAACCGGACGGCATC
CGACGAGTCGGCGGGCACCGGCACATGTGCCAAGCGCGCCGCCAGCAGTC
GCCCGCCACGCACCGCCAACTGGGGTTCGTCGCAGGCCAGAGCCGCCGTG
ACGGTGGTGTCGTCGGAGAGGTCGGCATCCAGCAGGACGAACCGCCCCGG
GTGTTCCGACTGCGCCGAACGCAGCAGGCCCCAGACCGCCGCTCCGGCGA
CGTCCGTCACCTCCTCACCGGTCCGGGTGGCCACGGCACCGTGTGTCACCA
CCACGAGCCGGGCCTCGGCAAGGCGATCGTCGGCCAGCCAGTCCTGCACC
ACGCTCAGCACTTCGCCGAGGACGTCCGCCACCGCGCCCTGGGAGCACGT
CAGCAGCACGGCGTCGGGGACGGGGGCGTCGTCGGTGTCCAGCCCGGAC
AGCAGGCCGGAGAGGTCCGCCGCCGCCCGGTCATGGGTGAGTACGGTCGA
CCGGACGGCCGTGTCCGGGGGCGGGGTGCCCGGTGTGACGTCCTTCCAGG
CCACGTCGAACAGCGCCGCGCGGCCGGCCGCCTGGGCAGAGGCTCGCAGT
TCGCCGGTGTCCAGCGGTCGTACGGCGAGAGAGTCGACCGACAACACGCC
CCGGCCGGTTTCGTCGGCCAGCGACACGGAGACGGCGGTCCGTTCGCCGT
CCCGCCCGGCCGGCGCCACCCGGACCCGTACCGCTGCCGCCTTCACCGCG
TGCAGGGTCACACCACTGAACGAGAACGGCACCGCCCCCGGCGGCAGGC
CCGTCGCCGCTCCGAGCGCCACCGCGTGCAGGGCGGCGTCCAGCAGAGCT
GGGTGCAGGTTGTACCGGGACGCCTCGTCGAGCACGGACTCCGGCAGGCG
GACCTCCGCGAAGACCTCTTCGCCCCGCCGCCAAGCCGCACGCAGCCCCC
GGAACGCCGGTCCGTAGGCGAACCCGCGGGCCTCCTGTGCCGCGTAGAAG
CTTTCCAGTTCGTCCGCCGCGCACGGCAGGGCCCCTTCCGGCGGCCAGCTG
CGCAGGGCGTCGCCGTCGGCGGAGGGCTGGGCGTCCAGCAGGCCGGTGG
CGTGGTGCTGCCAGGGATCCTCCGGGCGGGCGTGCTCGCTCCGGGAGGAG
ACGGTGAGGGTGCGGGCCCCGGTGTCGTCGGGCGCCGACACGCGGACCTG
GAGGTCGACGGCCGCGTCGTGCGGGACGGCGAGGGGCGCGTGAAGGGTG
AGCTCTCGCACGTGCGCGGCACCGCCGGCTTGGAGGGCGAGTTCGAGGAG
GGCGGTGCCGGGGAGGAGGACGATGCCGCCGACGCTGTGGTCGGCGAGC
CAGGGGTGGGTGTGCAGGGACAGGCGGCCGGTGAGCAAGGTTCCGTCTCC
GTCGGCGAGTTCCACGGTGGCGCCGAGGAGAGGGTGCTCGGTGGGGTGCA
GTCCGGCGGCGGAGACGTCGCCGGTGCTGGTGGTGGGTGTGTGGAGCCAG
TAGTGGTGGTGTTGGAAGGGGTAGGTGGGCAGGTCGATGGCGGGGGTGTG
GGGGGTGGTGGGGTAGTGGGTGGTCCAGGTGACGGTGTGGCCGGTGGTGT
GGGCGTGGGCGAGGGCGGTGAGGAAGCGGTGGGTGTCGTTGTCGTGGCG
GCGCAGGGTGCCCAGGGCGGTGGTGTGGTCGTGGTCTTCGATGGCGGGGG
TCAGGGTGGGGTGGGGGCTGGTCTCGATGAAGAGGCGGTGGCCCTGGGCG
GTGAGGGTGCGGACGGCGTGGGTGAAGCGGACGGGCCGGCGCAGGTTGC
GGTACCAGTAGGCGGCGTCCAGGGTGGTGGTGTCGGTCCAGGCGTCTTCG
ACGGTGGAGTAGAACGGGATGCTGCCGGGCTGGGGGGTGATGCCGTGGA
GCATGTGGAGCAGGTCGTGTTCGATGGTTTCGGTGTGGGGGCAGTGGGAT
GCGTAGTCCACGGGGATGCGGCGGGCCCGTACCCCGGTTTCGGTGCAGTG

FIG.6-24

GGTGAGGAGTTCGTCCAGGGCGTCGGTGTCGCCGGAGACGGTGGTGGCCC
GTGGCCCGTTGAACGCGGCCCTCCACAGCCGTCCCGGCCAGTGGGTGGTG
ATGAGGTCCTCGGCCTCGGTTCCGGTCAGGGCGAGTGAGGCCATGCCGCC
GTGGCCCCGCAGCGCGGCCAGGGCCCGGCTGCGCAGTGCCACGATCTTCG
CGGCGTCCTCCAGGGTGAGTGCGCCGCAGACGTGGGCGGCGGCGATCTCG
CCCTGGGAGTGGCCGACCACCGCGTCGGGTTCGATGCCGTAGGACCGCCA
CAGCGCCGCCAGGGACACCATGACCGAGAACAGCACCGGCTGCACCACA
TCCGCCCGCTCCCACACCGGATCCTCCGCGTCCCGGTGGAGCATTTCGGTG
AGCGACCACTCCACCCACGGCGCCAGCGCGCGTTCACACGCACCGACATG
GTCGGCGAACACCTGGGAGTCGCGCAGCAGGTCGAGTCCCATGCCGGCCC
ACTGACCGCCCTGGCCGGGGAAGACGAACACCACCCCGCCACCGGAGTG
GCTGTTGGTCTGGCTGCCGGTCGTGTCTTCGATGAGTGCGGGGTGCGGTTC
ACCCGAGGCCAGTGCTTCCAGCGCGTCTTCGAACTCTGTCCGTTCCCGTGC
CACGATCACGGCGCGGTGTTCCAGGACGGCCCTGCCATGGGCGAGTTCGG
CTCCGACCGCCCGTAGTGCGGTGTCGGTGCCGGGGCCTTGGAGGAAGTCA
CGCAGGAGTGCGGCCTGTGCCCGCAGCGCGGCGTTTGAACGCGCCGACAT
CGCCCAGGGCACCGGGGCGCCGTCTTCTGGGGCGGGGTCCCCGGCCGGCT
GGGCGGGTGCCTCTTCCAGGATGACGTGGGCGTTGGTTCCGCTGACTCCG
AAGGAGGAGATGCCGGCGCGTCGGGGCCGGTCCCCCTGGCGTGGCCAGG
GGCGGGGCTCGGTCAGCAGGCTGACCGCGCCGGACGACCAGTCGACCTGG
GGGGTCGGCTCGTCGATGTGCAGCGTGCGCGGCAGCGTCTCGTGGCGCAG
TGCCATCACCATCTTGATGATCCCGCCGACACCTGCCGCTGCTTGGGCGTG
GCCGATGTTGGACTTCAGGGAGCCGAGCCAGAGCGGCTGGTCGGGGTGGT
GTTCCTGGCCGTAGGTGGCGAGCAGGGCCTGGGCTTCGATGGGGTCGCCG
AGTTTGGTTCCTGTGCCGTGGGCTTCGACGGCGTCGACATCGGCGCCGGTC
AGGCCGGAGTTGGCCAGGGCCTGGCGGATCACGCGCTGCTGGGAGGGGC
CGTTCGGTGCGGTCAGGCCGTTGGAGGCGCCGTCCTGGTTGACCGCGCTG
CCCCGCACCACCGCCAGAACCCGGTGCCCGTTGCGCTCGGCGTCCGACAA
CCGCTCCACGAGCAGCATGCCCACGCCCTCGCCCCAGCCGGTACCGTCGG
CCGCGGCCGCGAAGGACTTGCACCGCCCGTCCACCGACAAACCCCGCTGC
CGGGAGAAGTCGATGAAGGTGCCCGGTGAAGACATCACCGTCACGCCGCC
GGCGAGGGCCATCGAGCATTCGCCCGATCGCAGGGCTTGGCCTGCGAGGT
GCAGTGCGACGAGCGACGACGAGCACGCGGTGTCGACCGAGACGGCCGG
CCCCTCGAAACCGAAGGTGTAAGCCACCCGACCCGACACGACACTGCCCG
CGTTTCCGTTGCCGATGTAGCCCTCCGCCCCTTCGGGAACGGCGGTCAAAC
GGGCGGCGTAGTCGTGGTACATCACACCCGCGAACACGCCCGTTCGGGAA
CCGCGTACGGCAGCGGGATCGATCCCCGCGTGTTCGAGGGTCTCCCAGAC
GGTTTCGAGGAGGAGCCGCTGCTGGGGGTCCATGGCAAGGGCCTCACGCG
GGCTGATACCGAAGAACTCGGCGTCGAACTGCCCGGCGTCGTAGAGGAAA
CCACCGTGCCGGGTGTACGACGCTCCGGCCCGCTCCGGGTCCGGGTCGAA
CAGCCCGGCCAGGTCCCACCCGCGGTCGGCCGGGAACTCCCCGATCGCGT
CACCGCCCGAAGCCACCAGCCCCCACAACTCCTCCGGCGACCGCACACCG
CCCGGGAAGCGGCACGCCATCCCGACGATCGCCAGCGGCTCGTCACTGCC
GACGGCTGTGGTTTCGGCGTACGGCGAAGTGCTGTCCGCGGCGTCGTCCC
CGAGCAGTTCCGTGCGCAGCAGGCGGGCCACGGCCGCGGGGCTGGGCTG

FIG.6-25

GTCGAAGACCAGGCTCGCCGGCAGTCGCAGTCCCGTCTCCGCGCTCAGGC
GGTTTCGCAGATCCACGGCCGTCAGGGAGTCGAAGCCGAGGTCGCGGAAG
GCCGAGTCGACCGGGATGGCTTCCGGTGCTTGGTGGCCGAGGACGGTGGC
GACATGCGAGCGGACCAGCCCGAGCAGGGCCTGGTACTGCTGTTCGGGTG
TCCGTCCCGCAAGCCGTGCCCGCAGCGACGCACCGCTGTCAGTGGTGGGG
AGGGTGGTGCGGTGGCTGGTGCGGGCGGGCGCGAGGTGTTCCAGAAGGG
GCGGTGCGGGATGGGTGGGGCGTAGGTCGGCGGGCAGGAGTGCGGGACG
TCCGGCGGCCAGGGCGGTGTCGAGGAGGGCGAGGGCGTCGGGGGTGGTC
AGGGGATGCAGCCCCGAGCGGGTGATGCGGTGACGGTCACCGGCATCCA
GATGCCCGGTCATCCCGCTGGTCTCTTCCCACAGTCCCCAGGCCAGGGAG
AGGGCGGGCAGACCGGCGGCACGGCGCTGGTGGGCCAGGGCGTCCAGGG
CGGCGTTGGCGGCGGCGTAGTTCCCCTGCCCCGGCGAGCCCAGGACACCT
GCGGCGGAGGAGAACAGCACGAACGCCGACAGGTCCATCCCCGCGGTCA
GCTCGTGCAGATGCAGGGCACCGTCCACCTTCGCCCCGACCACCGCATCG
ATCTTCTCCCGGTCCAGACACGTCACGGTGGCGTCGTCCAGGACACCGGC
CGTATGCACCACAGCCGTCAGCGGATGCTCCGCGGGCACCTGCTCCAGCA
GGGCGGCGACCTGGGCACGGTCGGCGACATCGCACGCCGCCACCGACACC
GACACCCCCGCCCCACCCAGTTCCGCACACAGTTCTTCGGCACCGGTAGC
GGCCATGCCGCGCCGGCTCACCAGCAGCAGATGCCGCACCCCGTGCCCGG
CGGCCAGATGGCGCGCGACCACCGCTCCCAGAGTGCCGGTCcCACCCGTC
ACCAGCACCGTCCCCTCCGCATCGAACCGGACGGCATCCGACGACTCCGA
CAGCGGCGGCACCCGCTTCAACCGTGGTACGCGAACCACCCCGTCGCGTA
CGGCGAGTTGGCTCTCACCGCGGGCCAGAGCGGACGCGACGGCGGCATCG
TCGAGACCGGCGCCGGTGCCGACCTTCGCGTCGGCGGACACGTCGGTGTC
CCCGTCGGTGTCGGTGTCGGTGTCGGTGTCGGGGTCGGTCTTGGTGTCGGG
GTCGAGGTCCAGCAGGACGAACCGGTCGGGATGCTCGGACTGGGCCGAG
CGGACCAGCCCCCACACAGCGGCCCCCGCCACATCCCGCACCGGCTCACC
CGCATCCACCGCGACCGCACCACGCGTCACCACGACCAGCCGCGCATCCC
CCTCCCGCTCATCGGCGAGCCACTCCCGCACCACACCCAACGCCGCGGCC
GTGACCTCGGCCACCCCACCACCCGGGCACTCCCACGCCACCAACTCCCC
GCCCCCACCGGCCACCGAGGCCGGCACCCCCTCCACCGGCACCCACCCCA
GCTCGAACAACGACCCACGCCGCACCCGAGCCCCCAGCCCCTCCAACGGC
ACCGGACGCATCAGGAGCGACTCGAGGGTGAGAACGGGTGCTCCGGTCTC
GTCGGTGGCGTGCAGGCGAACGGCGGTCGAGGTCGCGTCGGTGGGAGTCA
TGCGCAGGCGCAGGACGGTGGCGCCCCGGGCGTGGAGCGAGACACCGTT
CCATGTGTGAGGGACGAGCCCGGCCTGCTGCTGGTCCGCCAGCAGCAGGG
TGACCGATTGCACGGCCGCGTCCAGGAGCGCCGGATGCACCCCGAAGCCC
GCGACATCGGCCAGCCCCTCGTCCGGCAGACGCACCTCGGCCACCACGTC
GTCCCCGTCCCGCCAGGCCGCACACAAACCCTGGAACACCGGACCGTAGA
CAAAACCCCCACCCGCCAGACGGTCGTAGAGACCGTCGAGAACGACCGGT
CGGGCGCCGGGTGGCGGCCACTCCCCGGCCGCCGCTGCCTCCGCGTTCGG
ATCGTCTTCGGTGGACGGGGACAGCACACCCTCGGCATGCCGTGTCCACT
CTCCGTCCGTCTCCTCGTCCCCGGCCGGCCGCGCGTACACATTCACGGCGC
GCCGCCCCGCCTCGTCCGGCACCGACACCGACACCTGCACCACCACGTGC
CCCGACTCGGGAATCACCAGAGGGGCGTGGAGAGTGAGCTCGTCGACAC

FIG.6-26

GAGGACAGCCGGTACGCAGACCGGCCTGAAAAGCCAGATCCAGGAGGGC
GGTGCCCGGGAGGAGGACGATTCCGCCGACACTGTGGTCGGCGAGCCAG
GTGTGGGTGCGCAGGGACAGGCTGCCGGTGAGGACGATCCCGTCCCCGTC
CGCGAGCTCCATCACCGCACCCAGCAGCGGATGGTCCGGCCGCTGGAGCC
CGGCAGCCGACACATCGCCCGCACCGGCACCGGGAGTCGCCTGGAGCCAG
TAGTGCCGGCGTTGGAAGGGGTAGGTGGGGAGGTCGGGGATGGTGTGGG
GGTGGGGGTTGGTGTGGGTGTGGTGGTGGGTGTGCCAGGTGGTGGGGGTG
TGGGCGAGTGCGGTGAGGAGGTGGTGGGTGGGGTTGTGGTGGGGGTGGG
TGAGGGTGATGGCGGTGGGTTGGTGGTGGGGGAGGTTGTGGTGGGTGAGG
GTGGTGAGGGTGTGGTCGGGTCCGAGTTCGATGTAGGTGGTGACGCCGTT
GGTGTGGAGGGTGTGGATGGTGTCGGTCCAGTGGACGGGTTGGCGGGTCT
GGTGGGTCCAGTAGTGGGGGGTGAGGGGGTCGCCGGGGGTGCTGGTGAT
GAGGGGGGTGTGGGGTGGGTGGTAGGTGAGGGTGTGGGTGGTGGTGTCG
AGTTGTTCGAGGATGGTGTCGGTGTGGGGGGAGTGGAAGGCGTGGTTGGT
GGTGAGGGGTTTGGTGGTGATGCCTTGGGTGTGGCAGGTGGTGGTGATGT
GGTGGATGGTGTCGGGGTCGCCGCTGATGACGAGGGAGTGGGGGCTGTTG
ACGGCGGCGATGGTGGCTTTGCCGGGGTGTTGGTCGAGGAGGGGTTGGAT
GTGTTCGGGGGTGGTGTGGAGGGTGGTCATGGTGCCGGGGGGCATGGTTT
GCATGAGGCGGGCGCGGGTGGTGATGAGGTGGGTGGCGTCGGGGAGGGT
GAGGATGCCGGCGAGGTGGGCGGCGGTGATTTCGCCGAGGGAGTGTCCG
GCGAGGTAGTGGGGGGTGATGCCGTAGGTTTCGGTGATGAGGTGGTGGAG
GGCTTTTTGGAGGGTGAAGAGGGCGGGTTGGGCGTAGAGGGTGTGGGTGA
GGAGGTCGGTGGGGTCGTGGTTGAGGAGGAGGTCGCGCAGGGGGTGGTC
GAGGTGGGGGTCGAAGTGGGCGCAGGTTTCGTCGAGGGCGTCGGCGAAG
GCGGGGTAGGTGTGGTAGAGGCCGGTGGCCATGCCGGGGCGTTGGGTGCC
TTGTCCGGAGCAGAGGAAGGCGATTTTGTGGGTGTGGCCGGGTTCGGTGG
GGGGTGTGGGGATGAGGTGGGGGTGGGTGCGGCCGTCGGCCAGGGCGGT
GAGGGCGTCCAGGAGGGTGTCGCGGTCGGGGGCGATGAGGGTGGCGCGG
TGGTCGAACAGGGCGCGGGTGGTGGCCAGGCTGTAGCCGATGTCGGCCGC
GTCCTGTTCGGGGTGGTCCAGGACGTGGGCGTGCAGGGCGGCGGCCTGGG
CGCGTAGCGCGGCCTGCGACTTGCCCGACACGACCCACACCAACGGCACA
TCCGCCGACACCCGGCCCGCACCGTCCGTCTCCACCACCACCGCCGCAGC
CGCCGCAGTCTCCACCCCCGCCGGCGCGGCTTCCACCGCCTCCACCTCCGC
CCGCGCGGGCGCCTCCTCCAGGATCACGTGCGCGTTCGTCCCGCTCACCCC
GAAGGACGAGATTCCCGCTCGCCGGGGCCGGTCCTCCCGGCGTGGCCAGG
GCCGCGCCTCGGTCAGCAGGCTCACCGCTCCCGACGACCAGTCCACCTGC
GGCGACGGCTCATCCACATGCAACGTCCGCGGCAACGACTCGTGCCGCAA
CGCCATCACCATCTTGATGATCCCGCCGACACCTGCTGCCGCTTGGGCGTG
GCCGATGTTGGACTTCAGGGAGCCGAGCCAGAGCGGCTGGTCGGGGTGGT
GTTCCTGGCCGTAGGTGGCGAGCAGGGCCTGGGCTTCGATCGGGTCGCCC
AGCTTGGTCCCCGTGCCATGGGCTTCGACGGCGTCGACATCAACTGCGGA
GAGGTTCGCGTTGGCCAGGGCCTGGCGGATCACACGCTGCTGGGACGGAC
CGTTCGGCGCCGTCAGCCCGTTCGAGGCGCCGTCCTGGTTGACCGCGCTGC
CCCGCACCACCGCCAGAACCCGGTGCCCGTTGCGCTCGGCGTCCGACAAC
CGCTCCAGCAGGAGCATCCCGGCTCCCTCCGACCAGCCGGTACCGTCGGC

FIG. 6-27

CGAGGCGGAGAACGCCTTGCACCGGCCGTCCGCCGCCAGGCCCCGCTGCC
GCGAGAACTCCAGGAACGCGGTAGGCGTGGACATCACCGTCGCACCGCCC
GCCAAGGCCATGGTGCACTCGCCCGACCGCAGTGCCTGACAGGCCAGATG
CAGCGCGACGAGCGACGACGAGCACGCGGTGTCCACGGACACGGCGGGG
CCTTCGAGCCCGAACGTGTAGGCGACCCGGCCCGACGCCACGCTTCCGGA
CGTGCCGGTGAGAACGTACCCGTCGACGTCGGCGGCGACATGGTGCCGTG
AGCGGGACGCGTACTCCTGAGGCATGACGCCGGCGAACACGCCCGTCTGG
CTGCCGCGCACGGCACCGGGGTCGATACCCGCCCGCTCGAACGCCTCCCA
CGTCGTCTCCAGCAACAGCCGCTGCTGGGGGTCCATCGCGAGCGCCTCGC
GCGGGGAGATCCCGAAGAATCCCGCGTCGAACTCCCCCGCGTCGTAGAGG
AATCCCCCGTGACGGGTGTACGAGGTGCCCCGCTGCCCGGGCTCCGGGTC
GTAGAGCGCCTCCACGTCCCAGCCACGGTCGGCCGGGAACTCCCCGACCG
CGTCGCCGCCGGAGGCGACGAGTTGCCAGAGGTCCTCGGCCGAGGCGACA
CCTCCCGGATACCGGCATCCCACACCGATGATCGCGATGGGCTCGTGCTG
CCCGGCCTTCGGTTCGGCGGCGGCAGGTGCCGAAGGCGTCTTGGTGTCGT
TGGGGTTGAGGAGGGTGGTGAGGTGGTGGGTGAGTGCGGTGGGGGTGGG
GTGGTCGAAGGCGAGGGTGGTGGGCAGGCGCAGGCCGGTGGCGCGGGTG
AGCCGGTTGCGGAGTTCGACGGCGGTGAGGGAGTCGAAGCCGAGGTCGC
GGAAGGTGCGTTCGGGGTCGATGGTGTCGGGGGTGGGGTGGCCCAGGAC
GGCGGCGATGTGGGTACGGGCCAGGGCCAGCAGGGTGGCGTGCCGCTGTT
CGGAGGTCAGGGTGGCGAGGCGGTCGGCGAGGGAGACGTCCTGGCCTGC
GCCTGCACTGGTGCCGGTGTGTGCGGTGCGGGGGCTGGTGCGGGCGGGCG
CGAGGTGTTCCAGGAGGGGTGGTGCGGGGTGGGTGGGGCGTAGGTCGGC
GGGCAGGAGTGCGGGACGTCCGGTGGCCAGGGCGGTGTCGAGGAGGGCG
AGGGCGTCGGGGGTGGTCAGGGGATGCAGTCCCGAGCGGGTGATGCGGT
GACGGTCACCGGCGTCCAGGTGGCCGGTCATCCCGCTGGCCTCTTCCCAC
AGTCCCCAGGCCAGGGAGAGGGCGGGCAGACCGGCGGCGCGGCGCTGGT
GGGCCAGGGCGTCCAGGGCGGCGTTGGCGGCGGCGTAGTTGCCCTGCCCC
GGCGAGCCCAGGACACCTGCGGCGGAGGAGAACAGCACGAACGCCGACA
GGTCCATCCCCGCGGTCAGCTCGTGCAGATGCAGGGCACCGTCCACCTTC
GCCCCGACCACCGCATCGATCTTCTCCCGGTCCAGACACGTCACGGTGGC
GTCGTCCAGGACACCGGCCGTATGCACCACAGCCGTCAGCGGATGCTCCG
CGGGCACCTGCTCCAGCAGAGCGGCGACCTGGGCGCGGTCGGCGACATCG
CACGCCGCCACCGACACCGACACCCCTGCCTGACCCAGTTCCGCACACAG
TTCTTCGGCACCGGCGGCGGCCATGCCGCGCCGGCTCACCAGCAGCAGAT
GCCGCACCCCGTGCCCGGCGGCCAGATGGCGCGCGACCGCCGCCCCCAGA
GTGCCGGTCCCACCCGTCACCAGCACCGTCCCCTCCGCATCCAGGGGCAC
AGGCAGGGTCAGCACGTTCTTGCCGACATGCAGGCCCGACCGCATCGACC
GCAGCGCCTGGCGGGCCTGGCGCACGTCCCACGCGGTGACCGGCAACGGC
TCCAGCACCCCGCGCCGGAACAGATCCACCACCGTGTGCAGGATCTCCCC
CACCCGCTGCGCACCCGCGTCCATCAGGTCATACGCCCGGTAGGACACCC
CCGGGAACCGAGCGGCGACCTCACCGGCATCACGGATGTCGGTCTTGCCC
AGCTCCAGGAACCGGCCCCCCTGCGGCGAACACAGCCGCAACGAGGCATC
GGTGTACTCACCCGCCAGACAGTTCAGCACCACATCCACACCCCGCCCGC
CACTGGCCCGGCGGAAACGCGACTCGAACTCCACACTCCGCGAGGAAGCG

FIG.6-28

ATCCGCTGCGGCGCGACACCCGCCGCCCGCAGACGCGCCCACTTCGCCTC
ACTCGCCGTCGCATACACCTCCGCCCCAGATGACGGGCGAGCTGCACCG
CCGCCGTACCGACCCCGCCGGCCGCCGCATGGACCAGCACACTCTCCCCC
CGCCGCACCCCCGCCAGATCGACCAGCCCCAGGTAAGCGGTAGCGAACAC
CACCGGCACCGAAGCCGCCTGCGCGAACGACCAGCCCTCCGGGATACGGG
CCAGCAACACCTCCTGCGCCACCACCACCGGCGCGAACGCGTCCCCGAAC
ACCCCGAACACCCGGTCTCCCACCACCAGGCCCTCCACCCCGGGCCCCAC
CTCCACCACCACCCCCGCACCCTCACTGCCCACCCCCACCTGACCCGGCAC
CATCCCCAACGCCACCAGAACATCACGGAAGTTCACCCCGGCAGCCCGCA
CCGCCACCCGCACCTGCCCCCGACCCAGCACCACCCCAGCCGCATCCGAA
GCAACCACACCCACCCCCTCCAACAACCCCGACCCACCACCATCCAGCCG
CCACCCCACCCCACCAGGCAACGACAACCCTTCACCCGCACCCCCAAGCC
GCCCCCACCGCTCCAACCGCTCCAACCGCGGCACCCGCACGACCCCACCA
CGCACGGCAACCTGTGCCTCGCCACACGCGACAAACCCGGCCACATCGAC
ACCAGCACCAACACCGGCGCCCATGTCCTCATCGGCATCGACGACGGTCT
CCACGCCGGTGCCGGGGTCGAGGTCCAGCAGGACGAACCGGTCGGGATG
CTCGGACTGGGCCGAGCGGACCAGCCCCCACACAGCGGCCCCCGCCACGT
CCCGCACCGGCTCCCCCGCATCCACCGCGACCGCACCACGCGTCACCACG
ACCAGCCGCGCGTCCCCCTCCCGCTCATCGGCGAGCCACTCCCGCACCAC
ACCCAACGCCGCGGCCGTGACCTCGGCCACCCCACCACCCGGGCACTCCC
ACACCACCAACTCCCCGCCCCCACCGGCCAACGAGGCCGGCACCCCCTCC
ACCGGCACCCACCCCAACTCGAACAACGACCCACGCCGCACCCCCGCCCC
CAGCCCTTCCAACGGCACCGGACGCAGAACCAGAGACTCCAGCGCGAGC
ACCAGCGCACCGGTCTCATCGGCAACCCGAAGACTCACGGTCGTTCCGGC
CGCGTCGACAGACGTCACCCGGACTCGCAGTGCCCTGGCACCCCGGGCGT
GGAGGGAAGCACCGTTCCATGTGTAAGGCAGCAGACCGGCCTCTTGGTCC
TCGGGCAGCAGGAGGGTGACCGTCTGCACGGCCGCGTCCAGGAGCGCCG
GATGCACCCCGAAGCCCGCGACATCGGCCAGCCCCTCGTCCGGCAGACGC
ACCTCGGCCACCACGTCGTCCCCGTCCCGCCAGGCCGCACACAAACCCTG
GAACACCGGACCGTAGACAAAACCCCCACCCGCCAGACGACCGTAGAAC
TCATCGAGATCCACCGGCTGCGCACCGGACGGCGGCCACACCCCGTCCGC
CACCGGCTCAACAACCACCGACTCCCCAGGAACAGACGGACACACCACAC
CCTCGGCATGCCGCGTCCACTCACCCTCCAGCCCTCCGTCCTCCACCAGCC
GCCCGTACACACTCACACCACGACGACCCGCCTCGTCCGGCACCGAAACC
GACACCTGCACCACCACATGCCCCGACTCCGGAACCACCAGAGGAGCATG
GAGAGTCAGCTCATCGACACCAGGACAACCCGCACGCAGACCAGCCTGA
AAAGCCAGCTCCAGCAGAGCGGTACCGGGCAGCAGGACGACGCCGCCGA
CGCTGTGGTCGGCGAGCCAGGGGTGGGTGTGCAGGGACAGGCGCCCGGT
GAGGACGATTCCGTCCCCGTCCGCGAGCTCCATCACCGCGCCGAGCAGTG
GGTGGTCCGGTCGCTGGAGTCCGGCGGCGGAGACGTCGCCGGTGCTGGTG
GTGGGTGTGTGGAGCCAGTAGTGGTGGTGTTGGAAGGGGTAGGTGGGCAG
GTCGATGGCGGGGGTGTGGGGGGTGGTGGGGTAGTGGGTGGTCCAGGTG
ACGGTGTGGCCGGTGGTGTGGGCGTGGGCGAGGGCCGTGAGGAAGCGGT
GGGTGTCGTTGTCGTGGCGGCGCAGGGTGCCCAGGGCGGTGGTGTGGTCG
TGGTCTTCGATGGCGGGGGTCAGGGTGGGGTGGGGGCTGGTCTCGATGAA

FIG.6-29

GAGGCGGTGGCCCTGGGCGGTGAGGGTGCGGACGGCGTGGGTGAAGCGG
ACGGGCCGGCGCAGGTTGCGGTACCAGTAGGCGGCGTCCAGGGTGGTGGT
GTCGGTCCAGGCGTCCTCGACGGTGGAGTAGAACGGGATGCTGCCGGGCT
GGGGGGTGATGCCGTGGAGCATGTGGAGCAGGTCGTGTTCGATGGTTTCG
GTGTGGGGGCAGTGGGAGGCGTAGTCCACGGGGATGCGGCGGGCCCGTA
CCCCGGTTTCGGTGCAGTGGGTGAGGAGTTCGTCCAGGGCGTCGGTGTCG
CCGGAGACGGTGGTGGCCCGTGGCCCGTTGAACGCGGCCGTCCACAGCCG
TCCCGGCCAGTGGGTGGTGATGAGGTCCTCGGCCTCGGTTCCGGTCAGGG
CGAGTGAGGCCATGCCGCCGTGGCCCCGCAGCGCGGCCAGGGCCCGGCTG
CGCAGTGCCACGACCTTCGCGGCGTCCTCCAGGGTGAGGGCGCCGCAGAC
GTGGGCGGCGGCGATCTCGCCCTGGGAGTGGCCGACCACCGCGTCGGGTT
CGATGCCGTAGGACCGCCACAGCGCCGCCAGGGAGACCATGACCGAGAA
CAGCACCGGCTGGACCACATCGGCCCGCTCCCACACCGGATCCTCCGCCT
CGCGGTGGAGCATCTCGGTGAGCGACCACTCCACCCACGGCGCCAGCGCG
CGTTCACACGCACCGATATGGTCGGCGAACACCCCCGAGGTCGTCAGCAG
ATCAAGTCCCATGCCGGCCCACTGACCACCCTGGCCCGGGAACACGAACA
CCACCCCGCCACCGGAATGGCTGTGGCTGCCGGTCGCGTCTTCGATGAGT
GCGGGGTGCGGCTCACCCGAGGCCAGTGCTTCCAGCGCGCCTTCGAACTC
CGCCCGCTCCCGTGCCACGATCACCGCGCGGTGCTCCAGCACGGCCCTGC
CACGAGCCAACTCTGCCCCGATATCCCGCACCCCGGCATCCGTACCGGGG
CCGCGCAGGAACTCACGCAAGACCATGGCCTGCGCCCGCAACGCCGCACC
CGAACGCGCCGACACCACCCAGGGCACCGGAGCCCCGTCCTCTACCGCAG
CCTCCCCGGGCCGACGGGCGGGTGCCTCCTCCAGGATCACGTGCGCGTTG
GTTCCGCTCACCCCGAACGAGGACACCCCGGCCCGCCGGGGCCGGTCCTC
CCGACGCGGCCAGGGCCGCGCCTCGGACAGCAGGCTCACCGCCCCCGACG
ACCAGTCCACCTGCGGTGACGGCTCATCCACATGCAACGTCCGCGGCAGC
GACTCGTGCCGCAGCGCCATCACCATCTTGATGATCCCGCCCACACCCGCT
GCCGCCTGGGCGTGGCCGATGTTGGACTTCACCGAGCCCAGCCACAACGG
CTGTTCCCCGGAACGCTCCTGGCCATATGTGTCGAGCAGGGCCTGGGCTTC
GATCGGGTCACCGAGCCGTGTGCCGGTCCCGTGCCCCTCCACCGCGTCGA
CGTCCGCCACCGTCAGCCCCGCGTTGGCCAGTGCCTCGCGGATCACGCGC
TCCTGCGAGGGGCCGTTCGGTGCGGTCAGGCCGTTGGAGGCGCCGTCCTG
GTTGACCGCGCTGCCCCGCACCACCGCCAGAACCCGGTGCCCGTTGCGCT
CGGCGTCCGACAACCGCTCGACCAGCAGCATGCCCACGCCCTCGCCCATG
CCGGTACCGTCGGCCGCGGCCGCGAAGGACTTGCACCGCCCGTCCACCGA
CAGACCCCGCTGCCGGGAGAACTCCACGAACAGGAGCGGGGTGGACATC
ACGGTGACCCCACCGGCGAGGGCGAGATCGCACTCGCCCGTCCGCAGCGA
CTGGCAGGCCAGGTGCAGCGCCACCAGCGACGACGAACACGCCGTGTCG
ACGGTGACGGCCGGGCCTTCCAGACCGAGCGTGTAGGCGACGCGCCCGGA
GGCGACGGCGCCACCGCTGCCGTTGCCGATGTAGCCCTCGAACCCTTCGG
GGATGGTGGCGAGCCGGGAGGCGTAGTCGTGGTACATCATGCCGGTGAAG
ACACCCGCTCGGGCTCCCCGGACCGAGGAGGGGTCGATCCCGGCCCGCTC
GAAGACCTCCCACGAGGTCTCCAGCAGCAAGCGCTGCTGGGGGTCCATGG
CCAGGGCCTCACGCGGACTGATGCCGAAAAGCTCGGCGTCGAACTGTCCG
GCGTCGTAGAGGAAACCACCGTGGCGGGTGTACGACGCTCCGGCCCGCTC

FIG.6-30

CGGGTCCGGGTCGAACAGCCCGGCCAGGTCCCACCCGCGGTCGGCCGGGA
ACTCCCCGATCGCGTCACCGCCCGAAGCCACCAGCCCCCACAACTCCTCC
GGCGACCGCACACCGCCCGGGAACCGGCACGCCATCCCGACGATCGCCAG
CGGCTCCTGTGCCGCCTCGACGGCCGCTGTGAGCTGCTGGTTGCGCCGCCG
CAGGGCCTCATTGGCCTTCAGGGATGCCCGCAGCGCCTCGACGAGCTTCT
CGCTGGGCGTAGCCATCGGTGTCTCCAAGTCTGCGAATCCGGCAGGTGCG
GACGCGGTGGTGTGGACGGGGCGGGGGTCGGCGGGGACCGCGGCGGGCG
ACTCGGGTGGTGTCAGCGACGCCGCTGCTCGGTGAGCCCGGCCAGCCAGG
TGTGGACGTGCCGGGCCGTCGACTCCGCGTGCTCTTCGAGCATCGTGAAG
TGGTTGCCGTCGGTTTCGAGGACGGTGTGCGGCTCGCCCCACACCGGCGG
CGGCTGTTCGCTCTCACGGGCGCGGAGGAAGAGGGTGGGTGTCTCGAGGG
CGGGCGGCCGCCAGCCCGCGAAGATGCGGAAGTAGCCGCCCATCGCCACC
AGGCGGGCGTAGTCCAGGTCGATGAACTCGGTGACGCGGTCGAAGATTTC
GCTGGTGAGGGCGGCGGCGACGGGGGCCATCCCCTCGTCGGGCAGGTAG
GCGTCCATGACCACCACGGCCTGCGGCCGGACGCCCAGGTGTTCCAGGCG
GCTCGTGACGGTGTGGGTGAACCAGCCGCCGGCGGAGTGTCCGGCGAGGG
CGAAGGGCTCGCCGTCGGTGTGGCGGAGGATGGCGTCGGTGAACAGCCG
GGTGATGGTGTCGACGTCGGCGGGGAGGGGCTCGCCGTCGGCGAAGCCG
GGCGCCGGCACGTACCAGACGTCGCGGAGCCCGTCGAGGGCCGCCGCGA
AGCGGGAGTACTGGTAGACGCTGGACACGGCGGCGACGGTGGGCAGGCA
GATCAGCGCGGGCCCGGTGTCGCCCTGGGCGACGCGGACGAAGGGGGGT
CGGGTCATAGCCGAGGGGTCGGTGAAGCAGGGCCGGAAGGCGGAGGCCG
CCGACAGCAGGGCCATGGACTCCTCGACGCGGCCGCTGTCGTGACCGATC
CAGAACAGGGCTTCCACCGTGTCGGCGGACGGGCCGCTCCCGGCTCGCGA
CGAGGCGGTGGCATCGCGCTCCCCAGGGGCGCCGGCCGTTTCGGCGGTCA
TATCGGAGGCCGGCTCGGCGGCGAGGAGCCTTTCGAGGTGGTCGGCGAGC
GCTGCCGGGGTCGGGTGGTCGAAGACGAGCGTGGTGGCCAGGCGCAGCC
CGGTCGCTGCGTTGAGGCGGTTGCGCAGTTCCACGGCGGTCAGGGAGTCG
AAGCCGAACTCGCGGAACTCGCCGTCGGCGGTGACGGTGTCGGTGCCGCC
GTGGCCGAGGACGGCCGCGGCGTGGGTGCGGACCACCTCCGTCAGCAGG
GCGGTGCGCTCGGCGGGCTTCGGGGTCCCGGCCAGTCGCCCGCGGAGTTC
GGCGGCGGCGTCGGCCCCGACGCCGTGGTCGGCGGTCCGGCGGGCCGGG
GTGCGGACCAGGCCCCTGAGGACGGGCGGCAGGGTGCCGACGGCCGCCT
GCTCACGGAGGGTGCCCGGGTCGAGGGGGGTGGCGAGGAGCAGCGGTTC
GTCGAGGGCGAGGGCGGTGTCGAACAGGGCGAGCCCGTGGGCGTTGGTG
AGCGGGAGCAGGCCGCTGCGGGTCATCCGGGCGACGTCGGCGGCGGCGA
GGTGCTCGGCCATGCCGCCCGCCTCGGCCCAGCGTCCCCAGGCGAGGGAG
CGGCCGGGCAGGCCGAGGGCGTGCCGTTGCTGCATCAGAGCGTCGAGGA
AGGCGTTCGCGGCCGTGTAGTTGGCCTGTCCGGGGCTGCCGAAGGAGGCG
GCGGCGGACGAGAAGGCGATGAACGCGTCGAGCCCGGCGTCGCGGGTGA
GGTCGTGCAGGTGGGCGGCGCCGTGGGCCTTGGCGCTCAGGACGGCGTCC
AGGCGGTCGGGGGTCAGGGAGGTGAGGACGCCGTCGTCGACGACGCCGG
CGGTGTGGAGCACGGCCTTGAGCGGATGCCGTGCCGGGATCTCGGCCAGC
AGCGCCGCGACGGCCCGCCGGTCGGCGAGGTCGCAGGCGACGGCCGTCGT
CCGGGCGCCCAGCTCGGCGAGTTCGGCGACGAGTTCGGCGGTGCCGGGAG

FIG.6-31

CGGTGGGGCCGCTGCGGCTGGTCAGCAGCAGGTGCCGTACGCCGTGGGTG
ACGACGAGGTGGCGGGCGAGGAGCCGGCCGAGGTAGCCGGTGCCGCCGG
TGATGAGGACAGTGGCGTCGGGGTCCCAGTGTCCGCTGTCCGCTCGGGCG
CCGACCGGGATGCGGGCCAGCCGCGGGGTGTGGGCGCGGCCCTCGCGCA
GGACGGTCTGCGGCTCACCGGAGAGCAGGGCCGCGGCCAGGGCGCGCCG
GCTGGCGTCGGTGTCGTCGAGGTCGGTGAGGACGAACCGGCCGGGGTTCT
CGGTCTGGGCGGAGCGGACCATGCCCCAGACGGCGGCGTGCGCGAGGTC
GGGGACGGAGTCGCCCGGTGCGGCGGCGACCGCGCCGTGGGTGACGAAC
GCGAGCCGGGAGTCCGCGAACCGGTCGTCGGCGAGCCAGCTCTGCAGCAG
GTGCAGGACGCGGACGGTGGCCCGCCGGGTGGCGTCGGCCGCGTCGGCG
GCGCCGTCGCGGTGCGGGCAGGGGACGACGACCACGTCGGGTACGGGTG
TGCCGGCCGAGGCCAGTTCCTCCAGATCCGCGTATGTGCTCCACGGCACG
CCGGGGGCGTCGGGGCACTCGGCTTCGGAGCCGATCAGCGCCAGGCGCGT
CTTCGACGACGGTGTCCTGGGCAGCGGTACGGGCGCCCAGTCGAGCCGGA
AGAGGGCGTCGTGGTGGGCGGTGCGGGCCGAGTGGAGCTGTCCGGCCGTG
ACGGGCCGGAACGCGAGTGACTCGGCCGTGACGACGGTGTGTCCCGTGCT
GTCCGTGGCCAGCAGGGCGATCGTGTCGGGCGACCGCCGACTGAGGCGGA
CGCGCAGCGCCGATGCCCCGGAGGCCGTGACGGTGACGCCGCTCCAGGAG
AAGGGCAGCCAGCCGTGGCCCTCGTCCGGCTCGTCCTCGGCGAAGCCGAG
GACCACCGGGTGGAGTGCCGCGTCGAGCAGCGCCGGGTGGACGGCGTAG
CGGTCGGCGTCGCCCGACGGTCCGTCGGGCAGTGCGACCTCGGCGTACAG
GTCGTCCCCGTGCCGCCAGGCGGCCCGCAGTCCCTGGAACGCGGGTCCGT
ATCCGAGGCCCGCGTCGGCCAGTGTCCCGTACCAGTGGTCGAGGTCGACG
GGGACCGCGTCCGTGGGCGGCCACGGTGCGGCGGTGTCGTGGGCGGTCTC
CGCGCGCCGTGTCAGGACGCCCGTCGCGTGGCAGGTCCAGCCGGTCCCGT
CCGTGCCGGTCGGCGCGGCGGGGGTGAGTCCGTCGTCTTCCCGCGCGTAG
AGCGTGAAGGGGCGCCGCTCCACCCCGTCCGGCGCCGTCTCGGTCGCGCC
GACGGAGAGCTGCAGGACGACCGATCCGCGCTCCGGCAGGACCAGCGGG
ACCTGGAGTGCCAGTTCCTCGACGGTGTCGCAGCCGACTTCGTCGCCCGC
GCGGACGGCCAGTTCGAGGATGGCCGTGCCGGGCAGCAGGACGGTGCCG
AAGACGGCGTGGTCGGCGAGCCAGGGATGGGTGCGCAGCGAGATCCTGC
CGGTGAGCAGGCATTCCTGCGACTGCGGTGATCCGGCCAGGGGTACGGCG
GAGCCGAGCAGGGGGTGTCCGGCTGCGGTGAGTCCGGCGGCCGAGACGT
CCCCGGACAGGCTGGTGTCGGCGTCCAGCCAGTAGCGGCGGCGGTCGAAG
GGGTAGGTCGGCAGGTCGAGGTGGCGGGCGCGTTCCGGTGTCGCGCCGAT
GAGGGCCGGCCAGTGGACGGCCGTCCCGCCCTTCGGTGTGCCCTGCACGT
GGAGGTGGGCGAGCGCGGTGAGCAGCGCCAGGGGTTCGGGGCGGTCGGC
GCGCAGCAGCGGGACCAGGGCGGGACCGGGCTCGGTGGTGTTGTCGTCGG
CGGGCAGGCACTCTCCGGCGAGGGCGCAGAGGGTTCCGTCCGGGCCGAGT
TCCAGGAAGGTGCGTACCCCGTCGTCGTCGTGGAGGCGGCGTACGGCGTC
GCCGAAGCGTACGGTGCGGCGTAGCTGGCGGACCCAGTACTCCGGGTCGG
TGAGCGTGCCGGCCGTGGCGCGGTCGCCGGTGACGGTGGAGACCACCGGG
ATCGTCGGTTCGGCGTAGGCGATGCCGGTCGCGACCTGCCGGAACTCCTC
CAGGATCGGTTCCATCAGCGGGGAGTGGAAGGCGCGGTCGGTGCTGAGGC
GTTTGGTGCGCAGGCCCTGCTCGGCGAAGGCGGCGGCGGCTTCCAGTACG

FIG.6-32

TCCGGCTCGGCTCCGGAGATCACCACCGACGTGGGGCCGTTGACAGCGGC
GACGGCCACCCGTGCCTCCCGGCCGGCGAGCATCCGGGTGACCTGTTCCT
CGCTCGCGCGGACCGCCAGCATGGCTCCGCCGGGCGGCAGTTGTGTCTGC
GCCAGCCGGCCCCGGGCCGCGACCAGCCGGGCCGCGTCGGTCAGTGAGA
GGACGCCGGCGACGTGCGCGGCGGCCAGTTCGCCGATCGAGTGGCCGGCG
ACGTGGTCCGGGCGGATCCCGGCGCTCTCCAGCAGGCGGAAGAGGGCGA
CCTGGAGGGCGAAGAGCGCCGGCTGCGCGTCGCCGGTGCGGTCCAGCGGC
TGCGGCTCGTCGAGGAGGAGCGGGCGCAGGGGCCGGTCGAGATGGGGTT
CGAGCTCCGCGAGTACGTCGTCCAACGCCTGGGCGAAGGCGGGGTGGGCG
GCGTACAGCTCTCGGCCCATGCCGGGCCGTTGGGTTCCCTGGCCGGAGAA
GAGGAAGGCGACCTTGCCGTGGGCGGTGCGGGCGGGGGATTCGATCAGG
CCGGGGGCCGTGGTGCCCTCGGCCAGTGCGTCCAGGGTGCGCAGGAGTCC
CTCGTGGTCCTCGGCGACCAGCACGGCCCGGCGTTCGAATGTCGACCGGC
CGGTGGCCAGGGCGTGTGCGACGTCACCGATCGGGATGTCGGGGTTGGCG
GCGAGGTAGTCGCGCAGCCGCCTGGCCTGGGCGCGCAGGGCGGTGTCGGT
CCTGGCCGAGAGGAGACAGGGCACCGTCGCGGGTCCGGCCTCGTCCTGCG
ACGGTGCCTCCTCCGGCCGTACCTCTTCCTCCTGCGGTGCCTCTTCCAGGA
TGACGTGTGCGTTGGTGCCGCTCACCCCGAACGACGACACACCCGCACGA
CGCGGACGCTCACCCCGCTCCCACACCACCTCCTCCGTCAGCAACCGCAC
CGCACCCGACGACCAATCCACATGCGGCGACGGCTCATCCACATGCAACG
TCCGCGGCAGACGACCCCGCCACAACGCCATCACCATCTTGATCACACCA
GCCACCCCCGCCGCAGCCTGCGTATGACCCAGATTCGACTTCACCGACCC
CAACCACAACGGCACCCCACGACCCCGCCCATACGCCGCCAGCACCGCCT
GCGCCTCGATCGGATCACCCAACGACGTCCCCGTCCCATGCCCCTCCACCA
CATCCACCTCAGCAGCCGACAACCCCGCACACACCAACGCCTGACCGATC
ACCCGCTGCTGAGACGGACCATTCGGCGCCGTCAACCCATTCGACGCACC
ATCCTGATTCACCGCACTCCCCCGCACCACCGCCAACACCCGATGCCCCA
GCCGCCGCGCATCCGACAACCGCTCCACCAACAACACACCCACACCCTCG
GACCACCCCACCCCGTCCGCCGCCGCCGCGAACGCCTTGCACCGCCCGTC
CGCCGACAAACCCCGCTGCCGCGAGAACTCCACGAACGCCCCCGGCGTCG
ACATCACCGTCACACCCCCCGCCAACGCCAACTCCGACTCACCCGACCGC
AACGACTGACACGCCAGATGCAACGCCACCAACGACGACGAACACGCCG
TGTCCACCGTCACCGCCGGACCCTCCAACCCGAACGTGTACGACAACCGC
CCCGACAACACACTCCCCGACACACCCGTCAGCGCATACCCCTCCAGATC
CCGGCCACCCCGACGCACCAACTCCGCATAATCCTGATTCGCCACCCCCG
CGAACACACCCGTACGACTCCCCCGCAACGACACCGGATCGATCCCCGCC
CGCTCCAGCGCCTCCCAGGACACCTCCAGCAACAACCGCTGCTGCGGATC
CATCGCCAACGCCTCACGCGGCGAAATCCCGAAAAACCCCGCATCGAACT
CCGCCGCACCCGCCAAAAACCCACCCGACCGCGTATACGACGACCCCGGC
CGCCCCGCCTCCGGATCGTAAAGACCCTCCACATCCCAGCCCCGGTCCAC
CGGGAAGCCGCCGATCGCGTCCCCACCCGAGGCGACCAACTCCCACAAAT
CCTCCGGCGACCACACACCCCCCGGAAAACGACACGCCATCCCCACGATC
GCCACCGGCTCATCCACCACACCGGGTCGGGCCGCGACGGGCGGTGTCGC
CGGGGCGGTTCCGCACAGCTGGTCCCGGAGGTGCCGGGCCAGGACGGCG
GGGCGCGGGTAGTCGAAGACCAGTGTCGTGGGAAGGCGCAGTCCGGTGG

FIG.6-33

CCGTGTTGAGGCGGTTGCGCAGTTCGACGGCGGTGAGCGAGTCGAAGCCG
AGTTCGCGGAAGGCCCGGTCGGCCGGGACGGTGTCGGCCTCCCGGTGGCC
GAGCACCGCGGCCGTGTGGGTGCTGACCAGTTCCAGCAGGACGTCCGTCC
GGGCGTCCGGTTCCAGGGCGGCGAGCCGATCGCGCAGGTCGGTGCCGTGG
GCGGTGCCGGTGCCGGTGGCGCGGGTGAGCGCCCGGACGTCGGGGAGGT
CGCCGATCAGGGGCAGGCGGCTGCCGGCGGTGTGGGCGGTGAAGCGCTCC
CAGTCGATGTCGGCGACGGTCAAGCCGCTCTCGTCGTGGTCCAGCACCCG
GGCCAGGGCCGCCAGGGCGAGTTCGGGCGCCATCTCCGTCAGTCCCCGGC
GGTGCAGCCGGGCGGCCGCGTCCGGCCGGCCGGCGGCGCTGTGTCCGCGC
CAGGGGCCCCAGGCCACCGCGGTGGAAGGCAGTCCGAGACCGCGCCGGT
GGACGGCGAGAGCCTCGACATAGGCGTTGGCCGCCACATAGGCACCCTGG
CCACCGGAACCGAACGTGGCGGCGGCCGAGGAGAACACCACGAACGCCG
AAAGATCCGCACCCCGCGTCAGCTCGTGCAGGTTCCGCGCACCCACCGCC
CTGGCCGCCAGCACCCCCTCCAGCCGCTCCGGCGTCAACGCGTCCAGCAC
ACCGTCGTCCACCACCCCCGCCGTATGCACGACCGCCCCCAGCGGACAAT
CCTCGGGAACCGCCGTGGCCAGCAGCTCCGCGAGCGCCCCCCGATCGGCC
ACATCACAGGCGGCGATGGTCACCCGGGCGCCCCACTGGTCCGTCGTGTC
GGCGAGGCCGAAGCCGTCGCCGGAGGTACTGATCAGCAGCAGGTGTTCGG
CTCCGCGGTCGGCCAGCCATCGGGCGAGGTGGGCGGCCGGCTGCTCGGGG
TCGGCGTTCTCGCCGGTGATCAGGACGGTGCCGCGCGGCCGCCACCCACC
AGCCTCCGCTCCCCCTCCCGGAGCACGCACCAGACGCCGCACGAACACCC
CCGACGCCCGGACCGCGACCTCCCCCTCACCCCCGCCCCCCGACAGCACA
CCCAGCAAACCCTCCACCACCCGCTCGTCGACCACCTCCGGCAGATCGAC
CACCCCACCCCACCGATCCGGCAACTCCAACCCCGCCACCCGGCCCAAAC
CCCACACCACAGCCCCACCCGGATCCCCCAGCCGATCCCCCTCCCCCACC
GACACCGCACCCCGCGTCACACACCACAACGGCACCCCCAACCCCTCCAC
CGCCTGGACCAACCCCAGCACCAACCCGGCAACACCCACCCCACCCCCAC
ACACAGCCAGCACCCCCACCGGCCCCTCACCACCCCACACCTCACGCAAC
CGCTCCCCCAACACCACCCGATCCGCACAACCCCCCTCCACAGCCACCAC
CCGCACACACACCCCCGCCCACTCCAAACCCTCCACCACAGCAGCAGCAC
CCACCACCCCCTCAGGCACCACCACCACCCACACCCCACCCGACACCACA
CCACCACCCGACCGCGACACCGGACGCCACACCACCCGATACCGCCAGCC
ATCGACCACCGCACGCTCCCGAACACCCCGACGCCAGTCGCCGAGCGCGG
ACACCAGCGCGTCGAGCGGCGCGTCCTCGTCCACGGCGAGCAGCGCGGCC
ACGGCCGCCGGGTCCTCTCGTTCGACGGCTTCCCACAGCGGGCCGTCCTCC
GTGGTGGCCGGCGCGGCCGGTGTCTCCTCCGGGTCCAGCCAGTACCGCTC
ACGCTCGAAGGCGTACGTCGGCAGCTCCACCCGGCCGGCGGTCCCGGACG
GTTTGCCGCCCAGTACGGCCGCCCAGTCCACCCGTACCCCGCGCACGGAC
AGCTCCGCCGCGGAGGCCAGGAAGCGCCGCAGACCGCCCTCGCCCCGGCG
CAGTGAGCCGACCACCAGGGTGTCGGCGGCGCCGAGGTCGTCGAGCGTCT
CCTGGACCGCGACGGAGACCGCGGGGTGCGGGCCGGCCTCGACGAAGAC
GGTGTGCCCGTCGCGGGCGAGGGCCCGGGTGGCGTCCCGGAACCGGACG
GGCTCGCGCAGGTTGCGGTACCAGTACGCGGCGTCGAGTGCGGTGCCGTC
GACGGGCTCGCCGGTGACCGTGGAGTAGAGCGGGATGTCGGCGGGGCGG
GGGGTGACGGGAGCGAGAAGGCCGAGCAGGTCTGCGCGGATCGCCTCGA

FIG.6-34

CCTGCGGGGAGTGCGAGGCCCAGTCGACCTTCAGCAGGCGGGCCGGGAC
GCCGTCCCGGGTCAGGTCGTCGACCAGGGCGGTGACCGCGTCCGGGGAGC
CGGAGACCACGGCCGAGCGGGCCCCGTTGTCGGCGGCGACCACCAGGCTC
GGGTCCACGGCGGCGAGCCGCGGTTCCAGGTCCTCGGCCGGCAGACCGAC
CGAGGCCATGGCCCCCTGTCCGGCGAGCGCGGCGAGGGCCTGGCTGCGCA
GGGCGGTGACGCGCGCCGCGTCCTCCAGGGAGAGGGCACCGGCGACGCA
GGCCGCCGCGATCTCGCCCTGGGAGTGTCCGGCGACGGCGTCGGGGCGGA
CGCCGTAGGAGCGCCAGAGGGCCGCCAGGGACACCATGACCGCGAAGAG
CACGGGCTGGACGACGTCGACCCGGTCCAGCGGCGGGGCGTCCGGTTCGC
CGCGCAGGACGTCGAGCAGTTCCCAGTCGAGGTACGGACGCAGGGCGTCG
GCGCATTCGGTCATGCGCTGGGCGAAGACCGGTGAAGAGTCCAGGAGTTC
GGCGGCCATGCCGTCCCACTGGGTGCCCTGGCCGCCGAAGAGCAGCGCGA
TTTTGCCGTCCGCCTCGGGGCCGGTGCGTCCGGCCACGACTCCGGCCGTCG
GCAGGCCGGTGGCGAGGGCGTCGAGGCCGTGCCGGAAACCGTCGAGGTC
CTCGGCGAGCACGACCGCCCGGTGCTCCAGCCACGCCCGCTCCACCGCCA
GCGCACGCCCGACCTCCACCGGAGCCGCCCCCGCCCCATCGGCGAACACC
CGCAACCGCCGCGCCTGCCCCCGCAACGCCGACTCCGAACGAGCCGACAC
CACCCACGGCACCACCGCGGGTCCGGCCTCGCCCTGCGACGGTGCCTCCT
CCGGCCGTACCTCTTCCTCCTGCGGTGCCTCCTCCAGAATCACATGCGCGT
TGGTGCCGCTCACCCCGAACGACGACACACCCGCACGCCGCGGGCGCTCA
CCCCGCTCCCACACCACCTCCTCCGTCAGCAACCGCACCGCACCCGACGA
CCAATCCACATGCGGCGACGGCTCATCCACATGCAACGTCCGCGGCAGAC
GACCCCGCCACAACACCATCACCATCTTGATCACACCAGCCACCCCCGCC
GCAGCCTGCGTATGACCCAGATTCGACTTCACCGACCCCAACCACAACGG
CACCCCACGACCCCGCCCATACGCCGCCAGCACCGCCTGCGCCTCGATCG
GATCACCCAACGACGTCCCCGTCCCATGCCCCTCCACCACATCCACCTCAG
CAGCCGACAACCCCGCACACACCAACGCCTGACCGATCACCCGCTGCTGA
GACGGACCATTCGGCGCCGTCAACCCATTCGACGCACCATCCTGATTCAC
CGCACTCCCCCGCACCACCGGCAACACCCGATGCCCCAGCCGGCGCGCAT
CCGACAACCGCTCCACCAACAACACACCCACACCCTCGGACCACCCCACC
CCGTTCGTCGGCGTCGCGAACGCCTTGCACCGGCCGTCCGgCGACAAACCC
CGCTGTCGCGAGAACTCCACGAACGCCCCCGGCGTCGACATCACCGTCAC
ACCCCCCGGCAACGCCAACTTCGACTCACCCGAACGCAACGACTGACACG
CCAGATGCAACGCCACCAACGACGACGAACACGCCGTGTTCACCGTCACC
GGCGGACCCTTCAACCCGAACGTGTACGACAACCGCCCCGACAACACACT
CCCCGACACACCCGTCAGCGCATACCCCTCCAGATCCCGGCCACCCCGAC
GCACCAACTCCGCATAATCCTGATTCGCCACCCCCGCGAACACACCCGTA
CGACTCCCCCGCAACGACACCGGATCGATCCCCGCCCGCTCCAGCGCCTC
CCAGGACACCTCCAGCAACAACCGCTGCTGCGGATCCATCGCCAACGCCT
CACGCGGCGAAATCCCGAAAAACCCCGCATCGAACTCCGCCGCACCCGCC
AAAAACCCACCCGCCCGCGTATACGACGACCCCGGCCGCCCCGCCTCCGG
ATCGTAAAGACCCTCCACATCCCAGCCCCGGTCCACCGGGAAGCCGCCGA
TCGCGTCCCCGCCCGAGGCGACCAACTCCCACAAATCCTCCGGCGACCAC
ACACCCCCCGGAAAACGGCACGCCATCCCCACGATCGCCACCGGCTCATC
CACCACACCGGACCGGATGAAGGCGGGCCGGCCGGCCGGGGCTTCCCCGC

FIG.6-35

CGGTGCTCAGCAGTGTGCCGAGGTGTGTGGCCAGGGCGGACGGGTTGGGG
TAGTCGAACACCAGCGTGCTGGGCAACCGCAGTCCGGTGGCCGTGTTGAG
GCCGTTGCGCAGTTCGACGGCGTTGAGCGAGCCGAAGCCGAGCTCCCGGA
AGGCCCGGTCGGCCGGGACGGCGGTGGCGGTGCGGTGGCCGAGGACGGT
GGCGGTGTGGGTGCGGACGAGGTCGAGCAGGGCGCGGTCCCGTTCGGCCG
GTTCCAGGGCGGCCAGGCGTGCGCGGAGCGAGCCGGGGGCCTCCGTGCCG
GTGGCGGGCCGGGCGAGCCGGGCCTCGGGGATGTCGGAGAGCAGCCGGG
CGAGGCCGTCGGCGGCGGGCAGGCGCTCCCAGTCGATGTCGGCGATGGTG
AGGCAGGTCTCGTTGCGGTCCAGTACCTGGCCGAGGGCGGACAGCGCGGG
CTCGGTGTCCATGGGCCGGATCCCGCGGCGGTCCATCCGCGTGGCGGCCT
CCGCGTCCGCGGCCATGCCCCCGCCCGCCCAGGCGCCCCAGGCCACCGCG
GTGGAGGGCAGTCCGAGACCGCGCCGGTGGACGGCGAGAGCCTCGACAT
AGGCGTTGGCCGCCACATAGGCACCCTGGCCACCGGAACCGAACGTGGCG
GCGGCCGAGGAGAACACCACGAACGCCGACAGATCCGCACCCCGCGTCA
GTTCGTGCAGGTTCCGCGCACCCACCGCCTTGGCCGCCAGCACCCCCTCCA
GCCGCTCCGGCGTCAACGCGTCCAGCACACCGTCGTCCACCACCCCCGCC
GTATGCACGACGGCACCCAGCGGACAATCCTCGGGAACCGCCGTGGCCAG
CAGCTCCGCGAGCGCCCCCGGTCGGCCACATCACAGGCGGCGATGGTCA
CCCGGGCGCCCATCGCGGTGAGTTCCGCGCGGAGCTCCCCGGCACCCTTG
GCCTCGCGTCCGCTCCGGCTGACCAGCAGCAGGTGCTCGGCCCCGCGCCG
GACCATCCAGCGGGCGACGTGTGCTCCCAGAGCGCCGGTGCCGCCGGTGA
TCAGGACGGTGCCGCGCGGCCGCCACCCACCAGCCTCCGCTCCCCCTCCC
GGAGCACGCACCAGACGCCGCACGAACACCCCCGACGCCCGGACCGCGA
CCTCCCCCTCACCCCCGCCCCCGACAGCACACCCAGCAAACCCTCCACC
ACCCGCTCGTCGACCACCTCCGGCAGATCGACCACCCCACCCCACCGATC
CGGCAACTCCAACCCCGCCACCCGGCCCAAACCCCACACCACAGCCCCAC
CCGGATCCCCCAGCCGATCCCCCTCCCCCACCGACACCGCACCCCGCGTC
ACACACCACAACGGCACCCCCAACCCCTCCACCGCCTGGACCAGCCCCAG
CACCAACCCGGCAACACCCACCCCACCCCCACACACAGCCAGCACCCCCA
CCGGCCCCTCACCACCACACACCTCACGCAACCGCTCCCCCAACACCACC
CGATCCGCACAACCCCCCTCCACAGCCACCACCCGCACACACACCCCCGC
CCGCTCCAAACCCTCCACCACAGCAGCAGCACCCACCACCCCCTCAGGCA
CCACCACCACCCACACCCCACCCGACACCACACCACCACCCGACCGCGAC
ACCGGACGCCACACCACCCGATACCGCCAGCCATCGACCACCGCACGCTC
CCGAACACCCCGACGCCAGTCGCCGAGCGCGGACACCACGGATCCCAAA
GGCGCGTCCTCGTCGACTTCCAGCAGGGCCGCGACCGCCGGCAGGTCCGC
GCGCTCGACCGCCTGCCACAGCGGGCCGTCCTCCCCGGCCGGCAGCGCGG
CCGGTGTCTCGCCCGCGTCCAGCCAGTACCGCTCACGCTCGAACGCGTAC
GTCGGCAGCTCCACCCGGCCGGCGGTCCCGGACGGTGCGCCGCCCAGCAC
GGCCGCCCAGTCCACCCGCACCCCGCGCACGGACAGCCCGGCCACGGCGG
CGAGCACGGACACGGCCTCCGGCCGGTCCGGTCGCAGTGCGGGGAGCAG
GGGGGCGGGTTCGGTGAGGGCGTCCTGGCCGAGGGCGCAGAGTGTGCCGT
CCGGGCCGAGTTCGAGGTAGGCGGTGACGCCCTGGGCCTGGAGCCAGGCG
AGGCCGTCGCCGAAGCGGACGGTGTGGCGGGCGTGCTGGACCCAGTAGTC
AGCGGTGCCCATGGTGTCGGCGGAGACGGGGGCGCCGGTGAGGTTGGTG

FIG.6-36

ACCACGGGGATGCGCGGCGGGGCGAAGACGACCTGCTCCGCGACGCGGC
GGAAGTCGTCCAGTACGGCGTCCAGGTGCGGGGAGTGGAAGGCGTGGCT
GGTGCGCAGCCGCCGGGTCCGGCGGCCCTGTTCCGCCCAGTGGCGGGCGA
GCGTGAGTACGGCGTCCTCGTCGCCGGCGAGGACGACCGCGCGCGGGCCG
TTGACGGCGGCCAGGTCCGCGCGCCCCTCGGCATCCTGGAGCAGCGGCCG
GACTTCCTCCTCCGTCGCCTCGACGGCGACCATGGCGCCGGTGTCCGGCA
GCGCCTGCATCAGCCGGCCCCGGGCCGTCACCAGGGCGGCCGCGTCGGGG
AGGGAGAGCATCCCGGCGACGTGTGCGGCGGCCAGTTCACCGACGGAGT
GCCCCAGGAGGTAGTCGGGTGTCACCCCCCAGTTCTCGACCAGCCGGTAC
AGCGCGACCTCGACGGCGAACAGGGCGGGCTGGGCGTATTCCGTCTGTTC
GATCAGCTCGGCGCCGGGGGATCCGGGGGCCGCGAACACGATGTCGCGC
AGGGTGTGGCCTGCTTCCCCGATCGGGCCGAAGTGGGCGCACACCTCGTC
GAAGGCGTCCGCGAAGGCGGGGAAGTGCGCGTGGAGTTCGCGGCCCATG
GCCGGGCGCTGTGTGCCCTGGCCCGCGAAGAGGAACGCCAGCGGGCCTTC
GTCGGTCGCGGTGCCGGTGACGACTTCCGGGGCGGGACGGCCGGTGGCGA
GGGCGTCGAGGCCGTGCCGGAAACCGTCGAGGTCCTCGGCGAGCACGACC
GCCCGGTGCTCCAGCCACGCCCGCTCCACCGCCAGCGCACGCCCGACCTC
CACCGGAGCCGCCCCCGCCCCATCGGCGAACACCCGCAACCGCCGCGCCT
GCCCCCGCAACGCCGACTCCGAACGAGCCGACACCACCCACGGCACCACC
GCGGGTCCGGCCCCGTCCCCCGACGGAACCACCACCGGCCCGACGCCGTC
CCCCGACGGTGCCTCCTCCGGCCGTACCTCTTCCTCCTGCGGTGCCTCCTC
CAGAATCACATGCGCGTTGGTACCGCTCACCCCGAACGACGACACACCCG
CACGCCGCGGACGCTCACCCCGCTCCCACACCACCTCCTCCGTCAGCAAC
CGCACCGCACCCGACGACCAATCCACATGCGGCGACGGCTCATCCACATG
CAACGTCCGCGGCAGACGACCCCGCCACAACGCCATCACCATCTTGATCA
CACCAGCCACCCCCGCCGCAGCCTGCGTATGACCCAGATTCGACTTCACC
GACCCCAACCACAACGGCACCCCACGACCCCGCCCATACGCCGCCAGCAC
CGCCTGCGCCTCGATCGGATCACCCAACGACGTCCCCGTCCCATGCCCCTC
CACCACATCCACCTCAGCAGCCGACAACCCCGCACACACCAACGCCTGAC
CGATCACCCGCTGCTGAGACGGACCATTCGGCGCCGTCAACCCATTCGAC
GCACCATCCTGATTCACCGCACTCCCCCGCACCACCGCCAACACCCGATG
CCCCAGCCGCCGCGCATCCGACAACCGCTCCACCAGCAGCACACCGACAC
CCTCGGACATCCCGGTGCCGTCGGCCGCGGCGGCGTAGGGCTTGCAGCGG
CCGTCCGCCGACAGGCCCCGTTGGCGCGAGAACTCCACGAACATGGCGGG
GGTGGACATCACGGTGACCCCGCCGGCGAGTGCGAGGGAGGATTCGCCCG
ACCTGACGGACTGGCAGGCCAGGTGCAGTGCCACCAGCGATGACGAGCA
CGCCGTGTCGACCGTCACCGCGGGGCCTTCGAACCCGAAGGTGTAGGAGA
GCCGGCCGGACAGGACGCTCGCCGCGTTGCCGTTGCCGAGGAAGCCCTGA
AGGTGATCCGGAACGGACAGCAGACGGGTGGCGTAGTCGTGCGACATCAT
CCCCGCGAAGACGCCGGTGCGGCTGCCGCGCAGGGTGGCCGGGTCGATCC
CGGCCCGCTCCAGCGCCTCCCAGGACACCTCCAGCATCAACCGCTGCTGC
GGGTCCATCGCCAGCGCCTCGCGCGGGGAGAGACCGAAGAATCCCGCGTC
GAACTCCGCTGCCTCGTGCAGGAATCCGCCCGATCGCGTGTACGACCGCC
CTGCCCGGCCCGGCTCCGGGTCGTAGAGGTCCTCGACGTCCCAGCCCCGG
TCCACCGGGAAGTCGCCGATCGCGTCCCCGCCCGAGGCGACCAGCTCCCA

FIG.6-37

CAGGTCCTCGGGCGATCGCACACCTCCCGGGAACCGGCACGCCATGCCCA
CGATCGCGACCGGCTCCTGCCTGCCCGACTCGACCTGCTCCAGCCGGCGC
CGGACCCGCAGCAGATCGGCGGTCGCGCGCTTGAGGTACTCGCGGAGCAT
TTCCTCGTTGGCCATGACGGGGTCTCCTCGCCGCTGCGCTGGAGGTGGCAC
GGAACCCCGCCAGATTAGGGTGGGCAAGTCAACCCGAATACCCCCTATAC
ACCCCAGACTGGCTACGTGAAGCGAATACCCGTTCAAATAGGGGGAAGA
GCCGCAGGCATGGATCGTTACGCGAAGCGTTTCGAGGACCGGCTGGTCCT
GGTCACGGGGGCGGGGAGCGGCATCGGGCGGGCGACGGCCTGCCGGTTC
GGTGCCGCCGGGGCGCGGCTGGTGTGTGGACCGGGACGGGCCCGGCGC
GGAGGCGACCGCCGAACTGGCGCGTGCGCGGGGGGCGCGGGCGGCGTGC
GCCGAGGTGGCCGACGTCTCGGACGAGGTGGCGATGGAGCGGCTCGCCGC
GCGCGTCACGGCCGCGCACGGCGTGCTGGACGTGCTCGTGAACAATGCCG
GTATCGGCATGTCGGGGCGGTTTCTCGACACGTCGGCCGAGGACTGGCGC
CGCACCCTGGGGGTGAATCTGTGGGGCGTCATCCACGGGTGCCGGCTCCT
CGGCCGGGGCATGGCCGAGCGCCGGCAGGGCGGTCACATCGTGACGGTG
GCCTCGGCGGCCGCGTTCCAGCCGACCCGGGTCGTTCCGGTGTACGCCAC
CAGCAAGGCCGCGGCCCTGATGCTGAGCGAGTGTCTGCGCGCGGAGTTGG
CGGAGTTCGGCATCGGTGTGAGCGTGGTCTGCCCCGGCCTGGTCCGTACG
CCGTTCGCGTCCGCGATGTACTTCGCCGGCGCGTCCCCCGACGAGCACAC
CCGGCTGCGTGAGTCCTCCGCCCGCCGCTTCGCGGGCCGCGGCTGCCCGC
CGGAGAAGGTCGCGGACGCCGTCCTGCGCGCGATCATGCGGACGGCCTTG
CCGACGGTGACCGGGTCGACGCCGTAGAGCTGGATCAGCGCGGTCTCCTC
GCCCGTCTCCGGCTTGACCTCGAAGTACGCGAGCGGCTCGGCGTCGGCGG
CTGCCGCGTCGTACAGCAGGATGCGCAGATCCGGAAGTCCTGCTCTTCGA
CGAGCCGTTCAGCGCGCTGGACCCGCTGATCCCTTTAGTGAGGGTTAATTG
CGGCCGCGTTCCAGCCGACCCGGGTCGTTCCGGTGTACGCCACCAGCAAG
GCCGCGGCCCTGATGCTGAGCGAGTGTCTGCGCGCGGAGTTGGCGGAGTT
CGGCATCGGTGTGAGCGTGGTCTGCCCCGGCCTGGTCCGTACGCCGTTCGC
GTCCGCGATGTACTTCGCCGGCGCGTCCCCCGACGAGCACACCCGGCTGC
GTGAGTCCTCCGCCCGCCGCTTCGCGGGCCGCGGCTGCCCGCCGGAGAAG
GTCGCGGACGCCGTCCTGCGCGCGATCGTCCGCAATACGGCGGTGGTCGC
CGTCACCCCCGACGCCCGCGCCGTCCGTCTGATGAGCCGCTTCGCGCCCCG
CCTCCGCGCCGTCGTGGCCCGGCTGGACCCGTAGGCAGGGCCCGTACGGG
CAGCGGGCGTCCGGTTCGGGCCACCGGCCGCGGTATCCGCGCCCCTGCCC
GGAGCTGTGCCGCTCCGGGCAGGGGCGCGCGGACGAGGCGGTCCGGCCC
GGCGGCCCGGACCTGGCGGTCCGTTACTCAAACCGCGTGAGCGTCAGCCG
GATCCCGGTGGGAGCGGTGTCCTGGATGTAGGAGGCGAAGTCGGCCACGT
CGTCGAAGGCGAAGCCGTAGGCTCGGCCGTCCTCCGTGATCGCGTGCATC
GCCTTGGCGTAGTGGTTGGTCAGCGCGGTCCTGTAGAAGGCCGCGGGGTC
GGTCGTGGGCTGGGCGGCGGAGGTGAGCAGGGTCGAGCGGTTGAATCCG
GCGCCGAGGACCGCGGCGACGGGACCGGTGGTGCCGTCGTTCGGCGCGGC
GAGGGCACCGTGGCAGAAGAGCACGTCGCGCGTGGTGGGCTTGGCGAAG
GACACCTGGGCGGGCCCGTCGAAGGTCAGCCGCTCGCCGCGCACCCGGCC
GGTGAAGGTCCCGGCGTTGGTGGTGACCGTGAGGTCCCTGGCGGTGTAGG
TGCTCCACACCTCGTCGATGTACGGAGCGAGGTAGTCCTTCGGGAACAGG

FIG.6-38

CCGGCGTCCAGCCCGTGCCCGGGGGCGATCACACGGAGGTCGTCCAGGAC
CAGTGGCGCGAACTCCGCGACGCGGCGGACCGCTTCGAACGCCGCCGCCC
GGCCGCCGGCCCGCACGGTGCCGGTCGTCTGGTCCTTCGCGCCCGTCAGC
CGGATACTGAGCGGCACGCTGAACATGTCCACCATGGTCGTGTTGCAGAA
CATGCCGGAGGGGTTGTAGGTGAACTCGGCGCAGTCGTGCAGCACCCTGT
AGTTCGGATCGGACGCGACCCAGCCGGCCGGGTACTGCAGCGCGGCGTTC
CCGGCTCCGTCCGTGACCACCTTGAACTTGAGTTTCTGTCCGAGCGCGACA
TAGATCCGGCCGGACATGTACGGCAGGGAGAGCCGGGTCTCGCCGCTGCC
GGCCAGTGTGATCGCGTAGTCCGTGAAGCCGTCGGGGCCGTTGTCCGACA
GGGCGACGGGCGCGAGGGTGCCGTCGGGCGTGAGCCGTACCTGTCGGCCG
TCCTGGTTCCCCACGACGTAGACATGGACGTCGCCGTTGCCGAAGACGCC
GGTGTCGTTGACGACCGTCAGCGGCAGGGCGCCCGCCGTGGTCCCTTCCG
CGTCGCGGTCCCGGCCGGGGCCGGCGAGGGCGTGCGGTGCCAGGGCTGCG
ACGGCGGGAGCGGCCATCGCGGCGCCGCCGAGGGCGACGAGCAGGGTGC
GGCGGCCGAGGCTGCGCTGGTGTCGAGGAGTCATGTGGGGGGCCTCCTGG
TGGGCTTGCCGATGTTCTAATGACGGGAACATGACAGGTGAGAAGCGTGG
GAGCGCTCCTCAGGGCCCGATGGTACGCACGGGGAGGCGTCCCGCGTCCC
CGTGCCGGGACCGCTTAACCGACGCTTAAGGGCCGTTTA

FIG.6-39

MRGVSPSVSVREPQGLTFLGLGRQSHAVRTALEACAAGRVRVLVVEGGLGC
GKSAFLGEA LKHAAASGFL
VLRSAGSPPEGRRPFDLLRQLAVDPDIPDAQRSLLQDAVGTETPAAQRVRAAL
HQLTGAA PVVIGIDDLH
HADPQSLHCLLQAVDHPRATRLLLVCTALPSGLAADPAVEAELLCQPALQRV
MLGRLSLR AVSGLRAARP
GPAVEALPADDLLAVTGGNPLLVHALLEELVESHTQGHTDERAGRRRRAASP
VIGGRFYQ AVLASLSRTD
SLVRHSAGALAVLGDSGCAEVIARLLGIGRAMAARGLRALEATGLTASGRFR
HPVVEAAA LDTLDHDHRA
HLHRRAAALLYDVGAEPDEVARHLLAARHAAGPWAMSVLRDAAEQLLMRD
DVLTAVSCLE LARRSCAGGP
RRAEILLRLTVATRRTDPAAAEDHLAELVTELRAGRLTSAETERLGHLLLGCG
RLEEATE VMGRPGPHGD
PRTPRLETGFHASALWEPLIRPRTDPEPGDEESPRPRMPVTGIWDLPGDGTNAS
ASDAAE HVLRSLPLTD
TTLVIVVNAVRVLCRTGSYETAALWCTRLLGEAAGRRLPGWKAQFLALQAEI
ALCRGLLA DTEEYARQAL
ACVPRCSRSVFIGGPLASRVFAATAMGRYDEATRQLDHPVPEALFRSVYGPA
YLRARGHY YLALDRPLAA
VRDFLGAGRLLRRWGIDRPTLMPWRSDAAEAFLRLCEPRRADRLLREQLART
PDDDPHVR GVSLRLRAQI
AEPPDRLNLLTEAVNHLKSSGDRLALAGALADLGAAYRERGESTRAGATIRR
AWHLANDC GARALCERIL
PGGPGRQSFGDGTGRTEAALSGSELRVVELAANGHTNREIAARLCITVSTVEQ
HLTRAYR KLEISRRQEL PARLCAHIESPV

FIG.7

MPDLCETESLWLRRFQPAPAARTRLMCFPHAGGSASAYLRLARSLAPGIEVL
AVQYPGRQDRRAEPCPDS
VEGLADDLFAAVRHRVDASTALFGHSMGAVLAFELARRLERDAGVRCARIF
ASGRRAPSRFRDDSAPAAS
DASMLAEMRTLGGTDLRVLQDEELLIAALPALRADYRAIGTYRAADDAVVG
CPVTVLVGDADPRTSLDDA
HAWSAHTTAESEVLTFSGGHFFLDAHHDAVVEVVTARLRQDRAPRPDRV

FIG.8

MPELNDRTALVTGASRGIGKAIAQRLAAEGVRVAVHYGTQEKSAQETVETIE
RAGGRAFAVRADLLRDDA
VDELFTALERELEGRPLHILVNNAAVAPAPGDPALAAQDGYVPGLSDTTPEEF
DRVYRINVRAPFFVTQR
ALSLMADGGRIVNVSSAVTRIAWPLLPYAMTKGALEMMAPRLANELGSRGIT
VNTVAPGITDTDMNRWVR
ETPGAEAGISALTALGRLGRPNDIAGIVAFLVSDDARWITGQLLDASGGMALA
PAMM

FIG.9

VHETHAHGEEGSSDGSADAVVFVFPGQGSQWPGMGAELWDTSPVFRESVRA
CADALAPYLDWSVEGVLRG
APDAPAGPALDRADVAQPALFTLMVSLAELWRSHGVEPCAVLGHSLGEIAA
AHVAGALTLADAARVAALW
SRAQATLSGTGTLLAAKAAPEELAPHLQRWNGDDRHGTRLAIAGVNGPGST
VVAGDLDAIAALAADLASA
GVRTRRVAVDVPTHSPAMRTLRERILTDLASVAPCVSRLPFHSSLTGGLVDTR
GLDADYWYRNISETARF
DLAARGLLADGHRTFVELSPHPILTLGLQALADDVPGAADALVTGTLRRGRG
GMRQFQDALGRLSVPAGG
RPGREVSAAALAGRLAPLSPAQQEHLLVELVCAHFAALVGGDGGAPPTVRPS
AAFTDQGCDSATALELRD
RLREATGLRLPATLVFDHPTPAAVAGRLRRLALGIEETADTAPVAVRGHREG
EPIAIVGMACRFPGGVRS
PEDLWRLVTEGGDALGPFPTDRGWDTGRHAEDPATPGTYVQGEGGFLYDAG
EFDAEFFGISPREALAMDP
QQRLLLEMAWETFERAGIDPTSARGSRTGVFAGVLPLGYGPRMDETDQGTA
DLQGHLLTGTLPSVASGRI
SYTLGLEGPAVSVETACSSSLVALHLACRSLRAGECDLALTGGVSVLATLGLF
VEFSRQRGLSADGRCKA
YAAAADGTGWSEGAGLLLVERLSDARRLGHRVLAVVRGSAINQDGASNGLT
APSGPSQQRVIREALADAG
LTAADVDAVEGHGTGTRLGDPIEIEALLATYGQGRARERPLWLGSLKSNIGH
TMAAAGVGGVIKMVMALR
HGELPRTLHVDAPSPRADWSAGEVRLLTEAVAWPAAADGEPRRAGVSSFGV
SGTNAHAILEEAPAPEDEE
PAPPDGEALLPWAVSTRSEAALRTQARMLADVVRDDPGVGLADVGAELARG
RAALEHRAVVIASGRAEFA
RALEAVASGEPHPAVVRGHAGSERGGVVFVFPGQGGQWAGMGLDLLRSSPV
FAEHIAACGKALAPWVKWS
LTEVLHRDAEDPVWDRADVVQPVLFSVMTSLAALWRSYGVEPDAVTGHSQ
GEIAAAYVCGALGLEDAART
VALRSRALVALRGRGGMASVASAAPDVEELIARRWPGRLWVAAFNGPGAVT
VSGDGDALEEFLGHCADTE
VRARRVPVDYASHCPHTEAIERELLDALEDITPRPAAVPFYSTVDDAWLDTTR
LDASYWYRNLRRPVRFS
QAVRALTDGGHRVFIEASPHPTLVPAIEDHGDVTALGTLRRHGDDTERFLTAL
AHLHVTGAAGQDLWRHH
YARLRPAPRHVDLPTYAFQRDRYWWSGGAGRGDVTTAGLHPGGHPLLGAA
LDLADGGGRLHTGRVSLRTH
PWIADHGVAGITLLPGTAFLELALHTGESGNVRELTLHAPLVVPDEEGVDLQ
VHLARPDEAGLRALTRLL
PGRGVPTPRAPWQPHATGLLGPADRAPGSSGLEPHDLGGAWPPPGAVPLVPG

FIG.10

ELGDVPGCYARLADEGFE
YGPAFRGLRAVWRRGTEIFAEVALPAGDGSVFRLHPALLDAVLHPVVLGLVD
GVPARPLPFSWNGVALHA
PASGALRVRLAPADDGAVGITAATAAGEPVLSVAALALRSASAEQLRAAIRS
AAGSRDALYELDWLPLPA
DRAASPGGADIAALGTSELPCRTYETIAELSQALADGAPAPDAVVSDVGAVG
GPLDTVSLHGLCRRGLEL
VQAWLGEPRTADTRLVLVTRGAVGCAPAEPVADPAAAALWGLVRSAQAEH
PGRLLLLDLDPAGSRPVSGR
LVEQAVACGEPHIAVRGDGLRVPRLSRATAAPAHPPAGGREAQWDPEGTVLI
TGGTGSLGALFARHLVTA
HGVRRLLLASRSGPGAPGAAGLRDELTAHGATVTVAACDVADREAVAALLA
SVPSEHPLTAVVHTAGVLD
DGVLASLTADRLARVLRAKADAALHLHDLTRDLPLAAFVLFSSVTATLGTPG
QANYTAANAFLDALARHR
RAAGLPAVSLAWGLWEQTGGLTDHLGSVDLRRMARNGLVALPADAGLALF
DTALALDRANLVPARLDLPA
LRRATHVPPVLRRLVEVPGAPSADRSAGSGGEVRPLRETLAGLDDRKRPAAV
SRLVRRHVAWVLGADGPE
SVDEDRSFRDLGFDSLMAVELRNQLNTAAGIRLAATLVFDHPTPSAVARHLL
DRCSPDPAAPAAPSGTAV
ASALATLAELETALNGIPAEEWTAAGGPARLMTLASSLPAPASVPRTPAAGEA
AEKLAHASRDEIFAFID RELGRDSGPASPSRLGPQTPDSTDKAPFHGE

FIG. 10-1

MENEEKLLDYLKWVTADLHRSRERVTELEEAGREPIAIVGMACRFPGEVRSP
EELWGLVASGGDAIGAFP
DDRGWDLDGLFDPDPERAGTSYTRRGGFLYDAAEFDAGFFGISPREAMAMD
PQQRLLLETSWEAFERAGI
DPSSVRGSRVGVFAGLMYHDYAAAQGSTGDGDGEPDFEGYLGDGSVSSIAS
GRIAYTLGLAGAAITVDTA
CSSSLVALHLACQALRTGDSELALAGGVSVMSTPRTFVQFSRQRGLSADGRC
KAYAAAADGTGFSEGVGM
VLVERLSDARRLGHPVLAVVRGSAVNQDGASNGLTAPNGPSQERVIREALAN
AGLTAADVDAVEGHGTGT
RLGDPIELQALLATYGQGRARERPLWLGSVKSNIGHAQAAAGVGGVIKMVM
ALRHGELPRTLHVDAPSPR
VDWSAGEVRLLTEAVAWPAAADGEPRRAGVSSFGVSGTNAHVILEEAPASE
GEEAPPPEPGSPLPWVVSG
HSEAGLRAQAQALAEFARTAPGAELVDVGAALARGRAALGHRAVVVASERE
EFERALAALACGEPHPCVV
DGSADGRREDGVVFVFPGQGGQWAGMGLDLLTTSGVFAEHIGACERALAP
WVEWSLTEMLHREAEDPVWE
RADIVQPVLFSVMVSLAALWRSYGIEPDAVVGHSQGEIAAAHVCGALTLEDA
AKVVALRSRALAALRGRG
GMVSLSLSTADAGELVERRWAGRLWVAALNGPEATTVSGDVDALEELLAHC
AKSEVRARRVPVDYASHCP
HTEAIAEEIVDSLGDITPRAATVPFYSTVDDMWLDTTRLDASYWYRNLRLPV
RFSQAVRALTEEGHRLFI
ETSPHPTLVPAIEDHGDVTALGTLRRHGDDTERFLTALAHLHVTGAAGQDLW
RHHYARLRPAPRHVDLPT
YPFQRRRYWLEKPDPQTRPQRSRSTAPDLDRLEAEFWQAVEETDTDTLAHTL
HLDTQTLEPVLPALATWH
QQQRDHARINTWTYQETWKPLHLPTTRPTTPTSWLIAIPETHRNHPHTTNLLT
NLPHHNITPIPLTINHT
TDLHHAYHHAHHHTTPPITAVLSLLALDETPHPHHPHTPTGTLLNLTLTQTHT
QTHPPTPLWYLTTQATT
THPNDPLTHPTQAQTIGLARTTHLEHPHHTGGHIDLPTTPHPNTLTQLITALTH
PHHQHNLTIRTHTTHT
RRLTPTTLQPTTPTPPTNPHGTTLITGGTGALATTLAHHLATTGTQHLLLTSRR
GPHTPGARQLHTQLTQ
LGTNTTITACDLSDPDQLTHLLTHIPPEHPLTTVIHTAGILDDATLTNLTPTQLD
NVLRAKAHTAHLLHH
ATLHTPLDHFVLYSSAAATLGAPGQANYAAANAYLDALAHHRHTHNLPATT
IAWGTWQGNGLADSDKARA
NLDRRGFLPMPETLAAAAAVRAIESRRPSVVIAAIDWARAERTPDVEDLLPAA
DEGSSSGKPEAAPVDLR
GTLSRQSAADQQATLLGLVRTQAAVVLRHTEPEALAPGQAFRALGFDSLTAV

FIG.11

ELRNRLAKATDLALPASL
VFDHPTPVKLAEFLRTELLGTAPATTAAVPALQAHTDEPIAIIGMACRFPGAV
TTPEHLWNLIATEQDAI
GEFPTDRGWDLDNLYHPDPDHPGTTYTRHGGFLHDAGDFDADFFGINPREAL
AMDPQQRLLLETAWEAIE
HAGILPDALHGTPTGVFTGVNAQDYAAHTHTSPHTTEGYTLTGTAGSIASGRI
AYVLGLEGPAVTIDTAC
SSSLVALHLACQALRAGECTTALASGISIMTTPLAFTEFSRQRGLAADGRCKA
FAAAADGTGWSEGVGTL
LLERLSDAERNGHRVLAVVRGSAVNQDGASNGLTAPNGPSQQRVIRQALVN
ANLSAVDVDAVEAHGTGTK
LGDPIEAQALLATYGQGRAQEQPLWLGSVKSNLGHTQAAAGMAGLIKMVM
ALRHESLPRTLHVDEPSPEV
DWSSGAVSLLTEARPWPRVEDRPRRAGVSSFGVSGTNAHVIVEEAPAPTGVE
AVEAAPAGVETAAAAAVV
VETDGAGRVSADLPLVWVASGKSQAAIRAQAAALHAHVLDHPEQDADDIGY
SLATTRALFDHRATLIAPD
RHTVPEPLTGLGDGRTHPHLIPTPPTEPGHTHKIAFLCSGQGTQRPGMATGLY
HTYPAFAAALDETCAHF
DPHLDHPLHDLLLNHDPTDLLTHTLYAQPALFTLOKALHHLITETYGITPHYL
AGHSLGEITAAHLAGIL
TLPDATHLITTRARLMQTMPPGTMTTLHTTPEHIQPLLDOHPGKAAIAAVNSP
HSLVISGDPDTIHHITT
TCHNQGITTKPLATNHAFHSPHTDTILEQLDTTTHTLTYHQPHTPLITSTPGDP
LTPHYWTHQTRQPVHW
TDTIHTLHTHGVTTYIALGPEHTLTTLTHHNVPHHQPTAITLTHPHHNPTHHLL
TALAHLHTTQPTGPNI
WHHHYTPVAPAPRHVDLPTYPFPRRRYWVQASAGTGDVSAAGLQRPDHPLL
GAVMELADGDGIVLTGRLS
LHTHPWLADHSVGGVALLPGTALLELAFQAGLRAGCPGVDELTLHAPLVVPE
SGHVVVQVSVSVPGEAGR
RGVSVYGRLVEDGGLEGEWTRHAEGVVCPSVPGESVVVEPVADGVWPPSGA
QPVDLEEFYGRLAGGGFVY
GPVFQGLCAAWRDGDDVVAEVRLPDEGLADVAGFGVHPALLDAAVQAVTL
LFPDQQQAGLAAHTWNGVSL
HARGATVLRLRMTPTDATSTAVRLHATDETGAPVLTLDSLLMRPVPLEGLGA
GVRRGSLFELGWVPVEGM
PASVAGGGGELVAWECPGGGVAEVTAAALGVVQEWLADEREGDARLVVVT
RGAVAVDAGEPVRDVAGAAV
WGLVRSAQSEHPDRFALLDLDPDTKTDPGIDTDGDTDVSADAKVGTGDGLD
DAAVASALARGESQLAVRD
GVVRVARLGGLVGGLSLPGGVGWRLDGGGSGLLEGVGVVASDAAGVVLGR
GQVRVAVRAAGVNFRDVLVA
LGMVPGQVGVGSEGAGVVVEVGPGVEGLVVGDRVFGVFGDAFAPVVVAQE
VLLARIPEGWSFAQAASVPV

FIG.11-1

VFATAYLGLVDLAGVRRGESVLVHAAAGGVGTAAVQLARHLGAEVYATAS
EAKWARLRAAGVAPQRIASS
RSVEFESRFRRASGGRGVDVVLNCLAGEYTDASLRLCSPQGGRFLELGKTDIR
DAGEVAARFPGVSYRAY
DLMDAGAQRVGEILHTVVDLFRRGVLEPLPVTAWDVRQAHQALRSMRSGLH
VGKNVLTLPVPLDAEGTVL
VTGGTGTLGAAVARHLAAGHGVRHLLLVSRRGMAAAGAEKLCAELGQAGV
SVSVAGCDVADRAQVAALLE
QVPAEHPLTAVVHTAGVLDDATVTCLDRNKIDAVLGAKVDGALHLHELTAG
MDLSAFVLFSSAAGVLGSP
GQGNYAAANAALDALAHQRRAAGLPALSLAWGLWEEASGMTGHLDAADR
HRITRSGLHPLTTPDALALLD
TALAAGRPALLPADLRPTHPAPPLLEHLAPARTSHRTAHTSTATGVGQDVSLT
DRLATLTPEQRHDTLLA
LARTHIAAVLGHPSPDTIDPERTFRDLGFDSLTAVELRNRLTRATGLRLPATLA
FDHPTPTALTHHLTTL
LNPNDNDNVGPVLMELERLESALAALDRDDSACERVTLRLQSLMLRWSGSE
RQSAENTDDSSRFASATAE ELLEFIDRDLGLS

FIG.11-2

VANDEKVLEYLKRVTADLDRTRRRLYEVVEREQEPIAIVGMACRYPGGAGSP
AGLWDLVSSGTDAIGEFP
TDRGWDLERLYDPDPDHPGTTYTRHGGFLDGVGEFDAEFFGVSPREALAMD
PQQRLLLETAWEAIEHAGI
VPESLRGTSTGVFAGINPQDYTISQYGRDSEIEGYLLTGAAASIASGRISYTLGL
EGPAVTIDTACSSSL
VALHLACQALRAGECTMALAGGASVLSTPLIFVEFARHHGLSVDGRCKAFSA
SADGTGWGEGAGLLLLER
LSDAKRNGRRILALVRGSAVNQDGASNGLTAPNGPSQCRVIRRALANAHLAP
ADIDAVEAHGTGTTLGDP
IEAQALQEAYGADRPDDRPLWVGTLKSNIGHSIAAAGVGGVIKMVMALRHE
SLPRTLHVDEPSPQVDWSS
GAVSLLTEARPWPRDEDRPRRAGVSSFGVSGTNAHVILEEAPAPAEVQAVET
APVVRVDGGERSAPADVP
LVWVVSGKSQAALRAQAAALHAHVLDHPEQDAADIGYSLATTRALFDHRAT
LIAPDRDTLLDALTALADG
RTHPHLVPAPPTEPGHAHKIAFLCSGQGTQRPGMATGLYHTYPAFAAALDET
CAHFDPHLDHPLRDLLLN
HDPTGLLTHTLYAQPALFTLQKALHHLITETYGITPHYLAGHSLGEITAAHLA
GILTLPDATHLITTRAR
LMQTMPPGTMTTLHTTPEHIQPLLDQHPGKATIAAVNSPHSLVISGDPDTIHHI
TTTCHTQGITTKPLTT
NHAFHSPHTDTILEQLDTTTHTLTYHPPHTPLITSTPGDPLTPHYWTHQTRQPV
HWTDTIHTLHTNGVTT
YIELGPDHTLTTLTHHNLPHHQPTAITLTHPHHNPTHHLLTALAHTPTTWHTH
HHTHTNPHPHTIPDLPT
YPFQRRHYWLQAPTTSTDQPVAPTNDDAPAPRATSLRDTLAGRSPQEREEVL
LDLVLTQVAAVLGHTAPE
VVDPQRAFKDLGFDSLAAIKLRNRLAAATGLELPTTLVFDHPTPVALRQYFQS
QILGAEADAPNRLPLRA
ATTDEPIAIVGMACRFPGGVRTADDLWQLLSDEHDAVGGFPTNRGWDVANL
YDPDPDRHGTTYTQQGGFL
YEAGEFDAEFFGISPREALAMDPQQRLLLETAWEAIEHAGINPDALRNTSTGV
FAGVIYHDYASRFLTAP
AGYEGYLGHGSAGSIASGRVAYVLGLEGPAVTVDTACSSSLVALHLACQALR
SGECTMALAGGATVMSTP
QAFVEFSRQRGLAADGRCKAFSAAADGTGWGEGAGLLLLERLSEAERNGHR
VLAVVRGSAVNQDGASNGL
TAPNGPSQQRVIRQALANSGLTGADVDAVEAHGTGTKLGDPIEAQALLATYG
QEHHPDQPLWLGSLKSNI
GHAQAAAGVGSIIKMIMAMRNESLPRTLHVDEPSPHVDWSSGAVSLLTEPRP
WPRREDRPRRAGISSFGV
SGTNAHVIVEEPPARAEVEAVEAAPAGVETAAAAAVVVETDGAGRVSSDVP

FIG. 12

LVWVVSGKSQAALRAQAAA
LHAHVLDHPEQDAADIGYSLATTRALFDHRATLIAPDRDTLLDALTALADGR
THPHLIPTPPTEPGHTHK
IAFLCSGQGTQRPGMATGLYHTYPAFAAALDETCAHFDPHLDHPLRDLLLNH
DPTDLLTHTLYAQPALFT
LQKALHHLITETYGITPHYLAGHSLGEITAAHLAGILTLPDATHLITTRARLMQ
TMPPGTMTTLHTTPEH
IQPLLDQHPGKATIAAVNSPHSLVISGDPDTIHHITTTCHNQGITTKPLTTNHAF
HSPHTNTILEQLDTT
THTLTYHPPHTPLITSTPGNPLTPHYWTHQTRQPVHWADTIHTLHTNGVTTYI
GLGPDHTLSTLTHHNLP
QHQPTAITLTHPHHNPTHHLLTALAHTPTTWHTHHHTHTNPHPHTIPDLPTYP
FQRRHYWLEVPKPTAEA
SASASGPGRNRAAKLSALEAEFWQAVEETDTDTLAHTLDLDTQTLEPVLPAL
ATWHQQQRDHARINTWTY
QETWKPLHLPTTRPTTPTSWLIAIPETHRNHPHTTNLLTNLPHHNITPIPLTINH
TTDLHHAYHHAHHHT
TPPITAVLSLLALDETPHPHHPHTPTGTLLNLTLTQTHTQTHPPTPLWYLTTQA
TTTHPNDPLTHPTQAQ
TIGLARTTHLEHPHHTGGHIDLPTTPHPNTLTQLITALTHPHHQHNLTIRTHTT
HTRRLTPTTLQPTTPT
PPTNPHGTTLITGGTGALATTLAHHLATTGTQHLLLTSRRGPHTPGARQLHTQ
LTQLGTNTTITACDLSD
PDQLTHLLTHIPPEHPLTTVIHTAGILDDATLTNLTPTQLDNVLRAKAHTAHLL
HHATLHTPLDHFVLYS
SAAATLGAPGQANYAAANAYLDALAHHRHTHNLPATTIAWGTWQGNGLAS
GDIGEHLRRRGMIPLDPESA
VGAFDRAVASDRPSVFVADIDWPTFGRNTSSGLRALFEDIPEATQPEPTARSA
DQPNGHGSLQELLARQS
PAEQAETLLALVRTHSATVLGRDGADAVAAERPFRDLGFDSLSAVELRNHLT
ADTELALPTTLVFDHPTP
VKLAEFLRTELLGTAPATTAAVPALQSHTDEPIAIIGMACRFPGAVTTPEHLW
NLIATEQDAIGEFPTDR
GWDLDNLYHPDPDHPGTTYTRHGGFLYDAGDFDAEFFGINPREALAMDPQQ
RLLLETAWEAIEHAGILPD
ALHGTPTGVFTGVNAQDYAAHTHASPHTTEGYTLTGTAGSIASGRIAYTLGL
EGPAVTIDTACSSSLVAL
HLACQALRAGECTTALASGITVMTSPVTFTEFSRQRGLAPDGHCKAFSASAD
GTGWSEGVGTILVERLSD
AERNGHRILAVVRGSAVNQDGASNGLTAPNGPSQQRVIRQALANSGLTGAD
VDAVEAHGTGTKLGDPIEA
QALLATYGQGRAQEQPLWLGSVKSNLGHTQAAAGMAGLIKMVMALRHESL
PRTLHVDEPSPQVDWSSGAV
SLLTEARPWPRREDRPRRAGISSFGVSGTNAHVILEEAPAPAEAVETEQGVVP
QGDQECSAPVGVPLVWV

FIG. 12-1

VSGKSQAALRAQAAALHAHVLDHPEQDAADIGYSLATTRALFDHRATLIAPD
RDTLLDALTALADGRTHP
HLIPTPPTEPGHTHKIAFLCSGQGTQRPGMATGLYHTYPAFAAALDETCAHFD
PHLDHPLRDLLLNHDPT
DLLTHTLYAQPALFTLQKALHHLITETYGITPHYLAGHSLGEITAAHLAGILTL
PDATHLITTRARLMQT
MPPGTMTTLHTTPEHIQPLLDQHPGKATIAAVNSPHSLVISGDPDTIHHITTTC
HTQGITTKPLTTNHAF
HSPHTDTILEQLDTTTHTLTYHQPHTPLITSTPGDPLTPHYWTHQTRQPVHWA
DTIHTLHTNGVTTYIGL
GPDHTLSTLTHHNLPQHQPTAITLTHPHHNPTHHLLTALAHTPTTWHTHHHT
HTNPHPHTIPDLPTYPFQ
RRHYWLEVPKPTAEASASASGPGRNRAAKLSALEAEFWQAVEETDTDTLAH
TLDLDTQTLEPVLPALATW
HQQQRDHARINTWTYQETWKPLHLPTTRPTTPTSWLIAIPETHRNHPHTTNLL
TNLPHHNITPIPLTINH
TTDLHHAYHHAHHHTTPPITAVLSLLALDETPHPHHPHTPTGTLLNLTLTQTH
TQTHPPTPLWYLTTQAT
TTHPNDPLTHPTQAQTIGLARTTHLEHPHHTGGHIDLPTTPHPNTLTQLITALT
HPHHQHNLTIRTHTTH
TRRLTPTTLQPTTPTPPTNPHGTTLITGGTGALATTLAHHLATTGTQHLLLTSR
RGPHTPGARQLHTQLT
QLGTNTTITACDLSDPDQLTHILTHIPPEHPLTTVIHTAGVNHYAPVAATDPST
FASVLAAKAAGAAHLH
ELLLELDTVEQFILFSSGSGAWGSGNQCAYAAANAYLDALAAHRQARGLPG
MSLAWGPWDGDGMSAGEDA
QRYLRERGVLPMDPRLAVAAFDEAVRARPNSNLVVADIDWERFVPTFTARG
HNPLIEDIPEVRRLAAEAE
AAQTTTAATDAPALLNRLSGLSATQQKQHLLRLVRSHMGEVLGREDVDTLD
ERHTFRDLGFDSLTSARFS
QRLAKDTGLHLPATLVFDHPTPADCVAHLRDQLLGETDDMTPRKRDHLGED
RRAATADDPIAIVGMACRF
PGGVRSADDLWDLLSSGTDAISGFPTDRGWDIESLYDPDPDRSGTTYTRHGGF
LYDAGQFDAEFFGISPR
EALAMDPQQRLLLETAWEAVEHAGINPQTLHGTPTGVFTGVNAQDYAAHLR
QASGNVEGYALTGSSGSVV
SGRVAYTFGFEGPAVSVDTACSSSLVALHLAGQALRSGECTMALAGGVMVM
SSPETFVEFSRQRGLSVDG
RCKSFAAAADGTGWGEGVGMLLVERLSDAERNGHRVLAVVRGSAVNQDGA
SNGLTAPNGPSQQRVIRQAL
ANSGLTGADVDAVEAHGTGTKLGDPIEAQALLATYGQEHHPDQPLWLGSLK
SNIGHAQAAAGVGGIIKMV
MALRHETLPRTLHIDEPTPQVDWSSGAVSLLTEPRPWPRQGDRPRRAGISSFG
VSGTNAHVILEEAPAQP
AGDPAPEDGAPVPWAMSARSNAALRAQAALLRDFLQGPGTDTALRAVGAEL

FIG. 12-2

AHGRAVLEHRAVIVARERT
EFEDALEALASGEPHPALIEDTTGSQTNSHSGGGVVFVFPGQGGQWAGMGLD
LLRDSQVFADHVGACERA
LAPWVEWSLTEMLHRDAEDPVWERADVVQPVLFSVMVSLAALWRSYGIEPE
AVVGHSQGEIAAAHVCGAL
TLEDAAKIVALRSRALAALRGHGGMASLALTGTEAEDLITTHWPGRLWTAAF
NGPRATTVSGDTDALDEL
LTHCTETGVRARRIPVDYASHCPHTETIEHDLLHMLHGITPQPGSIPFYSTVED
AWTDTTTLDAAYWYRN
LRRPVRFTHAVRTLTAQGHRLFIETSPHPTLTPAIEDHDHTTALGTLRRHDND
THRFLTALAHAHTTGHT
VTWTTHYPTTPHTPAIDLPTYPFQHHHYWLHTPTTSTGDVSAAGLHPTEHPLL
GATVELADGDGTLLTGR
LSLHTHPWLADHSVGGIVLLPGTALLELALEAGTRTGCPHVQELTLHTPLVIP
ETGHVVFQLTVSAPDET
GQRPFTVHFRSEAVTGADDPADRTWTRCATGALSTAAAPDHSEAATWPPPSA
QPLDLDGLYDRMAEAGLV
YGPVFQGLREAWLDGEDIVAEVRLPQEAAADTQGFGLHPALLDAALHVTAL
TSQAGTADEDAQERRRLPF
AWAGVSLFARECAALRVRVAPCAPHPGDAVAITATDEDGRPVLAVESLTLRP
VSPDQLRAAAPAAGRDSL
FRLEWVPVTASASASARPTGPWAAIGTGPAVAGLAGHADLTVYAEAGDLLR
DLDGGAPAPAVVVLSVTPD
ADEFATPRAATGRALSVLQAWLADERLADSRLVAVTSGAVVAAPGDDTVDV
PGAAVWGLVRSGQSEHPDR
ITLLDCASGARPGPDLVAAALASGEPQLAARAGVLYTPRLARPHRDASAVPR
SLPSHGTVLITGGTGLLG
GLVARRLVEAHGVRRLLLAGRRGPAAEGLDSLTSELRERGATVEVAACDAA
DRTQLEALLAGVPEEHPLS
AVVHAAGVLDDGVLTSLTNERLGAVLRAKADSALLLHELTQDLDLSAFVLFS
SAAGVLGSPGQGSYAAAN
AVLDALAHQRSAAGLPALSLAWGLWAEGSGMTGHLDADDRSRINRAGMAP
LPTPDALDLFDAALSSDEPF
LVPARFDLSAVRTRTAYGPLPPLLRGLVRTSGAHRVRGAVGEARAAGVDEA
GRLRERLARQSDAERRNTL
LRLVQSNVAAVLGHRGTGTVAETRAFRELGFDSLTAVELRNRLKVATGLALR
ATVAFDFPTPAALAEHLG
ARLLPPDGAVSEAVGEKELRGLLTSIPIGRLREAGLIDRLLALAAAAPDSADQT
AEQPSRSVSVEDIDAM DVDSLIGLAHDTGTDSGHAPCEG

FIG.12-3

MTKAPHQGSPTPADVGDYYDRMTSLLNRALGGNTHLGYWPHPDDGSTLGQ
ASDRLTDHMIGKLREHTGRP
VRRVLDVGCGSGRPALRLAHSEPVDIVGITISPRQVELATALAERSGLANRVR
FECADAMDLPFPDASFD
AVWALECLLHMPDPARVFQEMARVLRPGGRLAAMDVTLRASQPTGADWSS
SELAVPSLIPITAYAGMISD
AGLRLTELTDIGEHVIAPSYSAMGDDVRANAHAYAEALEMTADDLETFVGK
CSQWYTEDIGYVVLTAPCQ RAEV

FIG.13

VSSPPSTIPEAPGAWPVLGHLPALLRDPLGFLSAVTERGDLFRIRLGHNTVYLA
THPEIVRTMLVSGAAD
FTRSKGAAGASRFIGPILVAVSGDSHRRQRRMMQPGFHRGKLDHYVISMSAA
AEETADSWRPGQVVDVPK
MASDLSLAMITKALFQSDLGAAAEAELRTTGHDILKVARLSALAPQLYTSLPT
AAKRHMGRTSAAIREAV
TAYRADGRDHGDLLSTMLRARDAEGNTMTDDEVHNEIMGLAVAGIGGPAA
LTAWIFHELAHDHLIEQRLH
AEIDTVLGGRLPTSADLPRLPYTQRLVKEALRKYPGWVGSRRTVRPVRLGEH
ELPADVEIMYSSYALQRD
PRWYRDPEKLDPDRWESKETTRDVPKGAWVPFALGTYKCIGDNFALMETAV
AVAVIASRWRLRPLKGDRV
RPVAKATHVFPDRLRMIAEPRTPAIPRGHAPADASLEAAARPKELPEP

FIG.14

MATPSEKLVEALRASLKANEALRRRNQQLTAAVEAAQEPLAIVGMACRFPG
GVRSPEELWGLVASGGDAI
GEFPADRGWDLAGLFDPDPERAGASYTRHGGFLYDAGQFDAELFGISPREAL
AMDPQQRLLLETSWEVFE
RAGIDPSSVRGARAGVFTGMMYHDYASRLATIPEGFEGYIGNGSGGAVASGR
VAYTLGLEGPAVTVDTAC
SSSLVALHLACQSLRTGECDLALAGGVTVMSTPLLFVEFSRQRGLSVDGRCK
SFAAAADGTGMGEGVGML
LVERLSDAERNGHRVLAVVRGSAVNQDGASNGLTAPNGPSQERVIREALAN
AGLTVADVDAVEGHGTGTR
LGDPIEAQALLDTYGQERSGEQPLWLGSVKSNIGHAQAAAGVGGIIKMVMAL
RHESLPRTLHVDEPSPQV
DWSSGAVSLLSEARPWPRREDRPRRAGVSSFGVSGTNAHVILEEAPARRPGE
AAVEDGAPVPWVVSARSG
AALRAQAMVLREFLRGPGTDAGVRDIGAELARGRAVLEHRAVIVARERAEFE
GALEALASGEPHPALIED
ATGSHSHSGGGVVFVFPGQGGQWAGMGLDLLTTSGVFADHIGACERALAPW
VEWSLTEMLHREAEDPVWE
RADVVQPVLFSVMVSLAALWRSYGIEPDAVVGHSQGEIAAAHVCGALTLED
AAKVVALRSRALAALRGHG
GMASLALTGTEAEDLITTHWPGRLWTAAFNGPRATTVSGDTDALDELLTHCT
ETGVRARRIPVDYASHCP
HTETIEHDLLHMLHGITPQPGSIPFYSTVEDAWTDTTTLDAAYWYRNLRRPVR
FTHAVRTLTAQGHRLFI
ETSPHPTLTPAIEDHDHTTALGTLRRHDNDTHRFLTALAHAHTTGHTVTWTT
HYPTTPHTPAIDLPTYPF
QHHHYWLHTPTTSTGDVSAAGLQRPDHPLLGAVMELADGDGIVLTGRLSLH
THPWLADHSVGGVVLLPGT
ALLELAFQAGLRAGCPGVDELTLHAPLVVPESGHVVVQVSVSVPDEAGRRG
VSVYGRLVEDGGLEGEWTR
HAEGVVCPSVPGESVVVEPVADGVWPPSGAQPVDLDEFYGRLAGGGFVYGP
VFQGLCAAWRDGDDVVAEV
RLPDEGLADVAGFGVHPALLDAAVQTVTLLLPEDQEAGLLPYTWNGASLHA
RGARALRVRVTSVDAAGTT
VSLRVADETGALVLALESLVLRPVPLEGLGAGVRRGSLFELGWVPVEGVPAS
LAGGGGELVVWECPGGGV
AEVTAAALGVVREWLADEREGDARLVVVTRGAVAVDAGEPVRDVAGAAV
WGLVRSAQSEHPDRFVLLDLD
PGTGVETVVDADEDMGAGVGAGVDVAGFVACGEAQVAVRGGVVRVPRLE
RLERWGRLGGAGEGLSLPGGV
GWRLDGGGSGLLEGVGVVASDAAGVVLGRGQVRVAVRAAGVNFRDVLVA
LGMVPGQVGVGSEGAGVVVEV
GPGVEGLVVGDRVFGVFGDAFAPVVVAQEVLLARIPEGWSFAQAASVPVVF

FIG.15

ATAYLGLVDLAGVRRGESV
LVHAAAGGVGTAAVQLARHLGAEVYATASEAKWARLRAAGVAPQRIASSR
SVEFESRFRRASGGRGVDVV
LNCLAGEYTDASLRLCSPQGGRFLELGKTDIRDAGEVAARFPGVSYRAYDLM
DAGAQRVGEILHTVVDLF
RRGVLEPLPVTAWDVRQARQALRSMRSGLHVGKNVLTLPVPLDAEGTVLVT
GGTGTLGAAVARHLAAGHG
VRHLLLVSRRGMAAAGAEELCAELGQAGVSVSVAACDVADRAQVAALLEQ
VPAEHPLTAVVHTAGVLDDA
TVTCLDREKIDAVVGAKVDGALHLHELTAGMDLSAFVLFSSAAGVLGSPGQ
GNYAAANAALDALAHQRRA
AGLPALSLAWGLWEEASGMTGHLDAGDRHRITRSGLHPLTTPDALALLDTAL
ATGRPALLPADLRPTHPA
PPLLEHLAPARTSPRTAHTGTSAGAGQDVSLADRLATLTSEQRHATLLALART
HIAAVLGHPTPDTIDPE
RTFRDLGFDSLTAVELRNRLTRATGLRLPTTLAFDHPTPTALTHHLTTLLNPN
DTKTPSAPAAAEPKAGQ
HEPIAIIGVGCRYPGGVASAEDLWQLVASGGDAVGEFPADRGWDVEALYDPE
PGQRGTSYTRHGGFLYDA
GEFDAGFFGISPREALAMDPQQRLLLETTWEAFERAGIDPGAVRGSQTGVFA
GVMPQEYASRSRHHVAAD
VDGYVLTGTSGSVASGRVAYTFGLEGPAVSVDTACSSSLVALHLACQALRSG
ECTMALAGGATVMSTPTA
FLEFSRQRGLAADGRCKAFSASADGTGWSEGAGMLLLERLSDAERNGHRVL
AVVRGSAVNQDGASNGLTA
PNGPSQQRVIRQALANANLSAVDVDAVEAHGTGTKLGDPIEAQALLATYGQE
HHPDQPLWLGSLKSNIGH
AQAAAGVGGIIKMVMALRHESLPRTLHVDEPSPQVDWSSGAVSLLTEARPWP
RREDRPRRAGISSFGVSG
TNAHVILEEAPARAEVEAVEAAPAGVETAAAAAVVVETDGAGRVSADVPLV
WVVSGKSQAALRAQAAALH
AHVLDHPEQDAADIGYSLATTRALFDHRATLIAPDRDTLLDALTALADGRTH
PHLIPTPPTEPGHTHKIA
FLCSGQGTQRPGMATGLYHTYPAFADALDETCAHFDPHLDHPLRDLLLNHDP
TDLLTHTLYAQPALFTLQ
KALHHLITETYGITPHYLAGHSLGEITAAHLAGILTLPDATHLITTRARLMQTM
PPGTMTTLHTTPEHIQ
PLLDQHPGKATIAAVNSPHSLVISGDPDTIHHITTTCHTQGITTKPLTTNHAFHS
PHTDTILEQLDTTTH
TLTYHPPHTPLITSTPGDPLTPHYWTHQTRQPVHWTDTIHTLHTNGVTTYIEL
GPDHTLTTLTHHNLPHH
QPTAITLTHPHHNPTHHLLTALAHTPTTWHTHHHTHTNPHPHTIPDLPTYPFQ
RRHYWLQATPGAGAGDV
SAAGLQRPDHPLLGAVMELADGDGIVLTGSLSLRTHTWLADHSVGGIVLLPG
TALLDLAFQAGLRTGCPR

FIG. 15-1

VDELTLHAPLVIPESGHVVVQVSVSVPDEAGRRAVNVYARPAGDEETDGEW
TRHAEGVLSPSTEDDPNAE
AAAAGEWPPPGARPVVLDGLYDRLAGGGFVYGPVFQGLCAAWRDGDDVVA
EVRLPDEGLADVAGFGVHPA
LLDAAVQSVTLLLADQQQAGLVPHTWNGVSLHARGATVLRLRMTPTDATST
AVRLHATDETGAPVLTLES
LLMRPVPLEGLGARVRRGSLFELGWVPVEGVPASVAGGGGELVAWECPGGG
VAEVTAAALGVVREWLADE
REGDARLVVVTRGAVAVDAGEPVRDVAGAAVWGLVRSAQSEHPDRFVLLD
LDPDTKTDPDTDTDTDTDGD
TDVSADAKVGTGAGLDDAAVASALARGESQLAVRDGVVRVPRLKRVPPLSE
SSDAVRFDAEGTVLVTGGT
GTLGAVVARHLAAGHGVRHLLLVSRRGMAATGAEELCAELGGAGVSVSVA
ACDVADRAQVAALLEQVPAE
HPLTAVVHTAGVLDDATVTCLDREKIDAVVGAKVDGALHLHELTAGMDLSA
FVLFSSAAGVLGSPGQGNY
AAANAALDALAHQRRAAGLPALSLAWGLWEETSGMTGHLDAGDRHRITRS
GLHPLTTPDALALLDTALAA
GRPALLPADLRPTHPAPPLLEHLAPARTSHRTTLPTTDSGASLRARLAGRTPEQ
QYQALLGLVRSHVATV
LGHQAPEAIPVDSAFRDLGFDSLTAVDLRNRLSAETGLRLPASLVFDQPSPAA
VARLLRTELLGDDAADS
TSPYAETTAVGSDEPLAIVGMACRFPGGVRSPEELWGLVASGGDAIGEFPADR
GWDLAGLFDPDPERAGA
SYTRHGGFLYDAGQFDAEFFGISPREALAMDPQQRLLLETVWETLEHAGIDP
AAVRGSRTGVFAGVMYHD
YAARLTAVPEGAEGYIGNGNAGSVVSGRVAYTFGFEGPAVSVDTACSSSLVA
LHLAGQALRSGECSMALA
GGVTVMSSPGTFIDFSRQRGLSVDGRCKSFAAAADGTGWGEGVGMLLVERL
SDAERNGHRVLAVVRGSAV
NQDGASNGLTAPNGPSQQRVIRQALANSGLTGADVDAVEAHGTGTKLGDPIE
AQALLATYGQEHHPDQPL
WLGSLKSNIGHAQAAAGVGGIIKMVMALRHETLPRTLHIDEPTPQVDWSSGA
VSLLTEPRPWPRQGDRPR
RAGISSFGVSGTNAHVILEEAPAQPAGDPAPEDGAPVPWAMSARSNAALRAQ
AALLRDFLQGPGTDTALR
AVGAELAHGRAVLEHRAVIVARERTEFEDALEALASGEPHPALIEDTTGSQTN
SHSGGGVVFVFPGQGGQ
WAGMGLDLLRDSQVFADHVGACERALAPWVEWSLTEMLHRDAEDPVWER
ADVVQPVLFSVMVSLAALWRS
YGIEPDAVVGHSQGEIAAAHVCGALTLEDAAKIVALRSRALAALRGHGGMA
SLALTGTEAEDLITTHWPG
RLWRAAFNGPRATTVSGDTDALDELLTHCTETGVRARRIPVDYASHCPHTETI
EHDLLHMLHGITPQPGS
IPFYSTVEDAWTDTTTLDAAYWYRNLRRPVRFTHAVRTLTAQGHRLFIETSPH

FIG. 15-2

PTLTPAIEDHDHTTALG
TLRRHDNDTHRFLTALAHAHTTGHTVTWTTHYPTTPHTPAIDLPTYPFQHHH
YWLHTPTTSTGDVSAAGL
HPTEHPLLGATVELADGDGTLLTGRLSLHTHPWLADHSVGGIVLLPGTALLEL
ALQAGGAAHVRELTLHA
PLAVPHDAAVDLQVRVSAPDDTGARTLTVSSRSEHARPEDPWQHHATGLLD
AQPSADGDALRSWPPEGAL
PCAADELESFYAAQEARGFAYGPAFRGLRAAWRRGEEVFAEVRLPESVLDEA
SRYNLHPALLDAALHAVA
LGAATGLPPGAVPFSFSGVTLHAVKAAAVRVRVAPAGRDGERTAVSVSLAD
ETGRGVLSVDSLAVRPLDT
GELRASAQAAGRAALFDVAWKDVTPGTPPPDTAVRSTVLTHDRAAADLSGL
LSGLDTDDAPVPDAVLLTC
SQGAVADVLGEVLSVVQDWLADDRLAEARLVVVTHGAVATRTGEEVTDVA
GAAVWGLLRSAQSEHPGRFV
LLDADLSDDTTVTAALACDEPQLAVRGGRLLAARLAHVPVPADSSDAVRFD
AEGTVLVTGGTGTLGAAVA
RHLAAGHGVRHLLLVSRRGMAATGAEELCAELGQAGVSVSVAACDVADRA
QVAALLEQVPAEHPLTAVVH
TAGVLDDATVACLNREKIDAVVGAKVDGALHLHELTAGMDLSAFVLFSSAA
GVLGSPGQGNYAAANAALD
ALAHQRRAAGLPALSLAWGLWEEASGMTGHLDAGDRHRITRSGLHPLTTPD
ALALLDTALVTGRPALLPA
DLRPTHPAPPLLEHLAPARTSPRTAHTGTSAGAGQDVSLADRLATLTPEQQHD
TLFTVVRTQIATVLGHQ
TPEAVPADSAFRDLGFDSLTAVELRNRLSRATGLRLPATLAFDHPTATALTRH
LLTRLLPDDAATAPPEQ
SLFAEIGRLEAVLSSVASPLPGAQGLGEEARSRLASRLRSLAQVLGGEEAPRPD
LGEATDEEMFALIDQE TGSP

FIG. 15-3

MANEEMLREYLKRATADLLRVRRRLEQVESGRQEPVAIVGMACRFPGGVRS
PEDLWELVASGGDAIGDFP
VDRGWDVEDLYDPEPGRAGRSYTRSGGFLHEAAEFDAGFFGLSPREALAMD
PQQRLMLEVSWEALERAGI
DPATLRGSRTGVFAGMMSHDYATRLLSVPDHLQGFLGNGNAASVLSGRLSY
TFGFEGPAVTVDTACSSSL
VALHLACQSVRSGESSLALAGGVTVMSTPAMFVEFSRQRGLSADGRCKPYA
AAADGTGMSEGVGVLLVER
LSDARRLGHRVLAVVRGSAVNQDGASNGLTAPNGPSQQRVIGQALVCAGLS
AAEVDVVEGHGTGTSLGDP
IEAQAVLAAYGRGRGVPLWLGSVKSNLGHTQAAAGVAGVIKMVMALWRGR
LPRTLHVDEPSPHVDWSSGA
VRLLTEEVVWERGERPRRAGVSSFGVSGTNAHVILEEAPQEEEVRPEEAPSGD
GVGPVVVPSGDGAGPAV
VPWVVSARSESALRGQARRLRVFADGAGAAPVEVGRALAVERAWLEHRAV
VLAEDLDGFRHGLDALATGR
PAPEVVTGTATDEGPLAFLFAGQGTQRPAMGRELHAHFPAFADAFDEVCAHF
GPIGEAGHTLRDIVFAAP
GSPGAELIEQTEYAQPALFAVEVALYRLVENWGVTPDYLLGHSVGELAAAH
VAGMLSLPDAAALVTARGR
LMQALPDTGAMVAVEATEEEVRPLLQDAEGRADLAAVNGPRAVVLAGDED
AVLTLARHWAEQGRRTRRLR
TSHAFHSPHLDAVLDDFRRVAEQVVFAPPRIPVVTNLTGAPVSADTMGTADY
WVQHARHTVRFGDGLAWL
QAQGVTAYLELGPDGTLCALGQDALTEPAPLLPALRPDRPEAVSVLAAVAGL
SVRGVRVDWAAVLGGAPS
GTAGRVELPTYAFERERYWLDAGETPAALPAGEDGPLWQAVERADLPAVAA
LLEVDEDAPLGSVVSALGD
WRRGVRERAVVDGWRYRVVWRPVSRSGGGVVSGGVWVVVVPEGVVGAA
AVVEGLERAGVCVRVVAVEGGC
ADRVVLGERLREVCGGEGPVGVLAVCGGGVGVAGLVLGLVQAVEGLGVPL
WCVTRGAVSVGEGDRLGDPG
GAVVWGLGRVAGLELPDRWGGVVDLPEVVDERVVEGLLGVLSGGGGEGEV
AVRASGVFVRRLVRAPGGGA
EAGGWRPRGTVLITGGTGALGAHVARWMVRRGAEHLLLVSRSGREAKGAG
ELRAELTAMGARVTIAACDV
ADRGALAELLATAVPEDCPLGAVVHTAGVVDDGVLDALTPERLEGVLAAKA
VGARNLHELTRGADLSAFV
VFSSAAATFGSGGQGAYVAANAYVEALAVHRRGLGLPSTAVAWGAWAGGG
MAADAEAATRMDRRGIRPMD
TEPALSALGQVLDRNETCLTIADIDWERLPAADGLARLLSDIPEARLARPATG
TEAPGSLRARLAALEPA
ERDRALLDLVRTHTATVLGHRTATAVPADRAFRELGFGSLNAVELRNGLNTA

FIG.16

TGLRLPSTLVFDYPNPSA
LATHLGTLLSTGGEAPAGRPAFIRSGVVDEPVAIVGMACRFPGGVWSPEDLW
ELVASGGDAIGGFPVDRG
WDVEGLYDPEAGRPGSSYTRAGGFLAGAAEFDAGFFGISPREALAMDPQQRL
LLEVSWEALERAGIDPVS
LRGSRTGVFAGVANQDYAELVRRGGRDLEGYALTGVSGSVLSGRLSYTFGL
KGPPVTVNTACSSSLVALH
LACQSLRSGESKLALPGGVTVMSTPGAFVEFSRQRGLSPDGRCKAFATPTNG
VGWSEGVGVLLVERLSDA
RRLGHRVLPVVRGSAVNQDGASNGLTAPNGPSQQRVIGQALVCAGLSAAEV
DVVEGHGTGTSLGDPIEAQ
AVLAAYGRGRGVPLWLGSVKSNLGHTQAAAGVAGVIKMVMVLWRGRLPR
TLHVDEPSPHVDWSSGAVRLL
TEEVVWERGERPRRAGVSSFGVSGTNAHVILEEAPQEEEVRPEEAPSQGEAGP
AVVPWVVSARSESALRG
QARRLRVFADGAGAAPVEVGRALAVERAWLEHRAVVLAEDLDGFRHGLDA
LATGLPTAGVVAGRTGPEAD
GKIALLFGGQGTQWDGMAAELLDSSPVFAQRMTECADALRPYLDWELLDVL
RGEPDAPPLDRVDVVQPVL
FAVMVSLAALWRSYGVRPDAVAGHSQGEIAAACVAGALSLEDAARVTALRS
QALAALAGQGAMASVGLPA
EDLEPRLAAVDPSLVVAADNGARSAVVSGSPDAVTALVDDLTRDGVPARLL
KVDWASHSPQVEAIRADLL
GLLAPVTPRPADIPLYSTVTGEPVDGTALDAAYWYRNLREPVRFRDATRALA
RDGHTVFVEAGPHPAVSV
AVQETLDDLGAADTLVVGSLRRGEGGLRRFLASAAELSVRGVRVDWAAVLG
GKPSGTAGRVELPTYAFER
ERYWLDPEETPAAPATTEDGPLWEAVEREDPAAVAALLAVDEDAPLDALVS
ALGDWRRGVRERAVVDGWR
YRVVWRPVSRSGGGVVSGGVWVVVVPEGVVGAAAVVEGLEWAGVCVRVV
AVEGGCADRVVLGERLREVWG
GEGPVGVLAVCGGGVGVAGLVLGLVQAVEGLGVPLWCVTRGAVSVGEGDR
LGDPGGAVVWGLGRVAGLEL
PDRWGGVVDLPEVVDERVVEGLLGVLSGGGGEGEVAVRASGVFVRRLVRAP
GGGAEAGGWRPRGTVLITG
ENADPEQPAAHLARWLADRGAEHLLLISTSGDGFGLADTTDQWGARVTIAA
CDVADRGALAELLATAVPE
DCPLGAVVHTAGVVDDGVLDALTPERLEGVLAARAVGARNLHELTRGADLS
AFVVFSSAAATFGSGGQGA
YVAANAYVEALAVHRRGLGLPSTAVAWGPWRGHSAAGRPDAAARLHRRGL
TEMAPELALAALARVLDHDE
SGLTVADIDWERFTAHTAGSRLPLIGDLPDVRALTRATGTGTAHGTDLRDRL
AALEPDARTDVLLELVST
HTAAVLGHREADTVPADRAFRELGFDSLTAVELRNRLNTATGLRLPTTLVFD
YPRPAVLARHLRDQLCGT

FIG. 16-1

APATPPVAARPGVVDEPVAIVGMACRFPGGVWSPEDLWELVASGGDAIGGFP
VDRGWDVEGLYDPEAGRP
GSSYTRSGGFLAGAAEFDAGFFGISPREALAMDPQQRLLLEVSWEALERAGID
PVSLRGSRTGVFAGVAN
QDYAELVRRGGRDLEGYALTGVSGSVLSGRLSYTFGLEGPAVTVDTACSSSL
VALHLACQSLRSGESELA
LAGGVTVMSTPGAFVEFSRQRGLSADGRCKAFAAAADGVGWSEGVGVLLV
ERLSDARRLGHRVLAVVRGS
AVNQDGASNGLTAPNGPSQQRVIGQALVCAGLSAAEVDVVEGHGTGTSLGD
PIEAQAVLAAYGRGRGVPL
WLGSVKSNLGHTQAAAGVAGVIKMVMALWRGRLPRTLHVDEPSPHVDWSS
GAVRLLTEEVVWERGERPRR
AGVSSFGVSGTNAHVILEEAPQEEEVRPEEAPSQDEAGPATVPCLLSARTDTA
LRAQARRLRDYLAANPD
IPIGDVAHALATGRSTFERRAVLVAEDHEGLLRTLDALAEGTTAPGLIESPART
AHGKVAFLFSGQGTQR
PGMGRELYAAHPAFAQALDDVLAELEPHLDRPLRPLLLDEPQPLDRTGDAQP
ALFALQVALFRLLESAGI
RPDHVAGHSIGELAAAHVAGVLSLTDAARLVAARGRLAQTQLPPGGAMLAV
RASEEQVTRMLAGREARVA
VAAVNGPTSVVISGAEPDVLEAAAAFAEQGLRTKRLSTDRAFHSPLMEPILEE
FRQVATGIAYAEPTIPV
VSTVTGDRATAGTLTDPEYWVRQLRRTVRFGDAVRRLHDDDGVRTFLELGP
DGTLCALAGECLPADDNTT
EPGPALVPLLRADRPEPLALLTALAHLHVQGTPKGGTAVHWPALIGATPERA
RHLDLPTYPFDRRRYWLD
ADTSLSGDVSAAGLTAAGHPLLGSAVPLAGSPQSQECLLTGRISLRTHPWLAD
HAVFGTVLLPGTAILEL
AVRAGDEVGCDTVEELALQVPLVLPERGSVVLQLSVGATETAPDGVERRPFT
LYAREDDGLTPAAPTGTD
GTGWTCHATGVLTRRAETAHDTAAPWPPTDAVPVDLDHWYGTLADAGLGY
GPAFQGLRAAWRHGDDLYAE
VALPDGPSGDADRYAVHPALLDAALHPVVLGFAEDEPDEGHGWLPFSWSGV
TVTASGASALRVRLSRRSP
DTIALLATDSTGHTVVTAESLAFRPVTAGQLHSARTAHHDALFRLDWAPVPL
PRTPSSKTRLALIGSEAE
CPDAPGVPWSTYADLEELASAGTPVPDVVVVPCPHRDGAADAADATRRATV
RVLHLLQSWLADDRFADSR
LAFVTHGAVAAAPGDSVPDLAHAAVWGMVRSAQTENPGRFVLTDLDDTDA
SRRALAAALLSGEPQTVLRE
GRAHTPRLARIPVGARADSGHWDPDATVLITGGTGYLGRLLARHLVVTHGV
RHLLLTSRSGPTAPGTAEL
VAELAELGARTTAVACDLADRRAVAALLAEIPARHPLKAVLHTAGVVDDGV
LTSLTPDRLDAVLSAKAHG
AAHLHDLTRDAGLDAFIAFSSAAASFGSPGQANYTAANAFLDALMQQRHAL

FIG. 16-2

GLPGRSLAWGRWAEAGGMA
EHLAAADVARMTRSGLLPLTNAHGLALFDTALALDEPLLLATPLDPGTLREQ
AAVGTLPPVLRGLVRTPA
RRTADHGVGADAAAELRGRLAGTPKPAERTALLTEVVRTHAAAVLGHGGTD
TVTADGEFREFGFDSLTAV
ELRNRLNAATGLRLATTLVFDHPTPAALADHLERLLAAEPASDMTAETAGAP
GERDATASSRAGSGPSAD
TVEALFWIGHDSGRVEESMALLSAASAFRPCFTDPSAMTRPPFVRVAQGDTG
PALICLPTVAAVSSVYQY
SRFAAALDGLRDVWYVPAPGFADGEPLPADVDTITRLFTDAILRHTDGEPFAL
AGHSAGGWFTHTVTSRL
EHLGVRPQAVVVMDAYLPDEGMAPVAAALTSEIFDRVTEFIDLDYARLVAM
GGYFRIFAGWRPPALETPT
LFLRARESEQPPPVWGEPHTVLETDGNHFTMLEEHAESTARHVHTWLAGLTE
QRRR

FIG.16-3

MDRYAKRFEDRLVLVTGAGSGIGRATACRFGAAGARLVCVDRDGPGAEATA
ELARARGARAACAEVADVS
DEVAMERLAARVTAAHGVLDVLVNNAGIGMSGRFLDTSAEDWRRTLGVNL
WGVIHGCRLLGRGMAERRQG
GHIVTVASAAAFQPTRVVPVYATSKAAALMLSECLRAELAEFGIGVSVVCPG
LVRTPFASAMYFAGASPD
EHTRLRESSARRFAGRGCPPEKVADAVLRAIMRTALPTVTGSTP

FIG.17

SEQUENCE LISTING

<160> NUMBER OF SEQ ID NOS: 42

<210> SEQ ID NO 1
<211> LENGTH: 88400
<212> TYPE: DNA
<213> ORGANISM: bacteria

<400> SEQUENCE: 1
gagctcttcg ctcccgccgg accggttggt cgcgccggag aggacgagcc ggtagcgggt 60
gttgatctcg ttggtgccga gcccgttggc cgggcggccg tggaaccacc tcggatcggg 120
ctcgggggtc tcctggccct tcttcagcgg cagatggtac ggctggccga tcagcgagga 180
gccgacggcc ctgccgtccg ccgtgatctc ggagccgtcg gcccggtcgc ggaagagtgc 240
ctgggcgacg ccggtgacga ccagcgggta gccggcgccc gtcaccaggg tcagcacgag 300
gagggcccgc aggcccgccc cgagcagccg gacggtgtgg gtggcggagt tgttcatggc 360
ggtcagcacg ctttcgtgac gtcacggccc gggaacgagg gagatgaaca ggtcgatgat 420
cttgatgcct atgaagggcg ccaccaggcc gcccaggccg tagatcccga ggttgcgccg 480
cagcatccgg tccgcgctca ccggccggta ccgcacgccc ctcagggaca gcggcaccag 540
cgccacgatg accagcgcgt tgaagatcac cgcggagagg atcgcggagt cgggtgagga 600
caggcccatg acgtcgagtc gctccaggcc gggatgggcc ggcgcgaaca gcgccgggat 660
gatcgcgaag tacttcgcga cgtcgttggc cagggagaag gtcgtcagtg cgccgcgtgt 720
gatcagcagt tgcttgccga tctccacgat ctcgatcagt ttggtgggat cggagtcgag 780
gtcgaccatg ttgccggcct ccttcgcggc cgacgtaccg gtgttcatcg ccacgccgac 840
gtccgcctgg gccagagccg gggcgtcgtt ggtgccgtcc ccggtcatgg cgaccagcct 900
gccgcctgcc tgctcccgcc tgatcagcgc catcttgtcc tcgggagtcg cctccgcgag 960
gtagtcgtcg acgcccgcct cgcgcgcgac ggcctgcgcg gtcagcgggt tgtcacccgt 1020
gatcatgacg gtcctgatgc ccatgcggcg cagttcctcg aaccgcgcgc gcatgccgtc 1080
cttgacgacg tccttgaggt ggacggctcc cagcacccgg gcgccccgct cgtcccgcgc 1140
ggcgaccagc aggggcgtgc cccccgatcc ggcgatgcgg tcggcgatgg ccttcgcgtc 1200
ctgggcggcc tcaccgccct gctcctcgac ccaggcgagg atggaaccgg ccgcgccctt 1260
gcggatcctg cggccgccga cgtccacgcc cgacatgcgg gtccgggcgg tgaacgcgat 1320
ccattcggcg ccggcgagtt cgccccggtg ccgctcgcgc agtccgtact gctccttcgc 1380
caggacgacg acggaccggc cctcgggcgt ctcgtccgcg agcgaggaga gctgcgcggc 1440
gtccgccacc tcggcctccg tggtgccgga caccggcacg aacccggccg cccgccggtt 1500
gccgagcgtg atcgtgccgg tcttgtccag cagcagcgtg gagacgtcgc ccgcggcctc 1560
gaccgcccgg cccgacacgg ccagcacatt gcgctgcacc aggcggtcca tgcccgcgat 1620
gccgatcgcc gagagcagcg cgccgatcgt ggtcgggatg aggcagacca gcagcgccac 1680
cagcaccgtc ggtgtcaggt gggtgcccgc gtgatccgcg aagggcggca gcgtggcgca 1740
gaccagcagg aagacgatgg tcagcgaggc cagcaggatg ttcagcgcga tttcgttagg 1800
cgtcttctgc cgggccgcgc cttcgacgag gtcgatcatc cggtcgatga aggtctcacc 1860
gggcttggtc gtgatccgga tgacgacacg gtcggacagg accttggtgc cgccggtgac 1920
ggcgctccgg tctcccccg actcgcggat gacgggtgcc gactcgccgg tgatggcgga 1980
ctcgtcgacg gacgcgacgc cctcgacgac atcaccgtcg ccggggatga cgtccccggc 2040

-continued

```
ctcgcagacc accagatcgc cgatcctcag tccggtgccc ggcacccgct cctccgagcc   2100
gtcctcgcgc aggcggcggg cgacggtgcc ggtcctggtc ttgcgcaggg tgtcggcctg   2160
tgccttgccg cggccttcgg cgaccgcctc cgcgaggttg gcgaagagca cggtcatcca   2220
gagccaggcg gagacggtcc agccgaaccg gtcgccggga tccatgaggg cgaagacggt   2280
ggtgaggacc gagccgatcc acaccacgaa catcacgggc gtcttgatct gcacccgcgg   2340
gtccagcttg cggaaggcgt ccggcaacga cctgacgagc tggcccgggt cgaacagacc   2400
gccgccgacc cgcctttcgg acggctggtg accggtgggg gcgtcgcgct gcggcgtccg   2460
ggcgggagtg atcgtggaca tcgggttccc ttggtcgtcc gggtgtgcgc tcatgccgcc   2520
agcccttcgg cgagcggccc cagcgccagg gccgggaagt acgtcaagcc ggcgaggatc   2580
aggatcgcgc ccaccatcag gccgctgaac agcggcttgt cggtgcgcag ggtgccggtg   2640
gtgaccggca cgggccgttg cccggcgagc gagccggcca gcgccaggac gaacaccatc   2700
ggcaggaagc ggccgagcag catcgccagt ccgatggtgg tgttgaacca ctgcgtgtcc   2760
gcgtcgagac cggcgaaggc cgagccgttg ttgttggcgc cggaggtgta ggcgtagagg   2820
atctcggaga acccgtgcgc gccgctgccg gtcgtcgagt tcaccggcgt cggcagggcc   2880
atcgcgcacg cggtgaggat caggaccagc gccggggtga ccagcaggtg gcaagcggcc   2940
agtttgatct cgcgggtgcc gatcttcttg cccaggtact cgggcgtgcg gccgaccatc   3000
agaccggcga tgaacaccgc tgtgacggcc atgacgagca tgccgtagag gccggatccc   3060
accccgcccg gagcgatctc gcccagcatc atgccgagca tcgcgatgcc tccgccaagg   3120
ccggtgaagg aggagtggaa ggagtccacc gcgccggtcg aggtgagcgt ggtcgacacc   3180
gcgaagatgg acgaggcgcc gacaccgaag cggacctcct tgccctccat cgcgccaccg   3240
gcgatctcga gcgccgggcc gcggtgcgag aactcggtcc acatcatcag ggcgacgaag   3300
gcgatccaga aggtggccat cgtcgccagg atcgcgtagc cctgcctgac cgagccgacc   3360
atgacgccga acgtccgggt gatcgagaag gggatcacca ggatcaggaa gatctcgaag   3420
aggttggtga agggcgtcgg gttctcgaac gggtgggcgc tgttggcgtt gaaatagccg   3480
ccgccgttgg tgcccagcag tttgatggcc tcctgggagg cgaccgcgcc cccgttccac   3540
tgctgcgagc cgcccgtgaa ccggccgacc tcgtggatgc cggagaagtt ctggatgacc   3600
ccgcaggcgg ccagcaccac ggcgccgagg gtggccagcg gcaccaggac gcggaccgtt   3660
ccgcgcacca gatcggccca gaggtttccc agttcaccgg tgcgggagcg cgcgaacccg   3720
cgcaccagcg cgaccgcgac ggccatgccc acggcggccg aggtgaagtt ctgcacggcc   3780
aggccggcgg tctgcacgag gtgtcccatg gcctgttcgc cggagtacga ctgccagttg   3840
gtgttggtca cgaaggacac ggccgtgttg aacgcctggt ccgggtcgac ggctcgaaag   3900
ccgagggaca gcggcaggac gccttgcgcc cgctggacca ggtacaggaa gaggacgccg   3960
gccacggaga aggccagcac accgcggagg tacgcgggcc agcgcatctg ggcgccgggg   4020
tcgacaccga tgccccggta gatccatctc tcgacgcgcc agtgctcgtc ggaggagtag   4080
accttggcca tgtggttgcc gaggggtttg tggacgagtg ccagagcact cgtcagggcg   4140
agcagttgga gcacgccggc gagtacggga cccatggctg ctctcagaac ctctccggga   4200
agatcagggc gaggacgaga tagcccagca gggagacggc cacgaccagg ccgacgacgg   4260
tctcggcggt cacagcttcg tcaccccccct ggcgacaaca gccaccagcg cgaagagcgc   4320
gagcgtggtg acgacgaagg ccgtatcggc catcgcggac tcctggaatg aggtgcggtg   4380
```

-continued

```
gaaacggacc cttgcaggta agcgcctcac cgaccgaaac aggacgtccg ttgacgtttc   4440
ccttacggcg tgacgtacgt ctttgacgga actcttacgc ctgaggtccg tgtccatgcc   4500
cctcggtccg ttgcggacca tgcccccgcg gccaccggag agggcggcgt cccccctcagc   4560
gggccccgcc cgtctccccc ggggcctccg tctcccccac cttctccacg accgtctcct   4620
ccggcccgac cggccgtccg tccgcggcac ggatccgcaa ggggcgcagc gggcggccgg   4680
tgcggcggtc gagcaggcgg gagtggtcct cgccggggc gaagcactgc tcctcgcccc   4740
actggcgcag ggcgacgatc accgggaaca aggcgcggcc cttgtccgtg aggacgtact   4800
cacggtggga accgccgtcc ggcgcgggca cgttgcgcag taccccggcc tcctccagcg   4860
cgcgcagccg cgccgtcagg atgttcttgg cgatgccgag gctgcgctgg aactcgccga   4920
agcggcgact gccgtcgaag gcgtcccgca cgatcagcag cgaccaccag tcgccgatgg   4980
cgttcaccga ccgggcgacg ggacaggggt cggcgtcgaa acgggtgcgg gcgaccatcc   5040
gcgtctctcc tctcctccgg caccccggat ccctccaggg atggttgcaa catgctacct   5100
cgtacggcta ccgtcctcgc cggtagcaag atgcaaccga gtgagaggtg tgacggtatg   5160
gcggtccagt gctccggtgc ggacggcgga tgcggcgaag ccggtggtcg cggagcggcc   5220
ggcacggcgc cgcccgcgcg gctcgtgccc ctgctcgccc tggcctgtgg cagctccgtc   5280
gccaccgtct acttcgccca ccccctgctg gtgaccctcg gtgagcgctt cgcgctcggc   5340
cccgggctgc tcggcgcgat cgtcaccgtg acgcaactcg gttacgcggt gggcctgctg   5400
acactcgtgc cgctcggcga cctgctcggc caccggcggc tggtcaccgc tcagctcgga   5460
ctgctggcac tggcgctgct ggccgccggg ctggcgccgg gcgcggctgc gctgctcggc   5520
gcgctcgccg cggtcgggct gctcgccgtc gtcgcccaga cgatggtcgc ggctgccgcc   5580
gccctgagcc cgcccgaccg gcgaggccgc gccgtgggaa ccgtcaccgg cggcatcgtc   5640
accggcatcc tgctggcgcg cgccgccgcg ggcgtcctcg ccgacctcgc cggctggcgg   5700
gcggtctacc tggcgtcggc gggcgtcacc gccgtcctcg ccgtgctgct gcgccgtgcg   5760
ctgcccccgg gatcgccgtc cgcaaaggct cgcgagacgt cgtacgtacg gctggtggcc   5820
tcgaccgtca ccctgttcgc ccgccatccg ctgctgcgga tccggggggc cctggccctg   5880
ctggtgttcg cggccttcag cacgctgtgg agcggcgtgg cccagccctt gagcgatccg   5940
ccgtggtcgc tgtcgcacac cgcgatcggc gcgttcgggc tcgccggggc ggccggagcc   6000
gtcgccgcac aggtggccgg gcgctggaac gaccgggggc tcgcccggcg cacgaccggc   6060
gccggcctcg cgctgctggc gctctcctgg ctcccgatcg ccctgacccg gcaatcgctg   6120
tgggcgctgg cgatcggcgc cgtcctgctg gacttcgccg tgcaggccgt ccacgtcacc   6180
aaccagaccc tcatccacgc cgtccggccc gaggcgggca gcaggatcat cggtggttac   6240
atggtcttct actccgcggg cagcagcctc ggcgccctcg gttcctccct cgcctacgcc   6300
acggcgggct ggccggccgt gacggccctg ggcgcgtcgt tcagcgtcgc cgcgctgctg   6360
ctgtggacgg cgacccgtcg tacggggctg cccggcgacg acccggcggc cgaacggacg   6420
gaccctggcc gtccgtccgg ggacagggct gccgggaggc ccgcccgcag ccgctcttcc   6480
ggcccccggt gaacgtctgg ggtggcgcgg ggcgcgcgat aggggtccgc cgagagtcag   6540
gggttgtccc gcctgtacag cggcatcggc ggtcggtcca atggaaggcg tgcctccgga   6600
tgcggggcgg gtcgtcgacg accctgtgcc ggcggcggat tcccaccctc ccccggaagg   6660
cgaggtcgtg atgaccgacg tccgtcatga cagcaggcag acgggtccgg cgctgcgcgc   6720
gctcagcgcg gcccggcggg cgcgggcctt ggcgtccgcg atggcggcgg ccgccgcgga   6780
```

-continued

```
gacgcggcag gccgtcgagg ccgcggacgg cacggaccgc gcggccgccg tagccgagat   6840
cggcgcggta ctggaggacg cctcccggca cacggacgcc gccgccgagg ccgccgcctc   6900
ggctgccgag gccgccgccc gggccgagac ggccgaggcc gcccgcacgg tggccgccga   6960
gtcggccgag gccgtcgtcg ccgccgccga gacggcggtc cgggcggccc gggtcaccga   7020
ggccgccacg agcgccgccg cccaggccgc ggccggtacg gacgcggcgg gcgtgatggc   7080
ggacgccgcg gcgcacaccc ggcaggccac cgccgagacc gcggcgatcg ccgaggccgc   7140
cgccgcggcg gccagcgcgg cccgggccgc cgtcggcgac gaggcggcgg acggcgcgga   7200
cccgtgccga cgggctgacg aggcggaggc cgcggccctg cggctgtgcg aggacacgcc   7260
gtggctgcgc aggcacctcc ccgacgtgtg aggcagggtg cccggcggcg ccggcgcgag   7320
atggaacccg ggccgggcgg ccctcttccc tccgggtgcc ggcgacgaga ccgtcgcccc   7380
cacctcgaac cgggccttcc ggtcgctgta ccggcatccg gagatcgagc ggcggccgca   7440
ctccgagggg gaccgggtgc tcggcggccg ggccgccacc tggacggatc cgccgtcgct   7500
ggagctgacg ggccgggtgg tccacgacgc gctgcgcctg ttccccggac gggctgctca   7560
ccgggtcatc accgaggaca cggggcgcgc agggcgcgcg ccgccggccg gcggcgtcgt   7620
cgcctgggtc gatcagcagc cccccgcggc gggttgctca cgttcggcgg cgggcaggcg   7680
tccgcccggt gcgcgttcag accgggcttt cgatgtgcgc gcacagccgg gcgggcagtt   7740
cctgacggcg gctgatctcc agcttgcggt aggcgcgcgt caggtgctgc tccacggtgc   7800
tgacggtgat gcagagccgg gcggcgatct cccggttggt gtgcccgttg gcggcgagtt   7860
ccacgaccct gagctccgat ccgctcagcg ccgcctcggt ccgcccgtg ccgtccccga   7920
acgactgccg cccaggacct cccggcagga tccgctcgca cagagcccgc gccccgcagt   7980
cgttcgccag gtgccaggcg cggcggatcg tggcgcccgc ccgggtcgac tcgccgcgct   8040
cccggtaggc ggcgcccaga tcggccaggg cacccgccag ggccagccgg tcgccgctgc   8100
tcttcaggtg gttcacggcc tcggtcagca ggttcagccg atccggcggt tcggcgatct   8160
gcgcgcgcag ccgcagcgag acgccgcgca catgaggatc gtcgtccggg gtccgggcca   8220
gttgttcccg caggagccga tcggccctcc tcggctcgca cagccgcagg aacgcctccg   8280
ccgcgtccga gcgccacggc atcagcgtcg gccggtcgat cccccagcgc cgcagcagac   8340
ggccggcgcc gaggaagtcg cggacggcgg cgaggggccg gtccagggcg aggtagtagt   8400
ggccccgggc gcgcaggtag gcggggccgt acacgctgcg gaacagggcc tccggcaccg   8460
ggtggtcgag ctgccgggtg gcctcgtcgt agcgccccat cgcggtggcc gcgaacaccc   8520
ggctggccag cggcccgccg atgaagacgc tgcggctgca cctcggcacg caggccaggg   8580
cctgacgggc gtactcctcg gtgtcggcga gcagccccccg gcacagcgcg atctcggcct   8640
ggagggcgag gaactgcgcc ttccagcccg gcagccggcg accggcggcc tcgccgagca   8700
gacgtgtgca ccagagcgcc gcggtctcgt acgagccggt gcggcacagg acccggaccg   8760
cgttgacgac gatcaccagg gtggtgtcgg tgagcggcag gctcctcagg acgtgctccg   8820
ccgcgtcgga ggccgaggcg ttggtgccgt cgccggggag gtcccagatc ccggtcaccg   8880
gcatccgcgg gcgggggctc tcctcgtccc cgggctccgg gtccgtccgg ggacggatca   8940
gcggctccca gagcgcggag gcgtggaagc ccgtctccag ccggggagtt cgcgggtcgc   9000
cgtgggggcc cggccgtccc atgacctccg tggcctcctc cagccgtccg cagccgagca   9060
gcaggtgacc cagccgttcg gtctcggcgc tcgtcagtcg tccggcccgc agctcggtga   9120
```

-continued

```
cgagttcggc gaggtggtcc tccgccgccg ccgggtcggt gcgccgggtg gcgacggtca   9180
ggcgcagcag gatctcggcg cgccggggcc ctcccgcaca ggagcgccgg gccagttcga   9240
gacaggagac ggcggtcagg acgtcgtccc gcatcagcag ctgctcggcg gcgtcccgca   9300
gcacggacat cgcccagggc ccggccgcgt gccgggcggc gagcaggtgc cgggccacct   9360
cgtccggttc cgcgccgacg tcgtacagca gcgcggcggc gcggcggtgg aggtgtgcgc   9420
ggtggtcgtg gtccagggtg tccagggcgg ccgcctcgac cacggggtgc cggaagcggc   9480
cggacgccgt caggccggtc gcctccaggg cgcgcagccc gcgggccgcc atggcgcggc   9540
cgatgccgag cagccgggcg atcacctcgg cgcagccgga gtcaccgagg acggcgagcg   9600
cgccggcgct gtgcctaacc aggctgtcgg tgcgggacag tgaggcgagg acggcctggt   9660
agaaccgccc gccgatgacg ggcgacgctg ctctccggcg ccggccggca cgctcgtcgg   9720
tgtgcccttg ggtgtggctt tcgacgagtt cttcgagcag ggcatgcacc agcagcggat   9780
tgccgccggt gacggcgagg aggtcgtccg cgggcagggc ctcgacggcc ggtccggggc   9840
gggcggcgcg cagtccggac acggcgcgca gggagaggcg gccgagcatg acgcgctgga   9900
gggccggctg gcacagcagc tcggcctcca cggcggggtc ggccgccagg ccggacggca   9960
gcgcggtgca gaccagcagc agtcgggtgg cgcggggatg gtcgacggcc tggagcaggc  10020
agtgcaggga ctgcgggtcc gcgtggtgca ggtcgtcgat gccgatgacg accggcgcgg  10080
cgccggtgag ctggtggagc gccgcccgca cacgctgcgc ggccggggtc tccgtcccga  10140
cggcgtcctg gagcagtgag cgctgggcgt ccgggatgtc ggggtcgacc gccagttgcc  10200
gcaggaggtc gaaggggcgc cggccctccg gcgggcttcc ggcggaccgg aggaccagga  10260
agcccgatgc cgccgcgtgc ttgagcgcct cccccaggaa cgcgcttttc ccgcagccga  10320
gtcctccttc gacgaccagc acccgcaccc ggccggcggc gcacgcctcg agcgccgttc  10380
tcacggcatg ggactgcctg cccaggccga ggaacgtgag cccttgcggc tcccgcacgg  10440
acaccgaagg ggaaacgccc cgcataatct ccctctgact ccctcccccg aagaccgggg  10500
gctttacgga ttcgtaccaa caggaaagcc cacaagtcga cgagatactg cccctctccc  10560
gaagccgcca cacgcgcacc ccgatacgag aatgagccaa tgagcaagcg tggtggccga  10620
gttgatacga acccgtgaat ttacgttatt tcgctcaccc tttcgagcgt gtggagagtc  10680
ctcggaatgg gcggccggga ggttgggcag cctccgcggg acggcgagcc attcgcgagg  10740
tcacgcggac acgcgtgttg cgataatcgc acttaaggag aggacgagcg atgcccgacc  10800
tttgcgagac cgaatccctc tggctccggc ggttccagcc ggctcccgcg gcccggacgc  10860
ggctcatgtg cttcccgcac gcgggcgggt ccgccagcgc ctatctgcgc ctggcccggt  10920
ccctcgcccc cggcatcgag gtcctggcgg tccagtaccc cggacgacag gaccggcgcg  10980
ccgagccctg cccggactcc gtcgaaggcc tggcggacga tctgttcgcg gccgtccggc  11040
accgcgtgga cgcgtcgacc gcgctgttcg gacacagcat gggcgcggtc ctcgccttcg  11100
agctggcccg gcggctggag cgcgacgcgg gggtccgctg cgcccggatc ttcgcctcgg  11160
ggcgccgggc accctcccgg ttccgtgacg actccgcccc ggccgccagc gacgcctcga  11220
tgctcgccga gatgcggact ctcggcggaa ccgacctgcg ggtgctccag gacgaggaac  11280
tgctgatcgc cgcgctgccc gcgctgcgcg ccgactaccg cgcgatcggg acctaccgcg  11340
ccgccgacga cgccgtggtc ggctgcccgg tcaccgtgct ggtcggtgac gccgatccga  11400
ggaccagcct cgacgacgcc cacgcctgga gcgcccacac cacggcggag tccgaggtgc  11460
tcaccttctc cggcgggcac ttcttcctcg acgcccacca cgacgcggtg gtggaggtcg  11520
```

-continued

```
tcaccgcgcg cctgcggcag gaccgcgcgc cccggccgga ccgggtgtga gggggcccgg  11580
cccgaagggc cgggccgctc cgcgcgtctg ccggcaccgg gccgcaccgg acccggcgcc  11640
ggcagacgcg cggcgacctc acatcatggc gggcgccagg gccattcccc cgctggcgtc  11700
cagcagttgg ccggtgatcc agcgggcgtc gtcggagacc aggaaggcga cgatgccggc  11760
gatgtcgttc ggccggccca gccggccgag cgcggtcagg gccgagatgc ccgcctcggc  11820
ccccggggtc tcgcgcaccc agcggttcat gtcggtgtcc gtgatgccgg gggccacggt  11880
gttgacggtg atgccgcgcg aaccgagttc gttggcgagc cggggagcca tcatctccag  11940
cgccccccttg gtcatggcgt agggcagcag cggccaggcg atccgggtga cggccgagga  12000
gacattgacg atgcgtccgc cgtcggccat cagtgacagg gcccgctggg tcacgaagaa  12060
cggtgcccgg acgttgatgc ggtacacgcg gtcgaactcc tcgggcgtgg tgtccgacag  12120
gccggggaca tagccgtcct gtgccgcgag cgccgggtcg ccgggggcgg gggcgacggc  12180
cgcgttgttc accaggatgt gcagcggacg cccctccagc tcccgctcca gtgcggtgaa  12240
gagctcatcc acggcgtcgt cccggaggag gtccgcccgg accgcgaagg cccgtccccc  12300
cgcgcgttcg atcgtctcca ccgtctcctg ggcgctcttt tcctgcgttc cgtagtgcac  12360
ggcgacccgg acgccctcgg cggcgagtcg ctgggcgatg gcttttccga tgccgcgcga  12420
ggcacccgtg accaaggccg tcctgtcgtt caattccggc atcccgaatc cccttctgcc  12480
gattatctta cttttcctct tgatgcatgg ggtcggaccc gaggccagat ccgcaccccg  12540
gccacgcgtg aggtcgcgac ctcaccgatt actgtgccag agtccaggcg acacacggga  12600
gggcgggaat gcgatcgatt tccgcacccg gaactcgtag ggggagcaag aagatcggcc  12660
gaatacccct ggggtggata gggggtacca ggaccgtcgg gcgatcacta ttttgaaaca  12720
cgactccggc gcgcggccgg cggcgaaagt cctctccatg ccgggctgtc ccctgcctcg  12780
aaatacctgc ggcgactttc gccctgcgat gcggccgccc atccctgccg agcggtgagg  12840
agacgacaag tgcacgagac acacgcgcac ggcgaggaag ggtcgtccga cgggtccgcg  12900
gacgcagtgg tcttcgtctt ccccggacag gggtctcagt ggccggggat gggtgcggaa  12960
ctgtgggaca cctccccggt gttccgcgag agtgtgcgcg cctgcgccga cgcgctcgcc  13020
ccgtacctcg actggtccgt cgaaggcgtc ctgcgcggcg ccccggacgc cccggccggc  13080
ccggcgctcg atcgcgccga cgtcgcgcag ccggccctgt tcaccctcat ggtgtcgctg  13140
gccgagctct ggcgctcgca cggagtcgaa ccctgcgccg tcctcgggca cagcctcggc  13200
gagatcgccg ccgcgcatgt ggccggcgcc ctgaccctgg ccgacgccgc ccgggtggcg  13260
gccctgtgga gccgggccca ggccacgctg tcgggcaccg gcacccttct cgcggccaag  13320
gccgcccccg aggaactggc accgcacctt cagcggtgga acggcgacga ccggcacggc  13380
acccggctcg cgatcgccgg cgtcaacggg cccggcagca cggtggtggc gggggacctc  13440
gacgcgatcg ccgcgctggc cgccgacctg gcctcggcgg gggtgcggac ccgccgggtc  13500
gccgtcgacg tgcccaccca ctcccccgcg atgcggaccc tgcgggaacg gatcctcacc  13560
gacctggcct ccgtcgcccc gtgcgtctcc cgtctcccct tccactcctc gctcaccggc  13620
ggtctggtgg acacccgcgg gctggacgcc gactactggt accgcaacat cagcgagacc  13680
gcgcgcttcg acctcgccgc ccgcggtctc ctggccgacg gacaccggac gttcgtggag  13740
ctgagcccgc acccgatact caccctgggc ctgcaagcgc tcgccgacga cgtccccggc  13800
gccgccgacg cgctcgtgac gggcacgctg cgccgcgggc gcggcggaat gcggcagttc  13860
```

-continued

```
caggacgcgc tcggccggct cagcgtcccc gcgggcgggc ggcccggccg cgaggtgagc  13920
gccgcggccc tggccggccg gctggcgccg ctctccccgg cgcagcagga gcatctgctg  13980
gtggaattgg tctgcgccca cttcgccgca ctcgtcggcg gcgacggcgg ggcgccgccg  14040
acggtgcggc cgtcggccgc cttcaccgat cagggctgcg actccgccac cgccctggag  14100
ctgcgcgacc ggctccgcga ggcgaccggg ctgcgcctgc ccgccacgct ggtcttcgac  14160
cacccgacgc cggccgcggt cgccggccgg ttgcgccgac tcgccctcgg gatcgaggag  14220
acggcggaca cggcaccggt cgccgtccgc ggccaccggg agggcgaacc gatcgcgatc  14280
gtcgggatgg cctgccgctt cccgggaggt gtccggtcgc cggaggacct gtggcggctg  14340
gtcaccgaag gcggtgacgc gctcgggccg ttccccaccg accgcggctg ggacaccggc  14400
cgccacgcgg aggacccggc cacacccggc acctacgtcc agggcgaggg cggattcctg  14460
tacgacgcgg gcgagttcga cgccgagttc ttcgggatct ccccgcgtga ggcgctggcc  14520
atggacccgc agcagcggtt gctgctggag atggcgtggg agaccttcga acgggcggga  14580
atcgatccca cctcggcccg gggatcgcgt accggcgtct tcgccggggt cctcccgctc  14640
ggctacggcc cccgcatgga cgagacggac cagggcaccg ccgacctcca gggccatctc  14700
ctcaccggca cactgcccag cgtcgcctcg ggccgcatct cctacaccct cggcctggag  14760
ggcccggcgg tgtcggtgga gacggcctgc tcgtcgtcgc tcgtcgccct ccacctcgcc  14820
tgccgctcgc tgcgggcggg cgagtgcgac ctcgccctga cggggggcgt ctcggtgctg  14880
gccaccctcg gcctgttcgt cgagttctcc cggcagcgtg gactgtcggc ggacggccgg  14940
tgcaaggcgt acgcggcggc ggccgacggg accggatgga gcgagggtgc cgggctgctg  15000
ctggtcgaac ggctctccga cgcacggcgg ctggggcacc gggtgctcgc ggtggtccgg  15060
ggcagcgcga tcaaccagga cggcgcgtcg aacgggctga ccgcccccag cgggccgtcc  15120
cagcagcggg tcatccgcga ggccctggcc gacgcgggcc tgacggcggc ggacgtcgac  15180
gcggtggagg ggcacgggac cggcacacga ctgggcgacc cgatcgagat cgaggcgctg  15240
ctcgccacct acggacaggg acgcgcccgg gaacggccgc tgtggctcgg atcgctgaag  15300
tcgaacatcg gtcacaccat ggccgcggcg ggggtgggcg gggtcatcaa gatggtgatg  15360
gcgctgcggc acggggagct gccccgcacc ctgcacgtgg acgcgccctc gccccgggcc  15420
gactggtcgg cgggcgaggt acggctgctg acggaggccg tcgcgtggcc cgcggcggcg  15480
gacggtgagc cgcggcgggc cggggtgtcg tccttcggcg tgagcggcac caacgcgcac  15540
gccatcctgg aggaggcgcc cgccccggag gacgaggaac cggcgccgcc ggacggtgaa  15600
gcactactgc cgtgggcggt gtccacgcgg tcggaggccg cactgcggac gcaggcacgg  15660
atgctggcgg acgtcgtacg cgacgacccc ggagtcggac tcgccgatgt gggtgcggag  15720
ctggcccggg ggcgggcggc tctcgagcac cgggccgtcg tcatcgcctc cgggcgcgcg  15780
gagttcgcgc gggcgctgga ggcggtggcg tccggcgagc cgcacccggc cgtggtccgg  15840
ggccacgcgg ggagcgagcg cggcggagtg gtgttcgtct tcccgggcca gggcggtcag  15900
tgggccggca tgggactcga cctcctgcga agctcaccgg tgttcgcgga gcacatcgcg  15960
gcctgcggca aagctctggc cccgtgggtg aagtggtcgc tcacggaggt gctgcaccgg  16020
gacgccgagg atccggtctg ggaccgggcc gacgtcgtcc agccggtgct gttctcggtc  16080
atgacgtcgc tggcggcgct gtggcgctcg tacggcgtcg agccggacgc cgtgaccggg  16140
cactcgcagg gggagatcgc cgccgcgtac gtctgcggag cgctcggtct ggaggacgcc  16200
gcacggacgg tggcgctgcg cagccgcgcc ctggtggcgc tgcgcgggcg gggcggcatg  16260
```

-continued gcgtccgtcg cctccgccgc cccggacgtc gaggagctca tcgcgcggcg ctggcccggc 16320
cggctgtggg tcgcggcgtt caacggcccc ggcgcggtga ccgtttccgg ggacggtgat 16380
gcgctggagg agttcctggg ccactgcgcg gacacggagg tgagggctcg gcgcgtcccg 16440
gtggactacg cctcccactg cccgcacacg gaggcgatcg agcgggaact gctcgacgcc 16500
ctggaggaca tcacccccg gccggcggcg gtcccgttct attcgacggt cgacgacgcg 16560
tggctggaca ccacacggct ggacgcctcc tactggtacc gcaacctgcg ccggcccgtc 16620
cgtttcagcc aggccgtgcg cgccctcacg gacggcggcc accgcgtctt catcgaggcg 16680
agcccgcatc ccaccctcgt ccccgccatc gaggaccacg gcgacgtcac cgccctcggc 16740
accctgcgcc gccacggcga cgacaccgag cggttcctca ccgccctcgc ccacctccat 16800
gtcaccggag ccgccggcca ggacctctgg cgccaccact acgcccggct caggcccgcc 16860
ccccgccacg tcgacctgcc cacctacgcc ttccagcgcg accggtactg gtggagcggc 16920
ggcgccgggc gcggggacgt caccaccgcc ggtctgcacc ccggcggcca tcccctcctc 16980
ggcgccgcgc tggacctcgc cgacggcggc ggccgcctcc acaccggccg tgtctccctg 17040
cgcacccacc cctggatcgc cgaccacggc gtcgcgggca tcaccctcct gcccggcacc 17100
gccttcctcg aactcgccct gcacacgggc gagtcgggga acgtgcggga actcaccctg 17160
cacgcgcccc tggtcgttcc cgacgaggag ggcgtcgacc tgcaagtgca cctcgcccgg 17220
cccgacgaag cgggcctgcg cgccctgacc cgtcttctcc cgggccgcgg ggtgccgacc 17280
ccgagagccc cctggcagcc ccacgccacc ggccttctcg ggccggccga ccgagcaccc 17340
ggctcctccg gcctcgagcc gcacgacctg ggcggcgcct ggcctccgcc gggggcggtc 17400
cccctcgtcc ccggcgaact cggcgacgtg cccggctgct acgcccgcct ggccgacgag 17460
gggttcgagt acgggccggc cttccggggg ctgcgtgcgg tgtggcgccg cggcacggag 17520
atcttcgccg aggtcgccct cccggccggc gacggctccg tgttccggct gcatccggcg 17580
ctgctggacg ccgtgctgca ccccgtcgta ctcgggctgg tggacggcgt gccggcccgt 17640
ccgctgccct tctcctggaa cggcgtggcg ctgcacgccc ccgcgagcgg cgcgctgcgg 17700
gtgcgcctcg cgccggccga cgacggcgct gtcggcatca cggccgcgac ggccgccggt 17760
gagccggtgc tctcggtcgc cgcgctggcc ctgcggtccg cctcggcgga gcagttgcgc 17820
gcggcgatcc gctccgcggc gggctcgcgc gacgccctct acgagctgga ctggctgccg 17880
ctcccggcgg accgggccgc ttcgcccggt ggggccgaca tcgcggccct gggcacatcg 17940
gagctgccct gccgtacgta cgagaccatc gcggagctgt cgcaggccct cgccgacggt 18000
gctcccgccc ccgacgccgt cgtctccgac gtcggcgccg tcggcgggcc gctggacacc 18060
gtgagcctgc acggcctctg ccggcgcggg ctggaactcg tgcaagcctg gctgggcgag 18120
ccccggacgg ccgacacgcg gctggtgctc gtgacgcgtg gggcggtcgg ctgtgccccg 18180
gccgagccgg tcgccgatcc ggccgcggcc gcgctgtggg ggctggtgcg gtccgcgcag 18240
gcggagcacc ccggacggct gctcctgctg gacctcgacc ccgccgggtc gcggcccgtc 18300
tccggccgcc tggtggaaca ggcggtggcc tgcggtgagc cgcacatcgc cgtacggggc 18360
gacggcctgc gcgtcccccg gttgtcccgc gcgacggccg cccccgcaca ccctcccgcc 18420
ggtggccggg aagcgcagtg ggacccggaa gggaccgtcc tcatcaccgg cggcaccgga 18480
agtctcggcg cgctgttcgc ccggcatctg gtgaccgcgc acggggtacg gcggctgctc 18540
ctcgccagcc gcagtggccc cggcgccccc ggcgccgccg ggctgcggga cgaactgacc 18600

-continued

```
gctcacggag ccaccgtcac cgtcgccgcc tgtgatgtgg ccgaccggga ggccgtcgcc  18660
gccctcctgg cgtccgtgcc gtccgagcac ccgctgaccg ccgtagtgca caccgccggc  18720
gtgctggacg acggcgtact cgcctcgctc accgccgacc ggctggcccg cgtcctgcgt  18780
gccaaggccg acgccgcgct ccacctgcac gatctcaccc gcgatctgcc gctcgccgcc  18840
ttcgtcctct tctcctccgt cacggcgacg ctcggcacac ccggccaggc caactacacc  18900
gccgccaacg cgttcctcga cgcgctcgcc cggcatcggc gcgccgcggg cctgcccgcc  18960
gtctcactcg cctgggggct gtgggagcag accggcgggc tgaccgatca cctcggatcg  19020
gtcgacctgc ggcggatggc ccgcaacggc ctggtcgcgc tgcccgccga cgccggcctg  19080
gcgctcttcg acaccgcgct ggccctggac cgcgccaacc tggtcccggc gcggctcgac  19140
ctgcccgcgc tgcgccgcgc cacacacgtg ccgcccgttc tgcggcggct ggtcgaggtg  19200
ccgggggcgc cgagcgcgga ccggtccgcc gggtccggcg gcgaggtgag gccgctgcgt  19260
gagacgctgg ccgggctgga cgaccggaaa cgcccgctg ccgtctcccg cctggtccgc  19320
aggcacgtcg cgtgggtgct cggcgccgac ggtccggagt cggtggacga ggaccgcagc  19380
ttccgcgacc tcggcttcga ctcgctgatg gccgtcgaac tgcgcaacca gctcaacacc  19440
gccgccggca tccggctcgc ggccaccctc gtcttcgacc acccgacacc gtcggccgtg  19500
gcgcggcacc tcctcgaccg gtgctcgccg gacccggccg ccccggccgc tccctcgggt  19560
acggcggtcg cgtcggcgct cgccactctg gccgagctgg agacggcttt gaacggcatc  19620
ccggccgagg agtggacggc cgccgggggc ccggcccggc tgatgacgct ggcgtcctcg  19680
ctgcccgcgc ccgcgtccgt ccctcggaca ccggcggccg gcgaagccgc cgagaagctc  19740
gcccacgcct cgcgcgacga gatcttcgcg ttcatcgatc gggagctggg gcgtgactcc  19800
gggccagcct caccctctcg cctcggtccg cagacccccg actcgacaga caaggcgccc  19860
tttcatggag aatgaggaaa agctcctgga ctacctcaag tgggtcaccg ccgatctgca  19920
ccgctcgcgg gaacgcgtca ccgagctgga ggaggccggc cgggagccga tcgccatcgt  19980
cgggatggcc tgccggttcc cgggcgaggt gcggtcgccg gaggagctgt gggggctggt  20040
cgcctcgggc ggcgacgcga tcggggcgtt cccggacgac cgcgggtggg atctggacgg  20100
gctgttcgac cccgacccgg agcgtgcggg cacctcgtac acccggcgcg gcggtttcct  20160
gtacgacgcg gcggagttcg acgcgggctt cttcgggatc tccccgcgtg aggcgatggc  20220
gatggacccg cagcagcggc tgctgctgga gacctcgtgg gaggctttcg agcgggccgg  20280
catcgacccg tcctcggtac gcgggtcccg ggtcggtgtc ttcgccggcc tcatgtacca  20340
cgactacgcg gcggcccagg gcagcaccgg ggacggagac ggggagccgg acttcgaggg  20400
ctacctcggc gacggcagcg tcagcagcat cgcctcgggc cgtatcgcct acaccctcgg  20460
gctcgcgggc gcggcgatca ccgtcgacac ggcctgctcc tcttccctgg tcgccctgca  20520
cctcgcctgc caggcgctgc gcaccggcga ctccgagctg gccctggccg gcggggtcag  20580
cgtcatgtcc accccccgca ccttcgtcca gttctcgcgg cagcggggcc tgtcggcgga  20640
cggccggtgc aaggcgtacg cggcggcggc cgacgggacg gggttctccg agggcgtcgg  20700
catggtgctg gtcgaacggc tctccgacgc ccggcggctg gggcatccgg tactggcggt  20760
cgtgcggggc agcgcggtca accaggacgg cgcgtcgaac ggtctgacgg cgcccaacgg  20820
accgtcgcag gagagggtga tccgcgaggc gctggccaac gcgggcctga cggcggcgga  20880
cgtcgacgcg gtggaggggc acgggaccgg gacacggctg ggtgacccga tcgagttgca  20940
ggcgctgctc gccacctacg gacagggacg cgcccgggag cggccgctgt ggctcggatc  21000
```

-continued ggtgaagtcc aacatcggtc acgcgcaggc ggcggcgggg gtgggcggcg tcatcaagat 21060
ggtgatggcg ctgcggcacg gggagctgcc gcgcaccctg cacgtggacg cgccctcgcc 21120
ccgggtcgac tggtcggcgg gcgaggtacg gctgctgacg gaggccgtcg cgtggcccgc 21180
ggcggcggac ggtgagccgc ggcgggccgg ggtgtcgtcc ttcggggtga gcggcaccaa 21240
cgcccatgtg atcctggagg aggcgcccgc gtcggagggc gaggaagctc cgccgccgga 21300
gcccgggtcg ccgttgccgt gggtggtgtc cggtcactcg gaggcgggct tgcgcgccca 21360
ggcgcaggct ctggcggagt tcgcacggac cgcgcccggg gccgaactcg tggacgtggg 21420
agcggcgttg gcccgggggc gggcggcgct ggggcatcgg gcggtcgtcg tcgcctcgga 21480
gcgtgaggag ttcgagcggg cgctggccgc gctggcctgt ggcgaaccgc acccgtgtgt 21540
ggtcgacggg tcggcggacg gccggcgcga ggacggtgtg gtgttcgtct tcccgggcca 21600
gggcggtcag tgggccggca tggactcgga tctgctgacg acctcggggg tgttcgccga 21660
acatatcggt gcgtgtgaac gcgcgctggc gccgtgggtg gagtggtcgc tgacggagat 21720
gctccaccgc gaggcggagg acccggtgtg ggagcgggcg gacatcgtcc agccggtgct 21780
gttctcggtc atggtgtccc tggccgcgct gtggcggtcc tacggcatcg aacccgacgc 21840
ggtggtcggc cactcccagg gcgagatcgc cgccgcccac gtctgcggcg ccctcaccct 21900
cgaagacgcc gcgaaagtcg tggcactgcg cagccgggcc ctggccgcac tgcggggccg 21960
cggcggcatg gtctccctct cgctgtcgac cgcggatgcc ggggagctgg tggagcggcg 22020
gtgggccggg cggctgtggg tcgcggcgct caacgggccg gaggcgacga cggtctcggg 22080
ggacgtcgac gcgctggagg agctcctggc ccactgcgcg aaaagcgagg tgcgagcgcg 22140
gcgcgtcccg gtggactacg cctcccactg cccgcacacg gaagcgatcg cggaagagat 22200
cgtcgattca ctcggggaca tcacgccccg ggccgccacc gttccgttct actcgacggt 22260
cgacgacatg tggttggaca ccacacggct ggacgcctcc tactggtacc gcaacctgcg 22320
cctcccggtc cgcttcagcc aggccgtgcg cgccctcacg gaagaaggcc accgcctctt 22380
catcgagacg agcccgcatc ccaccctcgt ccccgccatc gaggaccacg gcgacgtcac 22440
cgccctcggg accctgcgcc gccacggcga cgacaccgag cggttcctca ccgccctcgc 22500
ccacctccat gtcaccggag ccgccggcca ggacctctgg cgccaccact acgccaggct 22560
caggcccgcc ccccgccacg tcgacctgcc cacctacccc ttccaacgcc ggcgctactg 22620
gctggagaaa cccgacccgc agaccaggcc ccagcggtcc cgctccaccg ccccggacct 22680
cgacaggctg gaggcggagt tctggcaggc cgtcgaggaa accgacaccg acaccctcgc 22740
ccacaccctc cacctcgaca cccagaccct cgaacccgtc ctccccgccc tcgccacctg 22800
gcaccaacaa caacgcgacc acgcccgcat caacacctgg acctaccagg aaacctggaa 22860
accactccac ctccccacca cccgacccac cacccccacc agctggctca tcgccatccc 22920
cgaaacccac cgcaaccacc cccacaccac caacctcctc accaacctcc cccaccacaa 22980
catcaccccc atcccccta ccatcaacca caccaccgac ctccaccacg cctaccacca 23040
cgcccaccac cacaccaccc cacccatcac cgccgtcctc tccctcctcg ccctcgacga 23100
aacaccccac ccccaccacc cccacacccc caccggcacc ctcctcaacc tcaccctcac 23160
ccaaacccac acccaaaccc acccaccaac cccctctgg tacctcacca cccaagccac 23220
caccacccac cccaacgacc ccctcaccca ccccacccaa gcccaaacca tcggactcgc 23280
ccgcaccacc cacctcgaac acccccacca caccggcgga cacatcgacc tccccaccac 23340

-continued accccacccc aacaccctca cccaactcat caccgccctc acccaccccc accaccaaca 23400
caacctcacc atccgcaccc acaccaccca cacccgacga ctcaccccca ccaccctcca 23460
acccaccacc cccacaccac ccaccaaccc ccacggcacc accctcatca ccggcggcac 23520
cggcgccctc gccaccaccc tcgcccacca cctcgccacc accggcaccc aacacctcct 23580
cctcaccagc cgacgcggcc cccacacccc cggcgcccga caactccaca cccaactcac 23640
ccaactcggc accaacacca ccatcaccgc ctgcgacctc tccgaccccg accaactcac 23700
ccacctcctc acccacatcc cccccgaaca cccccctcacc accgtcatcc acaccgccgg 23760
catcctcgac gacgccaccc tcaccaacct cacccccacc caactcgaca acgtcctgcg 23820
cgccaaagcc cacaccgccc acctcctcca ccacgccacc ctccacaccc ccctcgacca 23880
cttcgtcctc tactcctccg ccgccgccac cctcggcgcc cccggccaag ccaactacgc 23940
agccgccaac gcctacctcg acgccctcgc ccaccaccgc cacacccaca acctccccgc 24000
caccaccatc gcctggggaa cctggcaagg aaacggcctc gccgactcgg acaaggcccg 24060
cgccaacctc gaccgccggg gcttcctgcc catgcccgag acgctggccg cagccgcggc 24120
cgtgcgggcg atcgagagca ggcggccgtc cgtggtcatc gccgccatcg actgggccag 24180
agccgagcgc acccccgacg tcgaggatct cctccccgcg gccgacgagg ggtcgtcgag 24240
tggcaagccg gaggccgcgc cggtggacct gcgcggtacc ttgagccggc agtccgccgc 24300
cgaccaacag gccacactgc tcggcctggt gcggacccag gcagccgtcg tactgcgcca 24360
cacggagccc gaggcgctcg ccccgggcca ggccttccgg gcgctcggct tcgactccct 24420
caccgccgtc gaactccgca accgactggc caaggccacg gacctcgcgc tgcccgcctc 24480
actggtcttc gatcacccga ctccggtgaa gctcgcggag ttcctgcgca ccgagctgct 24540
cggcaccgca ccagctacca ccgccgccgt cccggccctc caggcacaca ccgacgaacc 24600
catcgccatc atcggcatgg cctgccgctt ccccggcgcc gtcaccacac ccgaacacct 24660
gtggaacctc atcgccaccg aacaagacgc catcggcgag ttccccaccg accgcggctg 24720
ggacctggac aacctctacc accccgaccc cgaccacccc ggcaccacct acacccgcca 24780
cggcggattc ctccacgacg ccggcgactt cgacgccgac ttcttcggca tcaacccacg 24840
cgaagccctc gccatggacc cccaacaacg actcctcctc gaaaccgcct gggaagccat 24900
cgaacacgcc ggcatcctcc ccgacgccct gcacggcacc cccaccggcg tcttcaccgg 24960
cgtcaacgcc caggactacg ccgcacacac ccacacctcc ccccacacca ccgagggcta 25020
caccctcacc ggaaccgccg gcagcatcgc ctccggccgc atcgcctacg tcctcggact 25080
cgaaggcccc gccgtcacca tcgacaccgc ctgctcctcc tccctcgtcg ccctccacct 25140
cgcctgccag gccctgcgag caggcgaatg caccacagcc ctcgccagcg gcatcagcat 25200
catgaccaca ccgctggcct tcaccgagtt ctcccggcag cggggtctgg cggcggacgg 25260
ccggtgcaag gcgttcgcgg cggccgccga cggtaccggc tggtcggagg gggtggggac 25320
gctgctgttg gagcggttgt cggacgccga gcggaacggg caccgggttc tggcggtggt 25380
gcggggcagc gcggtcaacc aggacggcgc ctccaacggg ctgacggcgc cgaacggtcc 25440
gtcccagcag cgtgtgatcc gccaggccct ggtcaacgcg aacctctccg cagttgatgt 25500
cgacgccgtc gaagcccacg gcacggggac caagctgggc gacccgatcg aagcccaggc 25560
cctgctcgcc acctacggcc agggacgtgc gcaggaacag ccactgtggc tcggttcggt 25620
caaatccaac ctgggtcaca cccaggcggc ggcaggcatg gccggcctga tcaagatggt 25680
gatggcgctg cggcacgagt cgttgccgcg gacgttgcat gtggatgagc cgtcgccgga 25740

-continued

```
ggtggactgg tcgtcggggg cggtgagtct gctgaccgag gcgcggccct ggccgcgggt  25800
cgaggaccgg ccccggcggg ccggggtgtc ctcgttcggg gtgagcggga cgaacgccca  25860
cgtcatcgtg gaggaggcgc ccgcgccgac gggagtggag gcggtggaag ccgcgccggc  25920
gggggtggag actgcggcgg ctgcggcggt ggtggtggag acggacggtg cgggccgggt  25980
gtcggcggat ctgccgttgg tgtgggtggc gtcgggcaag tcgcaggccg cgatacgcgc  26040
ccaagccgcc gccctgcacg cccacgtcct ggaccacccc gaacaggacg cggacgacat  26100
cggctacagc ctggccacca cccgcgccct gttcgaccac cgcgccaccc tcatcgcccc  26160
cgaccgccac accgtcccgg agcccctcac cgggctgggc gacggacgca cgcaccccca  26220
cctcatcccc acacccccca ccgaacccgg ccacacccac aaaatcgcct tcctctgctc  26280
cggacaaggc acccaacgcc ccggcatggc caccggcctc taccacacct accccgcctt  26340
cgccgccgcc ctcgacgaaa cctgcgccca cttcgacccc cacctcgacc acccccctgca  26400
cgacctcctc ctcaaccacg accccaccga cctcctcacc cacaccctct acgcccagcc  26460
cgccctcttc accctccaaa aagccctcca ccacctcatc accgaaacct acggcatcac  26520
cccccactac ctcgccggac actccctcgg cgaaatcacc gccgcccacc tcgccggcat  26580
cctcaccctc cccgacgcca cccacctcat caccacccgc gcccgcctca tgcaaaccat  26640
gcccccccggc accatgacca ccctccacac cacccccgaa cacatccaac ccctcctcga  26700
ccaacacccc ggcaaagccg ccatcgccgc cgtcaacagc cccactccc tcgtcatcag  26760
cggcgacccc gacaccatcc accacatcac caccacctgc cacaaccaag gcatcaccac  26820
caaacccctc gccaccaacc acgccttcca ctccccccac accgacacca tcctcgaaca  26880
actcgacacc accacccaca ccctcaccta ccaccaaccc cacaccccc tcatcaccag  26940
cacccccggc gacccccctca ccccccacta ctggacccac cagacccgcc aacccgtcca  27000
ctggaccgac accatccaca ccctccacac ccacggcgtg accacgtaca tcgcactcgg  27060
accagagcac accctcacca ccctcaccca ccacaacgtc ccccaccacc aacccaccgc  27120
catcaccctc acccacccc accacaaccc cacccaccac ctcctcaccg cactcgccca  27180
cctccacaca acccaaccca ccggccccaa catctggcac caccactaca ccccagtcgc  27240
acccgccccc cgccacgtcg acctgcccac ctaccccttc ccacgccggc gctactgggt  27300
gcaggcgtcc gccggtacgg gtgacgtgtc ggctgccggg ctccagcgac cggaccaccc  27360
actgctcggc gcggtgatgg agctcgcgga cggggacgga atcgtcctca ccgggcgctt  27420
gtccctgcac acccacccct ggctcgccga ccacagcgtc ggcggcgtcg ccctccttcc  27480
cggtaccgct ctgctggagc tggcttttca ggctggtctg cgtgcgggtt gtcctggtgt  27540
cgatgagctg actctccatg ctcctctggt ggttccggag tcggggcatg tggtggtgca  27600
ggtgtcggtt tcggtgccgg gcgaggcggg tcgtcgtggt gtgagtgtgt acgggcggct  27660
ggtggaggac ggggggctgg agggtgagtg gacgcggcat gccgagggtg tggtgtgtcc  27720
gtctgttcct ggggagtcgg tggttgtgga gccggtggcg gacggggtgt ggccgccgtc  27780
cggtgcgcag ccggtggatc ttgaggagtt ctacggtcgt ctggcgggtg ggggttttgt  27840
ctacggtccg gtgttccagg gtttgtgtgc ggcctggcgg gacggggacg acgtggtggc  27900
cgaggtgcgt ctgccggacg aggggctggc cgatgtcgcg ggcttcgggg tgcatccggc  27960
gctcctggac gcggccgtgc aggcagtcac cctcctgttc ccggaccagc agcaagccgg  28020
tctcgcggcc cacacatgga acggtgtctc gctccacgcc cggggcgcca ccgtcctgcg  28080
```

-continued

```
cctgcgcatg actcccaccg acgcgacctc gaccgccgtt cgcctgcacg ccaccgacga  28140
gaccggagca cccgttctca ccctcgactc gctcctgatg cgtccggtgc cgttggaggg  28200
gctgggggcg ggggtgcggc gtggctcgtt gttcgagctg gggtgggtgc cggtggaggg  28260
gatgccggcc tcggtggccg gtgggggcgg ggagttggtg gcgtgggagt gcccgggtgg  28320
tggggtggcc gaggtcacgg ccgcggcgtt gggagtggtg caggagtggc tcgccgatga  28380
gcgggagggg gacgcgcggc tggtcgtggt gacgcgtggt gcggtcgcgg tggatgcggg  28440
ggagccggtg cgggacgtgg cgggggccgc tgtgtggggg ctggtccgct cggcccagtc  28500
cgagcatccc gaccggttcg ccctgctcga cctcgacccc gacaccaaga ccgaccccgg  28560
catcgacacc gacggggaca ccgacgtgtc cgccgacgcg aaggtcggca ccggtgatgg  28620
tctcgacgat gccgccgtcg cgtccgctct ggcccgcggt gagagccaac tcgccgtacg  28680
cgacggggtg gttcgcgtag cgcggttggg gggtttggtt ggggggttgt cgttgcctgg  28740
tggggtgggg tggcggctgg atggtggtgg gtcggggttg ttggaggggg tgggtgtggt  28800
tgcttcggat gcggctgggg tggtgctggg tcgggggcag gtgcgggtgg cggtgcgggc  28860
tgccggggtg aacttccggg atgttctggt ggcgttgggg atggtgccgg gtcaggtggg  28920
ggtgggcagt gagggtgcgg gggtggtggt ggaggtgggg cccggggtgg agggcctggt  28980
ggtgggggac cgggtgttcg gggtgttcgg ggacgcgttc gcgccggtgg tggtggcgca  29040
ggaggtgttg ctggcccgta tcccggaggg ctggtcgttc gcgcaggcgg cttcggtgcc  29100
ggtggtgttc gctaccgctt acctgggact ggtcgatctg gcgggggtgc ggcgggggga  29160
gagtgtgctg gtccatgcgg cggccggcgg ggtcggtacc gccgcggtgc agctcgcccg  29220
tcatctgggg gcggaggtgt atgcgacggc cagtgaggcg aagtgggcgc gtctgcgggc  29280
ggcgggtgtc gcgccgcagc ggatcgcgtc ctcgcggagt gtggagttcg agtcccgttt  29340
ccgccgggcc agtggcggcc ggggtgtgga tgtggtgctg aactgtctgg cgggtgagta  29400
caccgatgcc tcgttgcggc tgtgttcgcc gcagggggcc cggttcctgg agctgggcaa  29460
gaccgacatc cgtgatgccg gtgaggtcgc cgctcggttc ccgggggtgt cctaccgggc  29520
gtatgacctg atggacgcgg gtgcgcagcg ggtgggggag atcctgcaca cggtggtgga  29580
tctgttccgg cgcggggtgc tggagccgtt gccggtcacc gcgtgggacg tgcgccaggc  29640
ccatcaggca ctgcggtcga tgcggtcggg cctgcacgtc ggcaagaacg tgctcaccct  29700
gcccgtgccc ctggatgcgg aggggacggt gctggtgacg ggcgggaccg gcactctggg  29760
ggcggcggtc gcgcgccatc tggccgccgg gcacggggtg cggcatctgc tgctggtgag  29820
ccggcgcggc atggccgccg ccggtgccga aaaactgtgt gcggaactgg gtcaggcagg  29880
ggtttcggtg tcggtggccg ggtgtgatgt cgccgaccgc gcccaggtcg ccgccctgct  29940
ggagcaggtg cccgcggagc atccgctgac cgctgtggtg cacacggccg gtgtcctgga  30000
cgacgccacc gtgacctgcc tggaccggaa caagatcgat gcggtgctcg ggcgaaggt  30060
ggacggtgcc ctgcacctgc acgagctgac cgcggggatg gacctgtcgg cgttcgtgct  30120
gttctcctcc gccgccgggg tcctgggctc gccggggcag ggcaactacg ccgccgccaa  30180
cgccgccctg gacgccctgg cccaccagcg ccgcgccgcc ggtctgcccg ccctctccct  30240
ggcctgggga ctgtgggaag aggccagcgg gatgaccggc catctggatg ccgctgaccg  30300
tcaccgcatc acccgctcgg ggctgcatcc cctgaccacc cccgacgccc tcgccctcct  30360
cgacaccgcc ctggccgccg gacgccccgc actcctgccc gccgacctac gccccaccca  30420
ccccgcaccg cccctcctgg aacacctcgc gcccgcccgc accagccacc gcaccgcaca  30480
```

-continued

```
caccagcacc gcaaccggcg tgggccagga cgtctccctc accgaccgcc tcgccaccct  30540
gacccccgaa cagcggcacg acaccctgct ggcgctggcc cgtacccaca tcgccgccgt  30600
cctgggccac cccagccccg acaccatcga ccccgaacgc accttccgcg acctcggctt  30660
cgactccctc accgccgtcg aactccgcaa ccggctcacc cgcgccaccg gcctgcgcct  30720
gcccgccacc ctcgccttcg accaccccac ccccaccgca ctcacccacc acctcaccac  30780
cctcctcaac cccaacgaca acgacaacgt cggtccggta ctgatggagc tcgaaagact  30840
ggaatccgct ctcgccgcgc tggacaggga cgacagcgcc tgcgagcggg tcactctgcg  30900
actgcaatcg ctgatgctca ggtggagcgg ctccgagcgg cagtcagccg aaaacacgga  30960
cgactccagc aggttcgcgt cggcgaccgc ggaggagcta ctcgaattca tcgaccgaga  31020
cctgggtctt tcctgaacca gctcggtctt ccctgaacca gctcgacgac gcggttttcc  31080
cgtgcgcgac ggactccaag gacgtgaacc agacgtggcg aatgacgaga aggtgctcga  31140
atacctcaag cgagtcaccg cggatttgga ccggaccagg cggcgcctgt acgaagtcgt  31200
cgagcgggag caggagccga tcgccatcgt ggggatggct tgccgttatc cgggcggggc  31260
cgggtcgccc gcaggtctct gggacctcgt cagctccggt acggacgcca tcggggagtt  31320
ccccaccgat cgtggctggg atctggaacg tctctacgac cccgaccccg atcacccggg  31380
caccacgtac acccgccacg gcggattcct cgacggcgta ggtgagttcg acgcggagtt  31440
cttcggcgtc agcccgcgtg aggccctggc gatggacccc cagcagcggc tcctcctcga  31500
aaccgcctgg gaagccatcg aacacgccgg catcgtcccc gagtcgctgc gcggcacgtc  31560
caccggcgtc ttcgccggta tcaacccgca ggactacacc atcagtcagt acggacggga  31620
ttcggagatc gagggctatc tgctgaccgg ggcagccgcc agtatcgcct ccggccgtat  31680
ctcctacacc ctcggcctcg aaggcccagc cgtcaccatc gacaccgcct gctcctcctc  31740
cctcgtcgcc ctccacctgg cttgccaagc gctgcgcgca ggggagtgca ccatggccct  31800
ggcgggcggc gcctcggtcc tgtccacacc gctgatcttc gtcgagttcg ctcgccatca  31860
cggcctgtcg gtcgacggcc ggtgcaaggc gttctccgct tcggccgacg gcacgggctg  31920
gggcgagggc gccggcctgc tcctcctcga acggctctcc gacgccaagc gcaacggccg  31980
ccgcatcctc gctctcgtac gggggagcgc ggtcaaccag gacggcgcct cgaacgggct  32040
gacggcgccg aacggaccct cccagtgcag ggtcatccgc cgggccttgg ccaacgccca  32100
tctcgccccg gccgacatcg atgccgtgga agctcacggc accggcacca ccctgggcga  32160
ccccatcgaa gcccaggccc tccaggaagc gtacggcgcg gaccgacccg acgatcggcc  32220
gctctgggtc ggcacgctca agtcgaacat cggccactcg atcgccgcgg cgggtgtggg  32280
cggggtcatc aagatggtga tggcgctgcg gcacgagtcg ttgccgcgga ccttgcatgt  32340
ggatgagccg tcgccgcagg tggactggtc gtcgggtgcg gtgagtctgc tgaccgaagc  32400
gcggccctgg ccgcgggacg aggaccggcc ccggcgggcc ggggtgtcct cgttcggggt  32460
gagcgggacc aacgcgcacg tgatcctgga ggaagcgccc gcgccggcgg aggtgcaggc  32520
ggtagaaact gcgccggtgg tgcgggtgga tggtggggag cgttccgcac cggcggatgt  32580
gccgttggtg tgggtcgtgt cgggcaagtc gcaggccgcg ctacgcgccc aggccgccgc  32640
cctgcacgcc cacgtcctgg accaccccga acaggacgcg gccgacatcg gctacagcct  32700
ggccaccacc cgcgccctgt tcgaccaccg cgccaccctc atcgcccccg accgcgacac  32760
cctcctggac gccctcaccg ccctggccga cggccgcacc cacccccacc tcgtccccgc  32820
```

-continued

```
acccccccacc gaacccggcc acgcccacaa aatcgccttc ctctgctccg gacagggcac  32880
ccaacgcccc ggcatggcca ccggcctcta ccacacctac cccgccttcg ccgccgccct  32940
cgacgaaacc tgcgcccact tcgacccccca cctcgaccac cccctgcgcg acctcctcct  33000
caaccacgac cccaccggcc tcctcaccca caccctctac gcccagcccg ccctcttcac  33060
cctccaaaaa gccctccacc acctcatcac cgaaacctac ggcatcaccc cccactacct  33120
cgccggacac tccctcggcg aaatcaccgc cgcccacctc gccggcatcc tcaccctccc  33180
cgacgccacc cacctcatca ccacccgcgc ccgcctcatg caaaccatgc cccccggcac  33240
catgaccacc ctccacacca cccccgaaca catccaaccc ctcctcgacc aacaccccgg  33300
caaagccacc atcgccgccg tcaacagccc ccactccctc gtcatcagcg gcgaccccga  33360
caccatccac cacatcacca ccacctgcca cacccaaggc atcaccacca aacccctcac  33420
caccaaccac gccttccact ccccccacac cgacaccatc ctcgaacaac tcgacaccac  33480
cacccacacc ctcacctacc acccacccca caccccccctc atcaccagca cccccggcga  33540
ccccctcacc ccccactact ggacccacca gacccgccaa cccgtccact ggaccgacac  33600
catccacacc ctccacacca acggcgtcac cacctacatc gaactcggac ccgaccacac  33660
cctcaccacc ctcacccacc acaacctccc ccaccaccaa cccaccgcca tcaccctcac  33720
ccacccccac cacaacccca cccaccacct cctcaccgca ctcgcccaca cccccaccac  33780
ctggcacacc caccaccaca cccacaccaa cccccacccc cacaccatcc ccgacctccc  33840
cacctacccc ttccaacgcc ggcactactg gctccaggcg cccaccacca gcaccgatca  33900
gccggtggcc ccgacgaacg acgacgcccc cgcgcctcga gcgacatcgc tccgggacac  33960
tcttgccgga cgaagccctc aagagcgcga agaagtgctc ctggatctcg tactgaccca  34020
ggtcgccgcc gtgctcggcc acaccgcgcc tgaggtggtg gatccccaaa gggcgttcaa  34080
ggacctcggc ttcgactcac tggccgccat caaactccgc aacaggctcg ccgcagccac  34140
cggactcgag ctgccgacca cccttgtctt cgaccacccc acgccggtgg cactccgcca  34200
gtacttccag tcgcagatcc tcggagcgga ggcggacgcc cccaaccgtc tgcccctccg  34260
ggcggcgacc accgacgaac ccatcgcgat cgtcggcatg gcgtgccgct tcccgggcgg  34320
cgttcggacg gccgacgacc tgtggcagct cctgagcgac gaacacgatg cggtcggcgg  34380
cttccccacc aaccggggtt gggacgtggc gaacctctac gacccggacc cggatcgcca  34440
cggcaccacg tacacccagc agggcggctt cctctacgaa gcgggggagt tcgacgccga  34500
gttcttcggc atcagcccgc gtgaggccct ggcgatggac ccccagcagc ggctcctcct  34560
cgaaaccgcc tgggaagcca tcgaacacgc cggcatcaac cccgatgccc tgcgcaacac  34620
gtccaccggt gttttcgccg gggtcatcta ccacgactac gcgagccggt tcctcaccgc  34680
gccggccggt tacgagggct acctcggcca cgggagtgcc ggcagcatcg cgtcgggccg  34740
tgtcgcgtac gtgctgggtc tcgagggtcc cgcggtcacg gtcgacaccg cgtgttcgtc  34800
gtcgctcgtc gcgctgcatc tggcctgtca ggcactgcgg tcgggcgagt gcacgatggc  34860
tctggcgggc ggcgcgacgg tgatgtcgac cccgcaggcg ttcgtggagt tctcccggca  34920
gcggggtctg gcggcggacg gccggtgcaa ggcgttctcc gctgcggccg acggcacggg  34980
ctggggcgag ggcgccggcc tgcttctcct cgaacggctc tccgaggccg agcggaacgg  35040
acaccgggtt ctggcggtgg tgcggggcag cgcggtcaac caggacggcg cctcgaacgg  35100
gctgacggcg ccgaacggtc cgtcccagca gcgcgtgatc cgccaagctt tggccaactc  35160
gggcctgacc ggcgccgatg tcgacgccgt cgaagcccac ggcacgggga ccaagctggg  35220
```

-continued

```
cgacccgatc gaagcccagg ccctgctcgc cacctacggc caggaacacc accccgacca  35280
gccgctctgg ctcggctccc tgaagtccaa catcggccac gcccaagcgg cagcaggcgt  35340
gggcagcatc atcaagatga tcatggctat gcgcaacgag tcgctgccgc ggacgttgca  35400
cgtggatgag ccgtcacccc atgtggactg gtcgtcgggg gcggtgagtc tgctgaccga  35460
gccacgcccc tggccacgcc gggaagaccg gccccggcga gcgggaatct cctccttcgg  35520
agtcagcggg acgaacgccc acgtcatcgt ggaggagccg cctgcgcggg cggaggtgga  35580
ggcggtggaa gccgcgccgg cgggggtgga gactgcggcg gctgccgcgg tggtggtgga  35640
gacagacggt gcgggccggg tgtcctccga tgtgccgttg gtgtgggtgg tgtccggcaa  35700
gtcgcaggcc gcgctacgcg cccaggccgc cgccctgcac gcccacgtcc tggaccaccc  35760
cgaacaggac gcggccgaca tcggctacag cctggccacc acccgcgccc tgttcgacca  35820
ccgcgccacc ctcatcgccc ccgaccgcga caccctcctg gacgccctca ccgccctggc  35880
cgacggccgc acccaccccc acctcatccc cacacccccc accgaacccg gccacaccca  35940
caaaatcgcc ttcctctgct ccggacaagg cacccaacgc cccggcatgg ccaccggcct  36000
ctaccacacc taccccgcct tcgccgccgc cctcgacgaa acctgcgccc acttcgaccc  36060
ccacctcgac cacccccctgc gcgacctcct cctcaaccac gaccccaccg acctcctcac  36120
ccacaccctc tacgcccagc ccgccctctt caccctccaa aaagccctcc accacctcat  36180
caccgaaacc tacggcatca ccccccacta cctcgccgga cactccctcg gcgaaatcac  36240
cgccgcccac ctcgccggca tcctcaccct ccccgacgcc acccacctca tcaccacccg  36300
cgcccgcctc atgcaaacca tgcccccccgg caccatgacc accctccaca ccacccccga  36360
acacatccaa cccctcctcg accaacaccc cggcaaagcc accatcgccg ccgtcaacag  36420
cccccactcc ctcgtcatca gcggcgaccc cgacaccatc caccacatca ccaccacctg  36480
ccacaaccaa ggcatcacca ccaaacccct caccaccaac cacgccttcc actcccccca  36540
caccaacacc atcctcgaac aactcgacac caccacccac accctcacct accacccacc  36600
ccacaccccc ctcatcacca gcacccccgg caaccccctc accccccact actggaccca  36660
ccagacccgc caacccgtcc actgggcgga caccatccac accctccaca ccaacggcgt  36720
caccacctac atcggactcg gacccgacca caccctctcc accctcaccc accacaacct  36780
cccccaacac caacccaccg ccatcaccct cacccacccc caccacaacc ccacccacca  36840
cctcctcacc gcactcgccc acaccccccac cacctggcac acccaccacc acacccacac  36900
caaccccccac ccccacacca tccccgacct ccccacctac cccttccaac gccggcacta  36960
ctggctggag gtcccgaagc cgactgccga agcatccgcc tcagccagtg gcccggggcg  37020
gaaccgggcc gccaaactct cagcgctcga ggcggagttc tggcaggccg tcgaggaaac  37080
cgacaccgac accctcgccc acaccctcga cctcgacacc cagaccctcg aacccgtcct  37140
ccccgccctc gccacctggc accaacaaca acgcgaccac gcccgcatca acacctggac  37200
ctaccaggaa acctggaaac cactccacct ccccaccacc cgacccacca cccccaccag  37260
ctggctcatc gccatccccg aaacccaccg caaccacccc cacaccacca acctcctcac  37320
caacctcccc caccacaaca tcacccccat cccccctcacc atcaaccaca ccaccgacct  37380
ccaccacgcc taccaccacg cccaccacca caccacccca cccatcaccg ccgtcctctc  37440
cctcctcgcc ctcgacgaaa caccccaccc ccaccacccc cacaccccca ccggcaccct  37500
cctcaacctc accctcaccc aaacccacac ccaaacccac ccaccaaccc ccctctggta  37560
```

-continued

```
cctcaccacc caagccacca ccacccaccc caacgacccc ctcacccacc ccacccaagc  37620
ccaaaccatc ggactcgccc gcaccaccca cctcgaacac ccccaccaca ccggcggaca  37680
catcgacctc cccaccacac cccaccccaa caccctcacc caactcatca ccgccctcac  37740
ccaccccca c caccaacaca acctcaccat ccgcacccac accacccaca cccgacgact  37800
caccccacc accctccaac ccaccacccc cacaccaccc accaaccccc acggcaccac  37860
cctcatcacc ggcggcaccg gcgccctcgc caccaccctc gcccaccacc tcgccaccac  37920
cggcacccaa cacctcctcc tcaccagccg acgcggcccc cacaccccg gcgcccgaca  37980
actccacacc caactcaccc aactcggcac caacaccacc atcaccgcct gcgacctctc  38040
cgaccccgac caactcaccc acctcctcac ccacatcccc cccgaacacc ccctcaccac  38100
cgtcatccac accgccggca tcctcgacga cgccaccctc accaacctca cccccaccca  38160
actcgacaac gtcctgcgcg ccaaagccca caccgcccac ctcctccacc acgccaccct  38220
ccacaccccc ctcgaccact tcgtcctcta ctcctccgcc gccgccaccc tcggcgcccc  38280
cggccaagcc aactacgcag ccgccaacgc ctacctcgac gccctcgccc accaccgcca  38340
cacccacaac ctccccgcca ccaccatcgc ctggggaacc tggcaaggaa acggcctcgc  38400
gagcggtgac atcggcgagc atctgcgccg ccgcgggatg atcccgctgg atcccgagtc  38460
cgctgtcggt gccttcgacc gggcggtcgc gagcgatcgg cccagcgtct tcgtcgcgga  38520
catcgactgg cccaccttcg gccgcaacac ctccagcggt cttcgcgccc tcttcgagga  38580
cattccggag gccacacagc ctgagccgac cgcccggagc gcggaccagc cgaacgggca  38640
cggtagcctc caggaacttc tcgcccgcca gtccccggcc gagcaggccg aaacgctcct  38700
ggcattggtc cggacgcatt ccgcgaccgt cctcgggcgt gacggggccg atgccgtcgc  38760
cgccgaacgt cccttcaggg acctgggatt cgactcactg tccgccgtcg agctccgcaa  38820
tcatctgacg gccgacacgg agctcgctct gccgacaacg ctggtcttcg atcacccgac  38880
tccggtgaag ctcgcggagt tcctgcgcac cgagctgctc ggcaccgcac cagccaccac  38940
cgccgccgtc ccggccctcc agtcccacac cgacgaaccc atcgccatca tcggcatggc  39000
ctgccgcttc ccggcgccg tcaccacacc cgaacacctg tggaacctca tcgccaccga  39060
acaagacgcc atcggcgagt tccccaccga ccgcggctgg gacctggaca acctctacca  39120
ccccgacccc gaccaccccg gcaccaccta cacccgccac ggtggtttcc tctacgacgc  39180
cggcgacttc gacgccgagt tcttcggcat caacccacgc gaagccctcg ccatggaccc  39240
ccagcaacga ctcctcctgg aaaccgcctg ggaagccatc gaacacgccg gcatcctccc  39300
cgacgccctg cacggcaccc ccaccggcgt cttcaccggc gtcaacgccc aggactacgc  39360
cgcacacacc cacgcctccc cccacaccac cgagggctac accctcaccg gaaccgccgg  39420
cagcatcgcc tccggccgca tcgcctacac cctcggactc gaaggccccg ccgtcaccat  39480
cgacaccgcc tgctcctcct ccctcgtcgc cctccacctc gcctgccagg ccctgcgagc  39540
aggcgaatgc accacagccc tcgccagcgg catcaccgtc atgaccagcc cggtcacgtt  39600
caccgagttc tcccggcagc gagggctcgc cccgacgga cactgcaagg cgttctccgc  39660
ctcggccgac ggcaccggct ggagcgaggg cgtgggcacc atcctcgtcg aacggctctc  39720
cgacgccgag cggaacgggc accggattct ggcggtggtg cggggcagcg cggtcaacca  39780
ggacggcgcc tccaacggcc tgacggcgcc gaacggcccc tcccagcaac gcgtcatccg  39840
ccaggccctg gccaactccg gcctgaccgg cgccgatgtc gacgccgtcg aagcccacgg  39900
cacgggaacc aaactcggcg accccatcga agcccaggcc ctgctcgcca cctacggcca  39960
```

-continued

```
gggacgtgcg caggaacagc cactgtggct cggctcggtc aaatccaacc tcggccacac  40020
ccaggcagcg gcaggcatgg ccggcctgat caagatggtg atggcgctgc ggcacgagtc  40080
gttgccgcgg acgttgcatg tggatgagcc gtcgccgcag gtggactggt cgtcgggtgc  40140
ggtcagcctg ctgaccgagg cgcggccctg gccacgccgg gaggaccggc cccggcgagc  40200
gggaatctcg tccttcgggg tgagcgggac gaacgcgcac gtgatcctgg aggaggcgcc  40260
cgcgccggcg gaggcggtgg agacggaaca gggtgtggtg ccgcagggcg accaggagtg  40320
ttccgcgccg gtgggtgtgc cgttggtgtg ggtggtgtcc ggcaagtcgc aggccgcgct  40380
acgcgcccag gccgccgccc tgcacgccca cgtcctggac caccccgaac aggacgcggc  40440
cgacatcggc tacagcctgg ccaccacccg cgccctgttc gaccaccgcg ccaccctcat  40500
cgcccccgac cgcgacaccc tcctggacgc cctcaccgcc ctggccgacg gccgcaccca  40560
cccccacctc atccccacac cccccaccga acccggccac acccacaaaa tcgccttcct  40620
ctgctccgga caaggcaccc aacgccccgg catggccacc ggcctctacc acacctaccc  40680
cgccttcgcc gccgccctcg acgaaacctg cgcccacttc gacccccacc tcgaccaccc  40740
cctgcgcgac ctcctcctca accacgaccc caccgacctc ctcacccaca ccctctacgc  40800
ccaacccgcc ctcttcaccc tccaaaaagc cctccaccac ctcatcaccg aaacctacgg  40860
catcaccccc cactacctcg ccggacactc cctcggcgaa atcaccgccg cccacctcgc  40920
cggcatcctc accctccccg acgccaccca cctcatcacc acccgcgccc gcctcatgca  40980
aaccatgccc cccggcacca tgaccaccct ccacaccacc cccgaacaca tccaacccct  41040
cctcgaccaa caccccggca aagccaccat cgccgccgtc aacagccccc actccctcgt  41100
catcagcggc gaccccgaca ccatccacca catcaccacc acctgccaca cccaaggcat  41160
caccaccaaa cccctcacca ccaaccacgc cttccactcc ccccacaccg acaccatcct  41220
cgaacaactc gacaccacca cccacaccct cacctaccac caaccccaca ccccccctcat  41280
caccagcacc cccggcgacc ccctcacccc ccactactgg acccaccaga cccgccaacc  41340
cgtccactgg gcggacacca tccacaccct ccacaccaac ggcgtcacca cctacatcgg  41400
actcggaccc gaccacaccc tctccaccct cacccaccac aacctccccc aacaccaacc  41460
caccgccatc accctcaccc acccccacca caaccccacc caccacctcc tcaccgcact  41520
cgcccacacc cccaccacct ggcacaccca ccaccacacc cacaccaacc cccaccccca  41580
caccatcccc gacctcccca cctacccctt ccaacgccgg cactactggc tggaggtccc  41640
gaagccgact gccgaagcat ccgcctcagc cagtggcccg gggcggaacc gggccgccaa  41700
actctcagcg ctcgaggcgg agttctggca ggccgtcgag gaaaccgaca ccgacaccct  41760
cgcccacacc ctcgacctcg acacccagac cctcgaaccc gtcctccccg ccctcgccac  41820
ctggcaccaa caacaacgcg accacgcccg catcaacacc tggacctacc aggaaacctg  41880
gaaaccactc cacctcccca ccacccgacc caccaccccc accagctggc tcatcgccat  41940
ccccgaaacc caccgcaacc acccccacac caccaacctc ctcaccaacc tcccccacca  42000
caacatcacc cccatccccc tcaccatcaa ccacaccacc gacctccacc acgcctacca  42060
ccacgcccac caccacacca ccccacccat caccgccgtc ctctccctcc tcgccctcga  42120
cgaaacaccc cacccccacc acccccacac ccccaccggc accctcctca acctcaccct  42180
cacccaaacc cacacccaaa cccacccacc aaccccccctc tggtacctca ccacccaagc  42240
caccaccacc caccccaacg accccctcac ccaccccacc caagcccaaa ccatcggact  42300
```

-continued cgcccgcacc acccacctcg aacaccccca ccacaccggc ggacacatcg acctccccac 42360
cacaccccac cccaacaccc tcacccaact catcaccgcc ctcacccacc cccaccacca 42420
acacaacctc accatccgca cccacaccac ccacacccga cgactcaccc ccaccaccct 42480
ccaacccacc acccccacac cacccaccaa cccccacggc accaccctca tcaccggcgg 42540
caccggcgcc ctcgccacca ccctcgccca ccacctcgcc accaccggca cccaacacct 42600
cctcctcacc agccgacgcg gcccccacac ccccggcgcc cgacaactcc acacccaact 42660
cacccaactc ggcaccaaca ccaccatcac cgcctgcgac ctctccgacc ccgaccaact 42720
cacccacatc ctcacccaca tcccccccga acaccccctc accaccgtca tccacaccgc 42780
cggcgtcaac cattacgctc ccgtggcggc gaccgacccg tccacgttcg cgtccgtcct 42840
cgccgcgaag gcggccggcg cggcacacct gcatgaactc ctgctggagc tggacacggt 42900
cgagcagttc atcctcttct cctccggttc gggggcctgg ggcagcggca accagtgcgc 42960
gtacgcggct gccaacgcct acctcgatgc gctggcggcg caccgccagg cccgcggcct 43020
gcctggcatg tcgctcgcct gggggccttg ggacggtgac gggatgtcgg ccggagagga 43080
cgcccagcgg tacctccgtg agcggggcgt actgcccatg gatccgcggc tcgccgtcgc 43140
ggccttcgac gaggcggtcc gggcgcggcc gaactccaac ctcgtcgtcg cggacatcga 43200
ctgggagcgt ttcgtcccga cgttcaccgc gcggggccac aaccccctga tcgaggacat 43260
ccccgaagtc cgccggctgg ccgcggaggc cgaggccgcc cagaccacga ccgccgccac 43320
ggacgccccc gcccttctca accgactctc aggtctgtcg gccactcagc agaagcagca 43380
tcttctccgg ctggtgcggt cacacatggg cgaggtcctc ggccgcgagg acgtcgacac 43440
gctcgacgag cgccacacct tccgggacct gggcttcgac tcgctcacct cggcccgatt 43500
cagccagcgg ctcgccaagg acacggggct gcaccttcct gccaccctcg tcttcgacca 43560
cccgacgccc gccgactgcg tggctcatct gcgggatcaa cttctgggtg aaacggacga 43620
catgactccg aggaagcgag atcacctcgg ggaggaccgg cgggcggcca ccgcggacga 43680
cccgatcgcg atcgtcggga tggcgtgccg gttcccgggc ggcgtgcggt ccgccgatga 43740
tctgtgggac ctgctgtcgt cgggcaccga cgccatcagc ggcttcccca ccgatcgcgg 43800
ctgggacatc gagagcctct acgaccccga ccccgaccgc tccggcacca cgtacacccg 43860
ccacggtggt ttcctctacg acgccgggca gttcgacgcc gagttcttcg gcatcagccc 43920
gcgtgaggcc ctggccatgg atccccagca gcggctcctt ctcgaaaccg cctgggaggc 43980
cgtcgaacac gcaggcatca acccgcagac actccacggc acccccaccg gcgtcttcac 44040
gggcgtcaac gcccaggact acgcagccca cctgcgccag gcgtcgggca acgtcgaggg 44100
gtacgccctg accggaagct cgggcagtgt cgtgtcgggt cgggtggctt acaccttcgg 44160
tttcgagggg ccggccgtct cggtcgacac cgcgtgctcg tcgtcgctcg tcgcactgca 44220
cctcgcaggc caagccctgc ggtccggcga gtgcacgatg gccctcgccg gcggcgtcat 44280
ggtgatgtcc tcccctgaga cgttcgtgga gttctcgcgg cagcggggtt tgtcggtgga 44340
cgggcggtgc aagtccttcg cggccgcggc cgacggtacc ggctggggcg agggcgtggg 44400
catgctgctc gtggagcggt tgtcggacgc cgagcgcaac gggcaccggg ttctggcggt 44460
ggtgcggggc agcgcggtca accaggacgg cgcctccaac ggcctgaccg caccgaacgg 44520
cccctcccag cagcgcgtga tccgccaggc cctggccaac tccggcctga ccggcgccga 44580
tgtcgacgcc gtcgaagccc acggcacagg aaccaaactc ggcgaccccca tcgaagccca 44640
ggccctgctc gccacctacg gccaggaaca ccaccccgac cagccgctct ggctcggctc 44700

-continued

```
cctgaagtcc aacatcggcc acgcccaagc agcggcaggt gtcggcggga tcatcaaaat  44760
ggtgatggca ctgcgccacg agacgctgcc gcgcacgctg cacatcgacg agccgacccc  44820
ccaggtcgac tggtcgtccg gcgcggtcag cctgctgacc gagccccgcc cctggccacg  44880
ccagggggac cggccccgac gcgccggcat ctcctccttc ggagtcagcg gaaccaacgc  44940
ccacgtcatc ctggaagagg cacccgccca gccggccggg gaccccgccc cagaagacgg  45000
cgccccggtg ccctgggcga tgtcggcgcg ttcaaacgcc gcgctgcggg cacaggccgc  45060
actcctgcgt gacttcctcc aaggccccgg caccgacacc gcactacggg cggtcggagc  45120
cgaactcgcc catggcaggg ccgtcctgga acaccgcgcc gtgatcgtgg cacgggaacg  45180
gacagagttc gaagacgcgc tggaagcact ggcctcgggt gaaccgcacc ccgcactcat  45240
cgaagacacg accggcagcc agaccaacag ccactccggt ggcggggtgg tgttcgtctt  45300
ccccggccag ggcggtcagt gggccggcat gggactcgac ctgctgcgcg actcccaggt  45360
gttcgccgac catgtcggtg cgtgtgaacg cgcgctggcg ccgtgggtgg agtggtcgct  45420
caccgaaatg ctccaccggg acgcggagga tccggtgtgg gagcgggcgg atgtggtcca  45480
gccggtgctg ttctcggtca tggtgtccct ggcggcgctg tggcggtcct acggcatcga  45540
acccgaagcg gtggtcggcc actcccaggg cgagatcgcc gccgcccacg tctgcggcgc  45600
actcaccctg gaggacgccg cgaagatcgt ggcactgcgc agccgggccc tggccgcgct  45660
gcggggccac ggcggcatgg cctcactcgc cctgaccgga accgaggccg aggacctcat  45720
caccacccac tggccaggac ggctgtggac ggccgcgttc aacgggccac gggccaccac  45780
cgtctccggc gacaccgacg ccctggacga actcctcacc cactgcaccg aaaccggggt  45840
acgggcccgc cgcatccccg tggactacgc atcccactgc ccccacaccg aaaccatcga  45900
acacgacctg ctccacatgc tccacggcat caccccccag cccggcagca tcccgttcta  45960
ctccaccgtc gaggacgcct ggaccgacac caccaccctg gacgccgcct actggtaccg  46020
caacctgcgc cggcccgtcc gcttcaccca cgccgtccgc accctcaccg cccagggcca  46080
ccgcctcttc atcgagacca gcccccaccc caccctgacc cccgccatcg aagaccacga  46140
ccacaccacc gccctgggca ccctgcgccg ccacgacaac gacacccacc gcttcctcac  46200
cgccctcgcc cacgcccaca ccaccggcca caccgtcacc tggaccaccc actaccccac  46260
caccccccac acccccgcca tcgacctgcc cacctacccc ttccaacacc accactactg  46320
gctccacaca cccaccacca gcaccggcga cgtctccgcc gccggactgc accccaccga  46380
gcaccctctc ctcggcgcca ccgtggaact cgccgacgga gacggaacct tgctcaccgg  46440
gcgcctgtcc ctgcacaccc accccctggct cgccgaccac agcgtcggcg gcatcgtcct  46500
cctccccggc accgccctcc tcgaactcgc cctcgaagcc gggacgcgca ccggttgccc  46560
ccacgtccag gaactcaccc tgcacacgcc cctggtgatt cccgagaccg gacacgtcgt  46620
cttccagctg acggtctcgg caccggacga gaccgggcag cgcccgttca ccgtccattt  46680
ccgttccgag gccgtcaccg gcgcggacga tccggcggac cggacctgga cgcggtgcgc  46740
caccggtgcg ctctcgaccg cggccgcccc cgatcactcc gaagccgcca cctggccgcc  46800
gccgtccgct cagccgctgg acctcgacgg tctgtacgac cgcatggcgg aggcgggtct  46860
ggtctacggt ccggtgttcc aggggctccg cgaggcttgg ctcgatggcg aggacatcgt  46920
cgccgaggtg cgcctgccgc aggaggcggc cgccgacacg cagggcttcg gcctgcatcc  46980
cgccctgctc gacgccgctc tgcatgtgac ggcgctgacc tcacaggccg gtacagcgga  47040
```

-continued

```
cgaagacgcg caggaacggc gtcggttgcc gttcgcgtgg gccggtgtct ccctgttcgc  47100
cagggagtgc gcggcgctgc gtgtgcgggt ggcgccgtgt gcgccgcacc cgggggacgc  47160
cgtggcgatc acagccaccg acgaggacgg ccgtccggtg ctggcggtgg aatcgctcac  47220
cctccggccc gtctccccg accagttgcg ggcggcggcc ccggccgccg ggcgggattc  47280
gctgttccgc ctggagtggg taccggtcac ggcctccgcc tccgcctccg cccggccgac  47340
cgggccctgg gccgccatcg gcaccggtcc ggcggtggcc ggcctggccg gccacgcaga  47400
cctgacggtg tacgcggagg ccggcgatct gctccgggat ctggacggag gggcccccgc  47460
gcccgctgtg gtcgtgctca gcgtcacgcc cgatgccgac gaattcgcca ctccccgtgc  47520
ggcgaccggc cgggccctct ccgtccttca ggcctggctg gcggacgagc gcctggccga  47580
cagccggctc gtggccgtca cttctggggc ggtcgtcgcc gcgcccgggg acgacacggt  47640
cgacgtcccg ggtgccgccg tgtggggctt ggtgcgttcc gggcagtccg agcacccgga  47700
ccgcatcacg ctgctcgact gtgcgagcgg cgcccggccc gggccggacc tcgtcgccgc  47760
cgccctcgcc tcgggcgagc cgcagctcgc cgcccgcgcc ggggtcctct acacgccccg  47820
gctggccagg ccgcaccgcg acgcctcggc cgtaccgcgg tcgctgccgt cccacggcac  47880
cgtgctcatc accggcggca ccggtctgct gggcgggttg gtcgcccggc gcctggtgga  47940
ggcgcacggt gtccgccgcc ttctcctggc cggccgcagg ggtccggcgg cggaggggct  48000
ggactcgctg acgtccgagt tgcgtgagcg cggggcgacc gtcgaggtcg ccgcgtgcga  48060
cgcggccgac cgcacacagt tggaggcgct gctggccggg gtgcccgagg agcatcccct  48120
gtccgcggtc gtgcacgccg cgggtgtgct cgacgacggg gttctcacgt ccctgacgaa  48180
cgagcggctg ggagctgtcc tgcgggcgaa ggcggattcg gcgctgcttc tgcacgagct  48240
cactcaggac ctcgacctgt ccgccttcgt cctgttctcc tccgccgccg gcgtcctcgg  48300
ctctcccggc cagggcagct acgccgccgc caacgccgtg ctcgacgcac tcgcccacca  48360
gcgcagcgcc gccggtctgc ccgctctctc cctggcctgg gggctgtggg cggagggcag  48420
cgggatgacc gggcacctcg acgccgacga ccgctcccgg atcaaccggg ccggtatggc  48480
gccgctcccg acgcccgatg ccctggatct gttcgacgcc gcgctgtcgt cggacgaacc  48540
cttcctggta ccggctcgct tcgacctttc cgccgtacgc accaggaccg cgtacggccc  48600
gctcccgccg ctgctgcgcg gcctggtccg gacctcgggc gcgcaccggg tccggggcgc  48660
agtcggcgaa gcccgggcgg ccggcgtgga cgaggccgga cggctgcggg aacggctggc  48720
ccgccagagt gacgccgaac gccggaacac cttgctgcgg ctcgtgcagt cgaacgtcgc  48780
ggcggtgctc ggtcaccgcg gcacggggac cgtcgccgag acacgcgcct tccgtgagct  48840
gggcttcgac tcgctcacgg cggtggagct gcggaaccgg ctgaaggtcg ccacagggct  48900
ggcgctgcgg gccacggtcg ccttcgactt cccgactccg gcggcgctgg ccgagcatct  48960
gggtgcccgc ctgcttccgc cggacggcgc cgtgtccgag gcggtgggcg agaaggagct  49020
gcgcgggctc ttgacgtcga tcccgatcgg ccggctgcgg gaggcggggc tgatcgaccg  49080
cctcctggcg ctcgccgctg cggcgccaga ctccgccgat cagacggcgg agcagccctc  49140
ccggtccgtg tcggtcgagg acatcgacgc catggacgtc gacagcctca tcggcctggc  49200
ccacgacacc ggcaccgact ccggtcacgc cccctgcgag ggctgacctc cacttcacgg  49260
atgcgagaga cgacatgacg cagattccgc caaccggtca cgacgccgtg gcagccgggc  49320
ccgcccccgg cgccgcggaa cagaaacgag gacggaaacg gaaaccagga cgggagcccc  49380
ggccagagca tcgacgggaa caggaacgag ggcagggagc agggctgggg caggggcagg  49440
```

-continued

```
aacgcgcgcg gcccgcggac ggtggtcggc ggctcgtgct tggctgggcg gcgctcggcg  49500
cggtgtgcct ggccctgcag gcgtacgtgc tcgtccgctg ggcggccgac ggtgggtatc  49560
gcctggtgga cgtacccggt gagggcggcg cggagcgtgg ccaccgaagg gtcctcgaca  49620
tcgtgttccc ggcgctgtcg gcggcaggtg tcgtggggct ggcgctgtgg ctctaccgca  49680
ggtgccgcgc ggagcggcgg gtgtcgttcg acgccctgct gttcgccgga gtgctgttcg  49740
cgggctggct gagcccgctg atgaactggt tccatcccgt cctggtctcc aacacgcacg  49800
tgtggggcgc ggtcggctcc tgggggccgt acacgccggg atggcagggg tccgcccccg  49860
ggatggaggc cgagctgccg ctggtgacgt tcagcgtgtg ctcgacagcg ctcctgggtg  49920
tgctggcctg ctgtcacgtg ctgtcccgcg tccgggaccg gtggcccggg gtccgcccgt  49980
ggcaactgat cggggtggcc gtcgccaccg cggtggccct ggacctgtcg gagccggcga  50040
tctccttgat cggtctagtc cgtctggtcg aaggcgctgc cggaggtgtc gctgtggagc  50100
ggtgcctggt accagttccc tctgtaccag ctcctgaccg cggccctggc cagcgggttg  50160
ctgagcgcgc tccggttctt ccgcgacgag cgggacgaga cgctggtgga gcgcggtgcc  50220
tggcgcctgc cgggccgtgt ccgcctctgg gcgcggttcc tggccgtcgt cggcggcgtc  50280
catgtcgtga tgggcggcta tacggccctt catgtgctgc tctcgttggt cggcggccaa  50340
ccgccggacg cgttgccggg gttcttccgt ccgccggccg tctactgagg gcggggcgga  50400
cggcacgcaa cgaggggagg ggccggcgtc tcatgctctg ctgtccggtc agacctcagc  50460
gcgctggcac ggcgcggtca ggacgacgta cccgatgtcc tccgtgtacc actggctgca  50520
cttgcccacg aacgtctcca ggtcgtccgc cgtcatctcc agggcttcgg cgtaggcgtg  50580
ggcgttggcg cgtacgtcgt cacccatcgc gctgtacgac ggggcgatga cgtgctcacc  50640
gatgtcggtg agctcggtca gccggagtcc ggcgtcgctg atcatcccgg catagccggt  50700
gatggggatc agcgagggga cggcgagttc gctggacgac cagtccgccc ccgtcggctg  50760
tgatgcgcgg agtgtgacgt ccatggccgc cagccgccca ccggggcgca gcacacgggc  50820
catctcctgg aacacccggg ccgggtcggg catgtgcagc aggcactcga gggcccagac  50880
ggcgtcgaag gaggcgtcgg ggaagggcag gtccatggcg tcggcgcact cgaagcggac  50940
ccggttcgcg agtccggacc gctcggcgag cgcggtggcc agctcgacct gccgggggct  51000
gatggtgatg ccgacgatgt ccaccggctc gctgtgcgcc aggcgcaggg ccggccggcc  51060
ggaaccgcag ccgacgtcca gcacacgtct gaccgggcgc ccggtgtgtt cccgaagctt  51120
gccgatcata tggtcggtga ggcggtcgga ggcctggccg agtgtgctgc cgtcgtccgg  51180
gtgcggccag tatccgaggt gcgtgttgcc gcccagggcc cggttcaaca ggctggtcat  51240
gcggtcgtag tagtcaccga cgtccgcggg ggtcggtgat ccctggtgag gcgccttggt  51300
catggttccg gcagctcctt cggtcgtgcg gcggcctcaa gggaggcgtc cgcgggggcg  51360
tggccgcgag ggatggcggg ggtcctgggc tcggctatca tccgcaggcg gtcggggaag  51420
acgtgggtcg ccttggcgac cgggcggacg cggtcgccct tgaggggacg cagacgccag  51480
cgcgaggcga tgaccgcgac ggcgacggcc gtctccatga gggcgaagtt gtcgccgatg  51540
cacttgtagg tgccgagcgc gaagggaacc caggcgccct tcggaacgtc gcgcgtggtc  51600
tctttcgact cccagcggtc ggggtcgagc ttctccggat cacggtacca gcgggggtca  51660
cgctggagcg cgtacgagct gtacatgatt tccacgtcgg ccggcagctc gtgttccccg  51720
agccggacgg ggcgcaccgt gcgccgcgag cccacccagc cggggtactt gcgcagcgcc  51780
```

-continued

```
tccttgacca ggcgctgggt gtacgggagg cgcgggaggt ccgcgctggt ggggagccgg  51840
cctccgagga cggtgtcgat ttcggcgtgc agcctctgtt cgatgaggtg gtcgtgagcg  51900
agttcgtgga agatccacgc ggtgagagcg gccggcccac cgattccggc gaccgcgagc  51960
cccatgatct cgttgtgcac ctcgtcgtcc gtcatggtgt tgccctcggc gtcccgcgcg  52020
cgcagcatcg tcgagagcag gtcgccgtgg tcgcggccgt cggcgcggta ggcggtgacc  52080
gcctcccgga tggcggcgct ggtgcggccc atgtggcgct tggcggcagt gggcagggag  52140
gtgtagagct gcggggcgag cgcgctcagc ctggccacct tcaggatgtc gtgccccgtg  52200
gtgcgcagtt ccgcctcggc cgccgcaccc aggtcggact ggaacaacgc cttcgtgatc  52260
atggccagtg agaggtcgct cgccatcttc gggacatcca cgacctggcc cggccgccag  52320
gaatcggcgg tctcctcggc ggcggcggac atgctgatga cgtagtggtc gagcttgccc  52380
cggtggaatc cgggttgcat catccgccgc tggcggcggt gcgagtcccc ggagacggcc  52440
acgaggatgg ggccgatgaa ccggctggcg cccgccgcgc ccttgctgcg ggtgaagtcc  52500
gccgcgccgg acaccagcat ggtccgcacg atttcggggt gggtggcgag gtagacggtg  52560
ttgtggccga ggcggatgcg gaagaggtcc ccgcgttccg tgacggcgga caggaagccc  52620
agggggtcgc ggaggagggc cggcaggtgg ccgaggaccg gccaggcacc gggggcctcg  52680
gggatggtcg acggaggtga ggacactgtt gctcctgagg ggagggccgg gcgagtcggc  52740
gtggggtggg gtgaggtgtg cggtcgggca ggtggtcgcg tcgccggtgg tcggcgacgg  52800
gtggtgggtc agggggatcc ggtttcctgg tcgatgagcg cgaacatctc ctcgtccgtc  52860
gcctccccga ggtcgggacg cggcgcctcc tccccgccga gcacctgggc gagtgagcga  52920
agccgcgacg ccagccggga ccgggcttcc tctcccaggc cctgcgcccc ggggagcggc  52980
gacgcgacgg aggagagcac cgcttccagc cggccgatct ccgcgaagag ggactgctcg  53040
ggcggcgccg tggccgcgtc gtcggggagg agccgggtca gcaggtgccg ggtgagcgcg  53100
gtggcggtgg ggtggtcgaa ggcgagggtg gcgggcaggc gcaggccggt ggcgcgggag  53160
agccggttgc ggagttcgac ggcggtgaga gagtcgaagc cgaggtcccg gaaggccgag  53220
tccgcaggga ccgcctccgg cgtctgatgg ccgaggaccg tggcgatctg ggtgcgcacc  53280
acggtgaaca gggtgtcgtg ttgttgctcg ggggtcaggg tggcgaggcg gtcggcgagg  53340
gagacgtcct ggcctgcgcc tgcactggtg ccggtgtgtg cggtgcgggg gctggtgcgg  53400
gcgggcgcga ggtgttccag aaggggcggt gcggggtggg tggggcgtag gtcggcgggc  53460
aggagtgcgg gacgtccggt gaccagggcg gtgtcgagga gggcgagggc gtcgggggtg  53520
gtcagggggt gcagccccga gcgggtgatg cggtgacggt caccggcgtc cagatgcccg  53580
gtcatcccgc tggcctcttc ccacagtccc caggccaggg agagggcggg caggccggcg  53640
gcgcggcgct ggtgggccag ggcgtccagg gcggcgttgg cggcggcgta gttgccctgc  53700
cccggcgagc ccaggacacc ggccgcggag gagaacagca cgaacgccga caggtccatc  53760
cccgcggtca gctcgtgcag atgcagggca ccgtccacct tcgccccgac caccgcatcg  53820
atcttctccc ggttcagaca ggccacggtg gcgtcgtcca ggacaccggc cgtgtgcacc  53880
acagccgtca gcggatgctc cgcgggcacc tgctccagca gggcggcgac ctgggcgcgg  53940
tcggcgacat cgcacgccgc caccgacacc gacacccctg cctgacccag ttccgcacac  54000
agttcttcgg caccggtggc ggccatgccg cgccggctca ccagcagcag atgccgcacc  54060
ccgtgcccgg cggccagatg gcgcgcgacc gccgctccca gagtgccggt cccacccgtc  54120
accagcaccg tcccctccgc atcgaaccgg acggcatccg acgagtcggc gggcaccggc  54180
```

-continued

```
acatgtgcca agcgcgccgc cagcagtcgc ccgccacgca ccgccaactg gggttcgtcg 54240
caggccagag ccgccgtgac ggtggtgtcg tcggagaggt cggcatccag caggacgaac 54300
cgccccgggt gttccgactg cgccgaacgc agcaggcccc agaccgccgc tccggcgacg 54360
tccgtcacct cctcaccggt ccgggtggcc acggcaccgt gtgtcaccac cacgagccgg 54420
gcctcggcaa ggcgatcgtc ggccagccag tcctgcacca cgctcagcac ttcgccgagg 54480
acgtccgcca ccgcgccctg ggagcacgtc agcagcacgg cgtcggggac gggggcgtcg 54540
tcggtgtcca gcccggacag caggccggag aggtccgccg ccgcccggtc atgggtgagt 54600
acggtcgacc ggacggccgt gtccgggggc ggggtgcccg gtgtgacgtc cttccaggcc 54660
acgtcgaaca gcgccgcgcg gccggccgcc tgggcagagg ctcgcagttc gccggtgtcc 54720
agcggtcgta cggcgagaga gtcgaccgac aacacgcccc ggccggtttc gtcggccagc 54780
gacacggaga cggcggtccg ttcgccgtcc cgcccggccg gcgccacccg gacccgtacc 54840
gctgccgcct tcaccgcgtg cagggtcaca ccactgaacg agaacggcac cgccccccggc 54900
ggcaggcccg tcgccgctcc gagcgccacc gcgtgcaggg cggcgtccag cagagctggg 54960
tgcaggttgt accgggacgc ctcgtcgagc acggactccg gcaggcggac ctccgcgaag 55020
acctcttcgc cccgccgcca agccgcacgc agcccccgga acgccggtcc gtaggcgaac 55080
ccgcgggcct cctgtgccgc gtagaagctt tccagttcgt ccgccgcgca cggcagggcc 55140
ccttccggcg gccagctgcg cagggcgtcg ccgtcggcgg agggctgggc gtccagcagg 55200
ccggtggcgt ggtgctgcca gggatcctcc gggcgggcgt gctcgctccg ggaggagacg 55260
gtgagggtgc gggccccggt gtcgtcgggc gccgacacgc ggacctggag gtcgacggcc 55320
gcgtcgtgcg ggacggcgag gggcgcgtga agggtgagct ctcgcacgtg cgcggcaccg 55380
ccggcttgga gggcgagttc gaggagggcg gtgccgggga ggaggacgat gccgccgacg 55440
ctgtggtcgg cgagccaggg gtgggtgtgc agggacaggc ggccggtgag caaggttccg 55500
tctccgtcgg cgagttccac ggtggcgccg aggagagggt gctcggtggg gtgcagtccg 55560
gcggcggaga cgtcgccggt gctggtggtg ggtgtgtgga gccagtagtg gtggtgttgg 55620
aaggggtagg tgggcaggtc gatggcgggg gtgtgggggg tggtggggta gtgggtggtc 55680
caggtgacgg tgtggccggt ggtgtgggcg tgggcgaggg cggtgaggaa gcggtgggtg 55740
tcgttgtcgt ggcggcgcag ggtgcccagg gcggtggtgt ggtcgtggtc ttcgatggcg 55800
ggggtcaggg tggggtgggg gctggtctcg atgaagaggc ggtggccctg ggcggtgagg 55860
gtgcggacgg cgtgggtgaa gcggacgggc cggcgcaggt tgcggtacca gtaggcggcg 55920
tccagggtgg tggtgtcggt ccaggcgtct tcgacggtgg agtagaacgg gatgctgccg 55980
ggctgggggg tgatgccgtg gagcatgtgg agcaggtcgt gttcgatggt ttcggtgtgg 56040
gggcagtggg atgcgtagtc cacggggatg cggcgggccc gtaccccggt ttcggtgcag 56100
tgggtgagga gttcgtccag ggcgtcggtg tcgccggaga cggtggtggc ccgtggcccg 56160
ttgaacgcgg ccctccacag ccgtcccggc cagtgggtgg tgatgaggtc ctcggcctcg 56220
gttccggtca gggcgagtga ggccatgccg ccgtggcccc gcagcgcggc cagggcccgg 56280
ctgcgcagtg ccacgatctt cgcggcgtcc tccagggtga gtgcgccgca gacgtgggcg 56340
gcggcgatct cgccctggga gtggccgacc accgcgtcgg gttcgatgcc gtaggaccgc 56400
cacagcgccg ccagggacac catgaccgag aacagcaccg gctgcaccac atccgcccgc 56460
tcccacaccg gatcctccgc gtcccggtgg agcatttcgg tgagcgacca ctccacccac 56520
```

-continued ggcgccagcg cgcgttcaca cgcaccgaca tggtcggcga acacctggga gtcgcgcagc 56580
aggtcgagtc ccatgccggc ccactgaccg ccctggccgg ggaagacgaa caccaccccg 56640
ccaccggagt ggctgttggt ctggctgccg gtcgtgtctt cgatgagtgc ggggtgcggt 56700
tcacccgagg ccagtgcttc cagcgcgtct tcgaactctg tccgttcccg tgccacgatc 56760
acggcgcggt gttccaggac ggccctgcca tgggcgagtt cggctccgac cgcccgtagt 56820
gcggtgtcgg tgccggggcc ttggaggaag tcacgcagga gtgcggcctg tgcccgcagc 56880
gcggcgtttg aacgcgccga catcgcccag ggcaccgggg cgccgtcttc tggggcgggg 56940
tccccggccg gctgggcggg tgcctcttcc aggatgacgt gggcgttggt tccgctgact 57000
ccgaaggagg agatgccggc gcgtcggggc cggtcccccct ggcgtggcca ggggcggggc 57060
tcggtcagca ggctgaccgc gccggacgac cagtcgacct ggggggtcgg ctcgtcgatg 57120
tgcagcgtgc gcggcagcgt ctcgtggcgc agtgccatca ccatcttgat gatcccgccg 57180
acacctgccg ctgcttgggc gtggccgatg ttggacttca gggagccgag ccagagcggc 57240
tggtcggggt ggtgttcctg gccgtaggtg gcgagcaggg cctgggcttc gatggggtcg 57300
ccgagtttgg ttcctgtgcc gtgggcttcg acggcgtcga catcggcgcc ggtcaggccg 57360
gagttggcca gggcctggcg gatcacgcgc tgctgggagg ggccgttcgg tgcggtcagg 57420
ccgttggagg cgccgtcctg gttgaccgcg ctgccccgca ccaccgccag aacccggtgc 57480
ccgttgcgct cggcgtccga caaccgctcc acgagcagca tgcccacgcc ctcgccccag 57540
ccggtaccgt cggccgcggc cgcgaaggac ttgcaccgcc cgtccaccga caaaccccgc 57600
tgccgggaga agtcgatgaa ggtgcccggt gaagacatca ccgtcacgcc gccggcgagg 57660
gccatcgagc attcgcccga tcgcagggct tggcctgcga ggtgcagtgc gacgagcgac 57720
gacgagcacg cggtgtcgac cgagacggcc ggcccctcga aaccgaaggt gtaagccacc 57780
cgacccgaca cgacactgcc cgcgtttccg ttgccgatgt agccctccgc cccttcggga 57840
acggcggtca aacgggcggc gtagtcgtgg tacatcacac ccgcgaacac gcccgttcgg 57900
gaaccgcgta cggcagcggg atcgatcccc gcgtgttcga gggtctccca gacggtttcg 57960
aggaggagcc gctgctgggg gtccatggca agggcctcac gcgggctgat accgaagaac 58020
tcggcgtcga actgcccggc gtcgtagagg aaaccaccgt gccgggtgta cgacgctccg 58080
gcccgctccg ggtccgggtc gaacagcccg gccaggtccc acccgcggtc ggccgggaac 58140
tccccgatcg cgtcaccgcc cgaagccacc agcccccaca actcctccgg cgaccgcaca 58200
ccgcccggga agcggcacgc catcccgacg atcgccagcg gctcgtcact gccgacggct 58260
gtggtttcgg cgtacggcga agtgctgtcc gcggcgtcgt ccccgagcag ttccgtgcgc 58320
agcaggcggg ccacggccgc ggggctgggc tggtcgaaga ccaggctcgc cggcagtcgc 58380
agtcccgtct ccgcgctcag gcggtttcgc agatccacgg ccgtcaggga gtcgaagccg 58440
aggtcgcgga aggccgagtc gaccgggatg gcttccggtg cttggtggcc gaggacggtg 58500
gcgacatgcg agcggaccag cccgagcagg gcctggtact gctgttcggg tgtccgtccc 58560
gcaagccgtg cccgcagcga cgcaccgctg tcagtggtgg ggagggtggt gcggtggctg 58620
gtgcgggcgg gcgcgaggtg ttccagaagg ggcggtgcgg gatgggtggg gcgtaggtcg 58680
gcgggcagga gtgcgggacg tccggcggcc agggcggtgt cgaggagggc gagggcgtcg 58740
ggggtggtca ggggatgcag ccccgagcgg gtgatgcggt gacggtcacc ggcatccaga 58800
tgcccggtca tcccgctggt ctcttcccac agtccccagg ccagggagag ggcgggcaga 58860
ccggcggcac ggcgctggtg ggccagggcg tccagggcgg cgttggcggc ggcgtagttc 58920

-continued

```
ccctgccccg gcgagcccag gacacctgcg gcggaggaga acagcacgaa cgccgacagg  58980
tccatccccg cggtcagctc gtgcagatgc agggcaccgt ccaccttcgc cccgaccacc  59040
gcatcgatct tctcccggtc cagacacgtc acggtggcgt cgtccaggac accggccgta  59100
tgcaccacag ccgtcagcgg atgctccgcg ggcacctgct ccagcagggc ggcgacctgg  59160
gcacggtcgg cgacatcgca cgccgccacc gacaccgaca cccccgcccc acccagttcc  59220
gcacacagtt cttcggcacc ggtagcggcc atgccgcgcc ggctcaccag cagcagatgc  59280
cgcaccccgt gcccggcggc cagatggcgc gcgaccaccg ctcccagagt gccggtccca  59340
cccgtcacca gcaccgtccc ctccgcatcg aaccggacgg catccgacga ctccgacagc  59400
ggcggcaccc gcttcaaccg tggtacgcga accacccccgt cgcgtacggc gagttggctc  59460
tcaccgcggg ccagagcgga cgcgacggcg gcatcgtcga gaccggcgcc ggtgccgacc  59520
ttcgcgtcgg cggacacgtc ggtgtccccg tcggtgtcgg tgtcggtgtc ggtgtcgggg  59580
tcggtcttgg tgtcggggtc gaggtccagc aggacgaacc ggtcgggatg ctcggactgg  59640
gccgagcgga ccagccccca cacagcggcc cccgccacat cccgcaccgg ctcacccgca  59700
tccaccgcga ccgcaccacg cgtcaccacg accagccgcg catccccctc ccgctcatcg  59760
gcgagccact cccgcaccac acccaacgcc gcggccgtga cctcggccac ccccaccccc  59820
gggcactccc acgccaccaa ctccccgccc ccaccggcca ccgaggccgg caccccctcc  59880
accggcaccc accccagctc gaacaacgac ccacgccgca cccgagcccc cagcccctcc  59940
aacggcaccg gacgcatcag gagcgactcg agggtgagaa cgggtgctcc ggtctcgtcg  60000
gtggcgtgca ggcgaacggc ggtcgaggtc gcgtcggtgg gagtcatgcg caggcgcagg  60060
acggtggcgc cccgggcgtg gagcgagaca ccgttccatg tgtgagggac gagcccggcc  60120
tgctgctggt ccgccagcag cagggtgacc gattgcacgg ccgcgtccag gagcgccgga  60180
tgcaccccga agcccgcgac atcggccagc ccctcgtccg gcagacgcac ctcggccacc  60240
acgtcgtccc cgtcccgcca ggccgcacac aaaccctgga acaccggacc gtagacaaaa  60300
cccccacccg ccagacggtc gtagagaccg tcgagaacga ccggtcgggc gccgggtggc  60360
ggccactccc cggccgccgc tgcctccgcg ttcggatcgt cttcggtgga cggggacagc  60420
acaccctcgg catgccgtgt ccactctccg tccgtctcct cgtccccggc cggccgcgcg  60480
tacacattca cggcgcgccg ccccgcctcg tccggcaccg acaccgacac ctgcaccacc  60540
acgtgccccg actcgggaat caccagaggg gcgtggagag tgagctcgtc gacacgagga  60600
cagccggtac gcagaccggc ctgaaaagcc agatccagga gggcggtgcc cgggaggagg  60660
acgattccgc cgacactgtg gtcggcgagc caggtgtggg tgcgcaggga caggctgccg  60720
gtgaggacga tcccgtcccc gtccgcgagc tccatcaccg cacccagcag cggatggtcc  60780
ggccgctgga gcccggcagc cgacacatcg cccgcaccgg caccgggagt cgcctggagc  60840
cagtagtgcc ggcgttggaa ggggtaggtg gggaggtcgg ggatggtgtg ggggtggggg  60900
ttggtgtggg tgtggtggtg ggtgtgccag gtggtggggg tgtgggcgag tgcggtgagg  60960
aggtggtggg tggggttgtg gtgggggtgg gtgagggtga tggcggtggg ttggtggtgg  61020
gggaggttgt ggtgggtgag ggtggtgagg gtgtggtcgg gtccgagttc gatgtaggtg  61080
gtgacgccgt tggtgtggag ggtgtggatg gtgtcggtcc agtggacggg ttggcgggtc  61140
tggtgggtcc agtagtgggg ggtgaggggg tcgccggggg tgctggtgat gagggggggtg  61200
tggggtgggt ggtaggtgag ggtgtgggtg gtggtgtcga gttgttcgag gatggtgtcg  61260
```

-continued

```
gtgtgggggg agtggaaggc gtggttggtg gtgaggggtt tggtggtgat gccttgggtg  61320
tggcaggtgg tggtgatgtg gtggatggtg tcggggtcgc cgctgatgac gagggagtgg  61380
gggctgttga cggcggcgat ggtggctttg ccggggtgtt ggtcgaggag gggttggatg  61440
tgttcggggg tggtgtggag ggtggtcatg gtgccggggg gcatggtttg catgaggcgg  61500
gcgcgggtgg tgatgaggtg ggtggcgtcg gggagggtga ggatgccggc gaggtgggcg  61560
gcggtgattt cgccgaggga gtgtccggcg aggtagtggg gggtgatgcc gtaggtttcg  61620
gtgatgaggt ggtggagggc tttttggagg gtgaagaggg cgggttgggc gtagagggtg  61680
tgggtgagga ggtcggtggg gtcgtggttg aggaggaggt cgcgcagggg gtggtcgagg  61740
tgggggtcga agtgggcgca ggtttcgtcg agggcgtcgg cgaaggcggg gtaggtgtgg  61800
tagaggccgg tggccatgcc ggggcgttgg gtgccttgtc cggagcagag gaaggcgatt  61860
ttgtgggtgt ggccgggttc ggtgggggt gtggggatga ggtgggggtg ggtgcggccg  61920
tcggccaggg cggtgagggc gtccaggagg gtgtcgcggt cgggggcgat gagggtggcg  61980
cggtggtcga acagggcgcg ggtggtggcc aggctgtagc cgatgtcggc cgcgtcctgt  62040
tcggggtggt ccaggacgtg ggcgtgcagg gcggcggcct gggcgcgtag cgcggcctgc  62100
gacttgcccg acacgaccca caccaacggc acatccgccg acacccggcc cgcaccgtcc  62160
gtctccacca ccaccgccgc agccgccgca gtctccaccc ccgccggcgc ggcttccacc  62220
gcctccacct ccgcccgcgc gggcgcctcc tccaggatca cgtgcgcgtt cgtcccgctc  62280
accccgaagg acgagattcc cgctcgccgg ggccggtcct cccggcgtgg ccagggccgc  62340
gcctcggtca gcaggctcac cgctcccgac gaccagtcca cctgcggcga cggctcatcc  62400
acatgcaacg tccgcggcaa cgactcgtgc cgcaacgcca tcaccatctt gatgatcccg  62460
ccgacacctg ctgccgcttg ggcgtggccg atgttggact tcagggagcc gagccagagc  62520
ggctggtcgg ggtggtgttc ctggccgtag gtggcgagca gggcctgggc ttcgatcggg  62580
tcgcccagct tggtccccgt gccatgggct tcgacggcgt cgacatcaac tgcggagagg  62640
ttcgcgttgg ccagggcctg gcggatcaca cgctgctggg acggaccgtt cggcgccgtc  62700
agcccgttcg aggcgccgtc ctggttgacc gcgctgcccc gcaccaccgc cagaacccgg  62760
tgcccgttgc gctcggcgtc cgacaaccgc tccagcagga gcatcccggc tccctccgac  62820
cagccggtac cgtcggccga ggcggagaac gccttgcacc ggccgtccgc cgccaggccc  62880
cgctgccgcg agaactccag gaacgcggta ggcgtggaca tcaccgtcgc accgcccgcc  62940
aaggccatgg tgcactcgcc cgaccgcagt gcctgacagg ccagatgcag cgcgacgagc  63000
gacgacgagc acgcggtgtc cacggacacg gcggggcctt cgagcccgaa cgtgtaggcg  63060
acccggcccg acgccacgct tccggacgtg ccggtgagaa cgtacccgtc gacgtcggcg  63120
gcgacatggt gccgtgagcg ggacgcgtac tcctgaggca tgacgccggc gaacacgccc  63180
gtctggctgc cgcgcacggc accggggtcg atacccgccc gctcgaacgc ctcccacgtc  63240
gtctccagca acagccgctg ctgggggtcc atcgcgagcg cctcgcgcgg ggagatcccg  63300
aagaatcccg cgtcgaactc cccgcgtcg tagaggaatc ccccgtgacg ggtgtacgag  63360
gtgccccgct gcccgggctc cgggtcgtag agcgcctcca cgtcccagcc acggtcggcc  63420
gggaactccc ccaccgcgtc gccgccggag gcgacgagtt gccagaggtc ctcggccgag  63480
gcgacacctc ccggataccg gcatcccaca ccgatgatcg cgatgggctc gtgctgcccg  63540
gccttcggtt cggcggcggc aggtgccgaa ggcgtcttgg tgtcgttggg gttgaggagg  63600
gtggtgaggt ggtgggtgag tgcggtgggg gtggggtggt cgaaggcgag ggtggtgggc  63660
```

-continued aggcgcaggc cggtggcgcg ggtgagccgg ttgcggagtt cgacggcggt gagggagtcg 63720
aagccgaggt cgcggaaggt gcgttcgggg tcgatggtgt cgggggtggg gtggcccagg 63780
acggcggcga tgtgggtacg ggccagggcc agcagggtgg cgtgccgctg ttcggaggtc 63840
agggtggcga ggcggtcggc gagggagacg tcctggcctg cgcctgcact ggtgccggtg 63900
tgtgcggtgc gggggctggt gcgggcgggc gcgaggtgtt ccaggagggg tggtgcgggg 63960
tgggtggggc gtaggtcggc gggcaggagt gcgggacgtc cggtggccag ggcggtgtcg 64020
aggagggcga gggcgtcggg ggtggtcagg ggatgcagtc ccgagcgggt gatgcggtga 64080
cggtcaccgg cgtccaggtg gccggtcatc ccgctggcct cttcccacag tccccaggcc 64140
agggagaggg cgggcagacc ggcggcgcgg cgctggtggg ccagggcgtc cagggcggcg 64200
ttggcggcgg cgtagttgcc ctgccccggc gagcccagga cacctgcggc ggaggagaac 64260
agcacgaacg ccgacaggtc catccccgcg gtcagctcgt gcagatgcag ggcaccgtcc 64320
accttcgccc cgaccaccgc atcgatcttc tcccggtcca gacacgtcac ggtggcgtcg 64380
tccaggacac cggccgtatg caccacagcc gtcagcggat gctccgcggg cacctgctcc 64440
agcagagcgg cgacctgggc gcggtcggcg acatcgcacg ccgccaccga caccgacacc 64500
cctgcctgac ccagttccgc acacagttct tcggcaccgg cggcggccat gccgcgccgg 64560
ctcaccagca gcagatgccg caccccgtgc ccggcggcca gatggcgcgc gaccgccgcc 64620
cccagagtgc cggtcccacc cgtcaccagc accgtcccct ccgcatccag gggcacaggc 64680
agggtcagca cgttcttgcc gacatgcagg cccgaccgca tcgaccgcag cgcctggcgg 64740
gcctggcgca cgtcccacgc ggtgaccggc aacggctcca gcaccccgcg ccggaacaga 64800
tccaccaccg tgtgcaggat ctcccccacc cgctgcgcac ccgcgtccat caggtcatac 64860
gcccggtagg acacccccgg gaaccgagcg gcgacctcac cggcatcacg gatgtcggtc 64920
ttgcccagct ccaggaaccg gccccccctgc ggcgaacaca gccgcaacga ggcatcggtg 64980
tactcacccg ccagacagtt cagcaccaca tccacacccc gcccgccact ggcccggcgg 65040
aaacgcgact cgaactccac actccgcgag gaagcgatcc gctgcggcgc gacacccgcc 65100
gcccgcagac gcgcccactt cgcctcactc gccgtcgcat acacctccgc ccccagatga 65160
cgggcgagct gcaccgccgc cgtaccgacc ccgccggccg ccgcatggac cagcacactc 65220
tccccccgcc gcacccccgc cagatcgacc agccccaggt aagcggtagc gaacaccacc 65280
ggcaccgaag ccgcctgcgc gaacgaccag ccctccggga tacgggccag caacacctcc 65340
tgcgccacca ccaccggcgc gaacgcgtcc ccgaacaccc cgaacacccg gtctcccacc 65400
accaggccct ccaccccggg ccccacctcc accaccaccc ccgcaccctc actgcccacc 65460
cccacctgac ccggcaccat ccccaacgcc accagaacat cacggaagtt caccccggca 65520
gcccgcaccg ccacccgcac ctgcccccga cccagcacca ccccagccgc atccgaagca 65580
accacaccca ccccctccaa caaccccgac ccaccaccat ccagccgcca ccccacccca 65640
ccaggcaacg acaacccttc acccgcaccc ccaagccgcc cccaccgctc caaccgctcc 65700
aaccgcggca cccgcacgac cccaccacgc acggcaacct gtgcctcgcc acacgcgaca 65760
aacccggcca catcgacacc agcaccaaca ccggcgccca tgtcctcatc ggcatcgacg 65820
acggtctcca cgccggtgcc ggggtcgagg tccagcagga cgaaccggtc gggatgctcg 65880
gactgggccg agcggaccag cccccacaca gcggccccccg ccacgtcccg caccggctcc 65940
cccgcatcca ccgcgaccgc accacgcgtc accacgacca gccgcgcgtc cccctcccgc 66000

-continued

```
tcatcggcga gccactcccg caccacaccc aacgccgcgg ccgtgacctc ggccacccca  66060
ccacccgggc actcccacac caccaactcc ccgcccccac cggccaacga ggccggcacc  66120
ccctccaccg gcacccaccc caactcgaac aacgacccac gccgcacccc cgcccccagc  66180
ccttccaacg gcaccggacg cagaaccaga gactccagcg cgagcaccag cgcaccggtc  66240
tcatcggcaa cccgaagact cacggtcgtt ccggccgcgt cgacagacgt cacccggact  66300
cgcagtgccc tggcaccccg ggcgtggagg gaagcaccgt tccatgtgta aggcagcaga  66360
ccggcctctt ggtcctcggg cagcaggagg gtgaccgtct gcacggccgc gtccaggagc  66420
gccggatgca ccccgaagcc cgcgacatcg gccagcccct cgtccggcag acgcacctcg  66480
gccaccacgt cgtccccgtc ccgccaggcc gcacacaaac cctggaacac cggaccgtag  66540
acaaaacccc cacccgccag acgaccgtag aactcatcga gatccaccgg ctgcgcaccg  66600
gacggcggcc acaccccgtc cgccaccggc tcaacaacca ccgactcccc aggaacagac  66660
ggacacacca caccctcggc atgccgcgtc cactcaccct ccagccctcc gtcctccacc  66720
agccgcccgt acacactcac accacgacga cccgcctcgt ccggcaccga aaccgacacc  66780
tgcaccacca catgccccga ctccggaacc accagaggag catggagagt cagctcatcg  66840
acaccaggac aacccgcacg cagaccagcc tgaaaagcca gctccagcag agcggtaccg  66900
ggcagcagga cgacgccgcc gacgctgtgg tcggcgagcc aggggtgggt gtgcagggac  66960
aggcgcccgg tgaggacgat tccgtccccg tccgcgagct ccatcaccgc gccgagcagt  67020
gggtggtccg gtcgctggag tccggcggcg gagacgtcgc cggtgctggt ggtgggtgtg  67080
tggagccagt agtggtggtg ttggaagggg taggtgggca ggtcgatggc gggggtgtgg  67140
ggggtggtgg ggtagtgggt ggtccaggtg acggtgtggc cggtggtgtg ggcgtgggcg  67200
agggccgtga ggaagcggtg ggtgtcgttg tcgtggcggc gcagggtgcc cagggcggtg  67260
gtgtggtcgt ggtcttcgat ggcgggggtc agggtggggt gggggctggt ctcgatgaag  67320
aggcggtggc cctgggcggt gagggtgcgg acggcgtggg tgaagcggac gggccggcgc  67380
aggttgcggt accagtaggc ggcgtccagg gtggtggtgt cggtccaggc gtcctcgacg  67440
gtggagtaga acgggatgct gccgggctgg ggggtgatgc cgtggagcat gtggagcagg  67500
tcgtgttcga tggtttcggt gtgggggcag tgggaggcgt agtccacggg gatgcggcgg  67560
gcccgtaccc cggtttcggt gcagtgggtg aggagttcgt ccagggcgtc ggtgtcgccg  67620
gagacggtgg tggcccgtgg cccgttgaac gcggccgtcc acagccgtcc cggccagtgg  67680
gtggtgatga ggtcctcggc ctcggttccg gtcagggcga gtgaggccat gccgccgtgg  67740
ccccgcagcg cggccagggc ccggctgcgc agtgccacga ccttcgcggc gtcctccagg  67800
gtgagggcgc cgcagacgtg ggcggcggcg atctcgccct gggagtggcc gaccaccgcg  67860
tcgggttcga tgccgtagga ccgccacagc gccgccaggg agaccatgac cgagaacagc  67920
accggctgga ccacatcggc ccgctcccac accggatcct ccgcctcgcg gtggagcatc  67980
tcggtgagcg accactccac ccacggcgcc agcgcgcgtt cacacgcacc gatatggtcg  68040
gcgaacaccc ccgaggtcgt cagcagatca agtcccatgc cggcccactg accaccctgg  68100
cccgggaaca cgaacaccac cccgccaccg gaatggctgt ggctgccggt cgcgtcttcg  68160
atgagtgcgg ggtgcggctc acccgaggcc agtgcttcca gcgcgccttc gaactccgcc  68220
cgctcccgtg ccacgatcac cgcgcggtgc tccagcacgg ccctgccacg agccaactct  68280
gccccgatat cccgcacccc ggcatccgta ccggggccgc gcaggaactc acgcaagacc  68340
atggcctgcg cccgcaacgc cgcacccgaa cgcgccgaca ccacccaggg caccggagcc  68400
```

-continued

```
ccgtcctcta ccgcagcctc cccgggccga cgggcgggtg cctcctccag gatcacgtgc  68460
gcgttggttc cgctcacccc gaacgaggac accccggccc gccggggccg gtcctcccga  68520
cgcggccagg gccgcgcctc ggacagcagg ctcaccgccc ccgacgacca gtccacctgc  68580
ggtgacggct catccacatg caacgtccgc ggcagcgact cgtgccgcag cgccatcacc  68640
atcttgatga tcccgcccac acccgctgcc gcctgggcgt ggccgatgtt ggacttcacc  68700
gagcccagcc acaacggctg ttccccggaa cgctcctggc catatgtgtc gagcagggcc  68760
tgggcttcga tcgggtcacc gagccgtgtg ccggtcccgt gcccctccac cgcgtcgacg  68820
tccgccaccg tcagccccgc gttggccagt gcctcgcgga tcacgcgctc ctgcgagggg  68880
ccgttcggtg cggtcaggcc gttggaggcg ccgtcctggt tgaccgcgct gccccgcacc  68940
accgccagaa cccggtgccc gttgcgctcg gcgtccgaca accgctcgac cagcagcatg  69000
cccacgccct cgcccatgcc ggtaccgtcg gccgcggccg cgaaggactt gcaccgcccg  69060
tccaccgaca gaccccgctg ccgggagaac tccacgaaca ggagcggggt ggacatcacg  69120
gtgaccccac cggcgagggc gagatcgcac tcgcccgtcc gcagcgactg gcaggccagg  69180
tgcagcgcca ccagcgacga cgaacacgcc gtgtcgacgg tgacggccgg gccttccaga  69240
ccgagcgtgt aggcgacgcg cccggaggcg acggcgccac cgctgccgtt gccgatgtag  69300
ccctcgaacc cttcggggat ggtggcgagc cgggaggcgt agtcgtggta catcatgccg  69360
gtgaagacac ccgctcgggc tccccggacc gaggaggggt cgatcccggc ccgctcgaag  69420
acctcccacg aggtctccag cagcaagcgc tgctgggggt ccatggccag ggcctcacgc  69480
ggactgatgc cgaaaagctc ggcgtcgaac tgtccggcgt cgtagaggaa accaccgtgg  69540
cgggtgtacg acgctccggc ccgctccggg tccgggtcga acagcccggc caggtcccac  69600
ccgcggtcgg ccgggaactc cccgatcgcg tcaccgcccg aagccaccag cccccacaac  69660
tcctccggcg accgcacacc gcccgggaac cggcacgcca tcccgacgat cgccagcggc  69720
tcctgtgccg cctcgacggc cgctgtgagc tgctggttgc gccgccgcag ggcctcattg  69780
gccttcaggg atgcccgcag cgcctcgacg agcttctcgc tgggcgtagc catcggtgtc  69840
tccaagtctg cgaatccggc aggtgcggac gcggtggtgt ggacggggcg ggggtcggcg  69900
gggaccgcgg cgggcgactc gggtggtgtc agcgacgccg ctgctcggtg agcccggcca  69960
gccaggtgtg gacgtgccgg gccgtcgact ccgcgtgctc ttcgagcatc gtgaagtggt  70020
tgccgtcggt ttcgaggacg gtgtgcggct cgccccacac cggcggcggc tgttcgctct  70080
cacgggcgcg gaggaagagg gtgggtgtct cgagggcggg cggccgccag cccgcgaaga  70140
tgcggaagta gccgcccatc gccaccaggc gggcgtagtc caggtcgatg aactcggtga  70200
cgcggtcgaa gatttcgctg gtgagggcgg cggcgacggg ggccatcccc tcgtcgggca  70260
ggtaggcgtc catgaccacc acggcctgcg gccggacgcc caggtgttcc aggcggctcg  70320
tgacggtgtg ggtgaaccag ccgccggcgg agtgtccggc gagggcgaag ggctcgccgt  70380
cggtgtggcg gaggatggcg tcggtgaaca gccgggtgat ggtgtcgacg tcggcgggga  70440
ggggctcgcc gtcggcgaag ccgggcgccg gcacgtacca gacgtcgcgg agcccgtcga  70500
gggccgccgc gaagcgggag tactggtaga cgctggacac ggcggcgacg gtgggcaggc  70560
agatcagcgc gggcccggtg tcgccctggg cgacgcggac gaagggggt  cgggtcatag  70620
ccgaggggtc ggtgaagcag ggccggaagg cggaggccgc cgacagcagg gccatggact  70680
cctcgacgcg gccgctgtcg tgaccgatcc agaacagggc ttccaccgtg tcggcggacg  70740
```

-continued

```
ggccgctccc ggctcgcgac gaggcggtgg catcgcgctc cccaggggcg ccggccgttt  70800
cggcggtcat atcggaggcc ggctcggcgg cgaggagcct ttcgaggtgg tcggcgagcg  70860
ctgccggggt cgggtggtcg aagacgagcg tggtggccag gcgcagcccg gtcgctgcgt  70920
tgaggcggtt gcgcagttcc acggcggtca gggagtcgaa gccgaactcg cggaactcgc  70980
cgtcggcggt gacggtgtcg gtgccgccgt ggccgaggac ggccgcggcg tgggtgcgga  71040
ccacctccgt cagcagggcg gtgcgctcgg cgggcttcgg ggtcccggcc agtcgcccgc  71100
ggagttcggc ggcggcgtcg gccccgacgc cgtggtcggc ggtccggcgg gccggggtgc  71160
ggaccaggcc cctgaggacg ggcggcaggg tgccgacggc cgcctgctca cggagggtgc  71220
ccgggtcgag gggggtggcg aggagcagcg gttcgtcgag ggcgagggcg gtgtcgaaca  71280
gggcgagccc gtgggcgttg gtgagcggga gcaggccgct gcgggtcatc cgggcgacgt  71340
cggcggcggc gaggtgctcg gccatgccgc ccgcctcggc ccagcgtccc caggcgaggg  71400
agcggccggg caggccgagg gcgtgccgtt gctgcatcag agcgtcgagg aaggcgttcg  71460
cggccgtgta gttggcctgt ccggggctgc cgaaggaggc ggcggcggac gagaaggcga  71520
tgaacgcgtc gagcccggcg tcgcgggtga ggtcgtgcag gtgggcggcg ccgtgggcct  71580
tggcgctcag gacggcgtcc aggcggtcgg gggtcaggga ggtgaggacg ccgtcgtcga  71640
cgacgccggc ggtgtggagc acggccttga gcggatgccg tgccgggatc tcggccagca  71700
gcgccgcgac ggcccgccgg tcggcgaggt cgcaggcgac ggccgtcgtc cgggcgccca  71760
gctcggcgag ttcggcgacg agttcggcgg tgccgggagc ggtggggccg ctgcggctgg  71820
tcagcagcag gtgccgtacg ccgtgggtga cgacgaggtg gcgggcgagg agccggccga  71880
ggtagccggt gccgccggtg atgaggacag tggcgtcggg gtcccagtgt ccgctgtccg  71940
ctcgggcgcc gaccgggatg cgggccagcc gcggggtgtg ggcgcggccc tcgcgcagga  72000
cggtctgcgg ctcaccggag agcagggccg cggccagggc gcgccggctg gcgtcggtgt  72060
cgtcgaggtc ggtgaggacg aaccggccgg ggttctcggt ctgggcggag cggaccatgc  72120
cccagacggc ggcgtgcgcg aggtcgggga cggagtcgcc cggtgcggcg gcgaccgcgc  72180
cgtgggtgac gaacgcgagc cgggagtccg cgaaccggtc gtcggcgagc cagctctgca  72240
gcaggtgcag gacgcggacg gtggcccgcc gggtggcgtc ggccgcgtcg gcggcgccgt  72300
cgcggtgcgg gcaggggacg acgaccacgt cgggtacggg tgtgccggcc gaggccagtt  72360
cctccagatc cgcgtatgtg ctccacggca cgccgggggc gtcggggcac tcggcttcgg  72420
agccgatcag cgccaggcgc gtcttcgacg acggtgtcct gggcagcggt acgggcgccc  72480
agtcgagccg gaagagggcg tcgtggtggg cggtgcgggc cgagtggagc tgtccggccg  72540
tgacgggccg gaacgcgagt gactcggccg tgacgacggt gtgtcccgtg ctgtccgtgg  72600
ccagcagggc gatcgtgtcg ggcgaccgcc gactgaggcg gacgcgcagc gccgatgccc  72660
cggaggccgt gacggtgacg ccgctccagg agaagggcag ccagccgtgg ccctcgtccg  72720
gctcgtcctc ggcgaagccg aggaccaccg ggtggagtgc cgcgtcgagc agcgccgggt  72780
ggacggcgta gcggtcggcg tcgcccgacg gtccgtcggg cagtgcgacc tcggcgtaca  72840
ggtcgtcccc gtgccgccag gcggcccgca gtccctggaa cgcgggtccg tatccgaggc  72900
ccgcgtcggc cagtgtcccg taccagtggt cgaggtcgac ggggaccgcg tccgtgggcg  72960
gccacggtgc ggcggtgtcg tgggcggtct ccgcgcgccg tgtcaggacg cccgtcgcgt  73020
ggcaggtcca gccggtcccg tccgtgccgg tcggcgcggc gggggtgagt ccgtcgtctt  73080
cccgcgcgta gagcgtgaag gggcgccgct ccaccccgtc cggcgccgtc tcggtcgcgc  73140
```

-continued

```
cgacggagag ctgcaggacg accgatccgc gctccggcag gaccagcggg acctggagtg  73200
ccagttcctc gacggtgtcg cagccgactt cgtcgcccgc gcggacggcc agttcgagga  73260
tggccgtgcc gggcagcagg acggtgccga agacggcgtg gtcggcgagc cagggatggg  73320
tgcgcagcga gatcctgccg gtgagcaggc attcctgcga ctgcggtgat ccggccaggg  73380
gtacggcgga gccgagcagg gggtgtccgg ctgcggtgag tccggcggcc gagacgtccc  73440
cggacaggct ggtgtcggcg tccagccagt agcggcggcg gtcgaagggg taggtcggca  73500
ggtcgaggtg gcgggcgcgt tccggtgtcg cgccgatgag ggccggccag tggacggccg  73560
tcccgccctt cggtgtgccc tgcacgtgga ggtgggcgag cgcggtgagc agcgccaggg  73620
gttcggggcg gtcggcgcgc agcagcggga ccagggcggg accgggctcg gtggtgttgt  73680
cgtcggcggg caggcactct ccggcgaggg cgcagagggt tccgtccggg ccgagttcca  73740
ggaaggtgcg taccccgtcg tcgtcgtgga ggcggcgtac ggcgtcgccg aagcgtacgg  73800
tgcggcgtag ctggcggacc cagtactccg ggtcggtgag cgtgccggcc gtggcgcggt  73860
cgccggtgac ggtggagacc accgggatcg tcggttcggc gtaggcgatg ccggtcgcga  73920
cctgccggaa ctcctccagg atcggttcca tcagcgggga gtggaaggcg cggtcggtgc  73980
tgaggcgttt ggtgcgcagg ccctgctcgg cgaaggcggc ggcggcttcc agtacgtccg  74040
gctcggctcc ggagatcacc accgacgtgg ggccgttgac agcggcgacg gccacccgtg  74100
cctcccggcc ggcgagcatc cgggtgacct gttcctcgct cgcgcggacc gccagcatgg  74160
ctccgccggg cggcagttgt gtctgcgcca gccggccccg ggccgcgacc agccgggccg  74220
cgtcggtcag tgagaggacg ccggcgacgt gcgcggcggc cagttcgccg atcgagtggc  74280
cggcgacgtg gtccgggcgg atcccggcgc tctccagcag gcggaagagg gcgacctgga  74340
gggcgaagag cgccggctgc gcgtcgccgg tgcggtccag cggctgcggc tcgtcgagga  74400
ggagcgggcg caggggccgg tcgagatggg gttcgagctc cgcgagtacg tcgtccaacg  74460
cctgggcgaa ggcggggtgg gcggcgtaca gctctcggcc catgccgggc cgttgggttc  74520
cctggccgga gaagaggaag gcgaccttgc cgtgggcggt gcgggcgggg gattcgatca  74580
ggccgggggc cgtggtgccc tcggccagtg cgtccagggt gcgcaggagt ccctcgtggt  74640
cctcggcgac cagcacggcc cggcgttcga atgtcgaccg gccggtggcc agggcgtgtg  74700
cgacgtcacc gatcgggatg tcggggttgg cggcgaggta gtcgcgcagc cgcctggcct  74760
gggcgcgcag ggcggtgtcg gtcctggccg agaggagaca gggcaccgtc gcgggtccgg  74820
cctcgtcctg cgacggtgcc tcctccggcc gtacctcttc ctcctgcggt gcctcttcca  74880
ggatgacgtg tgcgttggtg ccgctcaccc cgaacgacga cacacccgca cgacgcggac  74940
gctcaccccg ctcccacacc acctcctccg tcagcaaccg caccgcaccc gacgaccaat  75000
ccacatgcgg cgacggctca tccacatgca acgtccgcgg cagacgaccc cgccacaacg  75060
ccatcaccat cttgatcaca ccagccaccc ccgccgcagc ctgcgtatga cccagattcg  75120
acttcaccga ccccaaccac aacggcaccc cacgaccccg cccatacgcc gccagcaccg  75180
cctgcgcctc gatcggatca cccaacgacg tccccgtccc atgcccctcc accacatcca  75240
cctcagcagc cgacaacccc gcacacacca acgcctgacc gatcacccgc tgctgagacg  75300
gaccattcgg cgccgtcaac ccattcgacg caccatcctg attcaccgca ctcccccgca  75360
ccaccgccaa cacccgatgc cccagccgcc gcgcatccga caaccgctcc accaacaaca  75420
cacccacacc ctcggaccac cccaccccgt ccgccgccgc cgcgaacgcc ttgcaccgcc  75480
```

-continued

```
cgtccgccga caaaccccgc tgccgcgaga actccacgaa cgccccggc gtcgacatca  75540
ccgtcacacc ccccgccaac gccaactccg actcacccga ccgcaacgac tgacacgcca  75600
gatgcaacgc caccaacgac gacgaacacg ccgtgtccac cgtcaccgcc ggaccctcca  75660
acccgaacgt gtacgacaac cgccccgaca acacactccc cgacacaccc gtcagcgcat  75720
acccctccag atcccggcca ccccgacgca ccaactccgc ataatcctga ttcgccaccc  75780
ccgcgaacac acccgtacga ctcccccgca acgacaccgg atcgatcccc gcccgctcca  75840
gcgcctccca ggacacctcc agcaacaacc gctgctgcgg atccatcgcc aacgcctcac  75900
gcggcgaaat cccgaaaaac cccgcatcga actccgccgc acccgccaaa aacccacccg  75960
accgcgtata cgacgacccc ggccgccccg cctccggatc gtaaagaccc tccacatccc  76020
agccccggtc caccgggaag ccgccgatcg cgtccccacc cgaggcgacc aactcccaca  76080
aatcctccgg cgaccacaca ccccccggaa aacgacacgc catccccacg atcgccaccg  76140
gctcatccac cacaccgggt cgggccgcga cgggcggtgt cgccggggcg gttccgcaca  76200
gctggtcccg gaggtgccgg gccaggacgg cggggcgcgg gtagtcgaag accagtgtcg  76260
tgggaaggcg cagtccggtg gccgtgttga ggcggttgcg cagttcgacg gcggtgagcg  76320
agtcgaagcc gagttcgcgg aaggcccggt cggccgggac ggtgtcggcc tcccggtggc  76380
cgagcaccgc ggccgtgtgg gtgctgacca gttccagcag gacgtccgtc cgggcgtccg  76440
gttccagggc ggcgagccga tcgcgcaggt cggtgccgtg ggcggtgccg gtgccggtgg  76500
cgcgggtgag cgcccggacg tcggggaggt cgccgatcag gggcaggcgg ctgccggcgg  76560
tgtgggcggt gaagcgctcc cagtcgatgt cggcgacggt caagccgctc tcgtcgtggt  76620
ccagcacccg ggccagggcc gccagggcga gttcgggcgc catctccgtc agtccccggc  76680
ggtgcagccg ggcggccgcg tccggccggc cggcggcgct gtgtccgcgc caggggcccc  76740
aggccaccgc ggtggaaggc agtccgagac cgcgccggtg gacggcgaga gcctcgacat  76800
aggcgttggc cgccacatag gcaccctggc caccggaacc gaacgtggcg gcggccgagg  76860
agaacaccac gaacgccgaa agatccgcac cccgcgtcag ctcgtgcagg ttccgcgcac  76920
ccaccgccct ggccgccagc accccctcca gccgctccgg cgtcaacgcg tccagcacac  76980
cgtcgtccac cacccccgcc gtatgcacga ccgcccccag cggacaatcc tcgggaaccg  77040
ccgtggccag cagctccgcg agcgcccccc gatcggccac atcacaggcg gcgatggtca  77100
cccgggcgcc ccactggtcc gtcgtgtcgg cgaggccgaa gccgtcgccg gaggtactga  77160
tcagcagcag gtgttcggct ccgcggtcgg ccagccatcg ggcgaggtgg gcggccggct  77220
gctcggggtc ggcgttctcg ccggtgatca ggacggtgcc gcgcggccgc cacccaccag  77280
cctccgctcc ccctcccgga gcacgcacca gacgccgcac gaacaccccc gacgcccgga  77340
ccgcgacctc cccctcaccc ccgcccccg acagcacacc cagcaaaccc tccaccaccc  77400
gctcgtcgac cacctccggc agatcgacca ccccacccca ccgatccggc aactccaacc  77460
ccgccacccg gcccaaaccc cacaccacag ccccacccgg atcccccagc cgatccccct  77520
cccccaccga caccgcaccc cgcgtcacac accacaacgg cacccccaac ccctccaccg  77580
cctggaccaa ccccagcacc aacccggcaa cacccacccc acccccacac acagccagca  77640
cccccaccgg cccctcacca ccccacacct cacgcaaccg ctcccccaac accacccgat  77700
ccgcacaacc cccctccaca gccaccaccc gcacacacac ccccgcccac tccaaaccct  77760
ccaccacagc agcagcaccc accaccccct caggcaccac caccacccac accccacccg  77820
acaccacacc accacccgac cgcgacaccg gacgccacac cacccgatac cgccagccat  77880
```

-continued

```
cgaccaccgc acgctcccga acaccccgac gccagtcgcc gagcgcggac accagcgcgt  77940
cgagcggcgc gtcctcgtcc acggcgagca gcgcggccac ggccgccggg tcctctcgtt  78000
cgacggcttc ccacagcggg ccgtcctccg tggtggccgg cgcggccggt gtctcctccg  78060
ggtccagcca gtaccgctca cgctcgaagg cgtacgtcgg cagctccacc cggccggcgg  78120
tcccggacgg tttgccgccc agtacggccg cccagtccac ccgtaccccg cgcacggaca  78180
gctccgccgc ggaggccagg aagcgccgca gaccgccctc gccccggcgc agtgagccga  78240
ccaccagggt gtcggcggcg ccgaggtcgt cgagcgtctc ctggaccgcg acggagaccg  78300
cggggtgcgg gccggcctcg acgaagacgg tgtgcccgtc gcgggcgagg gcccgggtgg  78360
cgtcccggaa ccggacgggc tcgcgcaggt tgcggtacca gtacgcggcg tcgagtgcgg  78420
tgccgtcgac gggctcgccg gtgaccgtgg agtagagcgg gatgtcggcg gggcgggggg  78480
tgacgggagc gagaaggccg agcaggtctg cgcggatcgc ctcgacctgc ggggagtgcg  78540
aggcccagtc gaccttcagc aggcgggccg ggacgccgtc ccgggtcagg tcgtcgacca  78600
gggcggtgac cgcgtccggg gagccggaga ccacggccga gcgggccccg ttgtcggcgg  78660
cgaccaccag gctcgggtcc acggcggcga gccgcggttc caggtcctcg gccggcagac  78720
cgaccgaggc catggccccc tgtccggcga gcgcggcgag ggcctggctg cgcagggcgg  78780
tgacgcgcgc cgcgtcctcc agggagaggg caccggcgac gcaggccgcc gcgatctcgc  78840
cctgggagtg tccggcgacg gcgtcggggc ggacgccgta ggagcgccag agggccgcca  78900
gggacaccat gaccgcgaag agcacgggct ggacgacgtc gacccggtcc agcggcgggg  78960
cgtccggttc gccgcgcagg acgtcgagca gttcccagtc gaggtacgga cgcagggcgt  79020
cggcgcattc ggtcatgcgc tgggcgaaga ccggtgaaga gtccaggagt tcggcggcca  79080
tgccgtccca ctgggtgccc tggccgccga agagcagcgc gattttgccg tccgcctcgg  79140
ggccggtgcg tccggccacg actccggccg tcggcaggcc ggtggcgagg gcgtcgaggc  79200
cgtgccggaa accgtcgagg tcctcggcga gcacgaccgc ccggtgctcc agccacgccc  79260
gctccaccgc cagcgcacgc ccgacctcca ccggagccgc ccccgcccca tcggcgaaca  79320
cccgcaaccg ccgcgcctgc ccccgcaacg ccgactccga acgagccgac accacccacg  79380
gcaccaccgc gggtccggcc tcgccctgcg acggtgcctc ctccggccgt acctcttcct  79440
cctgcggtgc ctcctccaga atcacatgcg cgttggtgcc gctcaccccg aacgacgaca  79500
cacccgcacg ccgcgggcgc tcaccccgct cccacaccac ctcctccgtc agcaaccgca  79560
ccgcacccga cgaccaatcc acatgcggcg acggctcatc cacatgcaac gtccgcggca  79620
gacgaccccg ccacaacacc atcaccatct tgatcacacc agccaccccc gccgcagcct  79680
gcgtatgacc cagattcgac ttcaccgacc ccaaccacaa cggcaccccca cgaccccgcc  79740
catacgccgc cagcaccgcc tgcgcctcga tcggatcacc caacgacgtc cccgtcccat  79800
gcccctccac cacatccacc tcagcagccg acaaccccgc acacaccaac gcctgaccga  79860
tcacccgctg ctgagacgga ccattcggcg ccgtcaaccc attcgacgca ccatcctgat  79920
tcaccgcact cccccgcacc accggcaaca cccgatgccc cagccggcgc gcatccgaca  79980
accgctccac caacaacaca cccacaccct cggaccaccc caccccgttc gtcggcgtcg  80040
cgaacgcctt gcaccggccg tccggcgaca aaccccgctg tcgcgagaac tccacgaacg  80100
cccccggcgt cgacatcacc gtcacacccc ccggcaacgc caacttcgac tcacccgaac  80160
gcaacgactg acacgccaga tgcaacgcca ccaacgacga cgaacacgcc gtgttcaccg  80220
```

-continued

```
tcaccggcgg acccttcaac ccgaacgtgt acgacaaccg ccccgacaac acactccccg  80280
acacacccgt cagcgcatac ccctccagat cccggccacc ccgacgcacc aactccgcat  80340
aatcctgatt cgccaccccc gcgaacacac ccgtacgact cccccgcaac gacaccggat  80400
cgatccccgc ccgctccagc gcctcccagg acacctccag caacaaccgc tgctgcggat  80460
ccatcgccaa cgcctcacgc ggcgaaatcc cgaaaaaccc cgcatcgaac tccgccgcac  80520
ccgccaaaaa cccacccgcc cgcgtatacg acgaccccgg ccgcccccgcc tccggatcgt  80580
aaagaccctc cacatcccag ccccggtcca ccgggaagcc gccgatcgcg tccccgcccg  80640
aggcgaccaa ctcccacaaa tcctccggcg accacacacc ccccggaaaa cggcacgcca  80700
tccccacgat cgccaccggc tcatccacca caccggaccg gatgaaggcg ggccggccgg  80760
ccggggcttc cccgccggtg ctcagcagtg tgccgaggtg tgtggccagg gcggacgggt  80820
tggggtagtc gaacaccagc gtgctgggca accgcagtcc ggtggccgtg ttgaggccgt  80880
tgcgcagttc gacggcgttg agcgagccga agccgagctc ccggaaggcc cggtcggccg  80940
ggacggcggt ggcggtgcgg tggccgagga cggtggcggt gtgggtgcgg acgaggtcga  81000
gcagggcgcg gtcccgttcg gccggttcca gggcggccag gcgtgcgcgg agcgagccgg  81060
gggcctccgt gccggtggcg ggccgggcga gccgggcctc ggggatgtcg gagagcagcc  81120
gggcgaggcc gtcggcggcg ggcaggcgct cccagtcgat gtcggcgatg gtgaggcagg  81180
tctcgttgcg gtccagtacc tggccgaggg cggacagcgc gggctcggtg tccatgggcc  81240
ggatcccgcg gcggtccatc cgcgtggcgg cctccgcgtc cgcggccatg cccccgcccg  81300
cccaggcgcc ccaggccacc gcggtggagg gcagtccgag accgcgccgg tggacggcga  81360
gagcctcgac ataggcgttg gccgccacat aggcaccctg gccaccggaa ccgaacgtgg  81420
cggcggccga ggagaacacc acgaacgccg acagatccgc accccgcgtc agttcgtgca  81480
ggttccgcgc acccaccgcc ttggccgcca gcaccccctc cagccgctcc ggcgtcaacg  81540
cgtccagcac accgtcgtcc accacccccg ccgtatgcac gacggcaccc agcggacaat  81600
cctcgggaac cgccgtggcc agcagctccg cgagcgcccc ccggtcggcc acatcacagg  81660
cggcgatggt cacccgggcg cccatcgcgg tgagttccgc gcggagctcc ccggcaccct  81720
tggcctcgcg tccgctccgg ctgaccagca gcaggtgctc ggccccgcgc cggaccatcc  81780
agcgggcgac gtgtgctccc agagcgccgg tgccgccggt gatcaggacg gtgccgcgcg  81840
gccgccaccc accagcctcc gctccccctc ccggagcacg caccagacgc cgcacgaaca  81900
cccccgacgc ccggaccgcg acctccccct cacccccgcc ccccgacagc acacccagca  81960
aaccctccac cacccgctcg tcgaccacct ccggcagatc gaccacccca ccccaccgat  82020
ccggcaactc caaccccgcc acccggccca aaccccacac cacagcccca cccggatccc  82080
ccagccgatc cccctccccc accgacaccg caccccgcgt cacacaccac aacggcaccc  82140
ccaaccccctc caccgcctgg accagcccca gcaccaaccc ggcaacaccc accccacccc  82200
cacacacagc cagcaccccc accggcccct caccaccaca cacctcacgc aaccgctccc  82260
ccaacaccac ccgatccgca caaccccccct ccacagccac cacccgcaca cacacccccg  82320
cccgctccaa accctccacc acagcagcag cacccaccac cccctcaggc accaccacca  82380
cccacacccc acccgacacc acaccaccac ccgaccgcga caccggacgc cacaccaccc  82440
gataccgcca gccatcgacc accgcacgct cccgaacacc ccgacgccag tcgccgagcg  82500
cggacaccac ggatcccaaa ggcgcgtcct cgtcgacttc cagcagggcc gcgaccgccg  82560
gcaggtccgc gcgctcgacc gcctgccaca gcgggccgtc ctccccggcc ggcagcgcgg  82620
```

-continued ccggtgtctc gcccgcgtcc agccagtacc gctcacgctc gaacgcgtac gtcggcagct 82680
ccacccggcc ggcggtcccg gacggtgcgc cgcccagcac ggccgcccag tccacccgca 82740
ccccgcgcac ggacagcccg gccacggcgg cgagcacgga cacggcctcc ggccggtccg 82800
gtcgcagtgc ggggagcagg ggggcgggtt cggtgagggc gtcctggccg agggcgcaga 82860
gtgtgccgtc cgggccgagt tcgaggtagg cggtgacgcc ctgggcctgg agccaggcga 82920
ggccgtcgcc gaagcggacg gtgtggcggg cgtgctggac ccagtagtca gcggtgccca 82980
tggtgtcggc ggagacgggg gcgccggtga ggttggtgac cacggggatg cgcggcgggg 83040
cgaagacgac ctgctccgcg acgcggcgga agtcgtccag tacggcgtcc aggtgcgggg 83100
agtggaaggc gtggctggtg cgcagccgcc gggtccggcg gccctgttcc gcccagtggc 83160
gggcgagcgt gagtacggcg tcctcgtcgc cggcgaggac gaccgcgcgc gggccgttga 83220
cggcggccag gtccgcgcgc ccctcggcat cctggagcag cggccggact tcctcctccg 83280
tcgcctcgac ggcgaccatg gcgccggtgt ccggcagcgc ctgcatcagc cggccccggg 83340
ccgtcaccag ggcggccgcg tcggggaggg agagcatccc ggcgacgtgt gcggcggcca 83400
gttcaccgac ggagtgcccc aggaggtagt cgggtgtcac cccccagttc tcgaccagcc 83460
ggtacagcgc gacctcgacg gcgaacaggg cgggctgggc gtattccgtc tgttcgatca 83520
gctcggcgcc gggggatccg ggggccgcga acacgatgtc gcgcagggtg tggcctgctt 83580
ccccgatcgg gccgaagtgg gcgcacacct cgtcgaaggc gtccgcgaag gcggggaagt 83640
gcgcgtggag ttcgcggccc atggccgggc gctgtgtgcc ctggcccgcg aagaggaacg 83700
ccagcgggcc ttcgtcggtc gcggtgccgg tgacgacttc cggggcggga cggccggtgg 83760
cgagggcgtc gaggccgtgc cggaaaccgt cgaggtcctc ggcgagcacg accgcccggt 83820
gctccagcca cgcccgctcc accgccagcg cacgcccgac ctccaccgga gccgcccccg 83880
ccccatcggc gaacacccgc aaccgccgcg cctgccccg caacgccgac tccgaacgag 83940
ccgacaccac ccacggcacc accgcgggtc cggccccgtc ccccgacgga accaccaccg 84000
gcccgacgcc gtcccccgac ggtgcctcct ccggccgtac ctcttcctcc tgcggtgcct 84060
cctccagaat cacatgcgcg ttggtaccgc tcaccccgaa cgacgacaca cccgcacgcc 84120
gcggacgctc accccgctcc cacaccacct cctccgtcag caaccgcacc gcacccgacg 84180
accaatccac atgcggcgac ggctcatcca catgcaacgt ccgcggcaga cgaccccgcc 84240
acaacgccat caccatcttg atcacaccag ccaccccgc cgcagcctgc gtatgaccca 84300
gattcgactt caccgacccc aaccacaacg gcaccccacg accccgccca tacgccgcca 84360
gcaccgcctg cgcctcgatc ggatcaccca acgacgtccc cgtcccatgc ccctccacca 84420
catccacctc agcagccgac aaccccgcac acaccaacgc ctgaccgatc acccgctgct 84480
gagacggacc attcggcgcc gtcaacccat tcgacgcacc atcctgattc accgcactcc 84540
cccgcaccac cgccaacacc cgatgcccca gccgccgcgc atccgacaac cgctccacca 84600
gcagcacacc gacaccctcg gacatcccgg tgccgtcggc cgcggcggcg tagggcttgc 84660
agcggccgtc cgccgacagg ccccgttggc gcgagaactc cacgaacatg gcgggggtgg 84720
acatcacggt gaccccgccg gcgagtgcga gggaggattc gcccgacctg acggactggc 84780
aggccaggtg cagtgccacc agcgatgacg agcacgccgt gtcgaccgtc accgcggggc 84840
cttcgaaccc gaaggtgtag gagagccggc cggacaggac gctcgccgcg ttgccgttgc 84900
cgaggaagcc ctgaaggtga tccggaacgg acagcagacg ggtggcgtag tcgtgcgaca 84960

-continued

```
tcatccccgc gaagacgccg gtgcggctgc cgcgcagggt ggccgggtcg atcccggccc  85020
gctccagcgc ctcccaggac acctccagca tcaaccgctg ctgcgggtcc atcgccagcg  85080
cctcgcgcgg ggagagaccg aagaatcccg cgtcgaactc cgctgcctcg tgcaggaatc  85140
cgcccgatcg cgtgtacgac cgccctgccc ggcccggctc cgggtcgtag aggtcctcga  85200
cgtcccagcc ccggtccacc gggaagtcgc cgatcgcgtc cccgcccgag gcgaccagct  85260
cccacaggtc ctcgggcgat cgcacacctc ccgggaaccg gcacgccatg cccacgatcg  85320
cgaccggctc ctgcctgccc gactcgacct gctccagccg gcgccggacc cgcagcagat  85380
cggcggtcgc gcgcttgagg tactcgcgga gcatttcctc gttggccatg acggggtctc  85440
ctcgccgctg cgctggaggt ggcacggaac cccgccagat tagggtgggc aagtcaaccc  85500
gaataccccc tatacacccc agactggcta cgtgaagcga atacccgttc aaataggggg  85560
aagagccgca ggcatggatc gttacgcgaa gcgtttcgag gaccggctgg tcctggtcac  85620
gggggcgggg agcggcatcg ggcgggcgac ggcctgccgg ttcggtgccg ccggggcgcg  85680
gctggtgtgt gtggaccggg acgggcccgg cgcggaggcg accgccgaac tggcgcgtgc  85740
gcggggggcg cgggcggcgt gcgccgaggt ggccgacgtc tcggacgagg tggcgatgga  85800
gcggctcgcc gcgcgcgtca cggccgcgca cggcgtgctg gacgtgctcg tgaacaatgc  85860
cggtatcggc atgtcggggc ggtttctcga cacgtcggcc gaggactggc gccgcaccct  85920
gggggtgaat ctgtggggcg tcatccacgg gtgccggctc ctcggccggg gcatggccga  85980
gcgccggcag ggcggtcaca tcgtgacggt ggcctcggcg gccgcgttcc agccgacccg  86040
ggtcgttccg gtgtacgcca ccagcaaggc cgcggccctg atgctgagcg agtgtctgcg  86100
cgcggagttg gcggagttcg gcatcggtgt gagcgtggtc tgccccggcc tggtccgtac  86160
gccgttcgcg tccgcgatgt acttcgccgg cgcgtccccc gacgagcaca cccggctgcg  86220
tgagtcctcc gcccgccgct tcgcgggccg cggctgcccg ccggagaagg tcgcggacgc  86280
cgtcctgcgc gcgatcatgc ggacggcctt gccgacggtg accgggtcga cgccgtagag  86340
ctggatcagc gcggtctcct cgcccgtctc cggcttgacc tcgaagtacg cgagcggctc  86400
ggcgtcggcg gctgccgcgt cgtacagcag gatgcgcaga tccggaagtc ctgctcttcg  86460
acgagccgtt cagcgcgctg gacccgctga tccctttagt gagggttaat tgcggccgcg  86520
ttccagccga cccgggtcgt tccggtgtac gccaccagca aggccgcggc cctgatgctg  86580
agcgagtgtc tgcgcgcgga gttggcggag ttcggcatcg gtgtgagcgt ggtctgcccc  86640
ggcctggtcc gtacgccgtt cgcgtccgcg atgtacttcg ccggcgcgtc cccogacgag  86700
cacacccggc tgcgtgagtc ctccgcccgc cgcttcgcgg gccgcggctg cccgccggag  86760
aaggtcgcgg acgccgtcct gcgcgcgatc gtccgcaata cggcggtggt cgccgtcacc  86820
cccgacgccc gcgccgtccg tctgatgagc cgcttcgcgc cccgcctccg cgccgtcgtg  86880
gcccggctgg acccgtaggc agggcccgta cgggcagcgg gcgtccggtt cgggccaccg  86940
gccgcggtat ccgcgcccct gcccggagct gtgccgctcc gggcaggggc gcgcggacga  87000
ggcggtccgg cccggcggcc cggacctggc ggtccgttac tcaaaccgcg tgagcgtcag  87060
ccggatcccg gtgggagcgg tgtcctggat gtaggaggcg aagtcggcca cgtcgtcgaa  87120
ggcgaagccg taggctcggc cgtcctccgt gatcgcgtgc atcgccttgg cgtagtggtt  87180
ggtcagcgcg gtcctgtaga aggccgcggg gtcggtcgtg ggctgggcgg cggaggtgag  87240
cagggtcgag cggttgaatc cggcgccgag gaccgcggcg acgggaccgg tggtgccgtc  87300
gttcggcgcg gcgagggcac cgtggcagaa gagcacgtcg cgcgtggtgg gcttggcgaa  87360
```

-continued

```
ggacacctgg gcgggcccgt cgaaggtcag ccgctcgccg cgcacccggc cggtgaaggt  87420

cccggcgttg gtggtgaccg tgaggtccct ggcggtgtag gtgctccaca cctcgtcgat  87480

gtacggagcg aggtagtcct tcgggaacag gccggcgtcc agcccgtgcc cgggggcgat  87540

cacacggagg tcgtccagga ccagtggcgc gaactccgcg acgcggcgga ccgcttcgaa  87600

cgccgccgcc cggccgccgg cccgcacggt gccggtcgtc tggtccttcg cgcccgtcag  87660

ccggatactg agcggcacgc tgaacatgtc caccatggtc gtgttgcaga acatgccgga  87720

ggggttgtag gtgaactcgg cgcagtcgtg cagcaccctg tagttcggat cggacgcgac  87780

ccagccggcc gggtactgca gcgcggcgtt cccggctccg tccgtgacca ccttgaactt  87840

gagtttctgt ccgagcgcga catagatccg gccggacatg tacggcaggg agagccgggt  87900

ctcgccgctg ccggccagtg tgatcgcgta gtccgtgaag ccgtcggggc cgttgtccga  87960

cagggcgacg ggcgcgaggg tgccgtcggg cgtgagccgt acctgtcggc cgtcctggtt  88020

ccccacgacg tagacatgga cgtcgccgtt gccgaagacg ccggtgtcgt tgacgaccgt  88080

cagcggcagg gcgcccgccg tggtcccttc cgcgtcgcgg tcccggccgg ggccggcgag  88140

ggcgtgcggt gccagggctg cgacggcggg agcggccatc gcggcgccgc cgagggcgac  88200

gagcagggtg cggcggccga ggctgcgctg gtgtcgagga gtcatgtggg gggcctcctg  88260

gtgggcttgc cgatgttcta atgacgggaa catgacaggt gagaagcgtg ggagcgctcc  88320

tcagggcccg atggtacgca cggggaggcg tcccgcgtcc ccgtgccggg accgcttaac  88380

cgacgcttaa gggccgttta                                              88400
```

<210> SEQ ID NO 2
<211> LENGTH: 922
<212> TYPE: PRT
<213> ORGANISM: bacteria

<400> SEQUENCE: 2

```
Met Arg Gly Val Ser Pro Ser Val Ser Val Arg Glu Pro Gln Gly Leu
1               5                   10                  15

Thr Phe Leu Gly Leu Gly Arg Gln Ser His Ala Val Arg Thr Ala Leu
            20                  25                  30

Glu Ala Cys Ala Ala Gly Arg Val Arg Val Leu Val Val Glu Gly Gly
        35                  40                  45

Leu Gly Cys Gly Lys Ser Ala Phe Leu Gly Glu Ala Leu Lys His Ala
    50                  55                  60

Ala Ala Ser Gly Phe Leu Val Leu Arg Ser Ala Gly Ser Pro Pro Glu
65                  70                  75                  80

Gly Arg Arg Pro Phe Asp Leu Leu Arg Gln Leu Ala Val Asp Pro Asp
                85                  90                  95

Ile Pro Asp Ala Gln Arg Ser Leu Leu Gln Asp Ala Val Gly Thr Glu
            100                 105                 110

Thr Pro Ala Ala Gln Arg Val Arg Ala Ala Leu His Gln Leu Thr Gly
        115                 120                 125

Ala Ala Pro Val Val Ile Gly Ile Asp Asp Leu His His Ala Asp Pro
    130                 135                 140

Gln Ser Leu His Cys Leu Leu Gln Ala Val Asp His Pro Arg Ala Thr
145                 150                 155                 160

Arg Leu Leu Leu Val Cys Thr Ala Leu Pro Ser Gly Leu Ala Ala Asp
                165                 170                 175

Pro Ala Val Glu Ala Glu Leu Leu Cys Gln Pro Ala Leu Gln Arg Val
```

-continued

```
            180                 185                 190

Met Leu Gly Arg Leu Ser Leu Arg Ala Val Ser Gly Leu Arg Ala Ala
        195                 200                 205

Arg Pro Gly Pro Ala Val Glu Ala Leu Pro Ala Asp Asp Leu Leu Ala
    210                 215                 220

Val Thr Gly Gly Asn Pro Leu Leu Val His Ala Leu Leu Glu Glu Leu
225                 230                 235                 240

Val Glu Ser His Thr Gln Gly His Thr Asp Glu Arg Ala Gly Arg Arg
                245                 250                 255

Arg Arg Ala Ala Ser Pro Val Ile Gly Gly Arg Phe Tyr Gln Ala Val
            260                 265                 270

Leu Ala Ser Leu Ser Arg Thr Asp Ser Leu Val Arg His Ser Ala Gly
        275                 280                 285

Ala Leu Ala Val Leu Gly Asp Ser Gly Cys Ala Glu Val Ile Ala Arg
    290                 295                 300

Leu Leu Gly Ile Gly Arg Ala Met Ala Ala Arg Gly Leu Arg Ala Leu
305                 310                 315                 320

Glu Ala Thr Gly Leu Thr Ala Ser Gly Arg Phe Arg His Pro Val Val
                325                 330                 335

Glu Ala Ala Ala Leu Asp Thr Leu Asp His Asp His Arg Ala His Leu
            340                 345                 350

His Arg Arg Ala Ala Ala Leu Leu Tyr Asp Val Gly Ala Glu Pro Asp
        355                 360                 365

Glu Val Ala Arg His Leu Leu Ala Ala Arg His Ala Ala Gly Pro Trp
    370                 375                 380

Ala Met Ser Val Leu Arg Asp Ala Ala Glu Gln Leu Leu Met Arg Asp
385                 390                 395                 400

Asp Val Leu Thr Ala Val Ser Cys Leu Glu Leu Ala Arg Arg Ser Cys
                405                 410                 415

Ala Gly Gly Pro Arg Arg Ala Glu Ile Leu Leu Arg Leu Thr Val Ala
            420                 425                 430

Thr Arg Arg Thr Asp Pro Ala Ala Ala Glu Asp His Leu Ala Glu Leu
        435                 440                 445

Val Thr Glu Leu Arg Ala Gly Arg Leu Thr Ser Ala Glu Thr Glu Arg
    450                 455                 460

Leu Gly His Leu Leu Leu Gly Cys Gly Arg Leu Glu Glu Ala Thr Glu
465                 470                 475                 480

Val Met Gly Arg Pro Gly Pro His Gly Asp Pro Arg Thr Pro Arg Leu
                485                 490                 495

Glu Thr Gly Phe His Ala Ser Ala Leu Trp Glu Pro Leu Ile Arg Pro
            500                 505                 510

Arg Thr Asp Pro Glu Pro Gly Asp Glu Glu Ser Pro Arg Pro Arg Met
        515                 520                 525

Pro Val Thr Gly Ile Trp Asp Leu Pro Gly Asp Gly Thr Asn Ala Ser
    530                 535                 540

Ala Ser Asp Ala Ala Glu His Val Leu Arg Ser Leu Pro Leu Thr Asp
545                 550                 555                 560

Thr Thr Leu Val Ile Val Val Asn Ala Val Arg Val Leu Cys Arg Thr
                565                 570                 575

Gly Ser Tyr Glu Thr Ala Ala Leu Trp Cys Thr Arg Leu Leu Gly Glu
            580                 585                 590

Ala Ala Gly Arg Arg Leu Pro Gly Trp Lys Ala Gln Phe Leu Ala Leu
        595                 600                 605
```

-continued

```
Gln Ala Glu Ile Ala Leu Cys Arg Gly Leu Leu Ala Asp Thr Glu Glu
    610                 615                 620

Tyr Ala Arg Gln Ala Leu Ala Cys Val Pro Arg Cys Ser Arg Ser Val
625                 630                 635                 640

Phe Ile Gly Gly Pro Leu Ala Ser Arg Val Phe Ala Ala Thr Ala Met
                645                 650                 655

Gly Arg Tyr Asp Glu Ala Thr Arg Gln Leu Asp His Pro Val Pro Glu
            660                 665                 670

Ala Leu Phe Arg Ser Val Tyr Gly Pro Ala Tyr Leu Arg Ala Arg Gly
        675                 680                 685

His Tyr Tyr Leu Ala Leu Asp Arg Pro Leu Ala Ala Val Arg Asp Phe
    690                 695                 700

Leu Gly Ala Gly Arg Leu Leu Arg Arg Trp Gly Ile Asp Arg Pro Thr
705                 710                 715                 720

Leu Met Pro Trp Arg Ser Asp Ala Ala Glu Ala Phe Leu Arg Leu Cys
                725                 730                 735

Glu Pro Arg Arg Ala Asp Arg Leu Leu Arg Glu Gln Leu Ala Arg Thr
            740                 745                 750

Pro Asp Asp Asp Pro His Val Arg Gly Val Ser Leu Arg Leu Arg Ala
        755                 760                 765

Gln Ile Ala Glu Pro Pro Asp Arg Leu Asn Leu Leu Thr Glu Ala Val
    770                 775                 780

Asn His Leu Lys Ser Ser Gly Asp Arg Leu Ala Leu Ala Gly Ala Leu
785                 790                 795                 800

Ala Asp Leu Gly Ala Ala Tyr Arg Glu Arg Gly Glu Ser Thr Arg Ala
                805                 810                 815

Gly Ala Thr Ile Arg Arg Ala Trp His Leu Ala Asn Asp Cys Gly Ala
            820                 825                 830

Arg Ala Leu Cys Glu Arg Ile Leu Pro Gly Gly Pro Gly Arg Gln Ser
        835                 840                 845

Phe Gly Asp Gly Thr Gly Arg Thr Glu Ala Ala Leu Ser Gly Ser Glu
    850                 855                 860

Leu Arg Val Val Glu Leu Ala Ala Asn Gly His Thr Asn Arg Glu Ile
865                 870                 875                 880

Ala Ala Arg Leu Cys Ile Thr Val Ser Thr Val Glu Gln His Leu Thr
                885                 890                 895

Arg Ala Tyr Arg Lys Leu Glu Ile Ser Arg Arg Gln Glu Leu Pro Ala
            900                 905                 910

Arg Leu Cys Ala His Ile Glu Ser Pro Val
        915                 920


<210> SEQ ID NO 3
<211> LENGTH: 259
<212> TYPE: PRT
<213> ORGANISM: bacteria

<400> SEQUENCE: 3

Met Pro Asp Leu Cys Glu Thr Glu Ser Leu Trp Leu Arg Arg Phe Gln
1               5                   10                  15

Pro Ala Pro Ala Ala Arg Thr Arg Leu Met Cys Phe Pro His Ala Gly
            20                  25                  30

Gly Ser Ala Ser Ala Tyr Leu Arg Leu Ala Arg Ser Leu Ala Pro Gly
        35                  40                  45

Ile Glu Val Leu Ala Val Gln Tyr Pro Gly Arg Gln Asp Arg Arg Ala
```

-continued

```
    50                  55                  60

Glu Pro Cys Pro Asp Ser Val Glu Gly Leu Ala Asp Asp Leu Phe Ala
65                  70                  75                  80

Ala Val Arg His Arg Val Asp Ala Ser Thr Ala Leu Phe Gly His Ser
                85                  90                  95

Met Gly Ala Val Leu Ala Phe Glu Leu Ala Arg Arg Leu Glu Arg Asp
            100                 105                 110

Ala Gly Val Arg Cys Ala Arg Ile Phe Ala Ser Gly Arg Arg Ala Pro
        115                 120                 125

Ser Arg Phe Arg Asp Asp Ser Ala Pro Ala Ala Ser Asp Ala Ser Met
    130                 135                 140

Leu Ala Glu Met Arg Thr Leu Gly Gly Thr Asp Leu Arg Val Leu Gln
145                 150                 155                 160

Asp Glu Glu Leu Leu Ile Ala Ala Leu Pro Ala Leu Arg Ala Asp Tyr
                165                 170                 175

Arg Ala Ile Gly Thr Tyr Arg Ala Ala Asp Asp Ala Val Val Gly Cys
            180                 185                 190

Pro Val Thr Val Leu Val Gly Asp Ala Asp Pro Arg Thr Ser Leu Asp
        195                 200                 205

Asp Ala His Ala Trp Ser Ala His Thr Thr Ala Glu Ser Glu Val Leu
    210                 215                 220

Thr Phe Ser Gly Gly His Phe Phe Leu Asp Ala His His Asp Ala Val
225                 230                 235                 240

Val Glu Val Val Thr Ala Arg Leu Arg Gln Asp Arg Ala Pro Arg Pro
                245                 250                 255

Asp Arg Val


<210> SEQ ID NO 4
<211> LENGTH: 267
<212> TYPE: PRT
<213> ORGANISM: bacteria

<400> SEQUENCE: 4

Met Pro Glu Leu Asn Asp Arg Thr Ala Leu Val Thr Gly Ala Ser Arg
1               5                   10                  15

Gly Ile Gly Lys Ala Ile Ala Gln Arg Leu Ala Ala Glu Gly Val Arg
            20                  25                  30

Val Ala Val His Tyr Gly Thr Gln Glu Lys Ser Ala Gln Glu Thr Val
        35                  40                  45

Glu Thr Ile Glu Arg Ala Gly Gly Arg Ala Phe Ala Val Arg Ala Asp
    50                  55                  60

Leu Leu Arg Asp Asp Ala Val Asp Glu Leu Phe Thr Ala Leu Glu Arg
65                  70                  75                  80

Glu Leu Glu Gly Arg Pro Leu His Ile Leu Val Asn Asn Ala Ala Val
                85                  90                  95

Ala Pro Ala Pro Gly Asp Pro Ala Leu Ala Ala Gln Asp Gly Tyr Val
            100                 105                 110

Pro Gly Leu Ser Asp Thr Thr Pro Glu Glu Phe Asp Arg Val Tyr Arg
        115                 120                 125

Ile Asn Val Arg Ala Pro Phe Phe Val Thr Gln Arg Ala Leu Ser Leu
    130                 135                 140

Met Ala Asp Gly Gly Arg Ile Val Asn Val Ser Ser Ala Val Thr Arg
145                 150                 155                 160

Ile Ala Trp Pro Leu Leu Pro Tyr Ala Met Thr Lys Gly Ala Leu Glu
```

-continued

```
                165                 170                 175

Met Met Ala Pro Arg Leu Ala Asn Glu Leu Gly Ser Arg Gly Ile Thr
            180                 185                 190

Val Asn Thr Val Ala Pro Gly Ile Thr Asp Thr Asp Met Asn Arg Trp
        195                 200                 205

Val Arg Glu Thr Pro Gly Ala Glu Ala Gly Ile Ser Ala Leu Thr Ala
    210                 215                 220

Leu Gly Arg Leu Gly Arg Pro Asn Asp Ile Ala Gly Ile Val Ala Phe
225                 230                 235                 240

Leu Val Ser Asp Asp Ala Arg Trp Ile Thr Gly Gln Leu Leu Asp Ala
                245                 250                 255

Ser Gly Gly Met Ala Leu Ala Pro Ala Met Met
            260                 265


<210> SEQ ID NO 5
<211> LENGTH: 2341
<212> TYPE: PRT
<213> ORGANISM: bacteria

<400> SEQUENCE: 5

Val His Glu Thr His Ala His Gly Glu Glu Gly Ser Ser Asp Gly Ser
1               5                   10                  15

Ala Asp Ala Val Val Phe Val Phe Pro Gly Gln Gly Ser Gln Trp Pro
            20                  25                  30

Gly Met Gly Ala Glu Leu Trp Asp Thr Ser Pro Val Phe Arg Glu Ser
        35                  40                  45

Val Arg Ala Cys Ala Asp Ala Leu Ala Pro Tyr Leu Asp Trp Ser Val
    50                  55                  60

Glu Gly Val Leu Arg Gly Ala Pro Asp Ala Pro Ala Gly Pro Ala Leu
65                  70                  75                  80

Asp Arg Ala Asp Val Ala Gln Pro Ala Leu Phe Thr Leu Met Val Ser
                85                  90                  95

Leu Ala Glu Leu Trp Arg Ser His Gly Val Glu Pro Cys Ala Val Leu
            100                 105                 110

Gly His Ser Leu Gly Glu Ile Ala Ala Ala His Val Ala Gly Ala Leu
        115                 120                 125

Thr Leu Ala Asp Ala Ala Arg Val Ala Ala Leu Trp Ser Arg Ala Gln
    130                 135                 140

Ala Thr Leu Ser Gly Thr Gly Thr Leu Leu Ala Ala Lys Ala Ala Pro
145                 150                 155                 160

Glu Glu Leu Ala Pro His Leu Gln Arg Trp Asn Gly Asp Asp Arg His
                165                 170                 175

Gly Thr Arg Leu Ala Ile Ala Gly Val Asn Gly Pro Gly Ser Thr Val
            180                 185                 190

Val Ala Gly Asp Leu Asp Ala Ile Ala Ala Leu Ala Ala Asp Leu Ala
        195                 200                 205

Ser Ala Gly Val Arg Thr Arg Arg Val Ala Val Asp Val Pro Thr His
    210                 215                 220

Ser Pro Ala Met Arg Thr Leu Arg Glu Arg Ile Leu Thr Asp Leu Ala
225                 230                 235                 240

Ser Val Ala Pro Cys Val Ser Arg Leu Pro Phe His Ser Ser Leu Thr
                245                 250                 255

Gly Gly Leu Val Asp Thr Arg Gly Leu Asp Ala Asp Tyr Trp Tyr Arg
            260                 265                 270
```

-continued

```
Asn Ile Ser Glu Thr Ala Arg Phe Asp Leu Ala Ala Arg Gly Leu Leu
        275                 280                 285

Ala Asp Gly His Arg Thr Phe Val Glu Leu Ser Pro His Pro Ile Leu
    290                 295                 300

Thr Leu Gly Leu Gln Ala Leu Ala Asp Asp Val Pro Gly Ala Ala Asp
305                 310                 315                 320

Ala Leu Val Thr Gly Thr Leu Arg Arg Gly Arg Gly Gly Met Arg Gln
                325                 330                 335

Phe Gln Asp Ala Leu Gly Arg Leu Ser Val Pro Ala Gly Gly Arg Pro
            340                 345                 350

Gly Arg Glu Val Ser Ala Ala Ala Leu Ala Gly Arg Leu Ala Pro Leu
        355                 360                 365

Ser Pro Ala Gln Gln Glu His Leu Leu Val Glu Leu Val Cys Ala His
    370                 375                 380

Phe Ala Ala Leu Val Gly Gly Asp Gly Gly Ala Pro Pro Thr Val Arg
385                 390                 395                 400

Pro Ser Ala Ala Phe Thr Asp Gln Gly Cys Asp Ser Ala Thr Ala Leu
                405                 410                 415

Glu Leu Arg Asp Arg Leu Arg Glu Ala Thr Gly Leu Arg Leu Pro Ala
            420                 425                 430

Thr Leu Val Phe Asp His Pro Thr Pro Ala Ala Val Ala Gly Arg Leu
        435                 440                 445

Arg Arg Leu Ala Leu Gly Ile Glu Glu Thr Ala Asp Thr Ala Pro Val
    450                 455                 460

Ala Val Arg Gly His Arg Glu Gly Glu Pro Ile Ala Ile Val Gly Met
465                 470                 475                 480

Ala Cys Arg Phe Pro Gly Gly Val Arg Ser Pro Glu Asp Leu Trp Arg
                485                 490                 495

Leu Val Thr Glu Gly Gly Asp Ala Leu Gly Pro Phe Pro Thr Asp Arg
            500                 505                 510

Gly Trp Asp Thr Gly Arg His Ala Glu Asp Pro Ala Thr Pro Gly Thr
        515                 520                 525

Tyr Val Gln Gly Glu Gly Gly Phe Leu Tyr Asp Ala Gly Glu Phe Asp
    530                 535                 540

Ala Glu Phe Phe Gly Ile Ser Pro Arg Glu Ala Leu Ala Met Asp Pro
545                 550                 555                 560

Gln Gln Arg Leu Leu Leu Glu Met Ala Trp Glu Thr Phe Glu Arg Ala
                565                 570                 575

Gly Ile Asp Pro Thr Ser Ala Arg Gly Ser Arg Thr Gly Val Phe Ala
            580                 585                 590

Gly Val Leu Pro Leu Gly Tyr Gly Pro Arg Met Asp Glu Thr Asp Gln
        595                 600                 605

Gly Thr Ala Asp Leu Gln Gly His Leu Leu Thr Gly Thr Leu Pro Ser
    610                 615                 620

Val Ala Ser Gly Arg Ile Ser Tyr Thr Leu Gly Leu Glu Gly Pro Ala
625                 630                 635                 640

Val Ser Val Glu Thr Ala Cys Ser Ser Ser Leu Val Ala Leu His Leu
                645                 650                 655

Ala Cys Arg Ser Leu Arg Ala Gly Glu Cys Asp Leu Ala Leu Thr Gly
            660                 665                 670

Gly Val Ser Val Leu Ala Thr Leu Gly Leu Phe Val Glu Phe Ser Arg
        675                 680                 685

Gln Arg Gly Leu Ser Ala Asp Gly Arg Cys Lys Ala Tyr Ala Ala Ala
```

-continued

```
    690                 695                 700

Ala Asp Gly Thr Gly Trp Ser Glu Gly Ala Gly Leu Leu Leu Val Glu
705                 710                 715                 720

Arg Leu Ser Asp Ala Arg Arg Leu Gly His Arg Val Leu Ala Val Val
                725                 730                 735

Arg Gly Ser Ala Ile Asn Gln Asp Gly Ala Ser Asn Gly Leu Thr Ala
            740                 745                 750

Pro Ser Gly Pro Ser Gln Gln Arg Val Ile Arg Glu Ala Leu Ala Asp
        755                 760                 765

Ala Gly Leu Thr Ala Ala Asp Val Asp Ala Val Glu Gly His Gly Thr
    770                 775                 780

Gly Thr Arg Leu Gly Asp Pro Ile Glu Ile Glu Ala Leu Leu Ala Thr
785                 790                 795                 800

Tyr Gly Gln Gly Arg Ala Arg Glu Arg Pro Leu Trp Leu Gly Ser Leu
                805                 810                 815

Lys Ser Asn Ile Gly His Thr Met Ala Ala Ala Gly Val Gly Gly Val
            820                 825                 830

Ile Lys Met Val Met Ala Leu Arg His Gly Glu Leu Pro Arg Thr Leu
        835                 840                 845

His Val Asp Ala Pro Ser Pro Arg Ala Asp Trp Ser Ala Gly Glu Val
    850                 855                 860

Arg Leu Leu Thr Glu Ala Val Ala Trp Pro Ala Ala Ala Asp Gly Glu
865                 870                 875                 880

Pro Arg Arg Ala Gly Val Ser Ser Phe Gly Val Ser Gly Thr Asn Ala
                885                 890                 895

His Ala Ile Leu Glu Glu Ala Pro Ala Pro Glu Asp Glu Glu Pro Ala
            900                 905                 910

Pro Pro Asp Gly Glu Ala Leu Leu Pro Trp Ala Val Ser Thr Arg Ser
        915                 920                 925

Glu Ala Ala Leu Arg Thr Gln Ala Arg Met Leu Ala Asp Val Val Arg
    930                 935                 940

Asp Asp Pro Gly Val Gly Leu Ala Asp Val Gly Ala Glu Leu Ala Arg
945                 950                 955                 960

Gly Arg Ala Ala Leu Glu His Arg Ala Val Val Ile Ala Ser Gly Arg
                965                 970                 975

Ala Glu Phe Ala Arg Ala Leu Glu Ala Val Ala Ser Gly Glu Pro His
            980                 985                 990

Pro Ala Val Val Arg Gly His Ala  Gly Ser Glu Arg Gly  Gly Val Val
        995                 1000                1005

Phe Val  Phe Pro Gly Gln Gly  Gly Gln Trp Ala Gly  Met Gly Leu
    1010                1015                1020

Asp Leu  Leu Arg Ser Ser Pro  Val Phe Ala Glu His  Ile Ala Ala
    1025                1030                1035

Cys Gly  Lys Ala Leu Ala Pro  Trp Val Lys Trp Ser  Leu Thr Glu
    1040                1045                1050

Val Leu  His Arg Asp Ala Glu  Asp Pro Val Trp Asp  Arg Ala Asp
    1055                1060                1065

Val Val  Gln Pro Val Leu Phe  Ser Val Met Thr Ser  Leu Ala Ala
    1070                1075                1080

Leu Trp  Arg Ser Tyr Gly Val  Glu Pro Asp Ala Val  Thr Gly His
    1085                1090                1095

Ser Gln  Gly Glu Ile Ala Ala  Ala Tyr Val Cys Gly  Ala Leu Gly
    1100                1105                1110
```

-continued

```
Leu Glu  Asp Ala Ala Arg Thr  Val Ala Leu Arg Ser  Arg Ala Leu
    1115                 1120                 1125

Val Ala  Leu Arg Gly Arg Gly  Gly Met Ala Ser Val  Ala Ser Ala
    1130                 1135                 1140

Ala Pro  Asp Val Glu Glu Leu  Ile Ala Arg Arg Trp  Pro Gly Arg
    1145                 1150                 1155

Leu Trp  Val Ala Ala Phe Asn  Gly Pro Gly Ala Val  Thr Val Ser
    1160                 1165                 1170

Gly Asp  Gly Asp Ala Leu Glu  Glu Phe Leu Gly His  Cys Ala Asp
    1175                 1180                 1185

Thr Glu  Val Arg Ala Arg Arg  Val Pro Val Asp Tyr  Ala Ser His
    1190                 1195                 1200

Cys Pro  His Thr Glu Ala Ile  Glu Arg Glu Leu Leu  Asp Ala Leu
    1205                 1210                 1215

Glu Asp  Ile Thr Pro Arg Pro  Ala Ala Val Pro Phe  Tyr Ser Thr
    1220                 1225                 1230

Val Asp  Asp Ala Trp Leu Asp  Thr Thr Arg Leu Asp  Ala Ser Tyr
    1235                 1240                 1245

Trp Tyr  Arg Asn Leu Arg Arg  Pro Val Arg Phe Ser  Gln Ala Val
    1250                 1255                 1260

Arg Ala  Leu Thr Asp Gly Gly  His Arg Val Phe Ile  Glu Ala Ser
    1265                 1270                 1275

Pro His  Pro Thr Leu Val Pro  Ala Ile Glu Asp His  Gly Asp Val
    1280                 1285                 1290

Thr Ala  Leu Gly Thr Leu Arg  Arg His Gly Asp Asp  Thr Glu Arg
    1295                 1300                 1305

Phe Leu  Thr Ala Leu Ala His  Leu His Val Thr Gly  Ala Ala Gly
    1310                 1315                 1320

Gln Asp  Leu Trp Arg His His  Tyr Ala Arg Leu Arg  Pro Ala Pro
    1325                 1330                 1335

Arg His  Val Asp Leu Pro Thr  Tyr Ala Phe Gln Arg  Asp Arg Tyr
    1340                 1345                 1350

Trp Trp  Ser Gly Gly Ala Gly  Arg Gly Asp Val Thr  Thr Ala Gly
    1355                 1360                 1365

Leu His  Pro Gly Gly His Pro  Leu Leu Gly Ala Ala  Leu Asp Leu
    1370                 1375                 1380

Ala Asp  Gly Gly Gly Arg Leu  His Thr Gly Arg Val  Ser Leu Arg
    1385                 1390                 1395

Thr His  Pro Trp Ile Ala Asp  His Gly Val Ala Gly  Ile Thr Leu
    1400                 1405                 1410

Leu Pro  Gly Thr Ala Phe Leu  Glu Leu Ala Leu His  Thr Gly Glu
    1415                 1420                 1425

Ser Gly  Asn Val Arg Glu Leu  Thr Leu His Ala Pro  Leu Val Val
    1430                 1435                 1440

Pro Asp  Glu Glu Gly Val Asp  Leu Gln Val His Leu  Ala Arg Pro
    1445                 1450                 1455

Asp Glu  Ala Gly Leu Arg Ala  Leu Thr Arg Leu Leu  Pro Gly Arg
    1460                 1465                 1470

Gly Val  Pro Thr Pro Arg Ala  Pro Trp Gln Pro His  Ala Thr Gly
    1475                 1480                 1485

Leu Leu  Gly Pro Ala Asp Arg  Ala Pro Gly Ser Ser  Gly Leu Glu
    1490                 1495                 1500
```

-continued

```
Pro His  Asp Leu Gly Gly Ala  Trp Pro Pro Pro Gly  Ala Val Pro
    1505                 1510                 1515

Leu Val  Pro Gly Glu Leu Gly  Asp Val Pro Gly Cys  Tyr Ala Arg
    1520                 1525                 1530

Leu Ala  Asp Glu Gly Phe Glu  Tyr Gly Pro Ala Phe  Arg Gly Leu
    1535                 1540                 1545

Arg Ala  Val Trp Arg Arg Gly  Thr Glu Ile Phe Ala  Glu Val Ala
    1550                 1555                 1560

Leu Pro  Ala Gly Asp Gly Ser  Val Phe Arg Leu His  Pro Ala Leu
    1565                 1570                 1575

Leu Asp  Ala Val Leu His Pro  Val Val Leu Gly Leu  Val Asp Gly
    1580                 1585                 1590

Val Pro  Ala Arg Pro Leu Pro  Phe Ser Trp Asn Gly  Val Ala Leu
    1595                 1600                 1605

His Ala  Pro Ala Ser Gly Ala  Leu Arg Val Arg Leu  Ala Pro Ala
    1610                 1615                 1620

Asp Asp  Gly Ala Val Gly Ile  Thr Ala Ala Thr Ala  Ala Gly Glu
    1625                 1630                 1635

Pro Val  Leu Ser Val Ala Ala  Leu Ala Leu Arg Ser  Ala Ser Ala
    1640                 1645                 1650

Glu Gln  Leu Arg Ala Ala Ile  Arg Ser Ala Ala Gly  Ser Arg Asp
    1655                 1660                 1665

Ala Leu  Tyr Glu Leu Asp Trp  Leu Pro Leu Pro Ala  Asp Arg Ala
    1670                 1675                 1680

Ala Ser  Pro Gly Gly Ala Asp  Ile Ala Ala Leu Gly  Thr Ser Glu
    1685                 1690                 1695

Leu Pro  Cys Arg Thr Tyr Glu  Thr Ile Ala Glu Leu  Ser Gln Ala
    1700                 1705                 1710

Leu Ala  Asp Gly Ala Pro Ala  Pro Asp Ala Val Val  Ser Asp Val
    1715                 1720                 1725

Gly Ala  Val Gly Gly Pro Leu  Asp Thr Val Ser Leu  His Gly Leu
    1730                 1735                 1740

Cys Arg  Arg Gly Leu Glu Leu  Val Gln Ala Trp Leu  Gly Glu Pro
    1745                 1750                 1755

Arg Thr  Ala Asp Thr Arg Leu  Val Leu Val Thr Arg  Gly Ala Val
    1760                 1765                 1770

Gly Cys  Ala Pro Ala Glu Pro  Val Ala Asp Pro Ala  Ala Ala Ala
    1775                 1780                 1785

Leu Trp  Gly Leu Val Arg Ser  Ala Gln Ala Glu His  Pro Gly Arg
    1790                 1795                 1800

Leu Leu  Leu Leu Asp Leu Asp  Pro Ala Gly Ser Arg  Pro Val Ser
    1805                 1810                 1815

Gly Arg  Leu Val Glu Gln Ala  Val Ala Cys Gly Glu  Pro His Ile
    1820                 1825                 1830

Ala Val  Arg Gly Asp Gly Leu  Arg Val Pro Arg Leu  Ser Arg Ala
    1835                 1840                 1845

Thr Ala  Ala Pro Ala His Pro  Pro Ala Gly Gly Arg  Glu Ala Gln
    1850                 1855                 1860

Trp Asp  Pro Glu Gly Thr Val  Leu Ile Thr Gly Gly  Thr Gly Ser
    1865                 1870                 1875

Leu Gly  Ala Leu Phe Ala Arg  His Leu Val Thr Ala  His Gly Val
    1880                 1885                 1890

Arg Arg  Leu Leu Leu Ala Ser  Arg Ser Gly Pro Gly  Ala Pro Gly
```

-continued

```
    1895                1900                1905

Ala Ala Gly Leu Arg Asp Glu Leu Thr Ala His Gly Ala Thr Val
    1910                1915                1920

Thr Val Ala Ala Cys Asp Val Ala Asp Arg Glu Ala Val Ala Ala
    1925                1930                1935

Leu Leu Ala Ser Val Pro Ser Glu His Pro Leu Thr Ala Val Val
    1940                1945                1950

His Thr Ala Gly Val Leu Asp Asp Gly Val Leu Ala Ser Leu Thr
    1955                1960                1965

Ala Asp Arg Leu Ala Arg Val Leu Arg Ala Lys Ala Asp Ala Ala
    1970                1975                1980

Leu His Leu His Asp Leu Thr Arg Asp Leu Pro Leu Ala Ala Phe
    1985                1990                1995

Val Leu Phe Ser Ser Val Thr Ala Thr Leu Gly Thr Pro Gly Gln
    2000                2005                2010

Ala Asn Tyr Thr Ala Ala Asn Ala Phe Leu Asp Ala Leu Ala Arg
    2015                2020                2025

His Arg Arg Ala Ala Gly Leu Pro Ala Val Ser Leu Ala Trp Gly
    2030                2035                2040

Leu Trp Glu Gln Thr Gly Gly Leu Thr Asp His Leu Gly Ser Val
    2045                2050                2055

Asp Leu Arg Arg Met Ala Arg Asn Gly Leu Val Ala Leu Pro Ala
    2060                2065                2070

Asp Ala Gly Leu Ala Leu Phe Asp Thr Ala Leu Ala Leu Asp Arg
    2075                2080                2085

Ala Asn Leu Val Pro Ala Arg Leu Asp Leu Pro Ala Leu Arg Arg
    2090                2095                2100

Ala Thr His Val Pro Pro Val Leu Arg Arg Leu Val Glu Val Pro
    2105                2110                2115

Gly Ala Pro Ser Ala Asp Arg Ser Ala Gly Ser Gly Gly Glu Val
    2120                2125                2130

Arg Pro Leu Arg Glu Thr Leu Ala Gly Leu Asp Asp Arg Lys Arg
    2135                2140                2145

Pro Ala Ala Val Ser Arg Leu Val Arg Arg His Val Ala Trp Val
    2150                2155                2160

Leu Gly Ala Asp Gly Pro Glu Ser Val Asp Glu Asp Arg Ser Phe
    2165                2170                2175

Arg Asp Leu Gly Phe Asp Ser Leu Met Ala Val Glu Leu Arg Asn
    2180                2185                2190

Gln Leu Asn Thr Ala Ala Gly Ile Arg Leu Ala Ala Thr Leu Val
    2195                2200                2205

Phe Asp His Pro Thr Pro Ser Ala Val Ala Arg His Leu Leu Asp
    2210                2215                2220

Arg Cys Ser Pro Asp Pro Ala Ala Pro Ala Ala Pro Ser Gly Thr
    2225                2230                2235

Ala Val Ala Ser Ala Leu Ala Thr Leu Ala Glu Leu Glu Thr Ala
    2240                2245                2250

Leu Asn Gly Ile Pro Ala Glu Glu Trp Thr Ala Ala Gly Gly Pro
    2255                2260                2265

Ala Arg Leu Met Thr Leu Ala Ser Ser Leu Pro Ala Pro Ala Ser
    2270                2275                2280

Val Pro Arg Thr Pro Ala Ala Gly Glu Ala Ala Glu Lys Leu Ala
    2285                2290                2295
```

-continued

His Ala Ser Arg Asp Glu Ile Phe Ala Phe Ile Asp Arg Glu Leu
    2300                2305                2310

Gly Arg Asp Ser Gly Pro Ala Ser Pro Ser Arg Leu Gly Pro Gln
    2315                2320                2325

Thr Pro Asp Ser Thr Asp Lys Ala Pro Phe His Gly Glu
    2330                2335                2340

<210> SEQ ID NO 6
<211> LENGTH: 3723
<212> TYPE: PRT
<213> ORGANISM: bacteria

<400> SEQUENCE: 6

Met Glu Asn Glu Glu Lys Leu Leu Asp Tyr Leu Lys Trp Val Thr Ala
1               5                   10                  15

Asp Leu His Arg Ser Arg Glu Arg Val Thr Glu Leu Glu Glu Ala Gly
            20                  25                  30

Arg Glu Pro Ile Ala Ile Val Gly Met Ala Cys Arg Phe Pro Gly Glu
        35                  40                  45

Val Arg Ser Pro Glu Glu Leu Trp Gly Leu Val Ala Ser Gly Gly Asp
    50                  55                  60

Ala Ile Gly Ala Phe Pro Asp Asp Arg Gly Trp Asp Leu Asp Gly Leu
65                  70                  75                  80

Phe Asp Pro Asp Pro Glu Arg Ala Gly Thr Ser Tyr Thr Arg Arg Gly
                85                  90                  95

Gly Phe Leu Tyr Asp Ala Ala Glu Phe Asp Ala Gly Phe Phe Gly Ile
            100                 105                 110

Ser Pro Arg Glu Ala Met Ala Met Asp Pro Gln Gln Arg Leu Leu Leu
        115                 120                 125

Glu Thr Ser Trp Glu Ala Phe Glu Arg Ala Gly Ile Asp Pro Ser Ser
    130                 135                 140

Val Arg Gly Ser Arg Val Gly Val Phe Ala Gly Leu Met Tyr His Asp
145                 150                 155                 160

Tyr Ala Ala Ala Gln Gly Ser Thr Gly Asp Gly Asp Gly Glu Pro Asp
                165                 170                 175

Phe Glu Gly Tyr Leu Gly Asp Gly Ser Val Ser Ser Ile Ala Ser Gly
            180                 185                 190

Arg Ile Ala Tyr Thr Leu Gly Leu Ala Gly Ala Ala Ile Thr Val Asp
        195                 200                 205

Thr Ala Cys Ser Ser Ser Leu Val Ala Leu His Leu Ala Cys Gln Ala
    210                 215                 220

Leu Arg Thr Gly Asp Ser Glu Leu Ala Leu Ala Gly Gly Val Ser Val
225                 230                 235                 240

Met Ser Thr Pro Arg Thr Phe Val Gln Phe Ser Arg Gln Arg Gly Leu
                245                 250                 255

Ser Ala Asp Gly Arg Cys Lys Ala Tyr Ala Ala Ala Ala Asp Gly Thr
            260                 265                 270

Gly Phe Ser Glu Gly Val Gly Met Val Leu Val Glu Arg Leu Ser Asp
        275                 280                 285

Ala Arg Arg Leu Gly His Pro Val Leu Ala Val Val Arg Gly Ser Ala
    290                 295                 300

Val Asn Gln Asp Gly Ala Ser Asn Gly Leu Thr Ala Pro Asn Gly Pro
305                 310                 315                 320

Ser Gln Glu Arg Val Ile Arg Glu Ala Leu Ala Asn Ala Gly Leu Thr

-continued

```
                325                 330                 335

Ala Ala Asp Val Asp Ala Val Glu Gly His Gly Thr Gly Thr Arg Leu
            340                 345                 350

Gly Asp Pro Ile Glu Leu Gln Ala Leu Leu Ala Thr Tyr Gly Gln Gly
        355                 360                 365

Arg Ala Arg Glu Arg Pro Leu Trp Leu Gly Ser Val Lys Ser Asn Ile
    370                 375                 380

Gly His Ala Gln Ala Ala Ala Gly Val Gly Gly Val Ile Lys Met Val
385                 390                 395                 400

Met Ala Leu Arg His Gly Glu Leu Pro Arg Thr Leu His Val Asp Ala
                405                 410                 415

Pro Ser Pro Arg Val Asp Trp Ser Ala Gly Glu Val Arg Leu Leu Thr
            420                 425                 430

Glu Ala Val Ala Trp Pro Ala Ala Ala Asp Gly Glu Pro Arg Arg Ala
        435                 440                 445

Gly Val Ser Ser Phe Gly Val Ser Gly Thr Asn Ala His Val Ile Leu
    450                 455                 460

Glu Glu Ala Pro Ala Ser Glu Gly Glu Glu Ala Pro Pro Pro Glu Pro
465                 470                 475                 480

Gly Ser Pro Leu Pro Trp Val Val Ser Gly His Ser Glu Ala Gly Leu
                485                 490                 495

Arg Ala Gln Ala Gln Ala Leu Ala Glu Phe Ala Arg Thr Ala Pro Gly
            500                 505                 510

Ala Glu Leu Val Asp Val Gly Ala Ala Leu Ala Arg Gly Arg Ala Ala
        515                 520                 525

Leu Gly His Arg Ala Val Val Val Ala Ser Glu Arg Glu Glu Phe Glu
    530                 535                 540

Arg Ala Leu Ala Ala Leu Ala Cys Gly Glu Pro His Pro Cys Val Val
545                 550                 555                 560

Asp Gly Ser Ala Asp Gly Arg Arg Glu Asp Gly Val Val Phe Val Phe
                565                 570                 575

Pro Gly Gln Gly Gly Gln Trp Ala Gly Met Gly Leu Asp Leu Leu Thr
            580                 585                 590

Thr Ser Gly Val Phe Ala Glu His Ile Gly Ala Cys Glu Arg Ala Leu
        595                 600                 605

Ala Pro Trp Val Glu Trp Ser Leu Thr Glu Met Leu His Arg Glu Ala
    610                 615                 620

Glu Asp Pro Val Trp Glu Arg Ala Asp Ile Val Gln Pro Val Leu Phe
625                 630                 635                 640

Ser Val Met Val Ser Leu Ala Ala Leu Trp Arg Ser Tyr Gly Ile Glu
                645                 650                 655

Pro Asp Ala Val Val Gly His Ser Gln Gly Glu Ile Ala Ala Ala His
            660                 665                 670

Val Cys Gly Ala Leu Thr Leu Glu Asp Ala Ala Lys Val Val Ala Leu
        675                 680                 685

Arg Ser Arg Ala Leu Ala Ala Leu Arg Gly Arg Gly Gly Met Val Ser
    690                 695                 700

Leu Ser Leu Ser Thr Ala Asp Ala Gly Glu Leu Val Glu Arg Arg Trp
705                 710                 715                 720

Ala Gly Arg Leu Trp Val Ala Ala Leu Asn Gly Pro Glu Ala Thr Thr
                725                 730                 735

Val Ser Gly Asp Val Asp Ala Leu Glu Glu Leu Leu Ala His Cys Ala
            740                 745                 750
```

-continued

```
Lys Ser Glu Val Arg Ala Arg Arg Val Pro Val Asp Tyr Ala Ser His
        755                 760                 765

Cys Pro His Thr Glu Ala Ile Ala Glu Glu Ile Val Asp Ser Leu Gly
    770                 775                 780

Asp Ile Thr Pro Arg Ala Ala Thr Val Pro Phe Tyr Ser Thr Val Asp
785                 790                 795                 800

Asp Met Trp Leu Asp Thr Thr Arg Leu Asp Ala Ser Tyr Trp Tyr Arg
                805                 810                 815

Asn Leu Arg Leu Pro Val Arg Phe Ser Gln Ala Val Arg Ala Leu Thr
            820                 825                 830

Glu Glu Gly His Arg Leu Phe Ile Glu Thr Ser Pro His Pro Thr Leu
        835                 840                 845

Val Pro Ala Ile Glu Asp His Gly Asp Val Thr Ala Leu Gly Thr Leu
    850                 855                 860

Arg Arg His Gly Asp Asp Thr Glu Arg Phe Leu Thr Ala Leu Ala His
865                 870                 875                 880

Leu His Val Thr Gly Ala Ala Gly Gln Asp Leu Trp Arg His His Tyr
                885                 890                 895

Ala Arg Leu Arg Pro Ala Pro Arg His Val Asp Leu Pro Thr Tyr Pro
            900                 905                 910

Phe Gln Arg Arg Arg Tyr Trp Leu Glu Lys Pro Asp Pro Gln Thr Arg
        915                 920                 925

Pro Gln Arg Ser Arg Ser Thr Ala Pro Asp Leu Asp Arg Leu Glu Ala
    930                 935                 940

Glu Phe Trp Gln Ala Val Glu Glu Thr Asp Thr Asp Thr Leu Ala His
945                 950                 955                 960

Thr Leu His Leu Asp Thr Gln Thr Leu Glu Pro Val Leu Pro Ala Leu
                965                 970                 975

Ala Thr Trp His Gln Gln Gln Arg Asp His Ala Arg Ile Asn Thr Trp
            980                 985                 990

Thr Tyr Gln Glu Thr Trp Lys Pro  Leu His Leu Pro Thr  Thr Arg Pro
        995                 1000                1005

Thr Thr  Pro Thr Ser Trp Leu  Ile Ala Ile Pro Glu  Thr His Arg
    1010                1015                1020

Asn His  Pro His Thr Thr Asn  Leu Leu Thr Asn Leu  Pro His His
    1025                1030                1035

Asn Ile  Thr Pro Ile Pro Leu  Thr Ile Asn His Thr  Thr Asp Leu
    1040                1045                1050

His His  Ala Tyr His His Ala  His His His Thr Thr  Pro Pro Ile
    1055                1060                1065

Thr Ala  Val Leu Ser Leu Leu  Ala Leu Asp Glu Thr  Pro His Pro
    1070                1075                1080

His His  Pro His Thr Pro Thr  Gly Thr Leu Leu Asn  Leu Thr Leu
    1085                1090                1095

Thr Gln  Thr His Thr Gln Thr  His Pro Pro Thr Pro  Leu Trp Tyr
    1100                1105                1110

Leu Thr  Thr Gln Ala Thr Thr  Thr His Pro Asn Asp  Pro Leu Thr
    1115                1120                1125

His Pro  Thr Gln Ala Gln Thr  Ile Gly Leu Ala Arg  Thr Thr His
    1130                1135                1140

Leu Glu  His Pro His His Thr  Gly Gly His Ile Asp  Leu Pro Thr
    1145                1150                1155
```

-continued

```
Thr Pro  His Pro Asn Thr Leu  Thr Gln Leu Ile Thr  Ala Leu Thr
    1160                 1165                 1170

His Pro  His His Gln His Asn  Leu Thr Ile Arg Thr  His Thr Thr
    1175                 1180                 1185

His Thr  Arg Arg Leu Thr Pro  Thr Thr Leu Gln Pro  Thr Thr Pro
    1190                 1195                 1200

Thr Pro  Pro Thr Asn Pro His  Gly Thr Thr Leu Ile  Thr Gly Gly
    1205                 1210                 1215

Thr Gly  Ala Leu Ala Thr Thr  Leu Ala His His Leu  Ala Thr Thr
    1220                 1225                 1230

Gly Thr  Gln His Leu Leu Leu  Thr Ser Arg Arg Gly  Pro His Thr
    1235                 1240                 1245

Pro Gly  Ala Arg Gln Leu His  Thr Gln Leu Thr Gln  Leu Gly Thr
    1250                 1255                 1260

Asn Thr  Thr Ile Thr Ala Cys  Asp Leu Ser Asp Pro  Asp Gln Leu
    1265                 1270                 1275

Thr His  Leu Leu Thr His Ile  Pro Pro Glu His Pro  Leu Thr Thr
    1280                 1285                 1290

Val Ile  His Thr Ala Gly Ile  Leu Asp Asp Ala Thr  Leu Thr Asn
    1295                 1300                 1305

Leu Thr  Pro Thr Gln Leu Asp  Asn Val Leu Arg Ala  Lys Ala His
    1310                 1315                 1320

Thr Ala  His Leu Leu His His  Ala Thr Leu His Thr  Pro Leu Asp
    1325                 1330                 1335

His Phe  Val Leu Tyr Ser Ser  Ala Ala Ala Thr Leu  Gly Ala Pro
    1340                 1345                 1350

Gly Gln  Ala Asn Tyr Ala Ala  Ala Asn Ala Tyr Leu  Asp Ala Leu
    1355                 1360                 1365

Ala His  His Arg His Thr His  Asn Leu Pro Ala Thr  Thr Ile Ala
    1370                 1375                 1380

Trp Gly  Thr Trp Gln Gly Asn  Gly Leu Ala Asp Ser  Asp Lys Ala
    1385                 1390                 1395

Arg Ala  Asn Leu Asp Arg Arg  Gly Phe Leu Pro Met  Pro Glu Thr
    1400                 1405                 1410

Leu Ala  Ala Ala Ala Ala Val  Arg Ala Ile Glu Ser  Arg Arg Pro
    1415                 1420                 1425

Ser Val  Val Ile Ala Ala Ile  Asp Trp Ala Arg Ala  Glu Arg Thr
    1430                 1435                 1440

Pro Asp  Val Glu Asp Leu Leu  Pro Ala Ala Asp Glu  Gly Ser Ser
    1445                 1450                 1455

Ser Gly  Lys Pro Glu Ala Ala  Pro Val Asp Leu Arg  Gly Thr Leu
    1460                 1465                 1470

Ser Arg  Gln Ser Ala Ala Asp  Gln Gln Ala Thr Leu  Leu Gly Leu
    1475                 1480                 1485

Val Arg  Thr Gln Ala Ala Val  Val Leu Arg His Thr  Glu Pro Glu
    1490                 1495                 1500

Ala Leu  Ala Pro Gly Gln Ala  Phe Arg Ala Leu Gly  Phe Asp Ser
    1505                 1510                 1515

Leu Thr  Ala Val Glu Leu Arg  Asn Arg Leu Ala Lys  Ala Thr Asp
    1520                 1525                 1530

Leu Ala  Leu Pro Ala Ser Leu  Val Phe Asp His Pro  Thr Pro Val
    1535                 1540                 1545

Lys Leu  Ala Glu Phe Leu Arg  Thr Glu Leu Leu Gly  Thr Ala Pro
```

-continued

```
    1550                1555                1560

Ala Thr  Thr Ala Ala Val Pro  Ala Leu Gln Ala His  Thr Asp Glu
    1565                1570                1575

Pro Ile  Ala Ile Ile Gly Met  Ala Cys Arg Phe Pro  Gly Ala Val
    1580                1585                1590

Thr Thr  Pro Glu His Leu Trp  Asn Leu Ile Ala Thr  Glu Gln Asp
    1595                1600                1605

Ala Ile  Gly Glu Phe Pro Thr  Asp Arg Gly Trp Asp  Leu Asp Asn
    1610                1615                1620

Leu Tyr  His Pro Asp Pro Asp  His Pro Gly Thr Thr  Tyr Thr Arg
    1625                1630                1635

His Gly  Gly Phe Leu His Asp  Ala Gly Asp Phe Asp  Ala Asp Phe
    1640                1645                1650

Phe Gly  Ile Asn Pro Arg Glu  Ala Leu Ala Met Asp  Pro Gln Gln
    1655                1660                1665

Arg Leu  Leu Leu Glu Thr Ala  Trp Glu Ala Ile Glu  His Ala Gly
    1670                1675                1680

Ile Leu  Pro Asp Ala Leu His  Gly Thr Pro Thr Gly  Val Phe Thr
    1685                1690                1695

Gly Val  Asn Ala Gln Asp Tyr  Ala Ala His Thr His  Thr Ser Pro
    1700                1705                1710

His Thr  Thr Glu Gly Tyr Thr  Leu Thr Gly Thr Ala  Gly Ser Ile
    1715                1720                1725

Ala Ser  Gly Arg Ile Ala Tyr  Val Leu Gly Leu Glu  Gly Pro Ala
    1730                1735                1740

Val Thr  Ile Asp Thr Ala Cys  Ser Ser Ser Leu Val  Ala Leu His
    1745                1750                1755

Leu Ala  Cys Gln Ala Leu Arg  Ala Gly Glu Cys Thr  Thr Ala Leu
    1760                1765                1770

Ala Ser  Gly Ile Ser Ile Met  Thr Thr Pro Leu Ala  Phe Thr Glu
    1775                1780                1785

Phe Ser  Arg Gln Arg Gly Leu  Ala Ala Asp Gly Arg  Cys Lys Ala
    1790                1795                1800

Phe Ala  Ala Ala Ala Asp Gly  Thr Gly Trp Ser Glu  Gly Val Gly
    1805                1810                1815

Thr Leu  Leu Leu Glu Arg Leu  Ser Asp Ala Glu Arg  Asn Gly His
    1820                1825                1830

Arg Val  Leu Ala Val Val Arg  Gly Ser Ala Val Asn  Gln Asp Gly
    1835                1840                1845

Ala Ser  Asn Gly Leu Thr Ala  Pro Asn Gly Pro Ser  Gln Gln Arg
    1850                1855                1860

Val Ile  Arg Gln Ala Leu Val  Asn Ala Asn Leu Ser  Ala Val Asp
    1865                1870                1875

Val Asp  Ala Val Glu Ala His  Gly Thr Gly Thr Lys  Leu Gly Asp
    1880                1885                1890

Pro Ile  Glu Ala Gln Ala Leu  Leu Ala Thr Tyr Gly  Gln Gly Arg
    1895                1900                1905

Ala Gln  Glu Gln Pro Leu Trp  Leu Gly Ser Val Lys  Ser Asn Leu
    1910                1915                1920

Gly His  Thr Gln Ala Ala Ala  Gly Met Ala Gly Leu  Ile Lys Met
    1925                1930                1935

Val Met  Ala Leu Arg His Glu  Ser Leu Pro Arg Thr  Leu His Val
    1940                1945                1950
```

-continued

```
Asp Glu  Pro Ser Pro Glu Val  Asp Trp Ser Ser Gly  Ala Val Ser
    1955                 1960                 1965

Leu Leu  Thr Glu Ala Arg Pro  Trp Pro Arg Val Glu  Asp Arg Pro
    1970                 1975                 1980

Arg Arg  Ala Gly Val Ser Ser  Phe Gly Val Ser Gly  Thr Asn Ala
    1985                 1990                 1995

His Val  Ile Val Glu Glu Ala  Pro Ala Pro Thr Gly  Val Glu Ala
    2000                 2005                 2010

Val Glu  Ala Ala Pro Ala Gly  Val Glu Thr Ala Ala  Ala Ala Ala
    2015                 2020                 2025

Val Val  Val Glu Thr Asp Gly  Ala Gly Arg Val Ser  Ala Asp Leu
    2030                 2035                 2040

Pro Leu  Val Trp Val Ala Ser  Gly Lys Ser Gln Ala  Ala Ile Arg
    2045                 2050                 2055

Ala Gln  Ala Ala Ala Leu His  Ala His Val Leu Asp  His Pro Glu
    2060                 2065                 2070

Gln Asp  Ala Asp Asp Ile Gly  Tyr Ser Leu Ala Thr  Thr Arg Ala
    2075                 2080                 2085

Leu Phe  Asp His Arg Ala Thr  Leu Ile Ala Pro Asp  Arg His Thr
    2090                 2095                 2100

Val Pro  Glu Pro Leu Thr Gly  Leu Gly Asp Gly Arg  Thr His Pro
    2105                 2110                 2115

His Leu  Ile Pro Thr Pro Pro  Thr Glu Pro Gly His  Thr His Lys
    2120                 2125                 2130

Ile Ala  Phe Leu Cys Ser Gly  Gln Gly Thr Gln Arg  Pro Gly Met
    2135                 2140                 2145

Ala Thr  Gly Leu Tyr His Thr  Tyr Pro Ala Phe Ala  Ala Ala Leu
    2150                 2155                 2160

Asp Glu  Thr Cys Ala His Phe  Asp Pro His Leu Asp  His Pro Leu
    2165                 2170                 2175

His Asp  Leu Leu Leu Asn His  Asp Pro Thr Asp Leu  Leu Thr His
    2180                 2185                 2190

Thr Leu  Tyr Ala Gln Pro Ala  Leu Phe Thr Leu Gln  Lys Ala Leu
    2195                 2200                 2205

His His  Leu Ile Thr Glu Thr  Tyr Gly Ile Thr Pro  His Tyr Leu
    2210                 2215                 2220

Ala Gly  His Ser Leu Gly Glu  Ile Thr Ala Ala His  Leu Ala Gly
    2225                 2230                 2235

Ile Leu  Thr Leu Pro Asp Ala  Thr His Leu Ile Thr  Thr Arg Ala
    2240                 2245                 2250

Arg Leu  Met Gln Thr Met Pro  Pro Gly Thr Met Thr  Thr Leu His
    2255                 2260                 2265

Thr Thr  Pro Glu His Ile Gln  Pro Leu Leu Asp Gln  His Pro Gly
    2270                 2275                 2280

Lys Ala  Ala Ile Ala Ala Val  Asn Ser Pro His Ser  Leu Val Ile
    2285                 2290                 2295

Ser Gly  Asp Pro Asp Thr Ile  His His Ile Thr Thr  Thr Cys His
    2300                 2305                 2310

Asn Gln  Gly Ile Thr Thr Lys  Pro Leu Ala Thr Asn  His Ala Phe
    2315                 2320                 2325

His Ser  Pro His Thr Asp Thr  Ile Leu Glu Gln Leu  Asp Thr Thr
    2330                 2335                 2340
```

-continued

```
Thr His  Thr Leu Thr Tyr His  Gln Pro His Thr Pro  Leu Ile Thr
    2345                 2350                 2355

Ser Thr  Pro Gly Asp Pro Leu  Thr Pro His Tyr Trp  Thr His Gln
    2360                 2365                 2370

Thr Arg  Gln Pro Val His Trp  Thr Asp Thr Ile His  Thr Leu His
    2375                 2380                 2385

Thr His  Gly Val Thr Thr Tyr  Ile Ala Leu Gly Pro  Glu His Thr
    2390                 2395                 2400

Leu Thr  Thr Leu Thr His His  Asn Val Pro His His  Gln Pro Thr
    2405                 2410                 2415

Ala Ile  Thr Leu Thr His Pro  His His Asn Pro Thr  His His Leu
    2420                 2425                 2430

Leu Thr  Ala Leu Ala His Leu  His Thr Thr Gln Pro  Thr Gly Pro
    2435                 2440                 2445

Asn Ile  Trp His His His Tyr  Thr Pro Val Ala Pro  Ala Pro Arg
    2450                 2455                 2460

His Val  Asp Leu Pro Thr Tyr  Pro Phe Pro Arg Arg  Arg Tyr Trp
    2465                 2470                 2475

Val Gln  Ala Ser Ala Gly Thr  Gly Asp Val Ser Ala  Ala Gly Leu
    2480                 2485                 2490

Gln Arg  Pro Asp His Pro Leu  Leu Gly Ala Val Met  Glu Leu Ala
    2495                 2500                 2505

Asp Gly  Asp Gly Ile Val Leu  Thr Gly Arg Leu Ser  Leu His Thr
    2510                 2515                 2520

His Pro  Trp Leu Ala Asp His  Ser Val Gly Gly Val  Ala Leu Leu
    2525                 2530                 2535

Pro Gly  Thr Ala Leu Leu Glu  Leu Ala Phe Gln Ala  Gly Leu Arg
    2540                 2545                 2550

Ala Gly  Cys Pro Gly Val Asp  Glu Leu Thr Leu His  Ala Pro Leu
    2555                 2560                 2565

Val Val  Pro Glu Ser Gly His  Val Val Val Gln Val  Ser Val Ser
    2570                 2575                 2580

Val Pro  Gly Glu Ala Gly Arg  Arg Gly Val Ser Val  Tyr Gly Arg
    2585                 2590                 2595

Leu Val  Glu Asp Gly Gly Leu  Glu Gly Glu Trp Thr  Arg His Ala
    2600                 2605                 2610

Glu Gly  Val Val Cys Pro Ser  Val Pro Gly Glu Ser  Val Val Val
    2615                 2620                 2625

Glu Pro  Val Ala Asp Gly Val  Trp Pro Pro Ser Gly  Ala Gln Pro
    2630                 2635                 2640

Val Asp  Leu Glu Glu Phe Tyr  Gly Arg Leu Ala Gly  Gly Gly Phe
    2645                 2650                 2655

Val Tyr  Gly Pro Val Phe Gln  Gly Leu Cys Ala Ala  Trp Arg Asp
    2660                 2665                 2670

Gly Asp  Asp Val Val Ala Glu  Val Arg Leu Pro Asp  Glu Gly Leu
    2675                 2680                 2685

Ala Asp  Val Ala Gly Phe Gly  Val His Pro Ala Leu  Leu Asp Ala
    2690                 2695                 2700

Ala Val  Gln Ala Val Thr Leu  Leu Phe Pro Asp Gln  Gln Gln Ala
    2705                 2710                 2715

Gly Leu  Ala Ala His Thr Trp  Asn Gly Val Ser Leu  His Ala Arg
    2720                 2725                 2730

Gly Ala  Thr Val Leu Arg Leu  Arg Met Thr Pro Thr  Asp Ala Thr
```

-continued

```
    2735                2740                2745

Ser Thr  Ala Val Arg Leu His  Ala Thr Asp Glu Thr  Gly Ala Pro
    2750                2755                2760

Val Leu  Thr Leu Asp Ser Leu  Leu Met Arg Pro Val  Pro Leu Glu
    2765                2770                2775

Gly Leu  Gly Ala Gly Val Arg  Arg Gly Ser Leu Phe  Glu Leu Gly
    2780                2785                2790

Trp Val  Pro Val Glu Gly Met  Pro Ala Ser Val Ala  Gly Gly Gly
    2795                2800                2805

Gly Glu  Leu Val Ala Trp Glu  Cys Pro Gly Gly Gly  Val Ala Glu
    2810                2815                2820

Val Thr  Ala Ala Ala Leu Gly  Val Val Gln Glu Trp  Leu Ala Asp
    2825                2830                2835

Glu Arg  Glu Gly Asp Ala Arg  Leu Val Val Val Thr  Arg Gly Ala
    2840                2845                2850

Val Ala  Val Asp Ala Gly Glu  Pro Val Arg Asp Val  Ala Gly Ala
    2855                2860                2865

Ala Val  Trp Gly Leu Val Arg  Ser Ala Gln Ser Glu  His Pro Asp
    2870                2875                2880

Arg Phe  Ala Leu Leu Asp Leu  Asp Pro Asp Thr Lys  Thr Asp Pro
    2885                2890                2895

Gly Ile  Asp Thr Asp Gly Asp  Thr Asp Val Ser Ala  Asp Ala Lys
    2900                2905                2910

Val Gly  Thr Gly Asp Gly Leu  Asp Asp Ala Ala Val  Ala Ser Ala
    2915                2920                2925

Leu Ala  Arg Gly Glu Ser Gln  Leu Ala Val Arg Asp  Gly Val Val
    2930                2935                2940

Arg Val  Ala Arg Leu Gly Gly  Leu Val Gly Gly Leu  Ser Leu Pro
    2945                2950                2955

Gly Gly  Val Gly Trp Arg Leu  Asp Gly Gly Gly Ser  Gly Leu Leu
    2960                2965                2970

Glu Gly  Val Gly Val Val Ala  Ser Asp Ala Ala Gly  Val Val Leu
    2975                2980                2985

Gly Arg  Gly Gln Val Arg Val  Ala Val Arg Ala Ala  Gly Val Asn
    2990                2995                3000

Phe Arg  Asp Val Leu Val Ala  Leu Gly Met Val Pro  Gly Gln Val
    3005                3010                3015

Gly Val  Gly Ser Glu Gly Ala  Gly Val Val Val Glu  Val Gly Pro
    3020                3025                3030

Gly Val  Glu Gly Leu Val Val  Gly Asp Arg Val Phe  Gly Val Phe
    3035                3040                3045

Gly Asp  Ala Phe Ala Pro Val  Val Val Ala Gln Glu  Val Leu Leu
    3050                3055                3060

Ala Arg  Ile Pro Glu Gly Trp  Ser Phe Ala Gln Ala  Ala Ser Val
    3065                3070                3075

Pro Val  Val Phe Ala Thr Ala  Tyr Leu Gly Leu Val  Asp Leu Ala
    3080                3085                3090

Gly Val  Arg Arg Gly Glu Ser  Val Leu Val His Ala  Ala Ala Gly
    3095                3100                3105

Gly Val  Gly Thr Ala Ala Val  Gln Leu Ala Arg His  Leu Gly Ala
    3110                3115                3120

Glu Val  Tyr Ala Thr Ala Ser  Glu Ala Lys Trp Ala  Arg Leu Arg
    3125                3130                3135
```

-continued

```
Ala Ala  Gly Val Ala Pro Gln  Arg Ile Ala Ser Ser  Arg Ser Val
    3140                 3145                 3150

Glu Phe  Glu Ser Arg Phe Arg  Arg Ala Ser Gly Gly  Arg Gly Val
    3155                 3160                 3165

Asp Val  Val Leu Asn Cys Leu  Ala Gly Glu Tyr Thr  Asp Ala Ser
    3170                 3175                 3180

Leu Arg  Leu Cys Ser Pro Gln  Gly Gly Arg Phe Leu  Glu Leu Gly
    3185                 3190                 3195

Lys Thr  Asp Ile Arg Asp Ala  Gly Glu Val Ala Ala  Arg Phe Pro
    3200                 3205                 3210

Gly Val  Ser Tyr Arg Ala Tyr  Asp Leu Met Asp Ala  Gly Ala Gln
    3215                 3220                 3225

Arg Val  Gly Glu Ile Leu His  Thr Val Val Asp Leu  Phe Arg Arg
    3230                 3235                 3240

Gly Val  Leu Glu Pro Leu Pro  Val Thr Ala Trp Asp  Val Arg Gln
    3245                 3250                 3255

Ala His  Gln Ala Leu Arg Ser  Met Arg Ser Gly Leu  His Val Gly
    3260                 3265                 3270

Lys Asn  Val Leu Thr Leu Pro  Val Pro Leu Asp Ala  Glu Gly Thr
    3275                 3280                 3285

Val Leu  Val Thr Gly Gly Thr  Gly Thr Leu Gly Ala  Ala Val Ala
    3290                 3295                 3300

Arg His  Leu Ala Ala Gly His  Gly Val Arg His Leu  Leu Leu Val
    3305                 3310                 3315

Ser Arg  Arg Gly Met Ala Ala  Ala Gly Ala Glu Lys  Leu Cys Ala
    3320                 3325                 3330

Glu Leu  Gly Gln Ala Gly Val  Ser Val Ser Val Ala  Gly Cys Asp
    3335                 3340                 3345

Val Ala  Asp Arg Ala Gln Val  Ala Ala Leu Leu Glu  Gln Val Pro
    3350                 3355                 3360

Ala Glu  His Pro Leu Thr Ala  Val Val His Thr Ala  Gly Val Leu
    3365                 3370                 3375

Asp Asp  Ala Thr Val Thr Cys  Leu Asp Arg Asn Lys  Ile Asp Ala
    3380                 3385                 3390

Val Leu  Gly Ala Lys Val Asp  Gly Ala Leu His Leu  His Glu Leu
    3395                 3400                 3405

Thr Ala  Gly Met Asp Leu Ser  Ala Phe Val Leu Phe  Ser Ser Ala
    3410                 3415                 3420

Ala Gly  Val Leu Gly Ser Pro  Gly Gln Gly Asn Tyr  Ala Ala Ala
    3425                 3430                 3435

Asn Ala  Ala Leu Asp Ala Leu  Ala His Gln Arg Arg  Ala Ala Gly
    3440                 3445                 3450

Leu Pro  Ala Leu Ser Leu Ala  Trp Gly Leu Trp Glu  Glu Ala Ser
    3455                 3460                 3465

Gly Met  Thr Gly His Leu Asp  Ala Ala Asp Arg His  Arg Ile Thr
    3470                 3475                 3480

Arg Ser  Gly Leu His Pro Leu  Thr Thr Pro Asp Ala  Leu Ala Leu
    3485                 3490                 3495

Leu Asp  Thr Ala Leu Ala Ala  Gly Arg Pro Ala Leu  Leu Pro Ala
    3500                 3505                 3510

Asp Leu  Arg Pro Thr His Pro  Ala Pro Pro Leu Leu  Glu His Leu
    3515                 3520                 3525
```

-continued

```
Ala Pro  Ala Arg Thr Ser His  Arg Thr Ala His Thr  Ser Thr Ala
    3530                 3535                 3540

Thr Gly  Val Gly Gln Asp Val  Ser Leu Thr Asp Arg  Leu Ala Thr
    3545                 3550                 3555

Leu Thr  Pro Glu Gln Arg His  Asp Thr Leu Leu Ala  Leu Ala Arg
    3560                 3565                 3570

Thr His  Ile Ala Ala Val Leu  Gly His Pro Ser Pro  Asp Thr Ile
    3575                 3580                 3585

Asp Pro  Glu Arg Thr Phe Arg  Asp Leu Gly Phe Asp  Ser Leu Thr
    3590                 3595                 3600

Ala Val  Glu Leu Arg Asn Arg  Leu Thr Arg Ala Thr  Gly Leu Arg
    3605                 3610                 3615

Leu Pro  Ala Thr Leu Ala Phe  Asp His Pro Thr Pro  Thr Ala Leu
    3620                 3625                 3630

Thr His  His Leu Thr Thr Leu  Leu Asn Pro Asn Asp  Asn Asp Asn
    3635                 3640                 3645

Val Gly  Pro Val Leu Met Glu  Leu Glu Arg Leu Glu  Ser Ala Leu
    3650                 3655                 3660

Ala Ala  Leu Asp Arg Asp Asp  Ser Ala Cys Glu Arg  Val Thr Leu
    3665                 3670                 3675

Arg Leu  Gln Ser Leu Met Leu  Arg Trp Ser Gly Ser  Glu Arg Gln
    3680                 3685                 3690

Ser Ala  Glu Asn Thr Asp Asp  Ser Ser Arg Phe Ala  Ser Ala Thr
    3695                 3700                 3705

Ala Glu  Glu Leu Leu Glu Phe  Ile Asp Arg Asp Leu  Gly Leu Ser
    3710                 3715                 3720


<210> SEQ ID NO 7
<211> LENGTH: 6043
<212> TYPE: PRT
<213> ORGANISM: bacteria

<400> SEQUENCE: 7

Val Ala Asn Asp Glu Lys Val Leu Glu Tyr Leu Lys Arg Val Thr Ala
1               5                   10                  15

Asp Leu Asp Arg Thr Arg Arg Arg Leu Tyr Glu Val Val Glu Arg Glu
            20                  25                  30

Gln Glu Pro Ile Ala Ile Val Gly Met Ala Cys Arg Tyr Pro Gly Gly
        35                  40                  45

Ala Gly Ser Pro Ala Gly Leu Trp Asp Leu Val Ser Ser Gly Thr Asp
    50                  55                  60

Ala Ile Gly Glu Phe Pro Thr Asp Arg Gly Trp Asp Leu Glu Arg Leu
65                  70                  75                  80

Tyr Asp Pro Asp Pro Asp His Pro Gly Thr Thr Tyr Thr Arg His Gly
                85                  90                  95

Gly Phe Leu Asp Gly Val Gly Glu Phe Asp Ala Glu Phe Phe Gly Val
            100                 105                 110

Ser Pro Arg Glu Ala Leu Ala Met Asp Pro Gln Gln Arg Leu Leu Leu
        115                 120                 125

Glu Thr Ala Trp Glu Ala Ile Glu His Ala Gly Ile Val Pro Glu Ser
    130                 135                 140

Leu Arg Gly Thr Ser Thr Gly Val Phe Ala Gly Ile Asn Pro Gln Asp
145                 150                 155                 160

Tyr Thr Ile Ser Gln Tyr Gly Arg Asp Ser Glu Ile Glu Gly Tyr Leu
                165                 170                 175
```

-continued

```
Leu Thr Gly Ala Ala Ala Ser Ile Ala Ser Gly Arg Ile Ser Tyr Thr
            180                 185                 190

Leu Gly Leu Glu Gly Pro Ala Val Thr Ile Asp Thr Ala Cys Ser Ser
        195                 200                 205

Ser Leu Val Ala Leu His Leu Ala Cys Gln Ala Leu Arg Ala Gly Glu
    210                 215                 220

Cys Thr Met Ala Leu Ala Gly Gly Ala Ser Val Leu Ser Thr Pro Leu
225                 230                 235                 240

Ile Phe Val Glu Phe Ala Arg His His Gly Leu Ser Val Asp Gly Arg
                245                 250                 255

Cys Lys Ala Phe Ser Ala Ser Ala Asp Gly Thr Gly Trp Gly Glu Gly
            260                 265                 270

Ala Gly Leu Leu Leu Leu Glu Arg Leu Ser Asp Ala Lys Arg Asn Gly
        275                 280                 285

Arg Arg Ile Leu Ala Leu Val Arg Gly Ser Ala Val Asn Gln Asp Gly
    290                 295                 300

Ala Ser Asn Gly Leu Thr Ala Pro Asn Gly Pro Ser Gln Cys Arg Val
305                 310                 315                 320

Ile Arg Arg Ala Leu Ala Asn Ala His Leu Ala Pro Ala Asp Ile Asp
                325                 330                 335

Ala Val Glu Ala His Gly Thr Gly Thr Thr Leu Gly Asp Pro Ile Glu
            340                 345                 350

Ala Gln Ala Leu Gln Glu Ala Tyr Gly Ala Asp Arg Pro Asp Asp Arg
        355                 360                 365

Pro Leu Trp Val Gly Thr Leu Lys Ser Asn Ile Gly His Ser Ile Ala
    370                 375                 380

Ala Ala Gly Val Gly Gly Val Ile Lys Met Val Met Ala Leu Arg His
385                 390                 395                 400

Glu Ser Leu Pro Arg Thr Leu His Val Asp Glu Pro Ser Pro Gln Val
                405                 410                 415

Asp Trp Ser Ser Gly Ala Val Ser Leu Leu Thr Glu Ala Arg Pro Trp
            420                 425                 430

Pro Arg Asp Glu Asp Arg Pro Arg Arg Ala Gly Val Ser Ser Phe Gly
        435                 440                 445

Val Ser Gly Thr Asn Ala His Val Ile Leu Glu Glu Ala Pro Ala Pro
    450                 455                 460

Ala Glu Val Gln Ala Val Glu Thr Ala Pro Val Val Arg Val Asp Gly
465                 470                 475                 480

Gly Glu Arg Ser Ala Pro Ala Asp Val Pro Leu Val Trp Val Val Ser
                485                 490                 495

Gly Lys Ser Gln Ala Ala Leu Arg Ala Gln Ala Ala Ala Leu His Ala
            500                 505                 510

His Val Leu Asp His Pro Glu Gln Asp Ala Ala Asp Ile Gly Tyr Ser
        515                 520                 525

Leu Ala Thr Thr Arg Ala Leu Phe Asp His Arg Ala Thr Leu Ile Ala
    530                 535                 540

Pro Asp Arg Asp Thr Leu Leu Asp Ala Leu Thr Ala Leu Ala Asp Gly
545                 550                 555                 560

Arg Thr His Pro His Leu Val Pro Ala Pro Pro Thr Glu Pro Gly His
                565                 570                 575

Ala His Lys Ile Ala Phe Leu Cys Ser Gly Gln Gly Thr Gln Arg Pro
            580                 585                 590
```

-continued

```
Gly Met Ala Thr Gly Leu Tyr His Thr Tyr Pro Ala Phe Ala Ala Ala
        595                 600                 605

Leu Asp Glu Thr Cys Ala His Phe Asp Pro His Leu Asp His Pro Leu
    610                 615                 620

Arg Asp Leu Leu Leu Asn His Asp Pro Thr Gly Leu Leu Thr His Thr
625                 630                 635                 640

Leu Tyr Ala Gln Pro Ala Leu Phe Thr Leu Gln Lys Ala Leu His His
                645                 650                 655

Leu Ile Thr Glu Thr Tyr Gly Ile Thr Pro His Tyr Leu Ala Gly His
            660                 665                 670

Ser Leu Gly Glu Ile Thr Ala Ala His Leu Ala Gly Ile Leu Thr Leu
        675                 680                 685

Pro Asp Ala Thr His Leu Ile Thr Thr Arg Ala Arg Leu Met Gln Thr
    690                 695                 700

Met Pro Pro Gly Thr Met Thr Thr Leu His Thr Thr Pro Glu His Ile
705                 710                 715                 720

Gln Pro Leu Leu Asp Gln His Pro Gly Lys Ala Thr Ile Ala Ala Val
                725                 730                 735

Asn Ser Pro His Ser Leu Val Ile Ser Gly Asp Pro Asp Thr Ile His
            740                 745                 750

His Ile Thr Thr Thr Cys His Thr Gln Gly Ile Thr Thr Lys Pro Leu
        755                 760                 765

Thr Thr Asn His Ala Phe His Ser Pro His Thr Asp Thr Ile Leu Glu
    770                 775                 780

Gln Leu Asp Thr Thr Thr His Thr Leu Thr Tyr His Pro Pro His Thr
785                 790                 795                 800

Pro Leu Ile Thr Ser Thr Pro Gly Asp Pro Leu Thr Pro His Tyr Trp
                805                 810                 815

Thr His Gln Thr Arg Gln Pro Val His Trp Thr Asp Thr Ile His Thr
            820                 825                 830

Leu His Thr Asn Gly Val Thr Thr Tyr Ile Glu Leu Gly Pro Asp His
        835                 840                 845

Thr Leu Thr Thr Leu Thr His His Asn Leu Pro His His Gln Pro Thr
    850                 855                 860

Ala Ile Thr Leu Thr His Pro His His Asn Pro Thr His His Leu Leu
865                 870                 875                 880

Thr Ala Leu Ala His Thr Pro Thr Thr Trp His Thr His His His Thr
                885                 890                 895

His Thr Asn Pro His Pro His Thr Ile Pro Asp Leu Pro Thr Tyr Pro
            900                 905                 910

Phe Gln Arg Arg His Tyr Trp Leu Gln Ala Pro Thr Thr Ser Thr Asp
        915                 920                 925

Gln Pro Val Ala Pro Thr Asn Asp Asp Ala Pro Ala Pro Arg Ala Thr
    930                 935                 940

Ser Leu Arg Asp Thr Leu Ala Gly Arg Ser Pro Gln Glu Arg Glu Glu
945                 950                 955                 960

Val Leu Leu Asp Leu Val Leu Thr Gln Val Ala Ala Val Leu Gly His
                965                 970                 975

Thr Ala Pro Glu Val Val Asp Pro Gln Arg Ala Phe Lys Asp Leu Gly
            980                 985                 990

Phe Asp Ser Leu Ala Ala Ile Lys  Leu Arg Asn Arg Leu  Ala Ala Ala
        995                 1000                1005

Thr Gly  Leu Glu Leu Pro Thr  Thr Leu Val Phe Asp  His Pro Thr
```

-continued

```
    1010                1015                1020

Pro Val  Ala Leu Arg Gln Tyr  Phe Gln Ser Gln Ile  Leu Gly Ala
    1025                1030                1035

Glu Ala  Asp Ala Pro Asn Arg  Leu Pro Leu Arg Ala  Ala Thr Thr
    1040                1045                1050

Asp Glu  Pro Ile Ala Ile Val  Gly Met Ala Cys Arg  Phe Pro Gly
    1055                1060                1065

Gly Val  Arg Thr Ala Asp Asp  Leu Trp Gln Leu Leu  Ser Asp Glu
    1070                1075                1080

His Asp  Ala Val Gly Gly Phe  Pro Thr Asn Arg Gly  Trp Asp Val
    1085                1090                1095

Ala Asn  Leu Tyr Asp Pro Asp  Pro Asp Arg His Gly  Thr Thr Tyr
    1100                1105                1110

Thr Gln  Gln Gly Gly Phe Leu  Tyr Glu Ala Gly Glu  Phe Asp Ala
    1115                1120                1125

Glu Phe  Phe Gly Ile Ser Pro  Arg Glu Ala Leu Ala  Met Asp Pro
    1130                1135                1140

Gln Gln  Arg Leu Leu Leu Glu  Thr Ala Trp Glu Ala  Ile Glu His
    1145                1150                1155

Ala Gly  Ile Asn Pro Asp Ala  Leu Arg Asn Thr Ser  Thr Gly Val
    1160                1165                1170

Phe Ala  Gly Val Ile Tyr His  Asp Tyr Ala Ser Arg  Phe Leu Thr
    1175                1180                1185

Ala Pro  Ala Gly Tyr Glu Gly  Tyr Leu Gly His Gly  Ser Ala Gly
    1190                1195                1200

Ser Ile  Ala Ser Gly Arg Val  Ala Tyr Val Leu Gly  Leu Glu Gly
    1205                1210                1215

Pro Ala  Val Thr Val Asp Thr  Ala Cys Ser Ser Ser  Leu Val Ala
    1220                1225                1230

Leu His  Leu Ala Cys Gln Ala  Leu Arg Ser Gly Glu  Cys Thr Met
    1235                1240                1245

Ala Leu  Ala Gly Gly Ala Thr  Val Met Ser Thr Pro  Gln Ala Phe
    1250                1255                1260

Val Glu  Phe Ser Arg Gln Arg  Gly Leu Ala Ala Asp  Gly Arg Cys
    1265                1270                1275

Lys Ala  Phe Ser Ala Ala Ala  Asp Gly Thr Gly Trp  Gly Glu Gly
    1280                1285                1290

Ala Gly  Leu Leu Leu Leu Glu  Arg Leu Ser Glu Ala  Glu Arg Asn
    1295                1300                1305

Gly His  Arg Val Leu Ala Val  Val Arg Gly Ser Ala  Val Asn Gln
    1310                1315                1320

Asp Gly  Ala Ser Asn Gly Leu  Thr Ala Pro Asn Gly  Pro Ser Gln
    1325                1330                1335

Gln Arg  Val Ile Arg Gln Ala  Leu Ala Asn Ser Gly  Leu Thr Gly
    1340                1345                1350

Ala Asp  Val Asp Ala Val Glu  Ala His Gly Thr Gly  Thr Lys Leu
    1355                1360                1365

Gly Asp  Pro Ile Glu Ala Gln  Ala Leu Leu Ala Thr  Tyr Gly Gln
    1370                1375                1380

Glu His  His Pro Asp Gln Pro  Leu Trp Leu Gly Ser  Leu Lys Ser
    1385                1390                1395

Asn Ile  Gly His Ala Gln Ala  Ala Ala Gly Val Gly  Ser Ile Ile
    1400                1405                1410
```

-continued

```
Lys Met  Ile Met Ala Met Arg  Asn Glu Ser Leu Pro  Arg Thr Leu
    1415                 1420                 1425

His Val  Asp Glu Pro Ser Pro  His Val Asp Trp Ser  Ser Gly Ala
    1430                 1435                 1440

Val Ser  Leu Leu Thr Glu Pro  Arg Pro Trp Pro Arg  Arg Glu Asp
    1445                 1450                 1455

Arg Pro  Arg Arg Ala Gly Ile  Ser Ser Phe Gly Val  Ser Gly Thr
    1460                 1465                 1470

Asn Ala  His Val Ile Val Glu  Glu Pro Pro Ala Arg  Ala Glu Val
    1475                 1480                 1485

Glu Ala  Val Glu Ala Ala Pro  Ala Gly Val Glu Thr  Ala Ala Ala
    1490                 1495                 1500

Ala Ala  Val Val Val Glu Thr  Asp Gly Ala Gly Arg  Val Ser Ser
    1505                 1510                 1515

Asp Val  Pro Leu Val Trp Val  Val Ser Gly Lys Ser  Gln Ala Ala
    1520                 1525                 1530

Leu Arg  Ala Gln Ala Ala Ala  Leu His Ala His Val  Leu Asp His
    1535                 1540                 1545

Pro Glu  Gln Asp Ala Ala Asp  Ile Gly Tyr Ser Leu  Ala Thr Thr
    1550                 1555                 1560

Arg Ala  Leu Phe Asp His Arg  Ala Thr Leu Ile Ala  Pro Asp Arg
    1565                 1570                 1575

Asp Thr  Leu Leu Asp Ala Leu  Thr Ala Leu Ala Asp  Gly Arg Thr
    1580                 1585                 1590

His Pro  His Leu Ile Pro Thr  Pro Pro Thr Glu Pro  Gly His Thr
    1595                 1600                 1605

His Lys  Ile Ala Phe Leu Cys  Ser Gly Gln Gly Thr  Gln Arg Pro
    1610                 1615                 1620

Gly Met  Ala Thr Gly Leu Tyr  His Thr Tyr Pro Ala  Phe Ala Ala
    1625                 1630                 1635

Ala Leu  Asp Glu Thr Cys Ala  His Phe Asp Pro His  Leu Asp His
    1640                 1645                 1650

Pro Leu  Arg Asp Leu Leu Leu  Asn His Asp Pro Thr  Asp Leu Leu
    1655                 1660                 1665

Thr His  Thr Leu Tyr Ala Gln  Pro Ala Leu Phe Thr  Leu Gln Lys
    1670                 1675                 1680

Ala Leu  His His Leu Ile Thr  Glu Thr Tyr Gly Ile  Thr Pro His
    1685                 1690                 1695

Tyr Leu  Ala Gly His Ser Leu  Gly Glu Ile Thr Ala  Ala His Leu
    1700                 1705                 1710

Ala Gly  Ile Leu Thr Leu Pro  Asp Ala Thr His Leu  Ile Thr Thr
    1715                 1720                 1725

Arg Ala  Arg Leu Met Gln Thr  Met Pro Pro Gly Thr  Met Thr Thr
    1730                 1735                 1740

Leu His  Thr Thr Pro Glu His  Ile Gln Pro Leu Leu  Asp Gln His
    1745                 1750                 1755

Pro Gly  Lys Ala Thr Ile Ala  Ala Val Asn Ser Pro  His Ser Leu
    1760                 1765                 1770

Val Ile  Ser Gly Asp Pro Asp  Thr Ile His His Ile  Thr Thr Thr
    1775                 1780                 1785

Cys His  Asn Gln Gly Ile Thr  Thr Lys Pro Leu Thr  Thr Asn His
    1790                 1795                 1800
```

-continued

```
Ala Phe His Ser Pro His Thr Asn Thr Ile Leu Glu Gln Leu Asp
    1805                1810                1815

Thr Thr Thr His Thr Leu Thr Tyr His Pro Pro His Thr Pro Leu
    1820                1825                1830

Ile Thr Ser Thr Pro Gly Asn Pro Leu Thr Pro His Tyr Trp Thr
    1835                1840                1845

His Gln Thr Arg Gln Pro Val His Trp Ala Asp Thr Ile His Thr
    1850                1855                1860

Leu His Thr Asn Gly Val Thr Thr Tyr Ile Gly Leu Gly Pro Asp
    1865                1870                1875

His Thr Leu Ser Thr Leu Thr His His Asn Leu Pro Gln His Gln
    1880                1885                1890

Pro Thr Ala Ile Thr Leu Thr His Pro His His Asn Pro Thr His
    1895                1900                1905

His Leu Leu Thr Ala Leu Ala His Thr Pro Thr Thr Trp His Thr
    1910                1915                1920

His His His Thr His Thr Asn Pro His Pro His Thr Ile Pro Asp
    1925                1930                1935

Leu Pro Thr Tyr Pro Phe Gln Arg Arg His Tyr Trp Leu Glu Val
    1940                1945                1950

Pro Lys Pro Thr Ala Glu Ala Ser Ala Ser Ala Ser Gly Pro Gly
    1955                1960                1965

Arg Asn Arg Ala Ala Lys Leu Ser Ala Leu Glu Ala Glu Phe Trp
    1970                1975                1980

Gln Ala Val Glu Glu Thr Asp Thr Asp Thr Leu Ala His Thr Leu
    1985                1990                1995

Asp Leu Asp Thr Gln Thr Leu Glu Pro Val Leu Pro Ala Leu Ala
    2000                2005                2010

Thr Trp His Gln Gln Gln Arg Asp His Ala Arg Ile Asn Thr Trp
    2015                2020                2025

Thr Tyr Gln Glu Thr Trp Lys Pro Leu His Leu Pro Thr Thr Arg
    2030                2035                2040

Pro Thr Thr Pro Thr Ser Trp Leu Ile Ala Ile Pro Glu Thr His
    2045                2050                2055

Arg Asn His Pro His Thr Thr Asn Leu Leu Thr Asn Leu Pro His
    2060                2065                2070

His Asn Ile Thr Pro Ile Pro Leu Thr Ile Asn His Thr Thr Asp
    2075                2080                2085

Leu His His Ala Tyr His His Ala His His His Thr Thr Pro Pro
    2090                2095                2100

Ile Thr Ala Val Leu Ser Leu Leu Ala Leu Asp Glu Thr Pro His
    2105                2110                2115

Pro His His Pro His Thr Pro Thr Gly Thr Leu Leu Asn Leu Thr
    2120                2125                2130

Leu Thr Gln Thr His Thr Gln Thr His Pro Pro Thr Pro Leu Trp
    2135                2140                2145

Tyr Leu Thr Thr Gln Ala Thr Thr Thr His Pro Asn Asp Pro Leu
    2150                2155                2160

Thr His Pro Thr Gln Ala Gln Thr Ile Gly Leu Ala Arg Thr Thr
    2165                2170                2175

His Leu Glu His Pro His His Thr Gly Gly His Ile Asp Leu Pro
    2180                2185                2190

Thr Thr Pro His Pro Asn Thr Leu Thr Gln Leu Ile Thr Ala Leu
```

-continued

```
    2195                2200                2205

Thr His  Pro His His Gln His  Asn Leu Thr Ile Arg  Thr His Thr
    2210                2215                2220

Thr His  Thr Arg Arg Leu Thr  Pro Thr Thr Leu Gln  Pro Thr Thr
    2225                2230                2235

Pro Thr  Pro Pro Thr Asn Pro  His Gly Thr Thr Leu  Ile Thr Gly
    2240                2245                2250

Gly Thr  Gly Ala Leu Ala Thr  Thr Leu Ala His His  Leu Ala Thr
    2255                2260                2265

Thr Gly  Thr Gln His Leu Leu  Leu Thr Ser Arg Arg  Gly Pro His
    2270                2275                2280

Thr Pro  Gly Ala Arg Gln Leu  His Thr Gln Leu Thr  Gln Leu Gly
    2285                2290                2295

Thr Asn  Thr Thr Ile Thr Ala  Cys Asp Leu Ser Asp  Pro Asp Gln
    2300                2305                2310

Leu Thr  His Leu Leu Thr His  Ile Pro Pro Glu His  Pro Leu Thr
    2315                2320                2325

Thr Val  Ile His Thr Ala Gly  Ile Leu Asp Asp Ala  Thr Leu Thr
    2330                2335                2340

Asn Leu  Thr Pro Thr Gln Leu  Asp Asn Val Leu Arg  Ala Lys Ala
    2345                2350                2355

His Thr  Ala His Leu Leu His  His Ala Thr Leu His  Thr Pro Leu
    2360                2365                2370

Asp His  Phe Val Leu Tyr Ser  Ser Ala Ala Ala Thr  Leu Gly Ala
    2375                2380                2385

Pro Gly  Gln Ala Asn Tyr Ala  Ala Ala Asn Ala Tyr  Leu Asp Ala
    2390                2395                2400

Leu Ala  His His Arg His Thr  His Asn Leu Pro Ala  Thr Thr Ile
    2405                2410                2415

Ala Trp  Gly Thr Trp Gln Gly  Asn Gly Leu Ala Ser  Gly Asp Ile
    2420                2425                2430

Gly Glu  His Leu Arg Arg Arg  Gly Met Ile Pro Leu  Asp Pro Glu
    2435                2440                2445

Ser Ala  Val Gly Ala Phe Asp  Arg Ala Val Ala Ser  Asp Arg Pro
    2450                2455                2460

Ser Val  Phe Val Ala Asp Ile  Asp Trp Pro Thr Phe  Gly Arg Asn
    2465                2470                2475

Thr Ser  Ser Gly Leu Arg Ala  Leu Phe Glu Asp Ile  Pro Glu Ala
    2480                2485                2490

Thr Gln  Pro Glu Pro Thr Ala  Arg Ser Ala Asp Gln  Pro Asn Gly
    2495                2500                2505

His Gly  Ser Leu Gln Glu Leu  Leu Ala Arg Gln Ser  Pro Ala Glu
    2510                2515                2520

Gln Ala  Glu Thr Leu Leu Ala  Leu Val Arg Thr His  Ser Ala Thr
    2525                2530                2535

Val Leu  Gly Arg Asp Gly Ala  Asp Ala Val Ala Ala  Glu Arg Pro
    2540                2545                2550

Phe Arg  Asp Leu Gly Phe Asp  Ser Leu Ser Ala Val  Glu Leu Arg
    2555                2560                2565

Asn His  Leu Thr Ala Asp Thr  Glu Leu Ala Leu Pro  Thr Thr Leu
    2570                2575                2580

Val Phe  Asp His Pro Thr Pro  Val Lys Leu Ala Glu  Phe Leu Arg
    2585                2590                2595
```

-continued

```
Thr Glu  Leu Leu Gly Thr Ala  Pro Ala Thr Thr Ala  Ala Val Pro
    2600                 2605                 2610

Ala Leu  Gln Ser His Thr Asp  Glu Pro Ile Ala Ile  Ile Gly Met
    2615                 2620                 2625

Ala Cys  Arg Phe Pro Gly Ala  Val Thr Thr Pro Glu  His Leu Trp
    2630                 2635                 2640

Asn Leu  Ile Ala Thr Glu Gln  Asp Ala Ile Gly Glu  Phe Pro Thr
    2645                 2650                 2655

Asp Arg  Gly Trp Asp Leu Asp  Asn Leu Tyr His Pro  Asp Pro Asp
    2660                 2665                 2670

His Pro  Gly Thr Thr Tyr Thr  Arg His Gly Gly Phe  Leu Tyr Asp
    2675                 2680                 2685

Ala Gly  Asp Phe Asp Ala Glu  Phe Phe Gly Ile Asn  Pro Arg Glu
    2690                 2695                 2700

Ala Leu  Ala Met Asp Pro Gln  Gln Arg Leu Leu Leu  Glu Thr Ala
    2705                 2710                 2715

Trp Glu  Ala Ile Glu His Ala  Gly Ile Leu Pro Asp  Ala Leu His
    2720                 2725                 2730

Gly Thr  Pro Thr Gly Val Phe  Thr Gly Val Asn Ala  Gln Asp Tyr
    2735                 2740                 2745

Ala Ala  His Thr His Ala Ser  Pro His Thr Thr Glu  Gly Tyr Thr
    2750                 2755                 2760

Leu Thr  Gly Thr Ala Gly Ser  Ile Ala Ser Gly Arg  Ile Ala Tyr
    2765                 2770                 2775

Thr Leu  Gly Leu Glu Gly Pro  Ala Val Thr Ile Asp  Thr Ala Cys
    2780                 2785                 2790

Ser Ser  Ser Leu Val Ala Leu  His Leu Ala Cys Gln  Ala Leu Arg
    2795                 2800                 2805

Ala Gly  Glu Cys Thr Thr Ala  Leu Ala Ser Gly Ile  Thr Val Met
    2810                 2815                 2820

Thr Ser  Pro Val Thr Phe Thr  Glu Phe Ser Arg Gln  Arg Gly Leu
    2825                 2830                 2835

Ala Pro  Asp Gly His Cys Lys  Ala Phe Ser Ala Ser  Ala Asp Gly
    2840                 2845                 2850

Thr Gly  Trp Ser Glu Gly Val  Gly Thr Ile Leu Val  Glu Arg Leu
    2855                 2860                 2865

Ser Asp  Ala Glu Arg Asn Gly  His Arg Ile Leu Ala  Val Val Arg
    2870                 2875                 2880

Gly Ser  Ala Val Asn Gln Asp  Gly Ala Ser Asn Gly  Leu Thr Ala
    2885                 2890                 2895

Pro Asn  Gly Pro Ser Gln Gln  Arg Val Ile Arg Gln  Ala Leu Ala
    2900                 2905                 2910

Asn Ser  Gly Leu Thr Gly Ala  Asp Val Asp Ala Val  Glu Ala His
    2915                 2920                 2925

Gly Thr  Gly Thr Lys Leu Gly  Asp Pro Ile Glu Ala  Gln Ala Leu
    2930                 2935                 2940

Leu Ala  Thr Tyr Gly Gln Gly  Arg Ala Gln Glu Gln  Pro Leu Trp
    2945                 2950                 2955

Leu Gly  Ser Val Lys Ser Asn  Leu Gly His Thr Gln  Ala Ala Ala
    2960                 2965                 2970

Gly Met  Ala Gly Leu Ile Lys  Met Val Met Ala Leu  Arg His Glu
    2975                 2980                 2985
```

-continued

Ser Leu Pro Arg Thr Leu His Val Asp Glu Pro Ser Pro Gln Val
2990 2995 3000

Asp Trp Ser Ser Gly Ala Val Ser Leu Leu Thr Glu Ala Arg Pro
3005 3010 3015

Trp Pro Arg Arg Glu Asp Arg Pro Arg Arg Ala Gly Ile Ser Ser
3020 3025 3030

Phe Gly Val Ser Gly Thr Asn Ala His Val Ile Leu Glu Glu Ala
3035 3040 3045

Pro Ala Pro Ala Glu Ala Val Glu Thr Glu Gln Gly Val Val Pro
3050 3055 3060

Gln Gly Asp Gln Glu Cys Ser Ala Pro Val Gly Val Pro Leu Val
3065 3070 3075

Trp Val Val Ser Gly Lys Ser Gln Ala Ala Leu Arg Ala Gln Ala
3080 3085 3090

Ala Ala Leu His Ala His Val Leu Asp His Pro Glu Gln Asp Ala
3095 3100 3105

Ala Asp Ile Gly Tyr Ser Leu Ala Thr Thr Arg Ala Leu Phe Asp
3110 3115 3120

His Arg Ala Thr Leu Ile Ala Pro Asp Arg Asp Thr Leu Leu Asp
3125 3130 3135

Ala Leu Thr Ala Leu Ala Asp Gly Arg Thr His Pro His Leu Ile
3140 3145 3150

Pro Thr Pro Pro Thr Glu Pro Gly His Thr His Lys Ile Ala Phe
3155 3160 3165

Leu Cys Ser Gly Gln Gly Thr Gln Arg Pro Gly Met Ala Thr Gly
3170 3175 3180

Leu Tyr His Thr Tyr Pro Ala Phe Ala Ala Ala Leu Asp Glu Thr
3185 3190 3195

Cys Ala His Phe Asp Pro His Leu Asp His Pro Leu Arg Asp Leu
3200 3205 3210

Leu Leu Asn His Asp Pro Thr Asp Leu Leu Thr His Thr Leu Tyr
3215 3220 3225

Ala Gln Pro Ala Leu Phe Thr Leu Gln Lys Ala Leu His His Leu
3230 3235 3240

Ile Thr Glu Thr Tyr Gly Ile Thr Pro His Tyr Leu Ala Gly His
3245 3250 3255

Ser Leu Gly Glu Ile Thr Ala Ala His Leu Ala Gly Ile Leu Thr
3260 3265 3270

Leu Pro Asp Ala Thr His Leu Ile Thr Thr Arg Ala Arg Leu Met
3275 3280 3285

Gln Thr Met Pro Pro Gly Thr Met Thr Thr Leu His Thr Thr Pro
3290 3295 3300

Glu His Ile Gln Pro Leu Leu Asp Gln His Pro Gly Lys Ala Thr
3305 3310 3315

Ile Ala Ala Val Asn Ser Pro His Ser Leu Val Ile Ser Gly Asp
3320 3325 3330

Pro Asp Thr Ile His His Ile Thr Thr Thr Cys His Thr Gln Gly
3335 3340 3345

Ile Thr Thr Lys Pro Leu Thr Thr Asn His Ala Phe His Ser Pro
3350 3355 3360

His Thr Asp Thr Ile Leu Glu Gln Leu Asp Thr Thr Thr His Thr
3365 3370 3375

Leu Thr Tyr His Gln Pro His Thr Pro Leu Ile Thr Ser Thr Pro

-continued 3380 3385 3390

Gly Asp Pro Leu Thr Pro His Tyr Trp Thr His Gln Thr Arg Gln
3395 3400 3405

Pro Val His Trp Ala Asp Thr Ile His Thr Leu His Thr Asn Gly
3410 3415 3420

Val Thr Thr Tyr Ile Gly Leu Gly Pro Asp His Thr Leu Ser Thr
3425 3430 3435

Leu Thr His His Asn Leu Pro Gln His Gln Pro Thr Ala Ile Thr
3440 3445 3450

Leu Thr His Pro His His Asn Pro Thr His His Leu Leu Thr Ala
3455 3460 3465

Leu Ala His Thr Pro Thr Thr Trp His Thr His His His Thr His
3470 3475 3480

Thr Asn Pro His Pro His Thr Ile Pro Asp Leu Pro Thr Tyr Pro
3485 3490 3495

Phe Gln Arg Arg His Tyr Trp Leu Glu Val Pro Lys Pro Thr Ala
3500 3505 3510

Glu Ala Ser Ala Ser Ala Ser Gly Pro Gly Arg Asn Arg Ala Ala
3515 3520 3525

Lys Leu Ser Ala Leu Glu Ala Glu Phe Trp Gln Ala Val Glu Glu
3530 3535 3540

Thr Asp Thr Asp Thr Leu Ala His Thr Leu Asp Leu Asp Thr Gln
3545 3550 3555

Thr Leu Glu Pro Val Leu Pro Ala Leu Ala Thr Trp His Gln Gln
3560 3565 3570

Gln Arg Asp His Ala Arg Ile Asn Thr Trp Thr Tyr Gln Glu Thr
3575 3580 3585

Trp Lys Pro Leu His Leu Pro Thr Thr Arg Pro Thr Thr Pro Thr
3590 3595 3600

Ser Trp Leu Ile Ala Ile Pro Glu Thr His Arg Asn His Pro His
3605 3610 3615

Thr Thr Asn Leu Leu Thr Asn Leu Pro His His Asn Ile Thr Pro
3620 3625 3630

Ile Pro Leu Thr Ile Asn His Thr Thr Asp Leu His His Ala Tyr
3635 3640 3645

His His Ala His His His Thr Thr Pro Pro Ile Thr Ala Val Leu
3650 3655 3660

Ser Leu Leu Ala Leu Asp Glu Thr Pro His Pro His His Pro His
3665 3670 3675

Thr Pro Thr Gly Thr Leu Leu Asn Leu Thr Leu Thr Gln Thr His
3680 3685 3690

Thr Gln Thr His Pro Pro Thr Pro Leu Trp Tyr Leu Thr Thr Gln
3695 3700 3705

Ala Thr Thr Thr His Pro Asn Asp Pro Leu Thr His Pro Thr Gln
3710 3715 3720

Ala Gln Thr Ile Gly Leu Ala Arg Thr Thr His Leu Glu His Pro
3725 3730 3735

His His Thr Gly Gly His Ile Asp Leu Pro Thr Thr Pro His Pro
3740 3745 3750

Asn Thr Leu Thr Gln Leu Ile Thr Ala Leu Thr His Pro His His
3755 3760 3765

Gln His Asn Leu Thr Ile Arg Thr His Thr Thr His Thr Arg Arg
3770 3775 3780

-continued

```
Leu Thr  Pro Thr Thr Leu Gln  Pro Thr Thr Pro Thr  Pro Pro Thr
    3785                 3790                 3795

Asn Pro  His Gly Thr Thr Leu  Ile Thr Gly Gly Thr  Gly Ala Leu
    3800                 3805                 3810

Ala Thr  Thr Leu Ala His His  Leu Ala Thr Thr Gly  Thr Gln His
    3815                 3820                 3825

Leu Leu  Leu Thr Ser Arg Arg  Gly Pro His Thr Pro  Gly Ala Arg
    3830                 3835                 3840

Gln Leu  His Thr Gln Leu Thr  Gln Leu Gly Thr Asn  Thr Thr Ile
    3845                 3850                 3855

Thr Ala  Cys Asp Leu Ser Asp  Pro Asp Gln Leu Thr  His Ile Leu
    3860                 3865                 3870

Thr His  Ile Pro Pro Glu His  Pro Leu Thr Thr Val  Ile His Thr
    3875                 3880                 3885

Ala Gly  Val Asn His Tyr Ala  Pro Val Ala Ala Thr  Asp Pro Ser
    3890                 3895                 3900

Thr Phe  Ala Ser Val Leu Ala  Ala Lys Ala Ala Gly  Ala Ala His
    3905                 3910                 3915

Leu His  Glu Leu Leu Leu Glu  Leu Asp Thr Val Glu  Gln Phe Ile
    3920                 3925                 3930

Leu Phe  Ser Ser Gly Ser Gly  Ala Trp Gly Ser Gly  Asn Gln Cys
    3935                 3940                 3945

Ala Tyr  Ala Ala Ala Asn Ala  Tyr Leu Asp Ala Leu  Ala Ala His
    3950                 3955                 3960

Arg Gln  Ala Arg Gly Leu Pro  Gly Met Ser Leu Ala  Trp Gly Pro
    3965                 3970                 3975

Trp Asp  Gly Asp Gly Met Ser  Ala Gly Glu Asp Ala  Gln Arg Tyr
    3980                 3985                 3990

Leu Arg  Glu Arg Gly Val Leu  Pro Met Asp Pro Arg  Leu Ala Val
    3995                 4000                 4005

Ala Ala  Phe Asp Glu Ala Val  Arg Ala Arg Pro Asn  Ser Asn Leu
    4010                 4015                 4020

Val Val  Ala Asp Ile Asp Trp  Glu Arg Phe Val Pro  Thr Phe Thr
    4025                 4030                 4035

Ala Arg  Gly His Asn Pro Leu  Ile Glu Asp Ile Pro  Glu Val Arg
    4040                 4045                 4050

Arg Leu  Ala Ala Glu Ala Glu  Ala Ala Gln Thr Thr  Thr Ala Ala
    4055                 4060                 4065

Thr Asp  Ala Pro Ala Leu Leu  Asn Arg Leu Ser Gly  Leu Ser Ala
    4070                 4075                 4080

Thr Gln  Gln Lys Gln His Leu  Leu Arg Leu Val Arg  Ser His Met
    4085                 4090                 4095

Gly Glu  Val Leu Gly Arg Glu  Asp Val Asp Thr Leu  Asp Glu Arg
    4100                 4105                 4110

His Thr  Phe Arg Asp Leu Gly  Phe Asp Ser Leu Thr  Ser Ala Arg
    4115                 4120                 4125

Phe Ser  Gln Arg Leu Ala Lys  Asp Thr Gly Leu His  Leu Pro Ala
    4130                 4135                 4140

Thr Leu  Val Phe Asp His Pro  Thr Pro Ala Asp Cys  Val Ala His
    4145                 4150                 4155

Leu Arg  Asp Gln Leu Leu Gly  Glu Thr Asp Asp Met  Thr Pro Arg
    4160                 4165                 4170
```

-continued

Lys Arg Asp His Leu Gly Glu Asp Arg Arg Ala Ala Thr Ala Asp
4175 4180 4185

Asp Pro Ile Ala Ile Val Gly Met Ala Cys Arg Phe Pro Gly Gly
4190 4195 4200

Val Arg Ser Ala Asp Asp Leu Trp Asp Leu Leu Ser Ser Gly Thr
4205 4210 4215

Asp Ala Ile Ser Gly Phe Pro Thr Asp Arg Gly Trp Asp Ile Glu
4220 4225 4230

Ser Leu Tyr Asp Pro Asp Pro Asp Arg Ser Gly Thr Thr Tyr Thr
4235 4240 4245

Arg His Gly Gly Phe Leu Tyr Asp Ala Gly Gln Phe Asp Ala Glu
4250 4255 4260

Phe Phe Gly Ile Ser Pro Arg Glu Ala Leu Ala Met Asp Pro Gln
4265 4270 4275

Gln Arg Leu Leu Leu Glu Thr Ala Trp Glu Ala Val Glu His Ala
4280 4285 4290

Gly Ile Asn Pro Gln Thr Leu His Gly Thr Pro Thr Gly Val Phe
4295 4300 4305

Thr Gly Val Asn Ala Gln Asp Tyr Ala Ala His Leu Arg Gln Ala
4310 4315 4320

Ser Gly Asn Val Glu Gly Tyr Ala Leu Thr Gly Ser Ser Gly Ser
4325 4330 4335

Val Val Ser Gly Arg Val Ala Tyr Thr Phe Gly Phe Glu Gly Pro
4340 4345 4350

Ala Val Ser Val Asp Thr Ala Cys Ser Ser Ser Leu Val Ala Leu
4355 4360 4365

His Leu Ala Gly Gln Ala Leu Arg Ser Gly Glu Cys Thr Met Ala
4370 4375 4380

Leu Ala Gly Gly Val Met Val Met Ser Ser Pro Glu Thr Phe Val
4385 4390 4395

Glu Phe Ser Arg Gln Arg Gly Leu Ser Val Asp Gly Arg Cys Lys
4400 4405 4410

Ser Phe Ala Ala Ala Ala Asp Gly Thr Gly Trp Gly Glu Gly Val
4415 4420 4425

Gly Met Leu Leu Val Glu Arg Leu Ser Asp Ala Glu Arg Asn Gly
4430 4435 4440

His Arg Val Leu Ala Val Val Arg Gly Ser Ala Val Asn Gln Asp
4445 4450 4455

Gly Ala Ser Asn Gly Leu Thr Ala Pro Asn Gly Pro Ser Gln Gln
4460 4465 4470

Arg Val Ile Arg Gln Ala Leu Ala Asn Ser Gly Leu Thr Gly Ala
4475 4480 4485

Asp Val Asp Ala Val Glu Ala His Gly Thr Gly Thr Lys Leu Gly
4490 4495 4500

Asp Pro Ile Glu Ala Gln Ala Leu Leu Ala Thr Tyr Gly Gln Glu
4505 4510 4515

His His Pro Asp Gln Pro Leu Trp Leu Gly Ser Leu Lys Ser Asn
4520 4525 4530

Ile Gly His Ala Gln Ala Ala Ala Gly Val Gly Gly Ile Ile Lys
4535 4540 4545

Met Val Met Ala Leu Arg His Glu Thr Leu Pro Arg Thr Leu His
4550 4555 4560

Ile Asp Glu Pro Thr Pro Gln Val Asp Trp Ser Ser Gly Ala Val

-continued

```
    4565                4570                4575

Ser Leu  Leu Thr Glu Pro Arg  Pro Trp Pro Arg Gln  Gly Asp Arg
    4580                4585                4590

Pro Arg  Arg Ala Gly Ile Ser  Ser Phe Gly Val Ser  Gly Thr Asn
    4595                4600                4605

Ala His  Val Ile Leu Glu Glu  Ala Pro Ala Gln Pro  Ala Gly Asp
    4610                4615                4620

Pro Ala  Pro Glu Asp Gly Ala  Pro Val Pro Trp Ala  Met Ser Ala
    4625                4630                4635

Arg Ser  Asn Ala Ala Leu Arg  Ala Gln Ala Ala Leu  Leu Arg Asp
    4640                4645                4650

Phe Leu  Gln Gly Pro Gly Thr  Asp Thr Ala Leu Arg  Ala Val Gly
    4655                4660                4665

Ala Glu  Leu Ala His Gly Arg  Ala Val Leu Glu His  Arg Ala Val
    4670                4675                4680

Ile Val  Ala Arg Glu Arg Thr  Glu Phe Glu Asp Ala  Leu Glu Ala
    4685                4690                4695

Leu Ala  Ser Gly Glu Pro His  Pro Ala Leu Ile Glu  Asp Thr Thr
    4700                4705                4710

Gly Ser  Gln Thr Asn Ser His  Ser Gly Gly Gly Val  Val Phe Val
    4715                4720                4725

Phe Pro  Gly Gln Gly Gly Gln  Trp Ala Gly Met Gly  Leu Asp Leu
    4730                4735                4740

Leu Arg  Asp Ser Gln Val Phe  Ala Asp His Val Gly  Ala Cys Glu
    4745                4750                4755

Arg Ala  Leu Ala Pro Trp Val  Glu Trp Ser Leu Thr  Glu Met Leu
    4760                4765                4770

His Arg  Asp Ala Glu Asp Pro  Val Trp Glu Arg Ala  Asp Val Val
    4775                4780                4785

Gln Pro  Val Leu Phe Ser Val  Met Val Ser Leu Ala  Ala Leu Trp
    4790                4795                4800

Arg Ser  Tyr Gly Ile Glu Pro  Glu Ala Val Val Gly  His Ser Gln
    4805                4810                4815

Gly Glu  Ile Ala Ala Ala His  Val Cys Gly Ala Leu  Thr Leu Glu
    4820                4825                4830

Asp Ala  Ala Lys Ile Val Ala  Leu Arg Ser Arg Ala  Leu Ala Ala
    4835                4840                4845

Leu Arg  Gly His Gly Gly Met  Ala Ser Leu Ala Leu  Thr Gly Thr
    4850                4855                4860

Glu Ala  Glu Asp Leu Ile Thr  Thr His Trp Pro Gly  Arg Leu Trp
    4865                4870                4875

Thr Ala  Ala Phe Asn Gly Pro  Arg Ala Thr Thr Val  Ser Gly Asp
    4880                4885                4890

Thr Asp  Ala Leu Asp Glu Leu  Leu Thr His Cys Thr  Glu Thr Gly
    4895                4900                4905

Val Arg  Ala Arg Arg Ile Pro  Val Asp Tyr Ala Ser  His Cys Pro
    4910                4915                4920

His Thr  Glu Thr Ile Glu His  Asp Leu Leu His Met  Leu His Gly
    4925                4930                4935

Ile Thr  Pro Gln Pro Gly Ser  Ile Pro Phe Tyr Ser  Thr Val Glu
    4940                4945                4950

Asp Ala  Trp Thr Asp Thr Thr  Thr Leu Asp Ala Ala  Tyr Trp Tyr
    4955                4960                4965
```

-continued

```
Arg Asn Leu Arg Arg Pro Val Arg Phe Thr His Ala Val Arg Thr
    4970                4975                4980

Leu Thr Ala Gln Gly His Arg Leu Phe Ile Glu Thr Ser Pro His
    4985                4990                4995

Pro Thr Leu Thr Pro Ala Ile Glu Asp His Asp His Thr Thr Ala
    5000                5005                5010

Leu Gly Thr Leu Arg Arg His Asp Asn Asp Thr His Arg Phe Leu
    5015                5020                5025

Thr Ala Leu Ala His Ala His Thr Thr Gly His Thr Val Thr Trp
    5030                5035                5040

Thr Thr His Tyr Pro Thr Thr Pro His Thr Pro Ala Ile Asp Leu
    5045                5050                5055

Pro Thr Tyr Pro Phe Gln His His His Tyr Trp Leu His Thr Pro
    5060                5065                5070

Thr Thr Ser Thr Gly Asp Val Ser Ala Ala Gly Leu His Pro Thr
    5075                5080                5085

Glu His Pro Leu Leu Gly Ala Thr Val Glu Leu Ala Asp Gly Asp
    5090                5095                5100

Gly Thr Leu Leu Thr Gly Arg Leu Ser Leu His Thr His Pro Trp
    5105                5110                5115

Leu Ala Asp His Ser Val Gly Gly Ile Val Leu Leu Pro Gly Thr
    5120                5125                5130

Ala Leu Leu Glu Leu Ala Leu Glu Ala Gly Thr Arg Thr Gly Cys
    5135                5140                5145

Pro His Val Gln Glu Leu Thr Leu His Thr Pro Leu Val Ile Pro
    5150                5155                5160

Glu Thr Gly His Val Val Phe Gln Leu Thr Val Ser Ala Pro Asp
    5165                5170                5175

Glu Thr Gly Gln Arg Pro Phe Thr Val His Phe Arg Ser Glu Ala
    5180                5185                5190

Val Thr Gly Ala Asp Asp Pro Ala Asp Arg Thr Trp Thr Arg Cys
    5195                5200                5205

Ala Thr Gly Ala Leu Ser Thr Ala Ala Ala Pro Asp His Ser Glu
    5210                5215                5220

Ala Ala Thr Trp Pro Pro Pro Ser Ala Gln Pro Leu Asp Leu Asp
    5225                5230                5235

Gly Leu Tyr Asp Arg Met Ala Glu Ala Gly Leu Val Tyr Gly Pro
    5240                5245                5250

Val Phe Gln Gly Leu Arg Glu Ala Trp Leu Asp Gly Glu Asp Ile
    5255                5260                5265

Val Ala Glu Val Arg Leu Pro Gln Glu Ala Ala Ala Asp Thr Gln
    5270                5275                5280

Gly Phe Gly Leu His Pro Ala Leu Leu Asp Ala Ala Leu His Val
    5285                5290                5295

Thr Ala Leu Thr Ser Gln Ala Gly Thr Ala Asp Glu Asp Ala Gln
    5300                5305                5310

Glu Arg Arg Arg Leu Pro Phe Ala Trp Ala Gly Val Ser Leu Phe
    5315                5320                5325

Ala Arg Glu Cys Ala Ala Leu Arg Val Arg Val Ala Pro Cys Ala
    5330                5335                5340

Pro His Pro Gly Asp Ala Val Ala Ile Thr Ala Thr Asp Glu Asp
    5345                5350                5355
```

-continued

```
Gly Arg Pro Val Leu Ala Val Glu Ser Leu Thr Leu Arg Pro Val
    5360                5365                5370

Ser Pro Asp Gln Leu Arg Ala Ala Ala Pro Ala Ala Gly Arg Asp
    5375                5380                5385

Ser Leu Phe Arg Leu Glu Trp Val Pro Val Thr Ala Ser Ala Ser
    5390                5395                5400

Ala Ser Ala Arg Pro Thr Gly Pro Trp Ala Ala Ile Gly Thr Gly
    5405                5410                5415

Pro Ala Val Ala Gly Leu Ala Gly His Ala Asp Leu Thr Val Tyr
    5420                5425                5430

Ala Glu Ala Gly Asp Leu Leu Arg Asp Leu Asp Gly Gly Ala Pro
    5435                5440                5445

Ala Pro Ala Val Val Val Leu Ser Val Thr Pro Asp Ala Asp Glu
    5450                5455                5460

Phe Ala Thr Pro Arg Ala Ala Thr Gly Arg Ala Leu Ser Val Leu
    5465                5470                5475

Gln Ala Trp Leu Ala Asp Glu Arg Leu Ala Asp Ser Arg Leu Val
    5480                5485                5490

Ala Val Thr Ser Gly Ala Val Val Ala Ala Pro Gly Asp Asp Thr
    5495                5500                5505

Val Asp Val Pro Gly Ala Ala Val Trp Gly Leu Val Arg Ser Gly
    5510                5515                5520

Gln Ser Glu His Pro Asp Arg Ile Thr Leu Leu Asp Cys Ala Ser
    5525                5530                5535

Gly Ala Arg Pro Gly Pro Asp Leu Val Ala Ala Ala Leu Ala Ser
    5540                5545                5550

Gly Glu Pro Gln Leu Ala Ala Arg Ala Gly Val Leu Tyr Thr Pro
    5555                5560                5565

Arg Leu Ala Arg Pro His Arg Asp Ala Ser Ala Val Pro Arg Ser
    5570                5575                5580

Leu Pro Ser His Gly Thr Val Leu Ile Thr Gly Gly Thr Gly Leu
    5585                5590                5595

Leu Gly Gly Leu Val Ala Arg Arg Leu Val Glu Ala His Gly Val
    5600                5605                5610

Arg Arg Leu Leu Leu Ala Gly Arg Arg Gly Pro Ala Ala Glu Gly
    5615                5620                5625

Leu Asp Ser Leu Thr Ser Glu Leu Arg Glu Arg Gly Ala Thr Val
    5630                5635                5640

Glu Val Ala Ala Cys Asp Ala Ala Asp Arg Thr Gln Leu Glu Ala
    5645                5650                5655

Leu Leu Ala Gly Val Pro Glu Glu His Pro Leu Ser Ala Val Val
    5660                5665                5670

His Ala Ala Gly Val Leu Asp Asp Gly Val Leu Thr Ser Leu Thr
    5675                5680                5685

Asn Glu Arg Leu Gly Ala Val Leu Arg Ala Lys Ala Asp Ser Ala
    5690                5695                5700

Leu Leu Leu His Glu Leu Thr Gln Asp Leu Asp Leu Ser Ala Phe
    5705                5710                5715

Val Leu Phe Ser Ser Ala Ala Gly Val Leu Gly Ser Pro Gly Gln
    5720                5725                5730

Gly Ser Tyr Ala Ala Ala Asn Ala Val Leu Asp Ala Leu Ala His
    5735                5740                5745

Gln Arg Ser Ala Ala Gly Leu Pro Ala Leu Ser Leu Ala Trp Gly
```

-continued

```
    5750                5755                5760

Leu Trp  Ala Glu Gly Ser Gly  Met Thr Gly His Leu  Asp Ala Asp
    5765                5770                5775

Asp Arg  Ser Arg Ile Asn Arg  Ala Gly Met Ala Pro  Leu Pro Thr
    5780                5785                5790

Pro Asp  Ala Leu Asp Leu Phe  Asp Ala Ala Leu Ser  Ser Asp Glu
    5795                5800                5805

Pro Phe  Leu Val Pro Ala Arg  Phe Asp Leu Ser Ala  Val Arg Thr
    5810                5815                5820

Arg Thr  Ala Tyr Gly Pro Leu  Pro Pro Leu Leu Arg  Gly Leu Val
    5825                5830                5835

Arg Thr  Ser Gly Ala His Arg  Val Arg Gly Ala Val  Gly Glu Ala
    5840                5845                5850

Arg Ala  Ala Gly Val Asp Glu  Ala Gly Arg Leu Arg  Glu Arg Leu
    5855                5860                5865

Ala Arg  Gln Ser Asp Ala Glu  Arg Arg Asn Thr Leu  Leu Arg Leu
    5870                5875                5880

Val Gln  Ser Asn Val Ala Ala  Val Leu Gly His Arg  Gly Thr Gly
    5885                5890                5895

Thr Val  Ala Glu Thr Arg Ala  Phe Arg Glu Leu Gly  Phe Asp Ser
    5900                5905                5910

Leu Thr  Ala Val Glu Leu Arg  Asn Arg Leu Lys Val  Ala Thr Gly
    5915                5920                5925

Leu Ala  Leu Arg Ala Thr Val  Ala Phe Asp Phe Pro  Thr Pro Ala
    5930                5935                5940

Ala Leu  Ala Glu His Leu Gly  Ala Arg Leu Leu Pro  Pro Asp Gly
    5945                5950                5955

Ala Val  Ser Glu Ala Val Gly  Glu Lys Glu Leu Arg  Gly Leu Leu
    5960                5965                5970

Thr Ser  Ile Pro Ile Gly Arg  Leu Arg Glu Ala Gly  Leu Ile Asp
    5975                5980                5985

Arg Leu  Leu Ala Leu Ala Ala  Ala Ala Pro Asp Ser  Ala Asp Gln
    5990                5995                6000

Thr Ala  Glu Gln Pro Ser Arg  Ser Val Ser Val Glu  Asp Ile Asp
    6005                6010                6015

Ala Met  Asp Val Asp Ser Leu  Ile Gly Leu Ala His  Asp Thr Gly
    6020                6025                6030

Thr Asp  Ser Gly His Ala Pro  Cys Glu Gly
    6035                6040


<210> SEQ ID NO 8
<211> LENGTH: 284
<212> TYPE: PRT
<213> ORGANISM: bacteria

<400> SEQUENCE: 8

Met Thr Lys Ala Pro His Gln Gly Ser Pro Thr Pro Ala Asp Val Gly
1               5                   10                  15

Asp Tyr Tyr Asp Arg Met Thr Ser Leu Leu Asn Arg Ala Leu Gly Gly
            20                  25                  30

Asn Thr His Leu Gly Tyr Trp Pro His Pro Asp Asp Gly Ser Thr Leu
        35                  40                  45

Gly Gln Ala Ser Asp Arg Leu Thr Asp His Met Ile Gly Lys Leu Arg
    50                  55                  60
```

-continued

```
Glu His Thr Gly Arg Pro Val Arg Arg Val Leu Asp Val Gly Cys Gly
65                  70                  75                  80

Ser Gly Arg Pro Ala Leu Arg Leu Ala His Ser Glu Pro Val Asp Ile
                85                  90                  95

Val Gly Ile Thr Ile Ser Pro Arg Gln Val Glu Leu Ala Thr Ala Leu
            100                 105                 110

Ala Glu Arg Ser Gly Leu Ala Asn Arg Val Arg Phe Glu Cys Ala Asp
        115                 120                 125

Ala Met Asp Leu Pro Phe Pro Asp Ala Ser Phe Asp Ala Val Trp Ala
    130                 135                 140

Leu Glu Cys Leu Leu His Met Pro Asp Pro Ala Arg Val Phe Gln Glu
145                 150                 155                 160

Met Ala Arg Val Leu Arg Pro Gly Gly Arg Leu Ala Ala Met Asp Val
                165                 170                 175

Thr Leu Arg Ala Ser Gln Pro Thr Gly Ala Asp Trp Ser Ser Ser Glu
            180                 185                 190

Leu Ala Val Pro Ser Leu Ile Pro Ile Thr Ala Tyr Ala Gly Met Ile
        195                 200                 205

Ser Asp Ala Gly Leu Arg Leu Thr Glu Leu Thr Asp Ile Gly Glu His
    210                 215                 220

Val Ile Ala Pro Ser Tyr Ser Ala Met Gly Asp Asp Val Arg Ala Asn
225                 230                 235                 240

Ala His Ala Tyr Ala Glu Ala Leu Glu Met Thr Ala Asp Asp Leu Glu
                245                 250                 255

Thr Phe Val Gly Lys Cys Ser Gln Trp Tyr Thr Glu Asp Ile Gly Tyr
            260                 265                 270

Val Val Leu Thr Ala Pro Cys Gln Arg Ala Glu Val
        275                 280


<210> SEQ ID NO 9
<211> LENGTH: 468
<212> TYPE: PRT
<213> ORGANISM: bacteria

<400> SEQUENCE: 9

Val Ser Ser Pro Pro Ser Thr Ile Pro Glu Ala Pro Gly Ala Trp Pro
1               5                   10                  15

Val Leu Gly His Leu Pro Ala Leu Leu Arg Asp Pro Leu Gly Phe Leu
            20                  25                  30

Ser Ala Val Thr Glu Arg Gly Asp Leu Phe Arg Ile Arg Leu Gly His
        35                  40                  45

Asn Thr Val Tyr Leu Ala Thr His Pro Glu Ile Val Arg Thr Met Leu
    50                  55                  60

Val Ser Gly Ala Ala Asp Phe Thr Arg Ser Lys Gly Ala Ala Gly Ala
65                  70                  75                  80

Ser Arg Phe Ile Gly Pro Ile Leu Val Ala Val Ser Gly Asp Ser His
                85                  90                  95

Arg Arg Gln Arg Arg Met Met Gln Pro Gly Phe His Arg Gly Lys Leu
            100                 105                 110

Asp His Tyr Val Ile Ser Met Ser Ala Ala Ala Glu Glu Thr Ala Asp
        115                 120                 125

Ser Trp Arg Pro Gly Gln Val Val Asp Val Pro Lys Met Ala Ser Asp
    130                 135                 140

Leu Ser Leu Ala Met Ile Thr Lys Ala Leu Phe Gln Ser Asp Leu Gly
145                 150                 155                 160
```

-continued

```
Ala Ala Ala Glu Ala Glu Leu Arg Thr Thr Gly His Asp Ile Leu Lys
                165                 170                 175

Val Ala Arg Leu Ser Ala Leu Ala Pro Gln Leu Tyr Thr Ser Leu Pro
            180                 185                 190

Thr Ala Ala Lys Arg His Met Gly Arg Thr Ser Ala Ala Ile Arg Glu
        195                 200                 205

Ala Val Thr Ala Tyr Arg Ala Asp Gly Arg Asp His Gly Asp Leu Leu
    210                 215                 220

Ser Thr Met Leu Arg Ala Arg Asp Ala Glu Gly Asn Thr Met Thr Asp
225                 230                 235                 240

Asp Glu Val His Asn Glu Ile Met Gly Leu Ala Val Ala Gly Ile Gly
                245                 250                 255

Gly Pro Ala Ala Leu Thr Ala Trp Ile Phe His Glu Leu Ala His Asp
            260                 265                 270

His Leu Ile Glu Gln Arg Leu His Ala Glu Ile Asp Thr Val Leu Gly
        275                 280                 285

Gly Arg Leu Pro Thr Ser Ala Asp Leu Pro Arg Leu Pro Tyr Thr Gln
    290                 295                 300

Arg Leu Val Lys Glu Ala Leu Arg Lys Tyr Pro Gly Trp Val Gly Ser
305                 310                 315                 320

Arg Arg Thr Val Arg Pro Val Arg Leu Gly Glu His Glu Leu Pro Ala
                325                 330                 335

Asp Val Glu Ile Met Tyr Ser Ser Tyr Ala Leu Gln Arg Asp Pro Arg
            340                 345                 350

Trp Tyr Arg Asp Pro Glu Lys Leu Asp Pro Asp Arg Trp Glu Ser Lys
        355                 360                 365

Glu Thr Thr Arg Asp Val Pro Lys Gly Ala Trp Val Pro Phe Ala Leu
    370                 375                 380

Gly Thr Tyr Lys Cys Ile Gly Asp Asn Phe Ala Leu Met Glu Thr Ala
385                 390                 395                 400

Val Ala Val Ala Val Ile Ala Ser Arg Trp Arg Leu Arg Pro Leu Lys
                405                 410                 415

Gly Asp Arg Val Arg Pro Val Ala Lys Ala Thr His Val Phe Pro Asp
            420                 425                 430

Arg Leu Arg Met Ile Ala Glu Pro Arg Thr Pro Ala Ile Pro Arg Gly
        435                 440                 445

His Ala Pro Ala Asp Ala Ser Leu Glu Ala Ala Ala Arg Pro Lys Glu
    450                 455                 460

Leu Pro Glu Pro
465


<210> SEQ ID NO 10
<211> LENGTH: 5674
<212> TYPE: PRT
<213> ORGANISM: bacteria

<400> SEQUENCE: 10

Met Ala Thr Pro Ser Glu Lys Leu Val Glu Ala Leu Arg Ala Ser Leu
1               5                   10                  15

Lys Ala Asn Glu Ala Leu Arg Arg Arg Asn Gln Gln Leu Thr Ala Ala
            20                  25                  30

Val Glu Ala Ala Gln Glu Pro Leu Ala Ile Val Gly Met Ala Cys Arg
        35                  40                  45

Phe Pro Gly Gly Val Arg Ser Pro Glu Glu Leu Trp Gly Leu Val Ala
```

-continued

```
    50                  55                  60

Ser Gly Gly Asp Ala Ile Gly Glu Phe Pro Ala Asp Arg Gly Trp Asp
65                  70                  75                  80

Leu Ala Gly Leu Phe Asp Pro Asp Pro Glu Arg Ala Gly Ala Ser Tyr
                85                  90                  95

Thr Arg His Gly Gly Phe Leu Tyr Asp Ala Gly Gln Phe Asp Ala Glu
            100                 105                 110

Leu Phe Gly Ile Ser Pro Arg Glu Ala Leu Ala Met Asp Pro Gln Gln
        115                 120                 125

Arg Leu Leu Leu Glu Thr Ser Trp Glu Val Phe Glu Arg Ala Gly Ile
    130                 135                 140

Asp Pro Ser Ser Val Arg Gly Ala Arg Ala Gly Val Phe Thr Gly Met
145                 150                 155                 160

Met Tyr His Asp Tyr Ala Ser Arg Leu Ala Thr Ile Pro Glu Gly Phe
                165                 170                 175

Glu Gly Tyr Ile Gly Asn Gly Ser Gly Gly Ala Val Ala Ser Gly Arg
            180                 185                 190

Val Ala Tyr Thr Leu Gly Leu Glu Gly Pro Ala Val Thr Val Asp Thr
        195                 200                 205

Ala Cys Ser Ser Ser Leu Val Ala Leu His Leu Ala Cys Gln Ser Leu
    210                 215                 220

Arg Thr Gly Glu Cys Asp Leu Ala Leu Ala Gly Gly Val Thr Val Met
225                 230                 235                 240

Ser Thr Pro Leu Leu Phe Val Glu Phe Ser Arg Gln Arg Gly Leu Ser
                245                 250                 255

Val Asp Gly Arg Cys Lys Ser Phe Ala Ala Ala Ala Asp Gly Thr Gly
            260                 265                 270

Met Gly Glu Gly Val Gly Met Leu Leu Val Glu Arg Leu Ser Asp Ala
        275                 280                 285

Glu Arg Asn Gly His Arg Val Leu Ala Val Val Arg Gly Ser Ala Val
    290                 295                 300

Asn Gln Asp Gly Ala Ser Asn Gly Leu Thr Ala Pro Asn Gly Pro Ser
305                 310                 315                 320

Gln Glu Arg Val Ile Arg Glu Ala Leu Ala Asn Ala Gly Leu Thr Val
                325                 330                 335

Ala Asp Val Asp Ala Val Glu Gly His Gly Thr Gly Thr Arg Leu Gly
            340                 345                 350

Asp Pro Ile Glu Ala Gln Ala Leu Leu Asp Thr Tyr Gly Gln Glu Arg
        355                 360                 365

Ser Gly Glu Gln Pro Leu Trp Leu Gly Ser Val Lys Ser Asn Ile Gly
    370                 375                 380

His Ala Gln Ala Ala Ala Gly Val Gly Gly Ile Ile Lys Met Val Met
385                 390                 395                 400

Ala Leu Arg His Glu Ser Leu Pro Arg Thr Leu His Val Asp Glu Pro
                405                 410                 415

Ser Pro Gln Val Asp Trp Ser Ser Gly Ala Val Ser Leu Leu Ser Glu
            420                 425                 430

Ala Arg Pro Trp Pro Arg Arg Glu Asp Arg Pro Arg Arg Ala Gly Val
        435                 440                 445

Ser Ser Phe Gly Val Ser Gly Thr Asn Ala His Val Ile Leu Glu Glu
    450                 455                 460

Ala Pro Ala Arg Arg Pro Gly Glu Ala Ala Val Glu Asp Gly Ala Pro
465                 470                 475                 480
```

-continued

```
Val Pro Trp Val Val Ser Ala Arg Ser Gly Ala Ala Leu Arg Ala Gln
                485                 490                 495

Ala Met Val Leu Arg Glu Phe Leu Arg Gly Pro Gly Thr Asp Ala Gly
            500                 505                 510

Val Arg Asp Ile Gly Ala Glu Leu Ala Arg Gly Arg Ala Val Leu Glu
        515                 520                 525

His Arg Ala Val Ile Val Ala Arg Glu Arg Ala Glu Phe Glu Gly Ala
    530                 535                 540

Leu Glu Ala Leu Ala Ser Gly Glu Pro His Pro Ala Leu Ile Glu Asp
545                 550                 555                 560

Ala Thr Gly Ser His Ser His Ser Gly Gly Gly Val Val Phe Val Phe
                565                 570                 575

Pro Gly Gln Gly Gly Gln Trp Ala Gly Met Gly Leu Asp Leu Leu Thr
            580                 585                 590

Thr Ser Gly Val Phe Ala Asp His Ile Gly Ala Cys Glu Arg Ala Leu
        595                 600                 605

Ala Pro Trp Val Glu Trp Ser Leu Thr Glu Met Leu His Arg Glu Ala
    610                 615                 620

Glu Asp Pro Val Trp Glu Arg Ala Asp Val Val Gln Pro Val Leu Phe
625                 630                 635                 640

Ser Val Met Val Ser Leu Ala Ala Leu Trp Arg Ser Tyr Gly Ile Glu
                645                 650                 655

Pro Asp Ala Val Val Gly His Ser Gln Gly Glu Ile Ala Ala Ala His
            660                 665                 670

Val Cys Gly Ala Leu Thr Leu Glu Asp Ala Ala Lys Val Val Ala Leu
        675                 680                 685

Arg Ser Arg Ala Leu Ala Ala Leu Arg Gly His Gly Gly Met Ala Ser
    690                 695                 700

Leu Ala Leu Thr Gly Thr Glu Ala Glu Asp Leu Ile Thr Thr His Trp
705                 710                 715                 720

Pro Gly Arg Leu Trp Thr Ala Ala Phe Asn Gly Pro Arg Ala Thr Thr
                725                 730                 735

Val Ser Gly Asp Thr Asp Ala Leu Asp Glu Leu Leu Thr His Cys Thr
            740                 745                 750

Glu Thr Gly Val Arg Ala Arg Arg Ile Pro Val Asp Tyr Ala Ser His
        755                 760                 765

Cys Pro His Thr Glu Thr Ile Glu His Asp Leu Leu His Met Leu His
    770                 775                 780

Gly Ile Thr Pro Gln Pro Gly Ser Ile Pro Phe Tyr Ser Thr Val Glu
785                 790                 795                 800

Asp Ala Trp Thr Asp Thr Thr Thr Leu Asp Ala Ala Tyr Trp Tyr Arg
                805                 810                 815

Asn Leu Arg Arg Pro Val Arg Phe Thr His Ala Val Arg Thr Leu Thr
            820                 825                 830

Ala Gln Gly His Arg Leu Phe Ile Glu Thr Ser Pro His Pro Thr Leu
        835                 840                 845

Thr Pro Ala Ile Glu Asp His Asp His Thr Thr Ala Leu Gly Thr Leu
    850                 855                 860

Arg Arg His Asp Asn Asp Thr His Arg Phe Leu Thr Ala Leu Ala His
865                 870                 875                 880

Ala His Thr Thr Gly His Thr Val Thr Trp Thr Thr His Tyr Pro Thr
                885                 890                 895
```

-continued

```
Thr Pro His Thr Pro Ala Ile Asp Leu Pro Thr Tyr Pro Phe Gln His
            900                 905                 910

His His Tyr Trp Leu His Thr Pro Thr Thr Ser Thr Gly Asp Val Ser
        915                 920                 925

Ala Ala Gly Leu Gln Arg Pro Asp His Pro Leu Leu Gly Ala Val Met
    930                 935                 940

Glu Leu Ala Asp Gly Asp Gly Ile Val Leu Thr Gly Arg Leu Ser Leu
945                 950                 955                 960

His Thr His Pro Trp Leu Ala Asp His Ser Val Gly Gly Val Val Leu
                965                 970                 975

Leu Pro Gly Thr Ala Leu Leu Glu Leu Ala Phe Gln Ala Gly Leu Arg
            980                 985                 990

Ala Gly Cys Pro Gly Val Asp Glu  Leu Thr Leu His Ala  Pro Leu Val
        995                 1000                 1005

Val Pro  Glu Ser Gly His Val  Val Val Gln Val Ser  Val Ser Val
    1010                 1015                 1020

Pro Asp  Glu Ala Gly Arg Arg  Gly Val Ser Val Tyr  Gly Arg Leu
    1025                 1030                 1035

Val Glu  Asp Gly Gly Leu Glu  Gly Glu Trp Thr Arg  His Ala Glu
    1040                 1045                 1050

Gly Val  Val Cys Pro Ser Val  Pro Gly Glu Ser Val  Val Val Glu
    1055                 1060                 1065

Pro Val  Ala Asp Gly Val Trp  Pro Pro Ser Gly Ala  Gln Pro Val
    1070                 1075                 1080

Asp Leu  Asp Glu Phe Tyr Gly  Arg Leu Ala Gly Gly  Gly Phe Val
    1085                 1090                 1095

Tyr Gly  Pro Val Phe Gln Gly  Leu Cys Ala Ala Trp  Arg Asp Gly
    1100                 1105                 1110

Asp Asp  Val Val Ala Glu Val  Arg Leu Pro Asp Glu  Gly Leu Ala
    1115                 1120                 1125

Asp Val  Ala Gly Phe Gly Val  His Pro Ala Leu Leu  Asp Ala Ala
    1130                 1135                 1140

Val Gln  Thr Val Thr Leu Leu  Leu Pro Glu Asp Gln  Glu Ala Gly
    1145                 1150                 1155

Leu Leu  Pro Tyr Thr Trp Asn  Gly Ala Ser Leu His  Ala Arg Gly
    1160                 1165                 1170

Ala Arg  Ala Leu Arg Val Arg  Val Thr Ser Val Asp  Ala Ala Gly
    1175                 1180                 1185

Thr Thr  Val Ser Leu Arg Val  Ala Asp Glu Thr Gly  Ala Leu Val
    1190                 1195                 1200

Leu Ala  Leu Glu Ser Leu Val  Leu Arg Pro Val Pro  Leu Glu Gly
    1205                 1210                 1215

Leu Gly  Ala Gly Val Arg Arg  Gly Ser Leu Phe Glu  Leu Gly Trp
    1220                 1225                 1230

Val Pro  Val Glu Gly Val Pro  Ala Ser Leu Ala Gly  Gly Gly Gly
    1235                 1240                 1245

Glu Leu  Val Val Trp Glu Cys  Pro Gly Gly Gly Val  Ala Glu Val
    1250                 1255                 1260

Thr Ala  Ala Ala Leu Gly Val  Val Arg Glu Trp Leu  Ala Asp Glu
    1265                 1270                 1275

Arg Glu  Gly Asp Ala Arg Leu  Val Val Val Thr Arg  Gly Ala Val
    1280                 1285                 1290

Ala Val  Asp Ala Gly Glu Pro  Val Arg Asp Val Ala  Gly Ala Ala
```

-continued

```
        1295                1300                1305

Val Trp Gly Leu Val Arg Ser Ala Gln Ser Glu His Pro Asp Arg
    1310                1315                1320

Phe Val Leu Leu Asp Leu Asp Pro Gly Thr Gly Val Glu Thr Val
    1325                1330                1335

Val Asp Ala Asp Glu Asp Met Gly Ala Gly Val Gly Ala Gly Val
    1340                1345                1350

Asp Val Ala Gly Phe Val Ala Cys Gly Glu Ala Gln Val Ala Val
    1355                1360                1365

Arg Gly Gly Val Val Arg Val Pro Arg Leu Glu Arg Leu Glu Arg
    1370                1375                1380

Trp Gly Arg Leu Gly Gly Ala Gly Glu Gly Leu Ser Leu Pro Gly
    1385                1390                1395

Gly Val Gly Trp Arg Leu Asp Gly Gly Gly Ser Gly Leu Leu Glu
    1400                1405                1410

Gly Val Gly Val Val Ala Ser Asp Ala Ala Gly Val Val Leu Gly
    1415                1420                1425

Arg Gly Gln Val Arg Val Ala Val Arg Ala Ala Gly Val Asn Phe
    1430                1435                1440

Arg Asp Val Leu Val Ala Leu Gly Met Val Pro Gly Gln Val Gly
    1445                1450                1455

Val Gly Ser Glu Gly Ala Gly Val Val Val Glu Val Gly Pro Gly
    1460                1465                1470

Val Glu Gly Leu Val Val Gly Asp Arg Val Phe Gly Val Phe Gly
    1475                1480                1485

Asp Ala Phe Ala Pro Val Val Val Ala Gln Glu Val Leu Leu Ala
    1490                1495                1500

Arg Ile Pro Glu Gly Trp Ser Phe Ala Gln Ala Ala Ser Val Pro
    1505                1510                1515

Val Val Phe Ala Thr Ala Tyr Leu Gly Leu Val Asp Leu Ala Gly
    1520                1525                1530

Val Arg Arg Gly Glu Ser Val Leu Val His Ala Ala Ala Gly Gly
    1535                1540                1545

Val Gly Thr Ala Ala Val Gln Leu Ala Arg His Leu Gly Ala Glu
    1550                1555                1560

Val Tyr Ala Thr Ala Ser Glu Ala Lys Trp Ala Arg Leu Arg Ala
    1565                1570                1575

Ala Gly Val Ala Pro Gln Arg Ile Ala Ser Ser Arg Ser Val Glu
    1580                1585                1590

Phe Glu Ser Arg Phe Arg Arg Ala Ser Gly Gly Arg Gly Val Asp
    1595                1600                1605

Val Val Leu Asn Cys Leu Ala Gly Glu Tyr Thr Asp Ala Ser Leu
    1610                1615                1620

Arg Leu Cys Ser Pro Gln Gly Gly Arg Phe Leu Glu Leu Gly Lys
    1625                1630                1635

Thr Asp Ile Arg Asp Ala Gly Glu Val Ala Ala Arg Phe Pro Gly
    1640                1645                1650

Val Ser Tyr Arg Ala Tyr Asp Leu Met Asp Ala Gly Ala Gln Arg
    1655                1660                1665

Val Gly Glu Ile Leu His Thr Val Val Asp Leu Phe Arg Arg Gly
    1670                1675                1680

Val Leu Glu Pro Leu Pro Val Thr Ala Trp Asp Val Arg Gln Ala
    1685                1690                1695
```

-continued

```
Arg Gln  Ala Leu Arg Ser Met  Arg Ser Gly Leu His  Val Gly Lys
    1700                 1705                 1710

Asn Val  Leu Thr Leu Pro Val  Pro Leu Asp Ala Glu  Gly Thr Val
    1715                 1720                 1725

Leu Val  Thr Gly Gly Thr Gly  Thr Leu Gly Ala Ala  Val Ala Arg
    1730                 1735                 1740

His Leu  Ala Ala Gly His Gly  Val Arg His Leu Leu  Leu Val Ser
    1745                 1750                 1755

Arg Arg  Gly Met Ala Ala Ala  Gly Ala Glu Glu Leu  Cys Ala Glu
    1760                 1765                 1770

Leu Gly  Gln Ala Gly Val Ser  Val Ser Val Ala Ala  Cys Asp Val
    1775                 1780                 1785

Ala Asp  Arg Ala Gln Val Ala  Ala Leu Leu Glu Gln  Val Pro Ala
    1790                 1795                 1800

Glu His  Pro Leu Thr Ala Val  Val His Thr Ala Gly  Val Leu Asp
    1805                 1810                 1815

Asp Ala  Thr Val Thr Cys Leu  Asp Arg Glu Lys Ile  Asp Ala Val
    1820                 1825                 1830

Val Gly  Ala Lys Val Asp Gly  Ala Leu His Leu His  Glu Leu Thr
    1835                 1840                 1845

Ala Gly  Met Asp Leu Ser Ala  Phe Val Leu Phe Ser  Ser Ala Ala
    1850                 1855                 1860

Gly Val  Leu Gly Ser Pro Gly  Gln Gly Asn Tyr Ala  Ala Ala Asn
    1865                 1870                 1875

Ala Ala  Leu Asp Ala Leu Ala  His Gln Arg Arg Ala  Ala Gly Leu
    1880                 1885                 1890

Pro Ala  Leu Ser Leu Ala Trp  Gly Leu Trp Glu Glu  Ala Ser Gly
    1895                 1900                 1905

Met Thr  Gly His Leu Asp Ala  Gly Asp Arg His Arg  Ile Thr Arg
    1910                 1915                 1920

Ser Gly  Leu His Pro Leu Thr  Thr Pro Asp Ala Leu  Ala Leu Leu
    1925                 1930                 1935

Asp Thr  Ala Leu Ala Thr Gly  Arg Pro Ala Leu Leu  Pro Ala Asp
    1940                 1945                 1950

Leu Arg  Pro Thr His Pro Ala  Pro Pro Leu Leu Glu  His Leu Ala
    1955                 1960                 1965

Pro Ala  Arg Thr Ser Pro Arg  Thr Ala His Thr Gly  Thr Ser Ala
    1970                 1975                 1980

Gly Ala  Gly Gln Asp Val Ser  Leu Ala Asp Arg Leu  Ala Thr Leu
    1985                 1990                 1995

Thr Ser  Glu Gln Arg His Ala  Thr Leu Leu Ala Leu  Ala Arg Thr
    2000                 2005                 2010

His Ile  Ala Ala Val Leu Gly  His Pro Thr Pro Asp  Thr Ile Asp
    2015                 2020                 2025

Pro Glu  Arg Thr Phe Arg Asp  Leu Gly Phe Asp Ser  Leu Thr Ala
    2030                 2035                 2040

Val Glu  Leu Arg Asn Arg Leu  Thr Arg Ala Thr Gly  Leu Arg Leu
    2045                 2050                 2055

Pro Thr  Thr Leu Ala Phe Asp  His Pro Thr Pro Thr  Ala Leu Thr
    2060                 2065                 2070

His His  Leu Thr Thr Leu Leu  Asn Pro Asn Asp Thr  Lys Thr Pro
    2075                 2080                 2085
```

-continued

```
Ser Ala  Pro Ala Ala Ala Glu  Pro Lys Ala Gly Gln  His Glu Pro
    2090                 2095                 2100

Ile Ala  Ile Ile Gly Val Gly  Cys Arg Tyr Pro Gly  Gly Val Ala
    2105                 2110                 2115

Ser Ala  Glu Asp Leu Trp Gln  Leu Val Ala Ser Gly  Gly Asp Ala
    2120                 2125                 2130

Val Gly  Glu Phe Pro Ala Asp  Arg Gly Trp Asp Val  Glu Ala Leu
    2135                 2140                 2145

Tyr Asp  Pro Glu Pro Gly Gln  Arg Gly Thr Ser Tyr  Thr Arg His
    2150                 2155                 2160

Gly Gly  Phe Leu Tyr Asp Ala  Gly Glu Phe Asp Ala  Gly Phe Phe
    2165                 2170                 2175

Gly Ile  Ser Pro Arg Glu Ala  Leu Ala Met Asp Pro  Gln Gln Arg
    2180                 2185                 2190

Leu Leu  Leu Glu Thr Thr Trp  Glu Ala Phe Glu Arg  Ala Gly Ile
    2195                 2200                 2205

Asp Pro  Gly Ala Val Arg Gly  Ser Gln Thr Gly Val  Phe Ala Gly
    2210                 2215                 2220

Val Met  Pro Gln Glu Tyr Ala  Ser Arg Ser Arg His  His Val Ala
    2225                 2230                 2235

Ala Asp  Val Asp Gly Tyr Val  Leu Thr Gly Thr Ser  Gly Ser Val
    2240                 2245                 2250

Ala Ser  Gly Arg Val Ala Tyr  Thr Phe Gly Leu Glu  Gly Pro Ala
    2255                 2260                 2265

Val Ser  Val Asp Thr Ala Cys  Ser Ser Ser Leu Val  Ala Leu His
    2270                 2275                 2280

Leu Ala  Cys Gln Ala Leu Arg  Ser Gly Glu Cys Thr  Met Ala Leu
    2285                 2290                 2295

Ala Gly  Gly Ala Thr Val Met  Ser Thr Pro Thr Ala  Phe Leu Glu
    2300                 2305                 2310

Phe Ser  Arg Gln Arg Gly Leu  Ala Ala Asp Gly Arg  Cys Lys Ala
    2315                 2320                 2325

Phe Ser  Ala Ser Ala Asp Gly  Thr Gly Trp Ser Glu  Gly Ala Gly
    2330                 2335                 2340

Met Leu  Leu Leu Glu Arg Leu  Ser Asp Ala Glu Arg  Asn Gly His
    2345                 2350                 2355

Arg Val  Leu Ala Val Val Arg  Gly Ser Ala Val Asn  Gln Asp Gly
    2360                 2365                 2370

Ala Ser  Asn Gly Leu Thr Ala  Pro Asn Gly Pro Ser  Gln Gln Arg
    2375                 2380                 2385

Val Ile  Arg Gln Ala Leu Ala  Asn Ala Asn Leu Ser  Ala Val Asp
    2390                 2395                 2400

Val Asp  Ala Val Glu Ala His  Gly Thr Gly Thr Lys  Leu Gly Asp
    2405                 2410                 2415

Pro Ile  Glu Ala Gln Ala Leu  Leu Ala Thr Tyr Gly  Gln Glu His
    2420                 2425                 2430

His Pro  Asp Gln Pro Leu Trp  Leu Gly Ser Leu Lys  Ser Asn Ile
    2435                 2440                 2445

Gly His  Ala Gln Ala Ala Ala  Gly Val Gly Gly Ile  Ile Lys Met
    2450                 2455                 2460

Val Met  Ala Leu Arg His Glu  Ser Leu Pro Arg Thr  Leu His Val
    2465                 2470                 2475

Asp Glu  Pro Ser Pro Gln Val  Asp Trp Ser Ser Gly  Ala Val Ser
```

-continued

```
    2480                2485                2490

Leu Leu  Thr Glu Ala Arg Pro  Trp Pro Arg Arg Glu  Asp Arg Pro
    2495                2500                2505

Arg Arg  Ala Gly Ile Ser Ser  Phe Gly Val Ser Gly  Thr Asn Ala
    2510                2515                2520

His Val  Ile Leu Glu Glu Ala  Pro Ala Arg Ala Glu  Val Glu Ala
    2525                2530                2535

Val Glu  Ala Ala Pro Ala Gly  Val Glu Thr Ala Ala  Ala Ala Ala
    2540                2545                2550

Val Val  Val Glu Thr Asp Gly  Ala Gly Arg Val Ser  Ala Asp Val
    2555                2560                2565

Pro Leu  Val Trp Val Val Ser  Gly Lys Ser Gln Ala  Ala Leu Arg
    2570                2575                2580

Ala Gln  Ala Ala Ala Leu His  Ala His Val Leu Asp  His Pro Glu
    2585                2590                2595

Gln Asp  Ala Ala Asp Ile Gly  Tyr Ser Leu Ala Thr  Thr Arg Ala
    2600                2605                2610

Leu Phe  Asp His Arg Ala Thr  Leu Ile Ala Pro Asp  Arg Asp Thr
    2615                2620                2625

Leu Leu  Asp Ala Leu Thr Ala  Leu Ala Asp Gly Arg  Thr His Pro
    2630                2635                2640

His Leu  Ile Pro Thr Pro Pro  Thr Glu Pro Gly His  Thr His Lys
    2645                2650                2655

Ile Ala  Phe Leu Cys Ser Gly  Gln Gly Thr Gln Arg  Pro Gly Met
    2660                2665                2670

Ala Thr  Gly Leu Tyr His Thr  Tyr Pro Ala Phe Ala  Asp Ala Leu
    2675                2680                2685

Asp Glu  Thr Cys Ala His Phe  Asp Pro His Leu Asp  His Pro Leu
    2690                2695                2700

Arg Asp  Leu Leu Leu Asn His  Asp Pro Thr Asp Leu  Leu Thr His
    2705                2710                2715

Thr Leu  Tyr Ala Gln Pro Ala  Leu Phe Thr Leu Gln  Lys Ala Leu
    2720                2725                2730

His His  Leu Ile Thr Glu Thr  Tyr Gly Ile Thr Pro  His Tyr Leu
    2735                2740                2745

Ala Gly  His Ser Leu Gly Glu  Ile Thr Ala Ala His  Leu Ala Gly
    2750                2755                2760

Ile Leu  Thr Leu Pro Asp Ala  Thr His Leu Ile Thr  Thr Arg Ala
    2765                2770                2775

Arg Leu  Met Gln Thr Met Pro  Pro Gly Thr Met Thr  Thr Leu His
    2780                2785                2790

Thr Thr  Pro Glu His Ile Gln  Pro Leu Leu Asp Gln  His Pro Gly
    2795                2800                2805

Lys Ala  Thr Ile Ala Ala Val  Asn Ser Pro His Ser  Leu Val Ile
    2810                2815                2820

Ser Gly  Asp Pro Asp Thr Ile  His His Ile Thr Thr  Thr Cys His
    2825                2830                2835

Thr Gln  Gly Ile Thr Thr Lys  Pro Leu Thr Thr Asn  His Ala Phe
    2840                2845                2850

His Ser  Pro His Thr Asp Thr  Ile Leu Glu Gln Leu  Asp Thr Thr
    2855                2860                2865

Thr His  Thr Leu Thr Tyr His  Pro Pro His Thr Pro  Leu Ile Thr
    2870                2875                2880
```

-continued

```
Ser Thr  Pro Gly Asp Pro Leu  Thr Pro His Tyr Trp  Thr His Gln
    2885                 2890                 2895

Thr Arg  Gln Pro Val His Trp  Thr Asp Thr Ile His  Thr Leu His
    2900                 2905                 2910

Thr Asn  Gly Val Thr Thr Tyr  Ile Glu Leu Gly Pro  Asp His Thr
    2915                 2920                 2925

Leu Thr  Thr Leu Thr His His  Asn Leu Pro His His  Gln Pro Thr
    2930                 2935                 2940

Ala Ile  Thr Leu Thr His Pro  His His Asn Pro Thr  His His Leu
    2945                 2950                 2955

Leu Thr  Ala Leu Ala His Thr  Pro Thr Thr Trp His  Thr His His
    2960                 2965                 2970

His Thr  His Thr Asn Pro His  Pro His Thr Ile Pro  Asp Leu Pro
    2975                 2980                 2985

Thr Tyr  Pro Phe Gln Arg Arg  His Tyr Trp Leu Gln  Ala Thr Pro
    2990                 2995                 3000

Gly Ala  Gly Ala Gly Asp Val  Ser Ala Ala Gly Leu  Gln Arg Pro
    3005                 3010                 3015

Asp His  Pro Leu Leu Gly Ala  Val Met Glu Leu Ala  Asp Gly Asp
    3020                 3025                 3030

Gly Ile  Val Leu Thr Gly Ser  Leu Ser Leu Arg Thr  His Thr Trp
    3035                 3040                 3045

Leu Ala  Asp His Ser Val Gly  Gly Ile Val Leu Leu  Pro Gly Thr
    3050                 3055                 3060

Ala Leu  Leu Asp Leu Ala Phe  Gln Ala Gly Leu Arg  Thr Gly Cys
    3065                 3070                 3075

Pro Arg  Val Asp Glu Leu Thr  Leu His Ala Pro Leu  Val Ile Pro
    3080                 3085                 3090

Glu Ser  Gly His Val Val Val  Gln Val Ser Val Ser  Val Pro Asp
    3095                 3100                 3105

Glu Ala  Gly Arg Arg Ala Val  Asn Val Tyr Ala Arg  Pro Ala Gly
    3110                 3115                 3120

Asp Glu  Glu Thr Asp Gly Glu  Trp Thr Arg His Ala  Glu Gly Val
    3125                 3130                 3135

Leu Ser  Pro Ser Thr Glu Asp  Asp Pro Asn Ala Glu  Ala Ala Ala
    3140                 3145                 3150

Ala Gly  Glu Trp Pro Pro Pro  Gly Ala Arg Pro Val  Val Leu Asp
    3155                 3160                 3165

Gly Leu  Tyr Asp Arg Leu Ala  Gly Gly Gly Phe Val  Tyr Gly Pro
    3170                 3175                 3180

Val Phe  Gln Gly Leu Cys Ala  Ala Trp Arg Asp Gly  Asp Asp Val
    3185                 3190                 3195

Val Ala  Glu Val Arg Leu Pro  Asp Glu Gly Leu Ala  Asp Val Ala
    3200                 3205                 3210

Gly Phe  Gly Val His Pro Ala  Leu Leu Asp Ala Ala  Val Gln Ser
    3215                 3220                 3225

Val Thr  Leu Leu Leu Ala Asp  Gln Gln Gln Ala Gly  Leu Val Pro
    3230                 3235                 3240

His Thr  Trp Asn Gly Val Ser  Leu His Ala Arg Gly  Ala Thr Val
    3245                 3250                 3255

Leu Arg  Leu Arg Met Thr Pro  Thr Asp Ala Thr Ser  Thr Ala Val
    3260                 3265                 3270
```

-continued

```
Arg Leu His Ala Thr Asp Glu Thr Gly Ala Pro Val Leu Thr Leu
    3275                3280                3285

Glu Ser Leu Leu Met Arg Pro Val Pro Leu Glu Gly Leu Gly Ala
    3290                3295                3300

Arg Val Arg Arg Gly Ser Leu Phe Glu Leu Gly Trp Val Pro Val
    3305                3310                3315

Glu Gly Val Pro Ala Ser Val Ala Gly Gly Gly Gly Glu Leu Val
    3320                3325                3330

Ala Trp Glu Cys Pro Gly Gly Gly Val Ala Glu Val Thr Ala Ala
    3335                3340                3345

Ala Leu Gly Val Val Arg Glu Trp Leu Ala Asp Glu Arg Glu Gly
    3350                3355                3360

Asp Ala Arg Leu Val Val Val Thr Arg Gly Ala Val Ala Val Asp
    3365                3370                3375

Ala Gly Glu Pro Val Arg Asp Val Ala Gly Ala Ala Val Trp Gly
    3380                3385                3390

Leu Val Arg Ser Ala Gln Ser Glu His Pro Asp Arg Phe Val Leu
    3395                3400                3405

Leu Asp Leu Asp Pro Asp Thr Lys Thr Asp Pro Asp Thr Asp Thr
    3410                3415                3420

Asp Thr Asp Thr Asp Gly Asp Thr Asp Val Ser Ala Asp Ala Lys
    3425                3430                3435

Val Gly Thr Gly Ala Gly Leu Asp Asp Ala Ala Val Ala Ser Ala
    3440                3445                3450

Leu Ala Arg Gly Glu Ser Gln Leu Ala Val Arg Asp Gly Val Val
    3455                3460                3465

Arg Val Pro Arg Leu Lys Arg Val Pro Pro Leu Ser Glu Ser Ser
    3470                3475                3480

Asp Ala Val Arg Phe Asp Ala Glu Gly Thr Val Leu Val Thr Gly
    3485                3490                3495

Gly Thr Gly Thr Leu Gly Ala Val Val Ala Arg His Leu Ala Ala
    3500                3505                3510

Gly His Gly Val Arg His Leu Leu Leu Val Ser Arg Arg Gly Met
    3515                3520                3525

Ala Ala Thr Gly Ala Glu Glu Leu Cys Ala Glu Leu Gly Gly Ala
    3530                3535                3540

Gly Val Ser Val Ser Val Ala Ala Cys Asp Val Ala Asp Arg Ala
    3545                3550                3555

Gln Val Ala Ala Leu Leu Glu Gln Val Pro Ala Glu His Pro Leu
    3560                3565                3570

Thr Ala Val Val His Thr Ala Gly Val Leu Asp Asp Ala Thr Val
    3575                3580                3585

Thr Cys Leu Asp Arg Glu Lys Ile Asp Ala Val Val Gly Ala Lys
    3590                3595                3600

Val Asp Gly Ala Leu His Leu His Glu Leu Thr Ala Gly Met Asp
    3605                3610                3615

Leu Ser Ala Phe Val Leu Phe Ser Ser Ala Ala Gly Val Leu Gly
    3620                3625                3630

Ser Pro Gly Gln Gly Asn Tyr Ala Ala Ala Asn Ala Ala Leu Asp
    3635                3640                3645

Ala Leu Ala His Gln Arg Arg Ala Ala Gly Leu Pro Ala Leu Ser
    3650                3655                3660

Leu Ala Trp Gly Leu Trp Glu Glu Thr Ser Gly Met Thr Gly His
```

-continued 3665 3670 3675

Leu Asp Ala Gly Asp Arg His Arg Ile Thr Arg Ser Gly Leu His
3680 3685 3690

Pro Leu Thr Thr Pro Asp Ala Leu Ala Leu Leu Asp Thr Ala Leu
3695 3700 3705

Ala Ala Gly Arg Pro Ala Leu Leu Pro Ala Asp Leu Arg Pro Thr
3710 3715 3720

His Pro Ala Pro Pro Leu Leu Glu His Leu Ala Pro Ala Arg Thr
3725 3730 3735

Ser His Arg Thr Thr Leu Pro Thr Thr Asp Ser Gly Ala Ser Leu
3740 3745 3750

Arg Ala Arg Leu Ala Gly Arg Thr Pro Glu Gln Gln Tyr Gln Ala
3755 3760 3765

Leu Leu Gly Leu Val Arg Ser His Val Ala Thr Val Leu Gly His
3770 3775 3780

Gln Ala Pro Glu Ala Ile Pro Val Asp Ser Ala Phe Arg Asp Leu
3785 3790 3795

Gly Phe Asp Ser Leu Thr Ala Val Asp Leu Arg Asn Arg Leu Ser
3800 3805 3810

Ala Glu Thr Gly Leu Arg Leu Pro Ala Ser Leu Val Phe Asp Gln
3815 3820 3825

Pro Ser Pro Ala Ala Val Ala Arg Leu Leu Arg Thr Glu Leu Leu
3830 3835 3840

Gly Asp Asp Ala Ala Asp Ser Thr Ser Pro Tyr Ala Glu Thr Thr
3845 3850 3855

Ala Val Gly Ser Asp Glu Pro Leu Ala Ile Val Gly Met Ala Cys
3860 3865 3870

Arg Phe Pro Gly Gly Val Arg Ser Pro Glu Glu Leu Trp Gly Leu
3875 3880 3885

Val Ala Ser Gly Gly Asp Ala Ile Gly Glu Phe Pro Ala Asp Arg
3890 3895 3900

Gly Trp Asp Leu Ala Gly Leu Phe Asp Pro Asp Pro Glu Arg Ala
3905 3910 3915

Gly Ala Ser Tyr Thr Arg His Gly Gly Phe Leu Tyr Asp Ala Gly
3920 3925 3930

Gln Phe Asp Ala Glu Phe Phe Gly Ile Ser Pro Arg Glu Ala Leu
3935 3940 3945

Ala Met Asp Pro Gln Gln Arg Leu Leu Leu Glu Thr Val Trp Glu
3950 3955 3960

Thr Leu Glu His Ala Gly Ile Asp Pro Ala Ala Val Arg Gly Ser
3965 3970 3975

Arg Thr Gly Val Phe Ala Gly Val Met Tyr His Asp Tyr Ala Ala
3980 3985 3990

Arg Leu Thr Ala Val Pro Glu Gly Ala Glu Gly Tyr Ile Gly Asn
3995 4000 4005

Gly Asn Ala Gly Ser Val Val Ser Gly Arg Val Ala Tyr Thr Phe
4010 4015 4020

Gly Phe Glu Gly Pro Ala Val Ser Val Asp Thr Ala Cys Ser Ser
4025 4030 4035

Ser Leu Val Ala Leu His Leu Ala Gly Gln Ala Leu Arg Ser Gly
4040 4045 4050

Glu Cys Ser Met Ala Leu Ala Gly Gly Val Thr Val Met Ser Ser
4055 4060 4065

-continued

```
Pro Gly  Thr Phe Ile Asp Phe  Ser Arg Gln Arg Gly  Leu Ser Val
    4070                 4075                 4080

Asp Gly  Arg Cys Lys Ser Phe  Ala Ala Ala Ala Asp  Gly Thr Gly
    4085                 4090                 4095

Trp Gly  Glu Gly Val Gly Met  Leu Leu Val Glu Arg  Leu Ser Asp
    4100                 4105                 4110

Ala Glu  Arg Asn Gly His Arg  Val Leu Ala Val Val  Arg Gly Ser
    4115                 4120                 4125

Ala Val  Asn Gln Asp Gly Ala  Ser Asn Gly Leu Thr  Ala Pro Asn
    4130                 4135                 4140

Gly Pro  Ser Gln Gln Arg Val  Ile Arg Gln Ala Leu  Ala Asn Ser
    4145                 4150                 4155

Gly Leu  Thr Gly Ala Asp Val  Asp Ala Val Glu Ala  His Gly Thr
    4160                 4165                 4170

Gly Thr  Lys Leu Gly Asp Pro  Ile Glu Ala Gln Ala  Leu Leu Ala
    4175                 4180                 4185

Thr Tyr  Gly Gln Glu His His  Pro Asp Gln Pro Leu  Trp Leu Gly
    4190                 4195                 4200

Ser Leu  Lys Ser Asn Ile Gly  His Ala Gln Ala Ala  Ala Gly Val
    4205                 4210                 4215

Gly Gly  Ile Ile Lys Met Val  Met Ala Leu Arg His  Glu Thr Leu
    4220                 4225                 4230

Pro Arg  Thr Leu His Ile Asp  Glu Pro Thr Pro Gln  Val Asp Trp
    4235                 4240                 4245

Ser Ser  Gly Ala Val Ser Leu  Leu Thr Glu Pro Arg  Pro Trp Pro
    4250                 4255                 4260

Arg Gln  Gly Asp Arg Pro Arg  Arg Ala Gly Ile Ser  Ser Phe Gly
    4265                 4270                 4275

Val Ser  Gly Thr Asn Ala His  Val Ile Leu Glu Glu  Ala Pro Ala
    4280                 4285                 4290

Gln Pro  Ala Gly Asp Pro Ala  Pro Glu Asp Gly Ala  Pro Val Pro
    4295                 4300                 4305

Trp Ala  Met Ser Ala Arg Ser  Asn Ala Ala Leu Arg  Ala Gln Ala
    4310                 4315                 4320

Ala Leu  Leu Arg Asp Phe Leu  Gln Gly Pro Gly Thr  Asp Thr Ala
    4325                 4330                 4335

Leu Arg  Ala Val Gly Ala Glu  Leu Ala His Gly Arg  Ala Val Leu
    4340                 4345                 4350

Glu His  Arg Ala Val Ile Val  Ala Arg Glu Arg Thr  Glu Phe Glu
    4355                 4360                 4365

Asp Ala  Leu Glu Ala Leu Ala  Ser Gly Glu Pro His  Pro Ala Leu
    4370                 4375                 4380

Ile Glu  Asp Thr Thr Gly Ser  Gln Thr Asn Ser His  Ser Gly Gly
    4385                 4390                 4395

Gly Val  Val Phe Val Phe Pro  Gly Gln Gly Gly Gln  Trp Ala Gly
    4400                 4405                 4410

Met Gly  Leu Asp Leu Leu Arg  Asp Ser Gln Val Phe  Ala Asp His
    4415                 4420                 4425

Val Gly  Ala Cys Glu Arg Ala  Leu Ala Pro Trp Val  Glu Trp Ser
    4430                 4435                 4440

Leu Thr  Glu Met Leu His Arg  Asp Ala Glu Asp Pro  Val Trp Glu
    4445                 4450                 4455
```

-continued

```
Arg Ala  Asp Val Val Gln Pro  Val Leu Phe Ser Val  Met Val Ser
    4460                 4465                 4470

Leu Ala  Ala Leu Trp Arg Ser  Tyr Gly Ile Glu Pro  Asp Ala Val
    4475                 4480                 4485

Val Gly  His Ser Gln Gly Glu  Ile Ala Ala Ala His  Val Cys Gly
    4490                 4495                 4500

Ala Leu  Thr Leu Glu Asp Ala  Ala Lys Ile Val Ala  Leu Arg Ser
    4505                 4510                 4515

Arg Ala  Leu Ala Ala Leu Arg  Gly His Gly Gly Met  Ala Ser Leu
    4520                 4525                 4530

Ala Leu  Thr Gly Thr Glu Ala  Glu Asp Leu Ile Thr  Thr His Trp
    4535                 4540                 4545

Pro Gly  Arg Leu Trp Arg Ala  Ala Phe Asn Gly Pro  Arg Ala Thr
    4550                 4555                 4560

Thr Val  Ser Gly Asp Thr Asp  Ala Leu Asp Glu Leu  Leu Thr His
    4565                 4570                 4575

Cys Thr  Glu Thr Gly Val Arg  Ala Arg Arg Ile Pro  Val Asp Tyr
    4580                 4585                 4590

Ala Ser  His Cys Pro His Thr  Glu Thr Ile Glu His  Asp Leu Leu
    4595                 4600                 4605

His Met  Leu His Gly Ile Thr  Pro Gln Pro Gly Ser  Ile Pro Phe
    4610                 4615                 4620

Tyr Ser  Thr Val Glu Asp Ala  Trp Thr Asp Thr Thr  Thr Leu Asp
    4625                 4630                 4635

Ala Ala  Tyr Trp Tyr Arg Asn  Leu Arg Arg Pro Val  Arg Phe Thr
    4640                 4645                 4650

His Ala  Val Arg Thr Leu Thr  Ala Gln Gly His Arg  Leu Phe Ile
    4655                 4660                 4665

Glu Thr  Ser Pro His Pro Thr  Leu Thr Pro Ala Ile  Glu Asp His
    4670                 4675                 4680

Asp His  Thr Thr Ala Leu Gly  Thr Leu Arg Arg His  Asp Asn Asp
    4685                 4690                 4695

Thr His  Arg Phe Leu Thr Ala  Leu Ala His Ala His  Thr Thr Gly
    4700                 4705                 4710

His Thr  Val Thr Trp Thr Thr  His Tyr Pro Thr Thr  Pro His Thr
    4715                 4720                 4725

Pro Ala  Ile Asp Leu Pro Thr  Tyr Pro Phe Gln His  His His Tyr
    4730                 4735                 4740

Trp Leu  His Thr Pro Thr Thr  Ser Thr Gly Asp Val  Ser Ala Ala
    4745                 4750                 4755

Gly Leu  His Pro Thr Glu His  Pro Leu Leu Gly Ala  Thr Val Glu
    4760                 4765                 4770

Leu Ala  Asp Gly Asp Gly Thr  Leu Leu Thr Gly Arg  Leu Ser Leu
    4775                 4780                 4785

His Thr  His Pro Trp Leu Ala  Asp His Ser Val Gly  Gly Ile Val
    4790                 4795                 4800

Leu Leu  Pro Gly Thr Ala Leu  Leu Glu Leu Ala Leu  Gln Ala Gly
    4805                 4810                 4815

Gly Ala  Ala His Val Arg Glu  Leu Thr Leu His Ala  Pro Leu Ala
    4820                 4825                 4830

Val Pro  His Asp Ala Ala Val  Asp Leu Gln Val Arg  Val Ser Ala
    4835                 4840                 4845

Pro Asp  Asp Thr Gly Ala Arg  Thr Leu Thr Val Ser  Ser Arg Ser
```

-continued

```
    4850                4855                4860

Glu His  Ala Arg Pro Glu Asp  Pro Trp Gln His His  Ala Thr Gly
    4865                4870                4875

Leu Leu  Asp Ala Gln Pro Ser  Ala Asp Gly Asp Ala  Leu Arg Ser
    4880                4885                4890

Trp Pro  Pro Glu Gly Ala Leu  Pro Cys Ala Ala Asp  Glu Leu Glu
    4895                4900                4905

Ser Phe  Tyr Ala Ala Gln Glu  Ala Arg Gly Phe Ala  Tyr Gly Pro
    4910                4915                4920

Ala Phe  Arg Gly Leu Arg Ala  Ala Trp Arg Arg Gly  Glu Glu Val
    4925                4930                4935

Phe Ala  Glu Val Arg Leu Pro  Glu Ser Val Leu Asp  Glu Ala Ser
    4940                4945                4950

Arg Tyr  Asn Leu His Pro Ala  Leu Leu Asp Ala Ala  Leu His Ala
    4955                4960                4965

Val Ala  Leu Gly Ala Ala Thr  Gly Leu Pro Pro Gly  Ala Val Pro
    4970                4975                4980

Phe Ser  Phe Ser Gly Val Thr  Leu His Ala Val Lys  Ala Ala Ala
    4985                4990                4995

Val Arg  Val Arg Val Ala Pro  Ala Gly Arg Asp Gly  Glu Arg Thr
    5000                5005                5010

Ala Val  Ser Val Ser Leu Ala  Asp Glu Thr Gly Arg  Gly Val Leu
    5015                5020                5025

Ser Val  Asp Ser Leu Ala Val  Arg Pro Leu Asp Thr  Gly Glu Leu
    5030                5035                5040

Arg Ala  Ser Ala Gln Ala Ala  Gly Arg Ala Ala Leu  Phe Asp Val
    5045                5050                5055

Ala Trp  Lys Asp Val Thr Pro  Gly Thr Pro Pro Pro  Asp Thr Ala
    5060                5065                5070

Val Arg  Ser Thr Val Leu Thr  His Asp Arg Ala Ala  Ala Asp Leu
    5075                5080                5085

Ser Gly  Leu Leu Ser Gly Leu  Asp Thr Asp Asp Ala  Pro Val Pro
    5090                5095                5100

Asp Ala  Val Leu Leu Thr Cys  Ser Gln Gly Ala Val  Ala Asp Val
    5105                5110                5115

Leu Gly  Glu Val Leu Ser Val  Val Gln Asp Trp Leu  Ala Asp Asp
    5120                5125                5130

Arg Leu  Ala Glu Ala Arg Leu  Val Val Val Thr His  Gly Ala Val
    5135                5140                5145

Ala Thr  Arg Thr Gly Glu Glu  Val Thr Asp Val Ala  Gly Ala Ala
    5150                5155                5160

Val Trp  Gly Leu Leu Arg Ser  Ala Gln Ser Glu His  Pro Gly Arg
    5165                5170                5175

Phe Val  Leu Leu Asp Ala Asp  Leu Ser Asp Asp Thr  Thr Val Thr
    5180                5185                5190

Ala Ala  Leu Ala Cys Asp Glu  Pro Gln Leu Ala Val  Arg Gly Gly
    5195                5200                5205

Arg Leu  Leu Ala Ala Arg Leu  Ala His Val Pro Val  Pro Ala Asp
    5210                5215                5220

Ser Ser  Asp Ala Val Arg Phe  Asp Ala Glu Gly Thr  Val Leu Val
    5225                5230                5235

Thr Gly  Gly Thr Gly Thr Leu  Gly Ala Ala Val Ala  Arg His Leu
    5240                5245                5250
```

```
Ala Ala Gly His Gly Val Arg His Leu Leu Leu Val Ser Arg Arg
    5255                5260                5265

Gly Met Ala Ala Thr Gly Ala Glu Glu Leu Cys Ala Glu Leu Gly
    5270                5275                5280

Gln Ala Gly Val Ser Val Ser Val Ala Ala Cys Asp Val Ala Asp
    5285                5290                5295

Arg Ala Gln Val Ala Ala Leu Leu Glu Gln Val Pro Ala Glu His
    5300                5305                5310

Pro Leu Thr Ala Val Val His Thr Ala Gly Val Leu Asp Asp Ala
    5315                5320                5325

Thr Val Ala Cys Leu Asn Arg Glu Lys Ile Asp Ala Val Val Gly
    5330                5335                5340

Ala Lys Val Asp Gly Ala Leu His Leu His Glu Leu Thr Ala Gly
    5345                5350                5355

Met Asp Leu Ser Ala Phe Val Leu Phe Ser Ser Ala Ala Gly Val
    5360                5365                5370

Leu Gly Ser Pro Gly Gln Gly Asn Tyr Ala Ala Ala Asn Ala Ala
    5375                5380                5385

Leu Asp Ala Leu Ala His Gln Arg Arg Ala Ala Gly Leu Pro Ala
    5390                5395                5400

Leu Ser Leu Ala Trp Gly Leu Trp Glu Glu Ala Ser Gly Met Thr
    5405                5410                5415

Gly His Leu Asp Ala Gly Asp Arg His Arg Ile Thr Arg Ser Gly
    5420                5425                5430

Leu His Pro Leu Thr Thr Pro Asp Ala Leu Ala Leu Leu Asp Thr
    5435                5440                5445

Ala Leu Val Thr Gly Arg Pro Ala Leu Leu Pro Ala Asp Leu Arg
    5450                5455                5460

Pro Thr His Pro Ala Pro Pro Leu Leu Glu His Leu Ala Pro Ala
    5465                5470                5475

Arg Thr Ser Pro Arg Thr Ala His Thr Gly Thr Ser Ala Gly Ala
    5480                5485                5490

Gly Gln Asp Val Ser Leu Ala Asp Arg Leu Ala Thr Leu Thr Pro
    5495                5500                5505

Glu Gln Gln His Asp Thr Leu Phe Thr Val Val Arg Thr Gln Ile
    5510                5515                5520

Ala Thr Val Leu Gly His Gln Thr Pro Glu Ala Val Pro Ala Asp
    5525                5530                5535

Ser Ala Phe Arg Asp Leu Gly Phe Asp Ser Leu Thr Ala Val Glu
    5540                5545                5550

Leu Arg Asn Arg Leu Ser Arg Ala Thr Gly Leu Arg Leu Pro Ala
    5555                5560                5565

Thr Leu Ala Phe Asp His Pro Thr Ala Thr Ala Leu Thr Arg His
    5570                5575                5580

Leu Leu Thr Arg Leu Leu Pro Asp Asp Ala Ala Thr Ala Pro Pro
    5585                5590                5595

Glu Gln Ser Leu Phe Ala Glu Ile Gly Arg Leu Glu Ala Val Leu
    5600                5605                5610

Ser Ser Val Ala Ser Pro Leu Pro Gly Ala Gln Gly Leu Gly Glu
    5615                5620                5625

Glu Ala Arg Ser Arg Leu Ala Ser Arg Leu Arg Ser Leu Ala Gln
    5630                5635                5640
```

-continued

```
Val Leu  Gly Gly Glu Glu Ala  Pro Arg Pro Asp Leu  Gly Glu Ala
    5645                5650                5655

Thr Asp  Glu Glu Met Phe Ala  Leu Ile Asp Gln Glu  Thr Gly Ser
    5660                5665                5670

Pro


<210> SEQ ID NO 11
<211> LENGTH: 5166
<212> TYPE: PRT
<213> ORGANISM: bacteria

<400> SEQUENCE: 11

Met Ala Asn Glu Glu Met Leu Arg Glu Tyr Leu Lys Arg Ala Thr Ala
1               5                   10                  15

Asp Leu Leu Arg Val Arg Arg Arg Leu Glu Gln Val Glu Ser Gly Arg
            20                  25                  30

Gln Glu Pro Val Ala Ile Val Gly Met Ala Cys Arg Phe Pro Gly Gly
        35                  40                  45

Val Arg Ser Pro Glu Asp Leu Trp Glu Leu Val Ala Ser Gly Gly Asp
    50                  55                  60

Ala Ile Gly Asp Phe Pro Val Asp Arg Gly Trp Asp Val Glu Asp Leu
65                  70                  75                  80

Tyr Asp Pro Glu Pro Gly Arg Ala Gly Arg Ser Tyr Thr Arg Ser Gly
                85                  90                  95

Gly Phe Leu His Glu Ala Ala Glu Phe Asp Ala Gly Phe Phe Gly Leu
            100                 105                 110

Ser Pro Arg Glu Ala Leu Ala Met Asp Pro Gln Gln Arg Leu Met Leu
        115                 120                 125

Glu Val Ser Trp Glu Ala Leu Glu Arg Ala Gly Ile Asp Pro Ala Thr
    130                 135                 140

Leu Arg Gly Ser Arg Thr Gly Val Phe Ala Gly Met Met Ser His Asp
145                 150                 155                 160

Tyr Ala Thr Arg Leu Leu Ser Val Pro Asp His Leu Gln Gly Phe Leu
                165                 170                 175

Gly Asn Gly Asn Ala Ala Ser Val Leu Ser Gly Arg Leu Ser Tyr Thr
            180                 185                 190

Phe Gly Phe Glu Gly Pro Ala Val Thr Val Asp Thr Ala Cys Ser Ser
        195                 200                 205

Ser Leu Val Ala Leu His Leu Ala Cys Gln Ser Val Arg Ser Gly Glu
    210                 215                 220

Ser Ser Leu Ala Leu Ala Gly Gly Val Thr Val Met Ser Thr Pro Ala
225                 230                 235                 240

Met Phe Val Glu Phe Ser Arg Gln Arg Gly Leu Ser Ala Asp Gly Arg
                245                 250                 255

Cys Lys Pro Tyr Ala Ala Ala Ala Asp Gly Thr Gly Met Ser Glu Gly
            260                 265                 270

Val Gly Val Leu Leu Val Glu Arg Leu Ser Asp Ala Arg Arg Leu Gly
        275                 280                 285

His Arg Val Leu Ala Val Val Arg Gly Ser Ala Val Asn Gln Asp Gly
    290                 295                 300

Ala Ser Asn Gly Leu Thr Ala Pro Asn Gly Pro Ser Gln Gln Arg Val
305                 310                 315                 320

Ile Gly Gln Ala Leu Val Cys Ala Gly Leu Ser Ala Ala Glu Val Asp
                325                 330                 335
```

-continued

```
Val Val Glu Gly His Gly Thr Gly Thr Ser Leu Gly Asp Pro Ile Glu
            340                 345                 350

Ala Gln Ala Val Leu Ala Ala Tyr Gly Arg Gly Arg Gly Val Pro Leu
        355                 360                 365

Trp Leu Gly Ser Val Lys Ser Asn Leu Gly His Thr Gln Ala Ala Ala
    370                 375                 380

Gly Val Ala Gly Val Ile Lys Met Val Met Ala Leu Trp Arg Gly Arg
385                 390                 395                 400

Leu Pro Arg Thr Leu His Val Asp Glu Pro Ser Pro His Val Asp Trp
                405                 410                 415

Ser Ser Gly Ala Val Arg Leu Leu Thr Glu Glu Val Val Trp Glu Arg
            420                 425                 430

Gly Glu Arg Pro Arg Arg Ala Gly Val Ser Ser Phe Gly Val Ser Gly
        435                 440                 445

Thr Asn Ala His Val Ile Leu Glu Glu Ala Pro Gln Glu Glu Glu Val
    450                 455                 460

Arg Pro Glu Glu Ala Pro Ser Gly Asp Gly Val Gly Pro Val Val Val
465                 470                 475                 480

Pro Ser Gly Asp Gly Ala Gly Pro Ala Val Val Pro Trp Val Val Ser
                485                 490                 495

Ala Arg Ser Glu Ser Ala Leu Arg Gly Gln Ala Arg Arg Leu Arg Val
            500                 505                 510

Phe Ala Asp Gly Ala Gly Ala Ala Pro Val Glu Val Gly Arg Ala Leu
        515                 520                 525

Ala Val Glu Arg Ala Trp Leu Glu His Arg Ala Val Val Leu Ala Glu
    530                 535                 540

Asp Leu Asp Gly Phe Arg His Gly Leu Asp Ala Leu Ala Thr Gly Arg
545                 550                 555                 560

Pro Ala Pro Glu Val Val Thr Gly Thr Ala Thr Asp Glu Gly Pro Leu
                565                 570                 575

Ala Phe Leu Phe Ala Gly Gln Gly Thr Gln Arg Pro Ala Met Gly Arg
            580                 585                 590

Glu Leu His Ala His Phe Pro Ala Phe Ala Asp Ala Phe Asp Glu Val
        595                 600                 605

Cys Ala His Phe Gly Pro Ile Gly Glu Ala Gly His Thr Leu Arg Asp
    610                 615                 620

Ile Val Phe Ala Ala Pro Gly Ser Pro Gly Ala Glu Leu Ile Glu Gln
625                 630                 635                 640

Thr Glu Tyr Ala Gln Pro Ala Leu Phe Ala Val Glu Val Ala Leu Tyr
                645                 650                 655

Arg Leu Val Glu Asn Trp Gly Val Thr Pro Asp Tyr Leu Leu Gly His
            660                 665                 670

Ser Val Gly Glu Leu Ala Ala Ala His Val Ala Gly Met Leu Ser Leu
        675                 680                 685

Pro Asp Ala Ala Ala Leu Val Thr Ala Arg Gly Arg Leu Met Gln Ala
    690                 695                 700

Leu Pro Asp Thr Gly Ala Met Val Ala Val Glu Ala Thr Glu Glu Glu
705                 710                 715                 720

Val Arg Pro Leu Leu Gln Asp Ala Glu Gly Arg Ala Asp Leu Ala Ala
                725                 730                 735

Val Asn Gly Pro Arg Ala Val Val Leu Ala Gly Asp Glu Asp Ala Val
            740                 745                 750

Leu Thr Leu Ala Arg His Trp Ala Glu Gln Gly Arg Arg Thr Arg Arg
```

-continued

```
        755                 760                 765

Leu Arg Thr Ser His Ala Phe His Ser Pro His Leu Asp Ala Val Leu
    770                 775                 780

Asp Asp Phe Arg Arg Val Ala Glu Gln Val Val Phe Ala Pro Pro Arg
785                 790                 795                 800

Ile Pro Val Val Thr Asn Leu Thr Gly Ala Pro Val Ser Ala Asp Thr
                805                 810                 815

Met Gly Thr Ala Asp Tyr Trp Val Gln His Ala Arg His Thr Val Arg
            820                 825                 830

Phe Gly Asp Gly Leu Ala Trp Leu Gln Ala Gln Gly Val Thr Ala Tyr
        835                 840                 845

Leu Glu Leu Gly Pro Asp Gly Thr Leu Cys Ala Leu Gly Gln Asp Ala
    850                 855                 860

Leu Thr Glu Pro Ala Pro Leu Leu Pro Ala Leu Arg Pro Asp Arg Pro
865                 870                 875                 880

Glu Ala Val Ser Val Leu Ala Ala Val Ala Gly Leu Ser Val Arg Gly
                885                 890                 895

Val Arg Val Asp Trp Ala Ala Val Leu Gly Gly Ala Pro Ser Gly Thr
            900                 905                 910

Ala Gly Arg Val Glu Leu Pro Thr Tyr Ala Phe Glu Arg Glu Arg Tyr
        915                 920                 925

Trp Leu Asp Ala Gly Glu Thr Pro Ala Ala Leu Pro Ala Gly Glu Asp
    930                 935                 940

Gly Pro Leu Trp Gln Ala Val Glu Arg Ala Asp Leu Pro Ala Val Ala
945                 950                 955                 960

Ala Leu Leu Glu Val Asp Glu Asp Ala Pro Leu Gly Ser Val Val Ser
                965                 970                 975

Ala Leu Gly Asp Trp Arg Arg Gly Val Arg Glu Arg Ala Val Val Asp
            980                 985                 990

Gly Trp Arg Tyr Arg Val Val Trp  Arg Pro Val Ser Arg  Ser Gly Gly
        995                 1000                1005

Gly Val  Val Ser Gly Gly Val  Trp Val Val Val Val  Pro Glu Gly
    1010                1015                1020

Val Val  Gly Ala Ala Ala Val  Val Glu Gly Leu Glu  Arg Ala Gly
    1025                1030                1035

Val Cys  Val Arg Val Val Ala  Val Glu Gly Gly Cys  Ala Asp Arg
    1040                1045                1050

Val Val  Leu Gly Glu Arg Leu  Arg Glu Val Cys Gly  Gly Glu Gly
    1055                1060                1065

Pro Val  Gly Val Leu Ala Val  Cys Gly Gly Gly Val  Gly Val Ala
    1070                1075                1080

Gly Leu  Val Leu Gly Leu Val  Gln Ala Val Glu Gly  Leu Gly Val
    1085                1090                1095

Pro Leu  Trp Cys Val Thr Arg  Gly Ala Val Ser Val  Gly Glu Gly
    1100                1105                1110

Asp Arg  Leu Gly Asp Pro Gly  Gly Ala Val Val Trp  Gly Leu Gly
    1115                1120                1125

Arg Val  Ala Gly Leu Glu Leu  Pro Asp Arg Trp Gly  Gly Val Val
    1130                1135                1140

Asp Leu  Pro Glu Val Val Asp  Glu Arg Val Val Glu  Gly Leu Leu
    1145                1150                1155

Gly Val  Leu Ser Gly Gly Gly  Gly Glu Gly Glu Val  Ala Val Arg
    1160                1165                1170
```

-continued

```
Ala Ser  Gly Val Phe Val Arg  Arg Leu Val Arg Ala  Pro Gly Gly
    1175                 1180                 1185

Gly Ala  Glu Ala Gly Gly Trp  Arg Pro Arg Gly Thr  Val Leu Ile
    1190                 1195                 1200

Thr Gly  Gly Thr Gly Ala Leu  Gly Ala His Val Ala  Arg Trp Met
    1205                 1210                 1215

Val Arg  Arg Gly Ala Glu His  Leu Leu Leu Val Ser  Arg Ser Gly
    1220                 1225                 1230

Arg Glu  Ala Lys Gly Ala Gly  Glu Leu Arg Ala Glu  Leu Thr Ala
    1235                 1240                 1245

Met Gly  Ala Arg Val Thr Ile  Ala Ala Cys Asp Val  Ala Asp Arg
    1250                 1255                 1260

Gly Ala  Leu Ala Glu Leu Leu  Ala Thr Ala Val Pro  Glu Asp Cys
    1265                 1270                 1275

Pro Leu  Gly Ala Val Val His  Thr Ala Gly Val Val  Asp Asp Gly
    1280                 1285                 1290

Val Leu  Asp Ala Leu Thr Pro  Glu Arg Leu Glu Gly  Val Leu Ala
    1295                 1300                 1305

Ala Lys  Ala Val Gly Ala Arg  Asn Leu His Glu Leu  Thr Arg Gly
    1310                 1315                 1320

Ala Asp  Leu Ser Ala Phe Val  Val Phe Ser Ser Ala  Ala Ala Thr
    1325                 1330                 1335

Phe Gly  Ser Gly Gly Gln Gly  Ala Tyr Val Ala Ala  Asn Ala Tyr
    1340                 1345                 1350

Val Glu  Ala Leu Ala Val His  Arg Arg Gly Leu Gly  Leu Pro Ser
    1355                 1360                 1365

Thr Ala  Val Ala Trp Gly Ala  Trp Ala Gly Gly Gly  Met Ala Ala
    1370                 1375                 1380

Asp Ala  Glu Ala Ala Thr Arg  Met Asp Arg Arg Gly  Ile Arg Pro
    1385                 1390                 1395

Met Asp  Thr Glu Pro Ala Leu  Ser Ala Leu Gly Gln  Val Leu Asp
    1400                 1405                 1410

Arg Asn  Glu Thr Cys Leu Thr  Ile Ala Asp Ile Asp  Trp Glu Arg
    1415                 1420                 1425

Leu Pro  Ala Ala Asp Gly Leu  Ala Arg Leu Leu Ser  Asp Ile Pro
    1430                 1435                 1440

Glu Ala  Arg Leu Ala Arg Pro  Ala Thr Gly Thr Glu  Ala Pro Gly
    1445                 1450                 1455

Ser Leu  Arg Ala Arg Leu Ala  Ala Leu Glu Pro Ala  Glu Arg Asp
    1460                 1465                 1470

Arg Ala  Leu Leu Asp Leu Val  Arg Thr His Thr Ala  Thr Val Leu
    1475                 1480                 1485

Gly His  Arg Thr Ala Thr Ala  Val Pro Ala Asp Arg  Ala Phe Arg
    1490                 1495                 1500

Glu Leu  Gly Phe Gly Ser Leu  Asn Ala Val Glu Leu  Arg Asn Gly
    1505                 1510                 1515

Leu Asn  Thr Ala Thr Gly Leu  Arg Leu Pro Ser Thr  Leu Val Phe
    1520                 1525                 1530

Asp Tyr  Pro Asn Pro Ser Ala  Leu Ala Thr His Leu  Gly Thr Leu
    1535                 1540                 1545

Leu Ser  Thr Gly Gly Glu Ala  Pro Ala Gly Arg Pro  Ala Phe Ile
    1550                 1555                 1560
```

-continued

```
Arg Ser  Gly Val Val Asp Glu  Pro Val Ala Ile Val  Gly Met Ala
    1565                 1570                 1575

Cys Arg  Phe Pro Gly Gly Val  Trp Ser Pro Glu Asp  Leu Trp Glu
    1580                 1585                 1590

Leu Val  Ala Ser Gly Gly Asp  Ala Ile Gly Gly Phe  Pro Val Asp
    1595                 1600                 1605

Arg Gly  Trp Asp Val Glu Gly  Leu Tyr Asp Pro Glu  Ala Gly Arg
    1610                 1615                 1620

Pro Gly  Ser Ser Tyr Thr Arg  Ala Gly Gly Phe Leu  Ala Gly Ala
    1625                 1630                 1635

Ala Glu  Phe Asp Ala Gly Phe  Phe Gly Ile Ser Pro  Arg Glu Ala
    1640                 1645                 1650

Leu Ala  Met Asp Pro Gln Gln  Arg Leu Leu Leu Glu  Val Ser Trp
    1655                 1660                 1665

Glu Ala  Leu Glu Arg Ala Gly  Ile Asp Pro Val Ser  Leu Arg Gly
    1670                 1675                 1680

Ser Arg  Thr Gly Val Phe Ala  Gly Val Ala Asn Gln  Asp Tyr Ala
    1685                 1690                 1695

Glu Leu  Val Arg Arg Gly Gly  Arg Asp Leu Glu Gly  Tyr Ala Leu
    1700                 1705                 1710

Thr Gly  Val Ser Gly Ser Val  Leu Ser Gly Arg Leu  Ser Tyr Thr
    1715                 1720                 1725

Phe Gly  Leu Lys Gly Pro Pro  Val Thr Val Asn Thr  Ala Cys Ser
    1730                 1735                 1740

Ser Ser  Leu Val Ala Leu His  Leu Ala Cys Gln Ser  Leu Arg Ser
    1745                 1750                 1755

Gly Glu  Ser Lys Leu Ala Leu  Pro Gly Gly Val Thr  Val Met Ser
    1760                 1765                 1770

Thr Pro  Gly Ala Phe Val Glu  Phe Ser Arg Gln Arg  Gly Leu Ser
    1775                 1780                 1785

Pro Asp  Gly Arg Cys Lys Ala  Phe Ala Thr Pro Thr  Asn Gly Val
    1790                 1795                 1800

Gly Trp  Ser Glu Gly Val Gly  Val Leu Leu Val Glu  Arg Leu Ser
    1805                 1810                 1815

Asp Ala  Arg Arg Leu Gly His  Arg Val Leu Pro Val  Val Arg Gly
    1820                 1825                 1830

Ser Ala  Val Asn Gln Asp Gly  Ala Ser Asn Gly Leu  Thr Ala Pro
    1835                 1840                 1845

Asn Gly  Pro Ser Gln Gln Arg  Val Ile Gly Gln Ala  Leu Val Cys
    1850                 1855                 1860

Ala Gly  Leu Ser Ala Ala Glu  Val Asp Val Val Glu  Gly His Gly
    1865                 1870                 1875

Thr Gly  Thr Ser Leu Gly Asp  Pro Ile Glu Ala Gln  Ala Val Leu
    1880                 1885                 1890

Ala Ala  Tyr Gly Arg Gly Arg  Gly Val Pro Leu Trp  Leu Gly Ser
    1895                 1900                 1905

Val Lys  Ser Asn Leu Gly His  Thr Gln Ala Ala Ala  Gly Val Ala
    1910                 1915                 1920

Gly Val  Ile Lys Met Val Met  Val Leu Trp Arg Gly  Arg Leu Pro
    1925                 1930                 1935

Arg Thr  Leu His Val Asp Glu  Pro Ser Pro His Val  Asp Trp Ser
    1940                 1945                 1950

Ser Gly  Ala Val Arg Leu Leu  Thr Glu Glu Val Val  Trp Glu Arg
```

-continued

```
    1955                1960                1965

Gly Glu  Arg Pro Arg Arg Ala  Gly Val Ser Ser Phe  Gly Val Ser
    1970                1975                1980

Gly Thr  Asn Ala His Val Ile  Leu Glu Glu Ala Pro  Gln Glu Glu
    1985                1990                1995

Glu Val  Arg Pro Glu Glu Ala  Pro Ser Gln Gly Glu  Ala Gly Pro
    2000                2005                2010

Ala Val  Val Pro Trp Val Val  Ser Ala Arg Ser Glu  Ser Ala Leu
    2015                2020                2025

Arg Gly  Gln Ala Arg Arg Leu  Arg Val Phe Ala Asp  Gly Ala Gly
    2030                2035                2040

Ala Ala  Pro Val Glu Val Gly  Arg Ala Leu Ala Val  Glu Arg Ala
    2045                2050                2055

Trp Leu  Glu His Arg Ala Val  Val Leu Ala Glu Asp  Leu Asp Gly
    2060                2065                2070

Phe Arg  His Gly Leu Asp Ala  Leu Ala Thr Gly Leu  Pro Thr Ala
    2075                2080                2085

Gly Val  Val Ala Gly Arg Thr  Gly Pro Glu Ala Asp  Gly Lys Ile
    2090                2095                2100

Ala Leu  Leu Phe Gly Gly Gln  Gly Thr Gln Trp Asp  Gly Met Ala
    2105                2110                2115

Ala Glu  Leu Leu Asp Ser Ser  Pro Val Phe Ala Gln  Arg Met Thr
    2120                2125                2130

Glu Cys  Ala Asp Ala Leu Arg  Pro Tyr Leu Asp Trp  Glu Leu Leu
    2135                2140                2145

Asp Val  Leu Arg Gly Glu Pro  Asp Ala Pro Pro Leu  Asp Arg Val
    2150                2155                2160

Asp Val  Val Gln Pro Val Leu  Phe Ala Val Met Val  Ser Leu Ala
    2165                2170                2175

Ala Leu  Trp Arg Ser Tyr Gly  Val Arg Pro Asp Ala  Val Ala Gly
    2180                2185                2190

His Ser  Gln Gly Glu Ile Ala  Ala Ala Cys Val Ala  Gly Ala Leu
    2195                2200                2205

Ser Leu  Glu Asp Ala Ala Arg  Val Thr Ala Leu Arg  Ser Gln Ala
    2210                2215                2220

Leu Ala  Ala Leu Ala Gly Gln  Gly Ala Met Ala Ser  Val Gly Leu
    2225                2230                2235

Pro Ala  Glu Asp Leu Glu Pro  Arg Leu Ala Ala Val  Asp Pro Ser
    2240                2245                2250

Leu Val  Val Ala Ala Asp Asn  Gly Ala Arg Ser Ala  Val Val Ser
    2255                2260                2265

Gly Ser  Pro Asp Ala Val Thr  Ala Leu Val Asp Asp  Leu Thr Arg
    2270                2275                2280

Asp Gly  Val Pro Ala Arg Leu  Leu Lys Val Asp Trp  Ala Ser His
    2285                2290                2295

Ser Pro  Gln Val Glu Ala Ile  Arg Ala Asp Leu Leu  Gly Leu Leu
    2300                2305                2310

Ala Pro  Val Thr Pro Arg Pro  Ala Asp Ile Pro Leu  Tyr Ser Thr
    2315                2320                2325

Val Thr  Gly Glu Pro Val Asp  Gly Thr Ala Leu Asp  Ala Ala Tyr
    2330                2335                2340

Trp Tyr  Arg Asn Leu Arg Glu  Pro Val Arg Phe Arg  Asp Ala Thr
    2345                2350                2355
```

-continued

```
Arg Ala  Leu Ala Arg Asp Gly  His Thr Val Phe Val  Glu Ala Gly
    2360                 2365                 2370

Pro His  Pro Ala Val Ser Val  Ala Val Gln Glu Thr  Leu Asp Asp
    2375                 2380                 2385

Leu Gly  Ala Ala Asp Thr Leu  Val Val Gly Ser Leu  Arg Arg Gly
    2390                 2395                 2400

Glu Gly  Gly Leu Arg Arg Phe  Leu Ala Ser Ala Ala  Glu Leu Ser
    2405                 2410                 2415

Val Arg  Gly Val Arg Val Asp  Trp Ala Ala Val Leu  Gly Gly Lys
    2420                 2425                 2430

Pro Ser  Gly Thr Ala Gly Arg  Val Glu Leu Pro Thr  Tyr Ala Phe
    2435                 2440                 2445

Glu Arg  Glu Arg Tyr Trp Leu  Asp Pro Glu Glu Thr  Pro Ala Ala
    2450                 2455                 2460

Pro Ala  Thr Thr Glu Asp Gly  Pro Leu Trp Glu Ala  Val Glu Arg
    2465                 2470                 2475

Glu Asp  Pro Ala Ala Val Ala  Ala Leu Leu Ala Val  Asp Glu Asp
    2480                 2485                 2490

Ala Pro  Leu Asp Ala Leu Val  Ser Ala Leu Gly Asp  Trp Arg Arg
    2495                 2500                 2505

Gly Val  Arg Glu Arg Ala Val  Val Asp Gly Trp Arg  Tyr Arg Val
    2510                 2515                 2520

Val Trp  Arg Pro Val Ser Arg  Ser Gly Gly Gly Val  Val Ser Gly
    2525                 2530                 2535

Gly Val  Trp Val Val Val Val  Pro Glu Gly Val Val  Gly Ala Ala
    2540                 2545                 2550

Ala Val  Val Glu Gly Leu Glu  Trp Ala Gly Val Cys  Val Arg Val
    2555                 2560                 2565

Val Ala  Val Glu Gly Gly Cys  Ala Asp Arg Val Val  Leu Gly Glu
    2570                 2575                 2580

Arg Leu  Arg Glu Val Trp Gly  Gly Glu Gly Pro Val  Gly Val Leu
    2585                 2590                 2595

Ala Val  Cys Gly Gly Gly Val  Gly Val Ala Gly Leu  Val Leu Gly
    2600                 2605                 2610

Leu Val  Gln Ala Val Glu Gly  Leu Gly Val Pro Leu  Trp Cys Val
    2615                 2620                 2625

Thr Arg  Gly Ala Val Ser Val  Gly Glu Gly Asp Arg  Leu Gly Asp
    2630                 2635                 2640

Pro Gly  Gly Ala Val Val Trp  Gly Leu Gly Arg Val  Ala Gly Leu
    2645                 2650                 2655

Glu Leu  Pro Asp Arg Trp Gly  Gly Val Val Asp Leu  Pro Glu Val
    2660                 2665                 2670

Val Asp  Glu Arg Val Val Glu  Gly Leu Leu Gly Val  Leu Ser Gly
    2675                 2680                 2685

Gly Gly  Gly Glu Gly Glu Val  Ala Val Arg Ala Ser  Gly Val Phe
    2690                 2695                 2700

Val Arg  Arg Leu Val Arg Ala  Pro Gly Gly Gly Ala  Glu Ala Gly
    2705                 2710                 2715

Gly Trp  Arg Pro Arg Gly Thr  Val Leu Ile Thr Gly  Glu Asn Ala
    2720                 2725                 2730

Asp Pro  Glu Gln Pro Ala Ala  His Leu Ala Arg Trp  Leu Ala Asp
    2735                 2740                 2745
```

-continued

```
Arg Gly  Ala Glu His Leu Leu  Leu Ile Ser Thr Ser  Gly Asp Gly
    2750                 2755                 2760

Phe Gly  Leu Ala Asp Thr Thr  Asp Gln Trp Gly Ala  Arg Val Thr
    2765                 2770                 2775

Ile Ala  Ala Cys Asp Val Ala  Asp Arg Gly Ala Leu  Ala Glu Leu
    2780                 2785                 2790

Leu Ala  Thr Ala Val Pro Glu  Asp Cys Pro Leu Gly  Ala Val Val
    2795                 2800                 2805

His Thr  Ala Gly Val Val Asp  Asp Gly Val Leu Asp  Ala Leu Thr
    2810                 2815                 2820

Pro Glu  Arg Leu Glu Gly Val  Leu Ala Ala Arg Ala  Val Gly Ala
    2825                 2830                 2835

Arg Asn  Leu His Glu Leu Thr  Arg Gly Ala Asp Leu  Ser Ala Phe
    2840                 2845                 2850

Val Val  Phe Ser Ser Ala Ala  Ala Thr Phe Gly Ser  Gly Gly Gln
    2855                 2860                 2865

Gly Ala  Tyr Val Ala Ala Asn  Ala Tyr Val Glu Ala  Leu Ala Val
    2870                 2875                 2880

His Arg  Arg Gly Leu Gly Leu  Pro Ser Thr Ala Val  Ala Trp Gly
    2885                 2890                 2895

Pro Trp  Arg Gly His Ser Ala  Ala Gly Arg Pro Asp  Ala Ala Ala
    2900                 2905                 2910

Arg Leu  His Arg Arg Gly Leu  Thr Glu Met Ala Pro  Glu Leu Ala
    2915                 2920                 2925

Leu Ala  Ala Leu Ala Arg Val  Leu Asp His Asp Glu  Ser Gly Leu
    2930                 2935                 2940

Thr Val  Ala Asp Ile Asp Trp  Glu Arg Phe Thr Ala  His Thr Ala
    2945                 2950                 2955

Gly Ser  Arg Leu Pro Leu Ile  Gly Asp Leu Pro Asp  Val Arg Ala
    2960                 2965                 2970

Leu Thr  Arg Ala Thr Gly Thr  Gly Thr Ala His Gly  Thr Asp Leu
    2975                 2980                 2985

Arg Asp  Arg Leu Ala Ala Leu  Glu Pro Asp Ala Arg  Thr Asp Val
    2990                 2995                 3000

Leu Leu  Glu Leu Val Ser Thr  His Thr Ala Ala Val  Leu Gly His
    3005                 3010                 3015

Arg Glu  Ala Asp Thr Val Pro  Ala Asp Arg Ala Phe  Arg Glu Leu
    3020                 3025                 3030

Gly Phe  Asp Ser Leu Thr Ala  Val Glu Leu Arg Asn  Arg Leu Asn
    3035                 3040                 3045

Thr Ala  Thr Gly Leu Arg Leu  Pro Thr Thr Leu Val  Phe Asp Tyr
    3050                 3055                 3060

Pro Arg  Pro Ala Val Leu Ala  Arg His Leu Arg Asp  Gln Leu Cys
    3065                 3070                 3075

Gly Thr  Ala Pro Ala Thr Pro  Pro Val Ala Ala Arg  Pro Gly Val
    3080                 3085                 3090

Val Asp  Glu Pro Val Ala Ile  Val Gly Met Ala Cys  Arg Phe Pro
    3095                 3100                 3105

Gly Gly  Val Trp Ser Pro Glu  Asp Leu Trp Glu Leu  Val Ala Ser
    3110                 3115                 3120

Gly Gly  Asp Ala Ile Gly Gly  Phe Pro Val Asp Arg  Gly Trp Asp
    3125                 3130                 3135

Val Glu  Gly Leu Tyr Asp Pro  Glu Ala Gly Arg Pro  Gly Ser Ser
```

-continued

```
    3140                3145                3150

Tyr Thr Arg Ser Gly Gly Phe Leu Ala Gly Ala Ala Glu Phe Asp
    3155                3160                3165

Ala Gly Phe Phe Gly Ile Ser Pro Arg Glu Ala Leu Ala Met Asp
    3170                3175                3180

Pro Gln Gln Arg Leu Leu Leu Glu Val Ser Trp Glu Ala Leu Glu
    3185                3190                3195

Arg Ala Gly Ile Asp Pro Val Ser Leu Arg Gly Ser Arg Thr Gly
    3200                3205                3210

Val Phe Ala Gly Val Ala Asn Gln Asp Tyr Ala Glu Leu Val Arg
    3215                3220                3225

Arg Gly Gly Arg Asp Leu Glu Gly Tyr Ala Leu Thr Gly Val Ser
    3230                3235                3240

Gly Ser Val Leu Ser Gly Arg Leu Ser Tyr Thr Phe Gly Leu Glu
    3245                3250                3255

Gly Pro Ala Val Thr Val Asp Thr Ala Cys Ser Ser Ser Leu Val
    3260                3265                3270

Ala Leu His Leu Ala Cys Gln Ser Leu Arg Ser Gly Glu Ser Glu
    3275                3280                3285

Leu Ala Leu Ala Gly Gly Val Thr Val Met Ser Thr Pro Gly Ala
    3290                3295                3300

Phe Val Glu Phe Ser Arg Gln Arg Gly Leu Ser Ala Asp Gly Arg
    3305                3310                3315

Cys Lys Ala Phe Ala Ala Ala Ala Asp Gly Val Gly Trp Ser Glu
    3320                3325                3330

Gly Val Gly Val Leu Leu Val Glu Arg Leu Ser Asp Ala Arg Arg
    3335                3340                3345

Leu Gly His Arg Val Leu Ala Val Val Arg Gly Ser Ala Val Asn
    3350                3355                3360

Gln Asp Gly Ala Ser Asn Gly Leu Thr Ala Pro Asn Gly Pro Ser
    3365                3370                3375

Gln Gln Arg Val Ile Gly Gln Ala Leu Val Cys Ala Gly Leu Ser
    3380                3385                3390

Ala Ala Glu Val Asp Val Val Glu Gly His Gly Thr Gly Thr Ser
    3395                3400                3405

Leu Gly Asp Pro Ile Glu Ala Gln Ala Val Leu Ala Ala Tyr Gly
    3410                3415                3420

Arg Gly Arg Gly Val Pro Leu Trp Leu Gly Ser Val Lys Ser Asn
    3425                3430                3435

Leu Gly His Thr Gln Ala Ala Ala Gly Val Ala Gly Val Ile Lys
    3440                3445                3450

Met Val Met Ala Leu Trp Arg Gly Arg Leu Pro Arg Thr Leu His
    3455                3460                3465

Val Asp Glu Pro Ser Pro His Val Asp Trp Ser Ser Gly Ala Val
    3470                3475                3480

Arg Leu Leu Thr Glu Glu Val Val Trp Glu Arg Gly Glu Arg Pro
    3485                3490                3495

Arg Arg Ala Gly Val Ser Ser Phe Gly Val Ser Gly Thr Asn Ala
    3500                3505                3510

His Val Ile Leu Glu Glu Ala Pro Gln Glu Glu Glu Val Arg Pro
    3515                3520                3525

Glu Glu Ala Pro Ser Gln Asp Glu Ala Gly Pro Ala Thr Val Pro
    3530                3535                3540
```

-continued

```
Cys Leu  Leu Ser Ala Arg Thr  Asp Thr Ala Leu Arg  Ala Gln Ala
    3545                 3550                 3555

Arg Arg  Leu Arg Asp Tyr Leu  Ala Ala Asn Pro Asp  Ile Pro Ile
    3560                 3565                 3570

Gly Asp  Val Ala His Ala Leu  Ala Thr Gly Arg Ser  Thr Phe Glu
    3575                 3580                 3585

Arg Arg  Ala Val Leu Val Ala  Glu Asp His Glu Gly  Leu Leu Arg
    3590                 3595                 3600

Thr Leu  Asp Ala Leu Ala Glu  Gly Thr Thr Ala Pro  Gly Leu Ile
    3605                 3610                 3615

Glu Ser  Pro Ala Arg Thr Ala  His Gly Lys Val Ala  Phe Leu Phe
    3620                 3625                 3630

Ser Gly  Gln Gly Thr Gln Arg  Pro Gly Met Gly Arg  Glu Leu Tyr
    3635                 3640                 3645

Ala Ala  His Pro Ala Phe Ala  Gln Ala Leu Asp Asp  Val Leu Ala
    3650                 3655                 3660

Glu Leu  Glu Pro His Leu Asp  Arg Pro Leu Arg Pro  Leu Leu Leu
    3665                 3670                 3675

Asp Glu  Pro Gln Pro Leu Asp  Arg Thr Gly Asp Ala  Gln Pro Ala
    3680                 3685                 3690

Leu Phe  Ala Leu Gln Val Ala  Leu Phe Arg Leu Leu  Glu Ser Ala
    3695                 3700                 3705

Gly Ile  Arg Pro Asp His Val  Ala Gly His Ser Ile  Gly Glu Leu
    3710                 3715                 3720

Ala Ala  Ala His Val Ala Gly  Val Leu Ser Leu Thr  Asp Ala Ala
    3725                 3730                 3735

Arg Leu  Val Ala Ala Arg Gly  Arg Leu Ala Gln Thr  Gln Leu Pro
    3740                 3745                 3750

Pro Gly  Gly Ala Met Leu Ala  Val Arg Ala Ser Glu  Glu Gln Val
    3755                 3760                 3765

Thr Arg  Met Leu Ala Gly Arg  Glu Ala Arg Val Ala  Val Ala Ala
    3770                 3775                 3780

Val Asn  Gly Pro Thr Ser Val  Val Ile Ser Gly Ala  Glu Pro Asp
    3785                 3790                 3795

Val Leu  Glu Ala Ala Ala Ala  Phe Ala Glu Gln Gly  Leu Arg Thr
    3800                 3805                 3810

Lys Arg  Leu Ser Thr Asp Arg  Ala Phe His Ser Pro  Leu Met Glu
    3815                 3820                 3825

Pro Ile  Leu Glu Glu Phe Arg  Gln Val Ala Thr Gly  Ile Ala Tyr
    3830                 3835                 3840

Ala Glu  Pro Thr Ile Pro Val  Val Ser Thr Val Thr  Gly Asp Arg
    3845                 3850                 3855

Ala Thr  Ala Gly Thr Leu Thr  Asp Pro Glu Tyr Trp  Val Arg Gln
    3860                 3865                 3870

Leu Arg  Arg Thr Val Arg Phe  Gly Asp Ala Val Arg  Arg Leu His
    3875                 3880                 3885

Asp Asp  Asp Gly Val Arg Thr  Phe Leu Glu Leu Gly  Pro Asp Gly
    3890                 3895                 3900

Thr Leu  Cys Ala Leu Ala Gly  Glu Cys Leu Pro Ala  Asp Asp Asn
    3905                 3910                 3915

Thr Thr  Glu Pro Gly Pro Ala  Leu Val Pro Leu Leu  Arg Ala Asp
    3920                 3925                 3930
```

-continued

Arg Pro Glu Pro Leu Ala Leu Leu Thr Ala Leu Ala His Leu His
3935 3940 3945

Val Gln Gly Thr Pro Lys Gly Gly Thr Ala Val His Trp Pro Ala
3950 3955 3960

Leu Ile Gly Ala Thr Pro Glu Arg Ala Arg His Leu Asp Leu Pro
3965 3970 3975

Thr Tyr Pro Phe Asp Arg Arg Arg Tyr Trp Leu Asp Ala Asp Thr
3980 3985 3990

Ser Leu Ser Gly Asp Val Ser Ala Ala Gly Leu Thr Ala Ala Gly
3995 4000 4005

His Pro Leu Leu Gly Ser Ala Val Pro Leu Ala Gly Ser Pro Gln
4010 4015 4020

Ser Gln Glu Cys Leu Leu Thr Gly Arg Ile Ser Leu Arg Thr His
4025 4030 4035

Pro Trp Leu Ala Asp His Ala Val Phe Gly Thr Val Leu Leu Pro
4040 4045 4050

Gly Thr Ala Ile Leu Glu Leu Ala Val Arg Ala Gly Asp Glu Val
4055 4060 4065

Gly Cys Asp Thr Val Glu Glu Leu Ala Leu Gln Val Pro Leu Val
4070 4075 4080

Leu Pro Glu Arg Gly Ser Val Val Leu Gln Leu Ser Val Gly Ala
4085 4090 4095

Thr Glu Thr Ala Pro Asp Gly Val Glu Arg Arg Pro Phe Thr Leu
4100 4105 4110

Tyr Ala Arg Glu Asp Asp Gly Leu Thr Pro Ala Ala Pro Thr Gly
4115 4120 4125

Thr Asp Gly Thr Gly Trp Thr Cys His Ala Thr Gly Val Leu Thr
4130 4135 4140

Arg Arg Ala Glu Thr Ala His Asp Thr Ala Ala Pro Trp Pro Pro
4145 4150 4155

Thr Asp Ala Val Pro Val Asp Leu Asp His Trp Tyr Gly Thr Leu
4160 4165 4170

Ala Asp Ala Gly Leu Gly Tyr Gly Pro Ala Phe Gln Gly Leu Arg
4175 4180 4185

Ala Ala Trp Arg His Gly Asp Asp Leu Tyr Ala Glu Val Ala Leu
4190 4195 4200

Pro Asp Gly Pro Ser Gly Asp Ala Asp Arg Tyr Ala Val His Pro
4205 4210 4215

Ala Leu Leu Asp Ala Ala Leu His Pro Val Val Leu Gly Phe Ala
4220 4225 4230

Glu Asp Glu Pro Asp Glu Gly His Gly Trp Leu Pro Phe Ser Trp
4235 4240 4245

Ser Gly Val Thr Val Thr Ala Ser Gly Ala Ser Ala Leu Arg Val
4250 4255 4260

Arg Leu Ser Arg Arg Ser Pro Asp Thr Ile Ala Leu Leu Ala Thr
4265 4270 4275

Asp Ser Thr Gly His Thr Val Val Thr Ala Glu Ser Leu Ala Phe
4280 4285 4290

Arg Pro Val Thr Ala Gly Gln Leu His Ser Ala Arg Thr Ala His
4295 4300 4305

His Asp Ala Leu Phe Arg Leu Asp Trp Ala Pro Val Pro Leu Pro
4310 4315 4320

Arg Thr Pro Ser Ser Lys Thr Arg Leu Ala Leu Ile Gly Ser Glu

-continued

```
    4325                4330                4335

Ala Glu Cys Pro Asp Ala Pro Gly Val Pro Trp Ser Thr Tyr Ala
    4340                4345                4350

Asp Leu Glu Glu Leu Ala Ser Ala Gly Thr Pro Val Pro Asp Val
    4355                4360                4365

Val Val Val Pro Cys Pro His Arg Asp Gly Ala Ala Asp Ala Ala
    4370                4375                4380

Asp Ala Thr Arg Arg Ala Thr Val Arg Val Leu His Leu Leu Gln
    4385                4390                4395

Ser Trp Leu Ala Asp Asp Arg Phe Ala Asp Ser Arg Leu Ala Phe
    4400                4405                4410

Val Thr His Gly Ala Val Ala Ala Ala Pro Gly Asp Ser Val Pro
    4415                4420                4425

Asp Leu Ala His Ala Ala Val Trp Gly Met Val Arg Ser Ala Gln
    4430                4435                4440

Thr Glu Asn Pro Gly Arg Phe Val Leu Thr Asp Leu Asp Asp Thr
    4445                4450                4455

Asp Ala Ser Arg Arg Ala Leu Ala Ala Ala Leu Leu Ser Gly Glu
    4460                4465                4470

Pro Gln Thr Val Leu Arg Glu Gly Arg Ala His Thr Pro Arg Leu
    4475                4480                4485

Ala Arg Ile Pro Val Gly Ala Arg Ala Asp Ser Gly His Trp Asp
    4490                4495                4500

Pro Asp Ala Thr Val Leu Ile Thr Gly Gly Thr Gly Tyr Leu Gly
    4505                4510                4515

Arg Leu Leu Ala Arg His Leu Val Val Thr His Gly Val Arg His
    4520                4525                4530

Leu Leu Leu Thr Ser Arg Ser Gly Pro Thr Ala Pro Gly Thr Ala
    4535                4540                4545

Glu Leu Val Ala Glu Leu Ala Glu Leu Gly Ala Arg Thr Thr Ala
    4550                4555                4560

Val Ala Cys Asp Leu Ala Asp Arg Arg Ala Val Ala Ala Leu Leu
    4565                4570                4575

Ala Glu Ile Pro Ala Arg His Pro Leu Lys Ala Val Leu His Thr
    4580                4585                4590

Ala Gly Val Val Asp Asp Gly Val Leu Thr Ser Leu Thr Pro Asp
    4595                4600                4605

Arg Leu Asp Ala Val Leu Ser Ala Lys Ala His Gly Ala Ala His
    4610                4615                4620

Leu His Asp Leu Thr Arg Asp Ala Gly Leu Asp Ala Phe Ile Ala
    4625                4630                4635

Phe Ser Ser Ala Ala Ala Ser Phe Gly Ser Pro Gly Gln Ala Asn
    4640                4645                4650

Tyr Thr Ala Ala Asn Ala Phe Leu Asp Ala Leu Met Gln Gln Arg
    4655                4660                4665

His Ala Leu Gly Leu Pro Gly Arg Ser Leu Ala Trp Gly Arg Trp
    4670                4675                4680

Ala Glu Ala Gly Gly Met Ala Glu His Leu Ala Ala Ala Asp Val
    4685                4690                4695

Ala Arg Met Thr Arg Ser Gly Leu Leu Pro Leu Thr Asn Ala His
    4700                4705                4710

Gly Leu Ala Leu Phe Asp Thr Ala Leu Ala Leu Asp Glu Pro Leu
    4715                4720                4725
```

-continued

```
Leu Leu Ala Thr Pro Leu Asp Pro Gly Thr Leu Arg Glu Gln Ala
    4730                4735                4740

Ala Val Gly Thr Leu Pro Pro Val Leu Arg Gly Leu Val Arg Thr
    4745                4750                4755

Pro Ala Arg Arg Thr Ala Asp His Gly Val Gly Ala Asp Ala Ala
    4760                4765                4770

Ala Glu Leu Arg Gly Arg Leu Ala Gly Thr Pro Lys Pro Ala Glu
    4775                4780                4785

Arg Thr Ala Leu Leu Thr Glu Val Val Arg Thr His Ala Ala Ala
    4790                4795                4800

Val Leu Gly His Gly Gly Thr Asp Thr Val Thr Ala Asp Gly Glu
    4805                4810                4815

Phe Arg Glu Phe Gly Phe Asp Ser Leu Thr Ala Val Glu Leu Arg
    4820                4825                4830

Asn Arg Leu Asn Ala Ala Thr Gly Leu Arg Leu Ala Thr Thr Leu
    4835                4840                4845

Val Phe Asp His Pro Thr Pro Ala Ala Leu Ala Asp His Leu Glu
    4850                4855                4860

Arg Leu Leu Ala Ala Glu Pro Ala Ser Asp Met Thr Ala Glu Thr
    4865                4870                4875

Ala Gly Ala Pro Gly Glu Arg Asp Ala Thr Ala Ser Ser Arg Ala
    4880                4885                4890

Gly Ser Gly Pro Ser Ala Asp Thr Val Glu Ala Leu Phe Trp Ile
    4895                4900                4905

Gly His Asp Ser Gly Arg Val Glu Glu Ser Met Ala Leu Leu Ser
    4910                4915                4920

Ala Ala Ser Ala Phe Arg Pro Cys Phe Thr Asp Pro Ser Ala Met
    4925                4930                4935

Thr Arg Pro Pro Phe Val Arg Val Ala Gln Gly Asp Thr Gly Pro
    4940                4945                4950

Ala Leu Ile Cys Leu Pro Thr Val Ala Ala Val Ser Ser Val Tyr
    4955                4960                4965

Gln Tyr Ser Arg Phe Ala Ala Ala Leu Asp Gly Leu Arg Asp Val
    4970                4975                4980

Trp Tyr Val Pro Ala Pro Gly Phe Ala Asp Gly Glu Pro Leu Pro
    4985                4990                4995

Ala Asp Val Asp Thr Ile Thr Arg Leu Phe Thr Asp Ala Ile Leu
    5000                5005                5010

Arg His Thr Asp Gly Glu Pro Phe Ala Leu Ala Gly His Ser Ala
    5015                5020                5025

Gly Gly Trp Phe Thr His Thr Val Thr Ser Arg Leu Glu His Leu
    5030                5035                5040

Gly Val Arg Pro Gln Ala Val Val Val Met Asp Ala Tyr Leu Pro
    5045                5050                5055

Asp Glu Gly Met Ala Pro Val Ala Ala Ala Leu Thr Ser Glu Ile
    5060                5065                5070

Phe Asp Arg Val Thr Glu Phe Ile Asp Leu Asp Tyr Ala Arg Leu
    5075                5080                5085

Val Ala Met Gly Gly Tyr Phe Arg Ile Phe Ala Gly Trp Arg Pro
    5090                5095                5100

Pro Ala Leu Glu Thr Pro Thr Leu Phe Leu Arg Ala Arg Glu Ser
    5105                5110                5115
```

-continued

```
Glu Gln  Pro Pro Pro Val Trp  Gly Glu Pro His Thr  Val Leu Glu
    5120                5125                5130

Thr Asp  Gly Asn His Phe Thr  Met Leu Glu Glu His  Ala Glu Ser
    5135                5140                5145

Thr Ala  Arg His Val His Thr  Trp Leu Ala Gly Leu  Thr Glu Gln
    5150                5155                5160

Arg Arg  Arg
    5165


<210> SEQ ID NO 12
<211> LENGTH: 254
<212> TYPE: PRT
<213> ORGANISM: bacteria

<400> SEQUENCE: 12

Met Asp Arg Tyr Ala Lys Arg Phe Glu Asp Arg Leu Val Leu Val Thr
1               5                   10                  15

Gly Ala Gly Ser Gly Ile Gly Arg Ala Thr Ala Cys Arg Phe Gly Ala
            20                  25                  30

Ala Gly Ala Arg Leu Val Cys Val Asp Arg Asp Gly Pro Gly Ala Glu
        35                  40                  45

Ala Thr Ala Glu Leu Ala Arg Ala Arg Gly Ala Arg Ala Ala Cys Ala
    50                  55                  60

Glu Val Ala Asp Val Ser Asp Glu Val Ala Met Glu Arg Leu Ala Ala
65                  70                  75                  80

Arg Val Thr Ala Ala His Gly Val Leu Asp Val Leu Val Asn Asn Ala
                85                  90                  95

Gly Ile Gly Met Ser Gly Arg Phe Leu Asp Thr Ser Ala Glu Asp Trp
            100                 105                 110

Arg Arg Thr Leu Gly Val Asn Leu Trp Gly Val Ile His Gly Cys Arg
        115                 120                 125

Leu Leu Gly Arg Gly Met Ala Glu Arg Arg Gln Gly Gly His Ile Val
    130                 135                 140

Thr Val Ala Ser Ala Ala Ala Phe Gln Pro Thr Arg Val Val Pro Val
145                 150                 155                 160

Tyr Ala Thr Ser Lys Ala Ala Ala Leu Met Leu Ser Glu Cys Leu Arg
                165                 170                 175

Ala Glu Leu Ala Glu Phe Gly Ile Gly Val Ser Val Val Cys Pro Gly
            180                 185                 190

Leu Val Arg Thr Pro Phe Ala Ser Ala Met Tyr Phe Ala Gly Ala Ser
        195                 200                 205

Pro Asp Glu His Thr Arg Leu Arg Glu Ser Ser Ala Arg Arg Phe Ala
    210                 215                 220

Gly Arg Gly Cys Pro Pro Glu Lys Val Ala Asp Ala Val Leu Arg Ala
225                 230                 235                 240

Ile Met Arg Thr Ala Leu Pro Thr Val Thr Gly Ser Thr Pro
                245                 250


<210> SEQ ID NO 13
<211> LENGTH: 7
<212> TYPE: PRT
<213> ORGANISM: bacteria

<400> SEQUENCE: 13

Gly Gly Thr Gly Thr Leu Gly
1               5
```

-continued

<210> SEQ ID NO 14
<211> LENGTH: 7
<212> TYPE: PRT
<213> ORGANISM: bacteria

<400> SEQUENCE: 14

Gly Ala Ala Ser Thr Leu Gly
1               5

<210> SEQ ID NO 15
<211> LENGTH: 33
<212> TYPE: DNA
<213> ORGANISM: bacteria

<400> SEQUENCE: 15
ctggtgacgg gcgctgcaag cactctgggg gcg                                  33

<210> SEQ ID NO 16
<211> LENGTH: 33
<212> TYPE: DNA
<213> ORGANISM: bacteria

<400> SEQUENCE: 16
gaccactgcc cgcgacgttc gtgagacccc cgc                                  33

<210> SEQ ID NO 17
<211> LENGTH: 7
<212> TYPE: PRT
<213> ORGANISM: bacteria

<400> SEQUENCE: 17

Leu Val Ser Arg Arg Gly Met
1               5

<210> SEQ ID NO 18
<211> LENGTH: 7
<212> TYPE: PRT
<213> ORGANISM: bacteria

<400> SEQUENCE: 18

Leu Val Ala Ala Ala Gly Met
1               5

<210> SEQ ID NO 19
<211> LENGTH: 47
<212> TYPE: DNA
<213> ORGANISM: bacteria

<400> SEQUENCE: 19
gcggcatctg ctgctggtgg cagcggcagg catggccgcc gccggtg                   47

<210> SEQ ID NO 20
<211> LENGTH: 47
<212> TYPE: DNA
<213> ORGANISM: bacteria

<400> SEQUENCE: 20
cgccgtagac gacgaccacc gtcgccgtcc gtaccggcgg cggccac                   47

<210> SEQ ID NO 21
<211> LENGTH: 7
<212> TYPE: PRT
<213> ORGANISM: bacteria

-continued

<400> SEQUENCE: 21

His Thr Ala Gly Val Leu Asp
1 5

<210> SEQ ID NO 22
<211> LENGTH: 7
<212> TYPE: PRT
<213> ORGANISM: bacteria

<400> SEQUENCE: 22

His Thr Pro Pro Leu Leu Asp
1 5

<210> SEQ ID NO 23
<211> LENGTH: 46
<212> TYPE: DNA
<213> ORGANISM: bacteria

<400> SEQUENCE: 23
gaccgctgtg gtgcacacgc cacctctcct ggacgacgcc accgtg 46

<210> SEQ ID NO 24
<211> LENGTH: 46
<212> TYPE: DNA
<213> ORGANISM: bacteria

<400> SEQUENCE: 24
ctggcgacac cacgtgtgcg gtggagagga cctgctgcgg tggcac 46

<210> SEQ ID NO 25
<211> LENGTH: 5
<212> TYPE: PRT
<213> ORGANISM: bacteria

<400> SEQUENCE: 25

Gly Ala Lys Val Asp
1 5

<210> SEQ ID NO 26
<211> LENGTH: 5
<212> TYPE: PRT
<213> ORGANISM: bacteria

<400> SEQUENCE: 26

Gly Ala Ala Val Asp
1 5

<210> SEQ ID NO 27
<211> LENGTH: 39
<212> TYPE: DNA
<213> ORGANISM: bacteria

<400> SEQUENCE: 27
gatgcggtgc tcggggcggc tgtggacggt gccctgcac 39

<210> SEQ ID NO 28
<211> LENGTH: 39
<212> TYPE: DNA
<213> ORGANISM: bacteria

<400> SEQUENCE: 28
ctacgccacg agccccgccg acacctgcca cgggacgtg 39

-continued

<210> SEQ ID NO 29
<211> LENGTH: 7
<212> TYPE: PRT
<213> ORGANISM: bacteria

<400> SEQUENCE: 29

Val Leu Phe Ser Ser Ala Ala
1               5

<210> SEQ ID NO 30
<211> LENGTH: 7
<212> TYPE: PRT
<213> ORGANISM: bacteria

<400> SEQUENCE: 30

Val Leu Phe Ala Ala Ala Ala
1               5

<210> SEQ ID NO 31
<211> LENGTH: 41
<212> TYPE: DNA
<213> ORGANISM: bacteria

<400> SEQUENCE: 31
gtcggcgttc gtgctgttcg cagcggccgc cggggtcctg g 41

<210> SEQ ID NO 32
<211> LENGTH: 41
<212> TYPE: DNA
<213> ORGANISM: bacteria

<400> SEQUENCE: 32
cagccgcaag cacgacaagc gtcgccggcg gccccaggac c 41

<210> SEQ ID NO 33
<211> LENGTH: 23
<212> TYPE: DNA
<213> ORGANISM: bacteria

<400> SEQUENCE: 33
tactgcgcca cacggagccc gag 23

<210> SEQ ID NO 34
<211> LENGTH: 20
<212> TYPE: DNA
<213> ORGANISM: bacteria

<400> SEQUENCE: 34
tgggtaacgc cagggttttc 20

<210> SEQ ID NO 35
<211> LENGTH: 24
<212> TYPE: DNA
<213> ORGANISM: bacteria

<400> SEQUENCE: 35
ggaaacagct atgacatgat tacg 24

<210> SEQ ID NO 36
<211> LENGTH: 20
<212> TYPE: DNA
<213> ORGANISM: bacteria

<400> SEQUENCE: 36

-continued

```
tcggagccgc tccacctgag                                             20


<210> SEQ ID NO 37
<211> LENGTH: 20
<212> TYPE: DNA
<213> ORGANISM: bacteria

<400> SEQUENCE: 37

cctgatggac gcgggtgcgc                                             20


<210> SEQ ID NO 38
<211> LENGTH: 16
<212> TYPE: DNA
<213> ORGANISM: bacteria

<400> SEQUENCE: 38

gacaccgaaa cccctg                                                 16


<210> SEQ ID NO 39
<211> LENGTH: 20
<212> TYPE: DNA
<213> ORGANISM: bacteria

<400> SEQUENCE: 39

cctgatggac gcgggtgcgc                                             20


<210> SEQ ID NO 40
<211> LENGTH: 23
<212> TYPE: DNA
<213> ORGANISM: bacteria

<400> SEQUENCE: 40

gccgtgtgca ccacagcggt cag                                         23


<210> SEQ ID NO 41
<211> LENGTH: 28
<212> TYPE: DNA
<213> ORGANISM: bacteria

<400> SEQUENCE: 41

gtgtgatgtc gccgaccgcg cccaggtc                                    28


<210> SEQ ID NO 42
<211> LENGTH: 22
<212> TYPE: DNA
<213> ORGANISM: bacteria

<400> SEQUENCE: 42

gcgctggtgg gccagggcgt cc                                          22
```

CLONING GENES FROM *STREPTOMYCES CYANEOGRISEUS* SUBSP. *NONCYANOGENUS* FOR BIOSYNTHESIS OF ANTIBIOTICS AND METHODS OF USE

CROSS-REFERENCE TO RELATED U.S. APPLICATIONS

This nonprovisional application claims the benefit under 35 U.S.C. § 119(e) of U.S. Provisional Application No. 60/471,256, filed on May 16, 2003. The prior application is incorporated herein by reference in its entirety.

STATEMENT REGARDING FEDERALLY SPONSORED RESEARCH OR DEVELOPMENT

Not Applicable

BACKGROUND OF THE INVENTION

1. Field of the Invention

The present invention concerns the novel biosynthetic genes for encoding the proteins responsible for producing the LL-F28249 compounds and the use thereof to make the active metabolites from the fermentation of *Streptomyces cyaneogriseus* subsp. *noncyanogenus*. The invention further concerns the genetic manipulation of the biosynthetic pathway to make active semisynthetic derivatives of the natural metabolites.

2. Description of the Related Art

All patents and publications cited in this specification are hereby incorporated by reference in their entirety.

*Streptomyces* are producers of a wide variety of commercially important secondary metabolites, including the majority of active antibiotics known as the β-lactams and the macrocyclic lactone compounds or macrolides. Because of the commercial importance of the secondary metabolites produced by *Streptomyces*, there has been considerable recent investment in the development of methods for molecular genetic manipulation of *Streptomyces*. Procedures have been developed for the introduction of genetic material by polyethylene glycol mediated transformation and by conjugal transfer from *Escherichia coli*. Vectors have been developed including high and low copy number vectors, integrative vectors, and *E. coli-Streptomyces* shuttle vectors. These methods for molecular genetic manipulation of *Streptomyces* have been summarized in D. A. Hopwood et al., *Genetic Manipulation of Streptomyces. A Laboratory Manual*, John Innes Foundation Press, Norwich, UK (1985). In many cases, the genes for the production of secondary metabolites are clustered in *Streptomyces*. Thus, the identification of a single gene in a biosynthetic gene cluster may lead to the identification of all of the genes responsible for the biosynthesis of the metabolite. This observation has proven to be tremendously valuable, and secondary metabolite biosynthetic gene clusters have been cloned by reverse genetics, complementation of blocked mutants, resistance and use of heterologous probes. Using these methods, nucleotide and predicted amino acid sequence data have been obtained for many macrolide biosynthetic gene clusters including those directing the synthesis of erythromycin (see S. Donadio et al., Science 252:675-679 (1991) and S. F. Haydock et al., Molecular and General Genetics 230:120-128 (1991)); rapamycin (see T. Schwecke et al., Proceedings of the National Academy of Sciences USA 92:7839-7843 (1995) and X. Ruan et al., Gene 203:1-9 (1997)); FK506 (H. Motamedi and A. Shafiee, European Journal of Biochemistry 256:528-534 (1998)); oleandomycin (D. G. Swan et al., Molecular and General Genetics 242:358-362 (1994)) and rifamycin (see P. R. August et al., Chemistry & Biology 5:69-79 (1998)). However, the complete biosynthetic gene cluster for the macrocyclic lactone compounds known as the LL-F28249 compounds has not yet been described in the art.

There are many reports that molecular genetic manipulations can be used to alter the course of polyketide biosynthesis (see S. Donadio et al., Science 252:675-679 (1991) and S. Donadio et al., Proceedings of the National Academy of Sciences USA 90: 7119-7123 (1993)). In those studies, erythromycin-related lactones were produced following manipulation of the 6-deoxyerythronolide B synthase ("DEBS") gene cluster (the core polyketide synthase gene cluster responsible for erythromycin biosynthesis) such that either the module 4 enoylreductase or the module 5 ketoreductase domains were nonfunctional. Strains containing these variant DEBS gene clusters produced the expected erythromycin-related lactones. These pioneering studies have since been repeated and expanded upon, and the results of many such studies have been reviewed in the literature (see, for example, L. Katz and S. Donadio, Annual Reviews of Microbiology 47:875-912 (1993); C. R. Hutchinson and I. Fujii, Annual Reviews of Microbiology 49:201-238 (1995); D. A. Hopwood, Chemical Reviews 97:2465-2497 (1997); and C. W. Carreras and D. V. Santi, Current Opinions in Biotechnology 9:403-411 (1998)).

Data summarized in the literature suggest that the organization of catalytic domains in type I polyketide synthase ("PKS") modules is conserved, and many highly conserved amino acid sequence motifs have also been described in those biosynthetic gene clusters. For example, the organization of the biosynthetic gene cluster of avermectin, which is produced by *S. avermitilis*, has been reported (see D. J. MacNeil et al., Gene 115:119-125 (1992) and D. J. MacNeil et al., Annals of the New York Academy of Sciences 721:123-132 (1994)); and partial nucleotide sequences of that biosynthetic gene cluster have been reported or are otherwise available. MacNeil and colleagues have also predicted the modular organization and reported a limited restriction endonuclease map of the wild-type *S. cyaneogriseus* (NRRL 15773) nemadectin biosynthetic gene cluster (see D. J. MacNeil et al., Annals of the New York Academy of Sciences 721:123-132 (1994)), but their restriction map was incomplete. Their analysis only indicated the presence of nine modular repeats of PKS function and required six overlapping clones to define the 75 kb region of the *S. cyaneogriseus* genome. MacNeil et al. did not complete the DNA sequencing of the whole biosynthetic gene cluster. Instead, the authors sequenced only the ends of selected cosmids. From the limited sequence information, they could only generate a very sketchy restriction endonuclease map. Further C-13 labeling studies have been conducted, and a mechanism for synthesis of the LL-F28249α compound from its constituent acyl units has been proposed (H. R. Tsou et al., Journal of Antibiotics (Tokyo) 42:398-406 (1989)).

The highly active LL-F28249 compounds, which are natural endectocidal agents widely used for treatment of nematode and arthropod parasites, including the control or prevention of helmintic, arthropod ectoparasitic and acaridal infections, are isolated from the fermentation broth of *Streptomyces cyaneogriseus* subsp. *noncyanogenus* (hereinafter referred to as "*S. cyaneogriseus*"). The series of anti-parasitic LL-F28249 compounds produced from *S. cyaneogriseus* are structurally similar to, but patentably distinct from, the well-characterized avermectins. U.S. Pat. No. 5,106,994 and its continuation U.S. Pat. No. 5,169,956 describe the preparation of the major and minor components, LL-F28249α-λ. The LL-F28249 family of compounds further includes, but is not limited to, the semisynthetic 23-oxo derivatives and 23-imino derivatives of LL-F28249α-λ, which are shown in U.S. Pat. No. 4,916,154. Moxidectin, chemically known as 23-(O-methyloxime)-LL-F28249α, is a particularly potent 23-imino derivative. Other examples of LL-F28249 derivatives include, but are not limited to, 23-(O-methyloxime)-5-(phenoxyacetoxy)-LL-F28249α, 23-(semicarbazone)-LL-F28249α and 23-(thiosemicarbazone)-LL-F28249α.

One of the major nemadectin metabolites, LL-F28249α (hereinafter referred to as "Fα"), is converted to the commercially important compound moxidectin using a four-step chemical process. The determination of the biosynthetic gene cluster of Fα, heretofore unknown, would be of great commercial significance. Not only would isolation of the gene be highly desirable to make the active Fα compound and other natural members of the LL-F28249 family of compounds, but also to prepare the commercially potent semisynthetic derivatives such as moxidectin more quickly and efficiently.

It is therefore an important object of the present invention to isolate and characterize the entire nucleotide sequence encoding the proteins responsible for producing the LL-F28249 compounds, preferably the LL-F28249α metabolite, and then to isolate and determine the function of the amino acid sequences comprising the biosynthesis proteins.

Another object is to provide a new process for isolating natural and semisynthetic derivatives directly from the fermentation broth of bioengineered strains of *Streptomyces cyaneogriseus* subsp. *noncyanogenus.*

A further object is to provide a new method for the preparation of moxidectin in an efficient process with fewer steps than heretofore achievable.

Further purposes and objects of the present invention will appear as the specification proceeds.

The foregoing objects are accomplished by providing a new, purified and isolated nucleic acid molecule that encodes the proteins connected with the entire biosynthetic pathway for producing the LL-F28249 compounds.

BRIEF SUMMARY OF THE INVENTION

The present invention concerns the unique cloning and characterization of the complete biosynthetic pathway for the formation of the LL-F28249 compounds and, most importantly, the highly active, major component LL-F28249α. The full DNA gene cluster and its expression in a suitable host enable the efficient production of the highly active natural metabolites and semisynthetic derivatives. Remarkably, the whole biosynthetic pathway is efficiently contained in only three plasmids identified as Cosmid Numbers 11, 36 and 40 (hereinafter referred to as "Cos11," "Cos36" and "Cos40," respectively).

BRIEF DESCRIPTION OF THE DRAWINGS

The background of the invention and its departure from the art will be further described hereinbelow with reference to the accompanying drawings, wherein:

FIG. 6 to FIG. 6-39 show the full-length nucleotide sequence (88400 bp) of the biosynthetic genes for making the LL-F28249 compounds (which corresponds to SEQ ID NO:1).

FIG. 7 represents the putative amino acid sequence (922 aa) of the regulatory protein encoded by the ORF1 gene (which corresponds to SEQ ID NO:2).

FIG. 8 represents the putative amino acid sequence (259 aa) of the thioesterase protein encoded by the ORF2 gene (which corresponds to SEQ ID NO:3).

FIG. 9 represents the putative amino acid sequence (267 aa) of the reductase protein encoded by the ORF3 gene (which corresponds to SEQ ID NO:4).

FIG. 10 to FIG. 10-1 represent the putative amino acid sequence (2341 aa) of the loading domain protein for Mod1 encoded by the ORF4 gene (which corresponds to SEQ ID NO:5).

FIG. 11 to FIG. 11-2 represent the putative amino acid sequence (3723 aa) of the loading domain protein for Mod2-Mod3 encoded by the ORF5 gene (which corresponds to SEQ ID NO:6).

FIG. 12 to FIG. 12-3 represent the putative amino acid sequence (6043 aa) of the loading domain protein for Mod4-Mod7 encoded by the ORF6 gene (which corresponds to SEQ ID NO:7).

FIG. 13 represents the putative amino acid sequence (284 aa) of the methyltransferase protein encoded by the ORF7 gene (which corresponds to SEQ ID NO:8).

FIG. 14 represents the putative amino acid sequence (468 aa) of the p450 protein encoded by the ORF8 gene (which corresponds to SEQ ID NO:9).

FIG. 15 to FIG. 15-3 represent the putative amino acid sequence (5674 aa) of the loading domain protein for Mod8-Mod10 encoded by the ORF9 gene (which corresponds to SEQ ID NO:10).

FIG. 16 to FIG. 16-3 represent the putative amino acid sequence (5166 aa) of the loading domain protein for Mod 1'-Mod 13 encoded by the ORF10 gene (which corresponds to SEQ ID NO:11).

FIG. 17 represents the putative amino acid sequence (254 aa) of the oxidoreductase protein encoded by the ORF11 gene (which corresponds to SEQ ID NO:12).

DETAILED DESCRIPTION OF THE INVENTION

Figure 1:
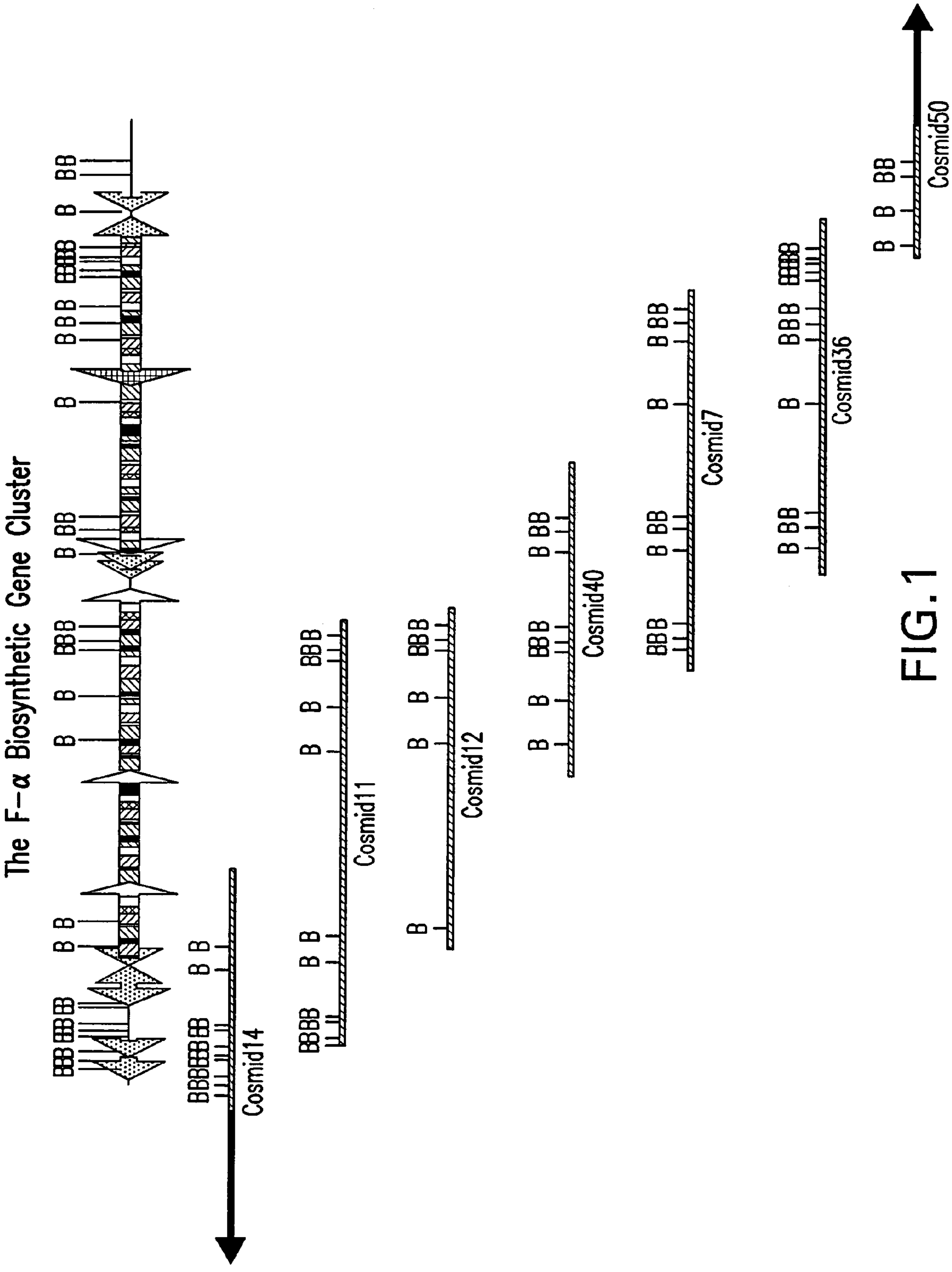
FIG. 1 illustrates the construction of the biosynthetic gene cluster for making the LL-F28249 compounds via the gene segments contained within cosmids made according to the present invention. *S. cyaneogriseus* cosmid libraries are constructed by ligating Sal3A fragments of *S. cyaneogriseus* genomic DNA into the BamH1 site of cosmid vector pSuperCos 1. The resultant cosmid libraries are transformed into *E. coli* VCS257. Various cosmids are identified by hybridization technique using the avermectin ketoacyl synthase probe or by a "walking" technique as described herein. The cosmids are characterized by restriction endonuclease mapping and DNA sequencing. The BamH1 restriction map of the Fα gene cluster is obtained from analyzing overlapping cosmids and confirmed by DNA sequencing. B denotes a BamH1 site.
Figure 2:
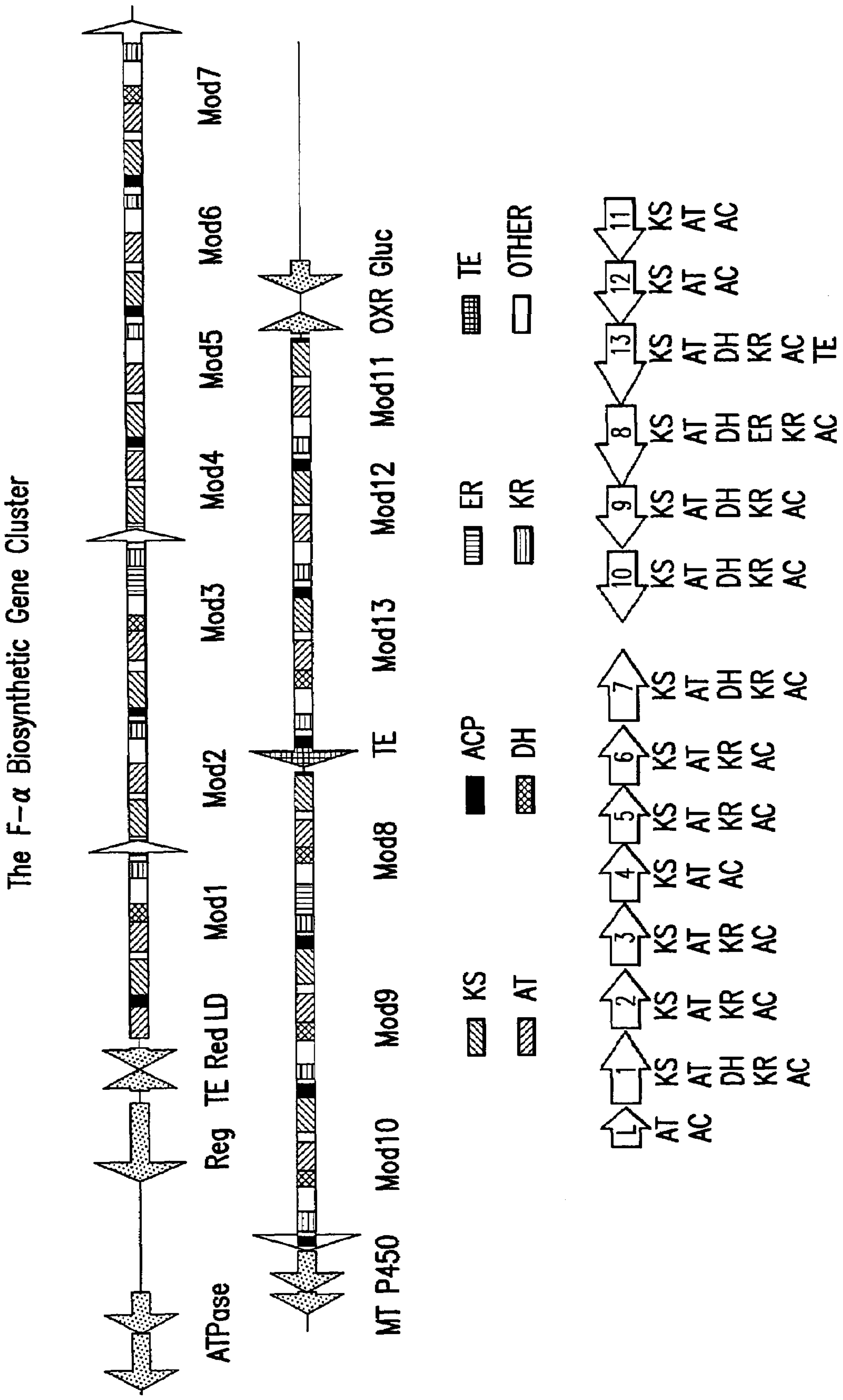
FIG. 2 illustrates the biosynthesis proteins and their positions encoded by the cloned biosynthetic gene cluster for making the LL-F28249 compounds. A contiguous nucleotide sequence of approximately 88 Kbp containing the entire Fα polyketide synthase gene cluster is obtained by sequencing overlapping cosmids and the subclones thereof. The 13 modules and respective domains are identified using BLAST alignment analysis. Other biosynthetic genes are identified in the same way. The following abbreviations are used in the figure: ACP, acyl carrier protein; DH, dehydratase; ER, enoylreductase; KR, ketoreductase; KS, ketoacyl synthase; LD, loading domain; TE, thioesterase; MT, methyl transferase; AT, acyl transferase.

In accordance with the present invention, there is provided a novel, purified and isolated nucleic acid molecule encoding the proteins of the entire biosynthetic pathway for producing the LL-F28249 compounds. The nucleic acid molecule of this invention is isolated from an antibiotic-producing wild-type or mutant *Streptomyces*. Surprisingly, the complete DNA for encoding all of the essential biosynthetic proteins is efficiently packaged in only three cosmids. These three cosmids, Cos11, Cos36 and Cos40, which have been constructed to contain the nucleic acid molecule according to the invention, are sufficient to regenerate the entire biosynthetic pathway for producing the LL-F28249 compounds. Thus, the present invention uniquely provides the entire biosynthetic gene cluster in three cosmids, as a preferred embodiment, which enables a substantially more efficient means for making the active anti-parasitic LL-F28249 compounds, particularly moxidectin, in fewer steps than previously contemplated. The success of this invention has overcome the prior failed attempts by others to isolate the full biosynthetic gene and satisfies a long-standing need.

The nucleotide sequence of this complete DNA gene cluster is fully described in FIG. 6 to FIG. 6-39 (which corresponds to SEQ ID NO:1). The scope of the invention also embraces its complementary strand, that is, those nucleotides that are the complement nucleotides (for example, A substituted for T, C substituted for G and vice versa) and/or reverse nucleotide sequences (i.e., a descending order instead of the forward or ascending strand, for example, changing the direction from reading 5' to the 3' end to reading 3' to the 5' end).

The present invention further includes the nucleic acid sequence that hybridizes to the sequence of the nucleic acid molecule of SEQ ID NO:1 isolated from the microbial source or its complementary strand and encodes a protein of the biosynthetic pathway for producing the LL-F28249 compounds. Typical hybridization procedures and conditions, which are well known to those of ordinary skill in the art, are illustrated in Sambrook et al., *Molecular Cloning: A Laboratory Manual, Second Edition*, Cold Spring Harbor Laboratory Press, Cold Spring Harbor, N.Y. (1989). While standard or stringent conditions are employed for homologous probes, less stringent hybridization conditions may be used for partially homologous probes that have less than 100% homology with the target nucleic acid sequence. In the latter case of partially homologous probes, a series of Southern and Northern hybridizations may be readily carried out at different stringencies. For instance, when hybridization is carried out in formamide-containing solvents, preferred conditions employ a temperature and ionic strength at a constant of about 42° C. with a solution containing 6×SSC, 50% formamide strength. Less stringent hybridization conditions may use the same temperature and ionic strength but less or lowering amounts of formamide in the annealing buffer at a range of about 45% to 0%. Alternatively, hybridization may be carried out in aqueous solutions containing no formamide. Usually for aqueous hybridization, the ionic strength of the solution is kept the same, often at about 1 M $Na^+$ while the temperature of annealing may be lowered from about 68° C. to 42° C.

In general, the isolation and characterization of the genomic DNA and the cloned, recombinant DNA from suitable host cells may be done via standard or stringent hybridization techniques, utilizing all or a portion of a nucleotide sequence as a probe to screen an appropriate library. As an alternative approach, oligonucleotide primers, which are constructed on the basis of other related, known DNA and protein sequences, can be used in polymerase chain reactions to amplify and identify other identical or related sequences. The nucleotides and proteins described herein are isolated and purified by routine methods to varying degrees. Preferably, the proteins are obtained in substantially pure form but a lower range of about 80% to about 90% pure is acceptable. It is contemplated that the scope of the invention also includes the DNA and proteins that are made by chemical synthesis, which have the same or substantially the same structures as those derived directly from the antibiotic-producing wild-type or mutant *Streptomyces* and are confirmed by routine testing or standard assays to be involved in the biosynthetic pathway of the LL-F28249 compounds.

Additionally, the invention encompasses and fully describes the isolated biosynthesis proteins comprising the amino acid sequences that include, but are not limited to, the regulatory protein encoded by the ORF1 gene (which corresponds to SEQ ID NO:2), the thioesterase protein encoded by the ORF2 gene (which corresponds to SEQ ID NO:3), the reductase protein encoded by the ORF3 gene (which corresponds to SEQ ID NO:4), the loading domain protein for Mod1 encoded by the ORF4 gene (which corresponds to SEQ ID NO:5), the loading domain protein for Mod2-Mod3 encoded by the ORF5 gene (which corresponds to SEQ ID NO:6), the loading domain protein for Mod4-Mod7 encoded by the ORF6 gene (which corresponds to SEQ ID NO:7), the methyltransferase protein encoded by the ORF7 gene (which corresponds to SEQ ID NO:8), the p450 protein encoded by the ORF8 gene (which corresponds to SEQ ID NO:9), the loading domain protein for Mod8-Mod10 encoded by the ORF9 gene (which corresponds to SEQ ID NO:10), the loading domain protein for Mod11-Mod13 encoded by the ORF10 gene (which corresponds to SEQ ID NO:11) and the oxidoreductase protein encoded by the ORF11 gene (which corresponds to SEQ ID NO:12).

The open reading frames of the genomic DNA cluster, which encode the biosynthesis proteins, may be identified using a variety of art-recognized techniques. The techniques include, but are not limited to, computer analysis to locate known start and stop codons, putative reading frame locations based on codon frequencies, similarity alignments to expressed genes in other known *Streptomyces* strains and the like. In this fashion, the proteins of the invention are identified using the nucleotide sequence of the present invention and the open reading frames or the encoded proteins may then be isolated and purified or, alternatively, synthesized by chemical means. Expressible genetic constructs based on the open reading frames and appropriate promoters, initiators, terminators and the like may be designed and introduced into a suitable host cell to express the protein encoded by the open reading frame.

As used herein, the term "proteins" means the polypeptides, the enzymes and the like, as those terms are commonly used in the art, which are encoded by the nucleic acid molecule comprising the biosynthetic pathway for producing the LL-F28249 compounds. The proteins of the invention encompass amino acid chains of varying length, including full-length, wherein the amino acid residues are linked by covalent peptide bonds, as well as the biologically active variants thereof. The proteins may be natural, recombinant or synthetic. For example, the biosynthesis proteins may be made through conventional recombinant technology by inserting a nucleotide sequence that encodes the protein into an appropriate expression vector and expressing the protein in a suitable host cell or through standard chemical synthesis by the Merrifield solid-phase synthesis method described in Merrifield, J. Am. Chem. Soc. 85:2149-2154 (1963), in which the amino acids are individually and sequentially attached to an amino acid chain. Alternatively, modern equipment is commercially available from a variety of manufacturers such as Perkin-Elmer, Inc. (Wellesley, Mass.) for the automated synthesis of proteins.

The biologically active variants that are included within the scope of the present invention comprise, at a minimum, the biologically functional portion of the amino acid sequence encoded by the nucleic acid molecule of the invention. As used herein, the "biologically functional portion" is that part of the protein structure which still retains the active function of the protein, for example, that part of the regulatory protein molecule encoded by the ORF1 gene which has the same or substantially the same activity and/or binding properties, i.e., at least about 90%, and more preferably, about 95%, similarities or potencies. The biologically active variants of the proteins include active amino acid structures having deleted, substituted or added amino acid residues, naturally occurring alleles, etc. The biologically functional portion may be easily identified by subjecting the full-length protein to chemical or enzymatic digestion to prepare fragments and then testing those fragments in standard assays to analyze which part of the amino acid structure retains the same or substantially the same biological activity as the full-length protein.

The determination of the full biosynthesis gene cluster of Fα, heretofore unknown, is of great commercial significance. The isolation and complete description of the gene according to the present methods permit the enhanced production of the active Fα compound and other natural members of the LL-F28249 family of compounds. Furthermore, the information about the gene enables an improved method for preparing the commercially potent semisynthetic derivatives such as moxidectin in a more quick and efficient fashion than the prior chemical process of manufacture. As a direct and beneficial consequence of the cloning and characterization the novel Fα biosynthesis gene cluster, which is described herein, unique processes for the direct fermentative production of moxidectin and other important LL-F28249 derivatives using bioengineered strains of *S. cyaneogriseus* are now obtainable.

One advantage of the present invention is the ability to enhance the production of the highly active Fα from the fermentation broth of *S. cyaneogriseus*. Cos11 contains a putative transcription activator gene (ORF1) for the PKS cluster. Increasing the expression level of the activator can result in a higher yield of Fα. This is achieved by increasing the copy number of the gene or by enhancing the regulatory sequence elements for this gene according to known techniques (see, for example, Perez-Llarena et al., Journal of Bacteriology 179:2053-2059 (1997)).

Another benefit derived from obtaining the full biosynthetic gene cluster of the present invention is to enable the efficient fermentative production and manufacture of the natural and semisynthetic derivatives of the LL-F28249 family of compounds such as, for example, LL-F28249α, LL-F28249β, LL-F28249γ, 23-(O-methyloxime)-LL-F28249α (moxidectin), 23-(O-methyloxime)-5-(phenoxyacetoxy)-LL-F28249α, 23-(semicarbazone)-LL-F28249α, 23-(thiosemicarbazone)-LL-F28249α, etc. Through the identification of the biosynthesis genes encoding the proteins responsible for the production of the LL-F28249 compounds and, desirably, the Fα metabolite as the major product, additional cloning and mutagenesis of the pathway readily produces other metabolites as by-products of the fermentation process. The biosynthesis genes are particularly useful to minimize the number of chemical reaction steps in preparing other semisynthetic members of the family.

The highly preferred utility of this invention involves the preparation of the commercially important compound moxidectin in fewer steps than previously done via known chemical processes. Moxidectin is currently produced by a four-step chemical process from Fα, which is first obtained by fermentation of *Streptomyces cyaneogriseus* subsp. *noncyanogenus*. The conversion of the natural metabolite Fα to moxidectin involves the following chemical reactions: (1) protection of the 5-hydroxyl group; (2) oxidation of the 23-hydroxyl group to a keto function; (3) conversion of the 23-keto to 23-O-methyloxime group; and (4) deprotection of the 5-hydroxyl group. The efficient method of the present invention now permits the chemical conversion of 23-keto Fα to moxidectin to be accomplished in a single step.

By generating mutants of the biosynthesis gene cluster, the specific activity responsible for reduction of the keto function at position 23 of the LL-F28249 compound structure is eliminated and the chemical synthesis is reduced to the one step. Surprisingly, the remainder of the modular polyketide synthase remains functional and the functional remainder of the polyketide synthase recognizes the unnatural polyketide intermediate. The unique bioengineered strain is then capable of being used, cloned and re-used for the direct fermentative production of 23-keto Fα further reducing the normal processing time.

In the below examples, selective mutagenesis illustrates how to modify Fα biosynthesis and to obtain the desired metabolites according to the present methods. Basically, mutants of the module 3 ketoreductase domain of the *S. cyaneogriseus* Fα biosynthetic gene cluster are generated by site-directed mutagenesis. These ketoreductase variants are designed by comparing the predicted amino acid sequence of the Fα module 3 ketoreductase domain to ketoreductase domains from a number of biologically active ketoreductase domains and several "cryptic" ketoreductase domains. The module 3 ketoreductase domain of the *S. cyaneogriseus* Fα biosynthetic gene cluster is then replaced with these variant domains by homologous recombination in order to alter Fα biosynthesis and obtain the desired metabolite.

Generally speaking, the site-directed mutagenesis introduces a small deletion or point mutation in the 23-keto (oxo) reductase gene (23-KR gene) to render the 23-ketoreductase domain nonfunctional while it retains the functions of other domains of the polyketide synthase. Mutations in the 23-KR gene are introduced by standard methods into a wild-type *Streptomyces cyaneogriseus* subsp. *noncyanogenus* strain or the mutant Fα production strain 142, resulting in the direct fermentative production of 23-keto (oxo) Fα. In addition, the whole Fα PKS gene cluster carrying mutations in the 23-KR gene may be introduced into a suitable host cell such as *S. lividans, S. coelicolor, E. coli* and the like to produce 23-keto Fα. The transformed host cells are used as the source of DNA for conjugal transfer to *S. cyaneogriseus* using methods described herein for the further fermentative production of 23-keto Fα.

The imino derivatives (23-oxime) of the 23-oxo compounds are then readily prepared by standard techniques such as procedures described by S. M. McElvain in The Characterization of Organic Compounds, published by MacMillian Company, New York, 1953, pages 204-205 and incorporated herein by reference. Typically, the 23-oxo compound is stirred in alcohol, such as methanol or ethanol, or dioxane in the presence of acetic acid and an excess of the amino derivatizing agent, such as hydroxylamine hydrochloride, O-methylhydroxylamine hydrochloride, semicarbazide hydrochloride and the like along with an equivalent amount of sodium acetate, at room temperature to about 50° C. The reaction is usually complete in several hours to several days at room temperature but can be readily speeded by heating. This subsequent conversion to moxidection via the 23-keto Fα compound is surprisingly and beneficially the only necessary chemical reaction to take place.

It is further contemplated that the genetic material contained within the three cosmids, Cos11, Cos36 and Cos40, may be reduced to fit into two plasmids or a single plasmid through genetic manipulations known to those of ordinary skill in the art. For example, the cloned Fα biosynthesis genes that are present in the Cos11, Cos36 and Cos40 prepared according to the methods of the present invention would be used to assemble the entire polyketide synthase (PKS) gene cluster on two plasmids or a single plasmid. The assembling can be achieved by use of cloning, PCR or synthetic genes, or a combination of any of these art-recognized techniques. The assembled Fα PKS gene cluster can be introduced into a suitable host cell such as *S. lividans, S. coelicolor, E. coli* and the like to produce Fα. Thereafter, the assembled PKS gene cluster can be used in a cell-free expression system such as, for example, a cell-free expression system described by Olsthoorn-Tieleman et al., Eur. J. Biochem. 268:3807-3815 (2001), to produce further amounts of Fα and related products.

Using the modular organization of the core LL-F28249α polyketide synthase and the functional domains within those modules, the biosynthesis gene cluster described herein is cloned and fully characterized. Generally, for the isolation of the biosynthetic genes, a cosmid library of *S. cyaneogriseus* genomic DNA is prepared in the commercially available vector pSuperCos (Stratagene, La Jolla, Calif.). This cosmid library is probed with fragments of DNA corresponding to the avermectin module 1 ketoacyl synthase, which has been amplified from *S. avermitilis* genomic DNA using the polymerase chain reaction. Subsequently, several regions of the Fα biosynthetic gene cluster, which have been amplified from previously characterized cosmids using the polymerase chain reaction, are used as probes to isolate additional cosmids. Using these methods, a series of cosmids are isolated that collectively span over 100 Kbp of genomic DNA. Complete restriction endonuclease mapping and thorough nucleotide sequence analysis identify the cosmids and result in a definitive, unambiguous contiguous nucleotide sequence spanning nearly 88 Kbp. Analysis of this nucleotide sequence reveals the presence of 13 complete modules of a modular polyketide synthase together with at least six additional genes involved in the biosynthesis or in the regulation of the biosynthesis of Fα.

The invention further embraces biologically functional plasmids or vectors containing the nucleic acid molecule of the present invention. The particular plasmids of the invention are selected for their ability to incorporate large DNA gene clusters but they are conventional and are derived from commonly available vectors, for example, pKR0.9, the pFDmod3/5.2 series, the pFDmod3/4.2 series and the like.

Although *E. coli* is used as the heterologous host in the examples, the heterologous expression of antibiotic biosynthetic genes is expected in a wide number of *Actinomycetales, Bacillus, Corynebacteria, Thermoactinomyces* and the like so long as they are capable of being transformed with the relatively large plasmid constructs described herein. Those that are transformed include, but are not limited to, *Streptomyces lividans, Streptomyces coelicolor, Streptomyces griseofuscus* and *Streptomyces ambofaciens*, which are known to be relatively non-restricting. Preferably, the suitable host cell that is stably transformed or transfected by the plasmid or vector is *Streptomyces coelicolor* or an *Escherichia coli-Streptomyces* cosmid vehicle. In vitro expression of the proteins may be performed, if desirable, using standard art methods.

The following section highlights general methods and materials, available to those of ordinary skill in the art, which have been used to successfully clone and characterize the entire, large biosynthetic pathway of the present invention.

General Methods and Materials

A. Materials Plasmids and Bacterial Strains

An *E. coli-Streptomyces* shuttle vector that contains elements required for replication and selection in *E. coli* and in *Streptomyces*, including antibiotic resistance markers for selection with apramycin, pKC1132, is used throughout this work (see M. Bierman et al., Gene 116:43-49 (1992)). In addition to pKC1132, commercially available cloning vectors are used as indicated herein. Those of ordinary skill in the art will be able to select other well known cloning vectors, which can readily be substituted for the exemplified vectors, and avoid or minimize instability problems encountered with certain older strains of the cosmid-harboring *E. coli* using standard techniques.

Plasmid DNA is manipulated using procedures similar to those established by work on other plasmids. Typical procedures are presented in Sambrook et al., *Molecular Cloning: A Laboratory Manual, Second Edition*, Cold Spring Harbor Laboratory Press, Cold Spring Harbor, N.Y. (1989). Typical procedures for *Streptomyces* are presented in D. A. Hopwood et al., *Genetic Manipulation of Streptomyces, A Laboratory Manual*, John Innes Foundation Press, Norwich, UK (1985). Specific methods used in this work are described herein unless they are identical to methods presented in the above-referenced laboratory manuals.

*E. coli* JM109 and DH5α, common laboratory strains used throughout this work, are readily available from a number of commercial sources (for example, Stratagene, La Jolla, Calif.). *E. coli* XL1-Blue MRF' strain is obtained from Stratagene (La Jolla, Calif.). *E. coli* ETS12567 (pUZ8002) is obtained from Professor Heinz Floss, of the Department of Chemistry, University of Washington (Seattle, Wash.). *E. coli* VCS257 is obtained from Stratagene (La Jolla, Calif.). *S. avermitilis* is obtained from the American Type Culture Collection under ATCC Deposit Accession No. 31,267 but it can also be obtained from the Agricultural Research Culture Collection (NRRL), 1815 N. University Street, Peoria, Ill. 61604, under NRRL 8165. “Wild-type” *Streptomyces cyaneogriseus* subsp. *noncyanogenus* LL-F28249 (NRRL 15773) and the mutant Fα production strain of *S. cyaneogriseus* designated “*S. cyaneogriseus* strain 142” are used separately throughout this written disclosure of the present invention but they are interchangeable and may substitute for each other in any given step of the disclosed process. Strain 142, which is derived from the wild-type strain, has undergone classic genetic manipulations to enhance antibiotic production but it retains the same polyketide synthase DNA sequence as the wild-type strain. Because their polyketide synthase sequences are identical, all of the plasmids described herein, including but not limited to Cos11, Cos36 and Cos40, can be derived from wild-type *Streptomyces cyaneogriseus* subsp. *noncyanogenus* or *S. cyaneogriseus* strain 142 with the same result.

B. Restriction Analysis of Plasmid DNA

Procedures for restriction analysis of plasmid DNA, procedures for agarose gel electrophoresis, and other standard techniques of recombinant DNA technology are described in Sambrook et al., *Molecular Cloning: A Laboratory Manual, Second Edition*, Cold Spring Harbor Laboratory Press, Cold Spring Harbor, N.Y. (1989). Plasmid DNA is digested with restriction endonucleases according to the manufacturer's procedures. Enzymes are obtained from New England Biolabs (Beverly, Mass.), Life Technologies (Rockville, Md.) or Promega (Madison, Wis.). Restriction digests are analyzed by electrophoresis in 0.8% w/v agarose using 40 mM tris-acetate, 1 mM EDTA as a buffer. The size of the fragments is determined by comparison to DNA fragments of known molecular weight (1 Kb ladder, Life Technologies, Rockville, Md.).

C. Preparation of Hybridization Probes

Hybridization probes are isolated from plasmids following restriction digestion or are generated using the polymerase chain reaction as described herein. Probes are radiolabeled to high specific radioactivity using EasyTides™ $\alpha^{32}$ P-dCTP (3000 Ci/mmol) from New England Nuclear (Boston, Mass.) and the rediprime™ II random prime labeling system from Amersham Pharmacia Biotech (Piscataway, N.J.) according to procedures provided by the manufacturer.

Hybridization probes are used to identify cosmids containing the Fα biosynthetic gene cluster (from both *S. cyaneogriseus* strain 142 and wild-type *S. cyaneogriseus* cosmid libraries), to confirm and characterize transconjugants and excisants, and to facilitate the generation of accurate restriction maps of the Fα biosynthetic gene cluster that confirm the identity of the gene. These hybridization probes are either generated by PCR amplification or the probes are excised from clones as summarized in the following Table 1.

TABLE 1

| Probe | PCR Primer Sequence or Restriction Sites | Use |
|---|---|---|
| Avermectin KS1 | F: GCCGAATTCCTTCGGCATCAGCCCC<br>R: GCTCGCACCGTCCTGGTTGACCGC | To Isolate Cosmids Containing the Fα Biosynthetic Gene Cluster (*S. cyaneogriseus* strain 142) |
| NE5.7 | 5.7 Kbp NotI/EcoRI Fragment of Cos7 | To Isolate Cosmids Containing the Fα Biosynthetic Gene Cluster (wild-type *S. cyaneogriseus*) (Contains Fα Module 3) |
| Apramycin | 750 bp SacI Fragment of pKC1132 | To Confirm and Characterize Transconjugants |
| Mod3 | F: GACAACGTCGGTCCGG<br>R: CGCGGTGACTCGCTTGAGGTATTC | To Confirm and Characterize Transconjugants, and in Restriction Mapping |
| Thioesterase | F: GCTTCACCGACCCCTCGGCTATGACC<br>R: GTGAAGTGGTTGCCGTCGGTTTCGAGG | To Restriction Map the Right End of the Fα Biosynthetic Gene Cluster |
| p450 | F: GATGACGTGCTCACCGATGTCGGTGAGC<br>R: GACGTGGAAATCATGTACAGCTCGTACG | To Restriction Map the Right End of the Fα Biosynthetic Gene Cluster |
| Cos36 (end) | 500 bp NotI Fragment of Cos36 | To Restriction Map the Right End of the Fα Biosynthetic Gene Cluster |
| Cos12 (end) | 1.1 Kbp BamHI/EcoRI Fragment of Cos12 | To Restriction Map the Left End of the Fα Biosynthetic Gene Cluster |
| B5.5 | 5.5 Kbp BamHI Fragment of Cos11 | To Restriction Map the Left End of the Fα Biosynthetic Gene Cluster, and To Isolate Cosmids Containing the Fα Biosynthetic Gene Cluster (wild-type *S. cyaneogriseus*) |

Isolation, Maintenance and Propagation of Plasmids

A. Plasmid Isolation

*E. coli* strains, both untransformed and those transformed with vectors as described herein, are grown using well-established methods similar to those described in Sambrook et al., *Molecular Cloning: A Laboratory Manual, Second Edition*, Cold Spring Harbor Laboratory Press, Cold Spring Harbor, N.Y. (1989).

Plasmid DNA is isolated from *E. coli* cultures using reagents and materials obtained from QIAGEN (Valencia, Calif.). Depending on the numbers of strains being analyzed, the miniprep plasmid isolation systems used included the QIAprep® Spin Miniprep Kits (for plasmid isolation from relatively small numbers of strains); the QIAprep® 8 Turbo Miniprep Kits (for higher-throughput plasmid isolation from somewhat larger numbers of strains); or the QIAprep® 96 Turbo Miniprep Kits (for partially automated isolation of plasmids from strains in 96-well blocks). For the isolation of larger quantities of plasmid DNA from *E. coli*, reagents and materials included in the QIAGEN Plasmid Midi (up to 100 μg) and Maxi (up to 500 μg) kits, or reagents and materials included in the Nucleobond AX-100 (up to 100 μg) kit from Clontech (Palo Alto, Calif.) are used.

B. Transformation of *Escherichia coli* by Plasmid DNA

Plasmid DNA is transformed into electrocompetent *E. coli* strains by electroporation or into chemically competent *E. coli* strains by heat shock using well-established procedures similar to those described in Sambrook et al., *Molecular Cloning: A Laboratory Manual, Second Edition*, Cold Spring Harbor Laboratory Press, Cold Spring Harbor, N.Y. (1989).

Transformants are selected using appropriate antibiotics, and after plasmids are isolated using methods described herein, they are characterized following digestion with restriction endonucleases, again using well-established methods described in Sambrook et al., *Molecular Cloning: A Laboratory Manual, Second Edition*, Cold Spring Harbor Laboratory Press, Cold Spring Harbor, N.Y. (1989).

C. Conjugal Transfer of Plasmid DNA from *Escherichia coli* to *Streptomyces cyaneogriseus*

In all cases, the plasmids of interest are first transformed into the *E. coli* strain designated ETS12567 (pUZ8002) by electroporation as described herein. This strain is $cm^r$, $tet^r$, $dam^-$, and $dcm^{-1}$. Additionally, pUZ8002, which is an $oriT^-$ version of the plasmid pRK2 (see R. Meyer et al., Science 190:1226-1228 (1975)), confers $kan^r$. The transformed cells are maintained in the presence of appropriate antibiotic selection, including 5 µg/ml kanamycin and 100 µg/ml apramycin. The conjugal transfer of plasmid DNA from these *E. coli* transformants to *S. cyaneogriseus* is accomplished using the following procedures, both of which are modified from a procedure described by M. Bierman et al., Gene 116: 43-49 (1992).

Conjugation Method #1: A 3 ml LB media supplemented with 5 µg/ml kanamycin, 5 µg/ml chloramphenicol, 50 µg/ml apramycin is inoculated with a single well-isolated transformed *E. coli* colony, and the culture is incubated at 37° C., with shaking at 220 rpm, for 16 hours. 10 ml TSB (27.5 g/L tryptic soy broth, 5 g/L yeast extract, 5 g/L $KH_2PO_4$, pH 7.0, 100 ml/L of a sterile solution of 20% (w/v) glucose added after autoclaving) media is inoculated with 100 µl of a frozen stock of *S. cyaneogriseus* mycelial fragments, and the culture is incubated at 31° C., with shaking at 220 rpm, for 16 hours. The next day, 10 ml LB media supplemented with 50 µg/ml apramycin is inoculated with a 100 µl aliquot of the overnight *E. coli* culture. At the same time, a 2 ml aliquot of the *S. cyaneogriseus* overnight culture is vortexed in a tube containing sterile glass beads for 2 minutes. The suspension is sonicated (3×, 5 second bursts at 100% output); and 1 ml of this suspension of mycelial fragments is transferred to 9 ml of TSB (27.5 g/L tryptic soy broth, 5 g/L yeast extract, 5 g/L $KH_2PO_4$, pH 7.0, 100 ml/L of a sterile solution of 20% (w/v) glucose added after autoclaving). Both cultures are incubated at 37° C., with shaking at 220 rpm, until the absorbance at 600 nm of the *E. coli* culture reached 0.4-0.6. The cells in each culture are collected by centrifugation, washed 2× with LB, and suspended in 500 µl 2XYT (16 g/L tryptone, 10 g/L yeast extract, 5 g/L NaCl, pH 7.0). Aliquots (100 µl) of the two preparations are combined; the mixture is incubated at 50° C. for 5 minutes; and the cells are collected by centrifugation. The supernatant is removed, and the cell pellet is suspended in 100 ml of 2XYT (16 g/L tryptone, 10 g/L yeast extract, 5 g/L NaCl, pH 7.0), and plated onto SFM (25 g/L soybean flour nutrisoy, 25 g/L mannitol, 20 g/L agar, 0.462 g/L L-cysteine, 0.462 g/L L-arginine, 0.462 g/L L-proline) plates. These plates are incubated at 37° C. for 16 hours, and then overlaid with 1 ml of sterile water containing 0.5 mg of nalidixic acid and 1 mg of apramycin (final concentrations 20 µg/ml and 40 µg/ml, respectively). The plates are incubated at 37° C. until colonies are well established.

Conjugation Method #2: 3 ml LB media supplemented with 5 µg/ml kanamycin, 5 µg/ml chloramphenicol, 100 µg/ml apramycin is inoculated with a single well-isolated transformed *E. coli* colony, and the culture is incubated at 37° C., with shaking at 220 rpm, for 16 hours. 25 ml KB3 medium (10 g/L Bacto-tryptone, 5 g/L yeast extract, 3 g/L beef extract, 1 g/L $KH_2PO_4$, 1 g/L $K_2HPO_4$, 1.5 g/L Difco agar, pH 6.8, and 0.5 ml/L of a trace metal solution containing 30 g/L $FeSO_4$, 30 g/L $ZnSO_4.7H_2O$, 4 g/L $MnSO_4$, 4 g/L $CuCl_2.5H_2O$, 0.4 g/L $CoCl_2.6H_2O$) is inoculated with 1 ml of a frozen stock of *S. cyaneogriseus*, and the culture is incubated at 31° C., with shaking at 220 rpm, for 16 hours. The next day, 1 ml of the overnight *E. coli* culture is combined with 9 ml of LB supplemented with 50 µg/ml apramycin. At the same time, a 5 ml aliquot of the *S. cyaneogriseus* overnight culture is vortexed in a tube containing sterile glass beads for 2 minutes. A 2.5 ml aliquot of the homogenized culture is inoculated into 25 ml of KB3 medium (10 g/L Bacto-tryptone, 5 g/L yeast extract, 3 g/L beef extract, 1 g/L $KH_2PO_4$, 1 g/L $K_2HPO_4$, 1.5 g/L Difco agar, pH 6.8 and 0.5 ml/L of a trace metal solution containing 30 g/L $FeSO_4$, 30 g/L $ZnSO_4.7H_2O$, 4 g/L $MnSO_4$, 4 g/L $CuCl_2.5H_2O$, 0.4 g/L $CoCl_2.6H_2O$), and both cultures are incubated at 37° C. for 3 hours. The cells in each culture are collected by centrifugation, and washed 2× with water. The *E. coli* and *S. cyaneogriseus* cell pellets are suspended in 1 ml and 2 ml, respectively, of TSB (27.5 g/L tryptic soy broth, 5 g/L yeast extract, 5 g/L $KH_2PO_4$, pH 7.0, 100 ml/L of a sterile solution of 20% (w/v) glucose added after autoclaving). 10 µl of the *S. cyaneogriseus* suspension, and 100 µl of the *E. coli* suspension are combined with 890 µl of TSB (27.5 g/L tryptic soy broth, 5 g/L yeast extract, 5 g/L $KH_2PO_4$, pH 7.0, 100 ml/L of a sterile solution of 20% (w/v) glucose added after autoclaving), and 100 µl of the mixture is plated onto AS-1 plates (1 g/L yeast extract, 0.2 g/L L-alanine, 0.2 g/L L-arginine, 0.5 g/L L-asparagine, 5 g/L soluble starch, 2.5 g/L NaCl, 10 g/L $Na_2SO_4$, 20 g/L agar, pH 7.5) supplemented with 10 mM $MgCl_2$. These plates are incubated at 37° C. for 16 hours, and then overlaid with 3 ml of R2 agar (100 g/L sucrose, 10 g/L glucose, 10 g/L $MgCl_2$, 0.25 g/L $K_2SO_4$, 0.1 g/L casamino acids, 25 g/L agar). At use, the following solutions are added to each 80 ml flask of R2 agar: 1 ml of 0.5% $K_2HPO_4$; 8 ml of 3.68% $CaCl_2.2H_2O$; 1.5 ml of 20% L-proline; 10 ml of 5.73% TES, pH 7.2; 0.5 ml of 1N NaOH; and 1 ml of a trace elements solution containing 40 mg/L $ZnCl_2$, 200 mg/L $FeCl_3.6H_2O$, 10 mg/L $CuCl_2.2H_2O$, 10 mg/L $MnCl_2.4H_2O$, 10 mg/L $Na_2B_4O_7.10H_2O$, 10 mg/L $(NH_4)_6Mo_7O_{24}.4H_2O$). The solution is also supplemented to 100 µg/ml apramycin and 100 µg/ml nalidixic acid (final concentrations). The plates are incubated at 37° C. until colonies are well established.

Using either method, putative transconjugants are repetitively picked onto fresh plates, in the presence of 100 µg/ml apramycin and 100 µg/ml nalidixic acid until cured of visible contamination by the *E. coli* strain used as the source of the plasmid.

The purified DNA derived from *Streptomyces cyaneogriseus* subsp. *noncyanogenus*, which encodes the entire biosynthetic pathway for the production of the LL-F28249 compounds, has been deposited in connection with the present patent application under the conditions mandated by 37 C.F.R. § 1.808 and maintained pursuant to the Budapest Treaty in the American Type Culture Collection (ATCC), 10801 University Boulevard, Manassas, Va. 20110-2209, U.S.A. More specifically, the purified cosmid DNA, described herein fully and identified as Cos11, Cos36 and Cos40, was deposited in the ATCC on May 24, 2002 and assigned ATCC Patent Deposit Designation Numbers PTA-4392, PTA-4393 and PTA-4394, respectively. It should be appreciated that related purified DNA, other cosmids or plasmids containing related nucleotide sequences, which may be readily constructed using site-directed mutagenesis and the techniques described herein, are also encompassed within the scope of the present invention.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

A further understanding of the invention may be obtained from the non-limiting examples that follow below.

EXAMPLE 1

Characterization of the Biosynthetic Gene Cluster for Making LL-F28249 Compounds A. Isolation and Characterization of Cosmids Containing the Fα Biosynthetic Gene Cluster 1. Construction of *Streptomyces cyaneogriseus* Cosmid Libraries Genomic DNA was isolated from *S. cyaneogriseus* (both wild-type and the Fα production strain designated 142) using a method presented in D. A. Hopwood et al., *Genetic Manipulation of Streptomyces, A Laboratory Manual*, John Innes Foundation Press, Norwich, UK (1985) ("Isolation of *Streptomyces* "Total" DNA: Procedure 3). The *S. cyaneogriseus* genomic DNA preparation was subjected to partial restriction endonuclease digestion with Sau3AI as follows. A reaction mixture was prepared containing Sau3AI and genomic DNA, and at time points (0, 5, 10, 15, 20, 30, and 45 minutes) aliquots were removed and the reactions were quenched by the addition of EDTA to a final concentration of 10 mM. A portion of each quenched reaction time point was resolved by electrophoresis through 0.3% w/v agarose at 25 volts for 16 hours. The reaction time point containing DNA fragments that were predominantly between 23 Kbp and 50 Kbp was selected for the cosmid library. At the same time, pSuperCos 1 (Stratagene, La Jolla, Calif.) was digested with the restriction endonuclease XbaI; dephosphorylated using calf intestine alkaline phosphatase; and after ethanol precipitation, the linear vector was digested with the restriction endonuclease BamHI in order to remove one of the Cos sites. The Sau3AI fragments of *S. cyaneogriseus* genomic DNA were ligated into linearized, BamHI treated pSuperCos 1 according to procedures provided by the manufacturer. The resultant recombinant cosmid DNA preparation was packaged using Gigapack® III XL Packaging Extract, and after lysis of the resultant lambda phage particles with chloroform, the cosmid DNA library was transformed into *E. coli* VCS257. These manipulations were all conducted using reagents, materials, and procedures provided by the manufacturer (Stratagene, La Jolla, Calif.).

2. Isolation of Cosmids Containing the Fα Biosynthetic Gene Cluster

Genomic DNA was isolated from *S. avermitilis* using a method presented in D. A. Hopwood et al., *Genetic Manipulation of Streptomyces, A Laboratory Manual*, John Innes Foundation Press, Norwich, UK (1985) ("Isolation of *Streptomyces* "Total" DNA: Procedure 3). This genomic DNA preparation was used as a template for amplification of a region of the module 1 ketoacyl synthase domain of the avermectin biosynthetic gene cluster using the polymerase chain reaction. The oligonucleotide primers used were designed on the basis of nucleotide sequences of the avermectin biosynthetic gene cluster that have been deposited into public databases. Colony lifts of the *S. cyaneogriseus* strain 142 cosmid library were screened for hybridization to the avermectin ketoacyl synthase probe, and more than 30 cosmids potentially containing type I polyketide synthase DNA were isolated. Initially, these cosmids were analyzed following digestion with BamHI, by agarose gel electrophoresis, by Southern blot using the avermectin module 1 ketoacyl synthase probe, and by limited nucleotide sequence analysis. Comparison of these data to data reported by MacNeil and colleagues (see D. J. MacNeil et al., Gene 115:119-125 (1992) and D. J. MacNeil et al., Annals of the New York Academy of Sciences 721:123-132 (1994)) suggested that two of these cosmids (designated Cos7 and Cos11) appeared to span the majority of the Fα biosynthetic gene cluster. The limited data presented by MacNeil and his colleagues were also used as the initial basis to support the isolation of a 5.7 Kbp NotI-EcoRI fragment that included most of module 3. A clone of this 5.7 Kbp NotI-EcoRI fragment was prepared (designated pNE57). The nucleotide sequence of this 5.7 Kbp fragment was determined in its entirety. This fragment of the Fα biosynthetic gene cluster (from genomic DNA isolated from the Fα production strain) was then used as a probe to screen the wild-type *S. cyaneogriseus* cosmid library and 45 cosmids potentially containing type I polyketide synthase DNA were isolated. These cosmids were extensively mapped with BamHI, NotI, and EcoRI using methods described herein, and on the basis of comparison of those restriction maps to the incomplete data presented by MacNeil and his colleagues, two cosmids (designated Cos36 and Cos40 from the wild-type strain), that appeared to span the majority of the Fα biosynthetic gene cluster, were identified.

In order to identify cosmids spanning the "ends" of the Fα biosynthetic gene cluster, but not containing significant stretches of core polyketide synthase DNA, the following strategy was employed. A 5.5 Kbp BamHI fragment isolated from Cos11 (from *S. cyaneogriseus* strain 142) was used to reprobe the wild-type *S. cyaneogriseus* cosmids that had been selected previously in order to identify additional cosmids that would extend the cluster to the "left." A number of cosmids were identified that hybridized to the probe, and after restriction mapping, one of these, Cos14, was identified that would support extending the cluster the furthest to the left. A 500 bp NotI fragment isolated from the 3' end of Cos36 was used to reprobe the wild-type *S. cyaneogriseus* cosmid library in order to identify additional cosmids that would extend the cluster to the "right." A number of additional cosmids were identified that hybridized to the probe, and after restriction mapping, one of these, Cos50, was identified that would support extending the cluster the furthest to the "right."

3. Restriction Mapping Cosmids Containing the Fα Biosynthetic Gene Cluster

Initially, more than 30 cosmids from the *S. cyaneogriseus* strain 142 cosmid library that hybridized to the avermectin ketoacyl synthase probe, and 45 cosmids from the wild-type *S. cyaneogriseus* cosmid library that hybridized to the Fα module 3 probe (pNE57), were mapped following digestion with BamHI, NotI, and EcoRI. On the basis of this preliminary analysis, and on the basis of comparison of the restriction maps to the incomplete data presented by MacNeil and his colleagues (see D. J. MacNeil et al., Gene 115:119-125 (1992) and D. J. MacNeil et al., Annals of the New York Academy of Sciences 721:123-132 (1994)), several cosmids were selected for more comprehensive analysis. These cosmids (designated Cos7 and Cos11 from *S. cyaneogriseus* strain 142; and Cos12, Cos14, Cos36, Cos40 and Cos50 from wild-type *S. cyaneogriseus*) were carefully mapped following digestion with BamHI, NotI, and EcoRI and double-digestion with BamHI/MluI, NotI/EcoRI, BamHI/EcoRI, SacI/EcoRI, and NotI/MluI. To resolve ambiguity in the restriction maps that were observed, subclones of these cosmids were constructed as summarized in the following Table 2, and these subclones were extensively mapped as described above.

TABLE 2

| Designation | Subcloned from: | Vector | Restriction Sites/Size |
|---|---|---|---|
| pB5.5 | Cos11 | pZeroBlunt | BamHI/5.5 Kbp |
| pB18.0 | Cos11 | pUC19 | BamHI/18.0 Kbp |
| PBE15.0 | Cos12 | pBluescript KS | BamHI/EcoRI/ 15.0 Kbp |
| pB2.5 | Cos14 | pBluescript KS | BamHI/2.5 Kbp |
| pB5.5 | Cos14 | PZeroBlunt | BamHI/5.5 Kbp |
| pBB14.0 | Cos14 | pBluescript KS | BamHI/BglII/14.0 Kbp |
| PM14.0 | Cos14 | pLitmus38 | MluI/14.0 Kbp |
| PN2.0 | Cos14 | pBluescript KS | NotI/2.0 Kbp |
| PN4.3 | Cos14 | pBluescript KS | NotI/4.3 Kbp |
| pS1.45 | Cos14 | pBluescript KS | SacI/1.45 Kbp |
| pS8.2 | Cos14 | pBluescript KS | SacI/8.2 Kbp |
| pS2.0 | Cos14 | pLitmus38 | SphI/2.0 |
| pB11.5 | Cos36 | pBluescript KS | BamHI/11.5 Kbp |
| PBE4.8 | Cos36 | pBluescript KS | BamHI/EcoRI/4.8 Kbp |
| PM4.6 | Cos36 | pLitmus38 | MluI 4.6 Kbp |
| PN1.6 | Cos36 | pBluescript KS | NotI/1.6 Kbp |
| PN4.8 | Cos36 | pBluescript KS | NotI/4.8 Kbp |
| PBE5.3 | Cos40 | pBluescript KS | BamHI/EcoRI/5.3 Kbp |
| PN5.2 | Cos50 | pBluescript KS | NotI/5.2 Kbp |
| PN10.0 | Cos50 | pBluescript KS | NotI/10.0 Kbp |
| pS3.3 | Cos50 | pBluescript KS | SacI/3.3 Kbp |

B. Nucleotide Sequence of the Fα Biosynthetic Gene Cluster

1. Sequencing Strategy

The vast majority of the nucleotide sequence data was obtained by end-sequencing random, size selected sublibraries of cosmid DNA that were prepared as described herein. Random sublibraries were sequenced until sufficient coverage (8-10× redundancy) should have existed over the entire fragment of DNA. In order to obtain nucleotide sequence data for regions of the biosynthetic gene cluster that were under-represented in the random sublibraries, or that for other reasons were difficult to sequence, two other sequencing strategies were used. In the first, products were generated using the polymerase chain reaction in such a way as to span the region of interest of the gene cluster. These PCR products were sequenced directly using the PCR primers as sequencing primers, or the products were cloned into the commercially available PCR product cloning vector pTOPO TA (Invitrogen, Carlsbad, Calif.), and sequenced using universal primers. Alternatively, sequencing primers were synthesized which facilitated obtaining nucleotide sequence by "walking" through regions of interest on cosmids or subclones prepared from the cosmids. Throughout, nucleotide sequence was obtained on Applied Biosystems Model 377 Automated sequencers, using ABI PRISM® BigDye™ Terminator Cycle Sequencing Ready Reaction reagents and materials according to detailed procedures provided by the manufacturer (Applied Biosystems, a Division of Perkin Elmer, Foster City, Calif.). Nucleotide sequence data was collected and analyzed using standard "Collection" and "Sequencing Analysis" algorithms (Applied Biosystems, a Division of Perkin Elmer, Foster City, Calif.). Nucleotide sequence assemblies were generated using the SeqMan™ II sequence analysis package that is commercially available from DNASTAR (Madison, Wis.), and using the custom Finch™-300 Assembly Server developed for us by Geospiza (Seattle, Wash.).

Two cosmids (designated Cos36 and Cos40) that appeared on the basis of extensive restriction mapping to span the majority of the Fα biosynthetic gene cluster were isolated from the wild-type *S. cyaneogriseus* cosmid library. These cosmids were sequenced in their entirety by end-sequencing random, size selected sublibraries that were prepared as described herein. In addition, random, size selected sublibraries prepared from the inserts in several subclones (as summarized in the following Table 3) were also sequenced. Finally, the majority of the subclones generated to support comprehensive restriction mapping of the Fα biosynthetic gene cluster were end-sequenced using universal primers.

TABLE 3

| Designation | Subcloned from Cosmid | Restriction Sites/Size |
|---|---|---|
| pNE57 (*S. cyaneogriseus* strain 142) | Cos7 | NotI-EcoRI/5.7 Kbp |
| pNE57 (wild-type *S. cyaneogriseus*) | Cos40 | NotI-EcoRI/5.7 Kbp |
| pB5.5 | Cos14 | BamHI/5.5 Kbp |
| pN4.3 | Cos14 | NotI/4.3 Kbp |
| pN10.0 | Cos50 | NotI/10.0 Kbp |
| pS8.2 | Cos14 | SacI/8.2 Kbp |

2. Construction of Sublibraries for Nucleotide Sequence Analysis

To generate large quantities of the inserts present in cosmids and in the subclones derived from those cosmids, large quantities of plasmid DNA were required. Media (typically 1 L) were inoculated with the clone of interest, and incubated at 37° C. overnight. Plasmid (cosmid) DNA was isolated from these cultures using materials and reagents included in the QIAGEN Plasmid Midi (up to 100 μg) and Maxi (up to 500 μg) kits, or reagents and materials included in the Nucleobond AX-100 (up to 100 μg) kit from Clontech (Palo Alto, Calif.). The inserts present in these plasmids (cosmids) were excised by digestion with appropriate restriction endonucleases, and the fragments were resolved by electrophoresis through 0.8% w/v agarose. The desired fragments were excised from these gels, and the DNA contained in those bands was isolated using reagents, materials, and procedures included in the QIAEX II® (for fragments larger than 10 Kbp) or QIAquick II (for fragments smaller than 10 Kbp) Gel Extraction Systems from QIAGEN (Valencia, Calif.). Then, the DNA was randomly sheared by sonication using a Microson cell disrupter at 10% output. Sonication times were optimized in order to generate fragments of the desired size (typically about 18 seconds for larger inserts isolated from cosmids, and about eight seconds for the smaller fragments isolated from plasmid subclones of those cosmids). Following ethanol precipitation, the DNA fragments were "blunted" using T4 DNA polymerase (New England Biolabs, Beverly, Mass.) in 25 μl reaction volumes containing 2.5 μl of 10×T4 DNA polymerase reaction buffer, 1 μl of 25 μg/ml BSA, and 1.5 μl of T4 DNA polymerase. The reaction mixtures were incubated at 16° C. for 20 minutes, and resolved by electrophoresis through 0.8% w/v agarose. The region of the gel containing DNA between 1.5 Kbp and 2.5 Kbp (by comparison to DNA fragments of known molecular weight) was excised, and the DNA was extracted from the agarose using reagents, materials, and procedures included in the QIAquick II Gel Extraction System from QIAGEN (Valencia, Calif.). Purified DNA was collected by ethanol precipitation and resuspended in 8 μl of water. These DNA fragments were then cloned into pCR®-Blunt, and the ligated products were transformed into chemically competent *E. coli* TOP10 using reagents, materials and procedures provided by the manufacturer (Invitrogen, Carlsbad, Calif.). Colonies were picked and used to inoculate 2 ml LB media supplemented with 50 μg/ml kanamycin, in 96-well deep well blocks. Plasmid DNA was purified from each of these cultures using reagents, materials and procedures included in QIAprep® 96 Turbo Miniprep Kits. Although the frequency of clones with insert generally exceeded 90%, each plasmid was digested with EcoRI and the fragments were resolved by electrophoresis through 0.8% w/v agarose in order to determine whether an insert of the desired size was present. Clones that did contain desired inserts were sequenced using universal sequencing primers as described herein.

3. Identification of Biosynthetic Modules and Domains Within Modules

Many modular polyketide biosynthetic gene clusters have been characterized and manipulated. In addition, a large number of nucleotide sequences of modular polyketide biosynthetic gene clusters have been deposited in the public databases. In general, modules of modular polyketide biosynthetic gene clusters, and the domains within those modules can be identified by performing BLAST searches against the public databases, and extensive use of those public databases was made to facilitate the present analysis of the Fα biosynthetic gene cluster (see S. F. Altschul et al., Nucleic Acids Research 25:3389-3402 (1997)). In addition, use of a recent literature reference that summarizes methods for identification of modular polyketide synthase domains, that in particular, describes the differentiation of malonyl-class from methylmalonyl-class acyltransferase domains was employed (S. J. Kakavas et al., Journal of Bacteriology 179:7515-7522 (1997). Leadlay and colleagues originally described methods for differentiation of malonyl-class from methylmalonyl-class acyltransferase domains (see T. Schwecke et al., Proceedings of the National Academy of Sciences USA 92:7839-7843 (1995)).

A description of five open reading frames, which together encode the loading domain and the 13 modules of the polyketide synthase, is illustrated in the below Table 4. For each open reading frame, the position in the Fα biosynthetic gene cluster (in nucleotides) and the length (in amino acids) of the predicted gene product are shown. In addition, the approximate location of each biosynthetic domain within that predicted gene product (again in amino acids) is also displayed. Abbreviations used are as follows: ACP, acyl carrier protein; ATm, malonyl-class acyltransferase; ATmm, methylmalonyl-class acyltransferase; DH, dehydratase; ER, enoylreductase; KR, ketoreductase; KS, ketoacyl synthase; LD, loading domain; TE, thioesterase.

TABLE 4

| | |
|---|---|
| ORF4: nt 12850-19875 (2341 aa) Designation: Loading Domain-Mod1 | |
| ATmm-LD | aa 22-350 |
| ACP-LD | aa 365-450 |
| KS-1 | aa 473-897 |
| ATmm-1 | aa 1006-1339 |
| DH-1 | aa 1359-1547 |
| KR-1 | aa 1865-2052 |
| ACP-1 | aa 2137-2223 |
| ORF5: nt 19865-31036 (3723 aa) Designation: Mod2-Mod3 | |
| KS-2 | aa 34-466 |
| ATmm-2 | aa 574-908 |
| KR-2 | aa 1211-1391 |
| ACP-2 | aa 1473-1559 |
| KS-3 | aa 1578-2005 |
| ATm-3 | aa 2136-2476 |
| DH-3 | aa 2486-2667 |
| ER-3 | aa 2925-3279 |
| KR-3 | aa 3287-3466 |
| ACP-3 | aa 3556-3640 |
| ORF6: nt 31115-49246 (6043 aa) Designation: Mod4-Mod7 | |
| KS-4 | aa 34-456 |
| ATm-4 | aa 582-907 |
| ACP-4 | aa 950-1031 |
| KS-5 | aa 1055-1481 |
| ATm-5 | aa 1613-1938 |
| KR-5 | aa 2247-2427 |
| ACP-5 | aa 2516-2601 |
| KS-6 | aa 2621-3047 |
| ATm-6 | aa 3168-3493 |
| KR-6 | aa 3802-3983 |
| ACP-6 | aa 4078-4164 |
| KS-7 | aa 4189-4615 |
| ATmm-7 | aa 4727-5056 |
| DH-7 | aa 5078-5257 |
| KR-7 | aa 5588-5768 |
| ACP-7 | aa 5868-5952 |
| ORF9: nt 52809-69833 (5674 aa) Designation: Mod8-Mod10 | |
| KS-8 | aa 39-465 |
| ATmm | aa 574-904 |
| DH-8 | aa 926-1106 |
| ER-8 | aa 1366-1718 |
| KR-8 | aa 1726-1908 |
| ACP-8 | aa 1995-2080 |
| KS-9 | aa 2102-2529 |
| ATm-9 | aa 2661-2986 |
| DH-9 | aa 3009-3188 |
| KR-9 | aa 3492-3674 |
| ACP-9 | aa 3753-3842 |
| KS-10 | aa 3864-4290 |
| ATmm-10 | aa 4402-4732 |
| DH-10 | aa 4753-4928 |
| KR-10 | aa 5234-5416 |
| ACP-10 | aa 5499-5586 |
| ORF10: nt 69929-85429 (5166 aa) Designation: Mod11-Mod13 | |
| KS-11 | aa 34-456 |
| ATm-11 | aa 578-916 |
| KR-11 | aa 1199-1380 |
| ACP-11 | aa 1464-1549 |
| KS-12 | aa 1570-1996 |
| ATmm-12 | aa 2105-2442 |
| KR-12 | aa 2724-2906 |
| ACP-12 | aa 2992-3076 |
| KS-13 | aa 3096-3519 |
| ATm-13 | aa 3631-3975 |
| DH-13 | aa 4003-4188 |
| KR-13 | aa 4505-4687 |
| ACP-13 | aa 4780-4866 |
| TE-13 | aa 4893-5167 |

4. Identification of Other Biosynthetic Pathway Genes

Whether the other open reading frames that were found to be clustered with the core modular polyketide synthase genes played a role in Fα biosynthesis, and if so, what that role might be was based on a BLAST comparison of the nucleotide and predicted amino acid sequences of these open reading frames to sequences that have been deposited in the public databases cluster (see S. F. Altschul et al., Nucleic Acids Research 25:3389-3402 (1997)). Using those methods, a tentative identification of at least six other genes that could be involved in Fα biosynthesis was made.

A description of six additional open reading frames, which encode genes that could be involved in Fα biosynthesis, is illustrated in the below Table 5. For each open reading frame, the position in the Fα biosynthetic gene cluster (in nucleotides) and the length (in amino acids) of the predicted gene product are shown. In addition, a brief description of the BLAST results used to assign a putative functional role in Fα biosynthesis, is also included here for each of the open reading frames.

TABLE 5

| |
|---|
| ORFA: nt 382-2514 (711 aa) |
| Designation: $K^+$-Translocating ATPase, Subunit B (Not related to Fα Biosynthetic Gene Cluster) |
| ORFB: nt 2511-4175 (555 aa) |
| Designation: $K^+$-Translocating ATPase, Subunit A (Not related to Fα Biosynthetic Gene Cluster) |
| ORF1: nt 7697-10465 (922 aa) |
| Designation: Regulatory Protein |
| ORF2: nt 10791-11570 (259 aa) |
| Designation: Thioesterase |
| ORF3: nt 11659-12462 (267 aa) |
| Designation: Reductase |
| ORF7: nt 50449-51303 (284 aa) |
| Designation: Methyltransferase |
| ORF8: nt 51300-52706 (468 aa) |
| Designation: p450 |
| ORF11: nt 85574-86338 (254 aa) |
| Designation: Oxidoreductase |
| ORFX: nt 87037-88293 (419 aa) |
| Designation: Endo-1,3-β-glucosidase (Not related to Fα Biosynthetic Gene Cluster) |

ORFA and ORFB: BLAST results reveal considerable homology between ORFA and ORFB and $K^+$-translocating ATPase subunits B and A, respectively, particularly the *Mycobacterium tuberculosis* genes (nucleotide sequences of which were directly submitted to the public databases). These genes are unrelated to the Fα biosynthetic gene cluster.

ORF1: BLAST results suggest that at the nucleotide level, ORF1 is related to a putative transcriptional activator in the pikCD operon of a macrolide biosynthetic gene cluster from *S. venezuelae* (see Y. Xue et al., Proceedings of the National Academy of Sciences USA 95:12111-12116 (1998)), and a putative regulatory protein in a Type-I polyketide synthase biosynthetic gene cluster from the rapamycin producing organism, *S. hygroscopicus* (see X. Ruan et al., Gene 203: 1-9 (1997)). At the predicted amino acid sequence level, the gene product exhibits limited homology to a family of hypothetical transcriptional activators related to the *E. coli* narL gene product. On the basis of these BLAST results, ORF1 appears to encode a transcriptional activator.

ORF2: BLAST results reveal significant homology between ORF2 and thioesterases at both the nucleotide and predicted amino acid sequence levels, including thioesterases in the *Amycolatopsis mediterranei* rifamycin biosynthetic gene cluster (see P. R. August et al., Chemistry & Biology 5:69-79 (1998)), and the *S. griseus* candicidin biosynthetic gene cluster (see L. M. Criado et al., Gene 126:135-139 (1993)). On the basis of these BLAST results, ORF2 appears to encode a thioesterase.

ORF3: An analysis of BLAST results suggests that ORF3 is homologous to reductases in the *S. cyanogenus* S136 landomycin biosynthetic gene cluster (see L. Westrich et al., FEMS Microbiological Letters 170:381-387 (1999)). At the predicted amino acid sequence level, BLAST results reveal homology between the ORF3 gene product and an oxidoreductase responsible for the conversion of versicolorin A to sterigmatocystin in the *Aspergillus parasiticus* aflatoxin biosynthetic pathway (see C. D. Skory et al., Applied and Environmental Microbiology 58:3527-3537 (1992)). On the basis of these BLAST results, ORF3 appears to encode a reductase.

ORF7: BLAST results reveal significant homology between ORF7 and methyltransferases at the nucleotide level, including methyltransferases in the *S. lavendulae* mitomycin C biosynthetic gene cluster (see Y. Q. Mao et al., Chemistry & Biology 6:251-263 (1999) and the *Saccharopolyspora erythraea* erythromycin biosynthetic gene cluster (see S. F. Haydock et al., Molecular and General Genetics 230:120-128 (1991)). On the basis of these BLAST results, ORF7 appears to encode a methyltransferase.

ORF8: BLAST results reveal limited homology between ORF8 and putative cytochrome P450's, including P450's in the *S. roseofulvus* frenolicin biosynthetic gene cluster and the *S. pristinaespiralis* pristinamycin biosynthetic gene cluster (see V. de Crecy-Lagard et al., Journal of Bacteriology 179: 705-713 (1997)). At the predicted amino acid sequence level, ORF8 exhibits homology to a large family of mammalian cytochrome P450's. On the basis of these BLAST results, ORF8 appears to encode a cytochrome P450.

ORF11: BLAST results reveal significant homology between ORF11 and oxidoreductases at both the nucleotide and predicted amino acid sequence levels, including oxidoreductases in the *S. violaceoruber* granaticin biosynthetic gene cluster (D. H. Sherman et al., EMBO Journal 8:2717-2725, (1989)), and the *S. cinnamonensis* monensin biosynthetic gene cluster (see T. J. Arrowsmith et al., Molecular and General genetics 234:254-264 (1992)). On the basis of these BLAST results, ORF11 appears to encode an oxidoreductase.

ORFX: BLAST results reveal homology between ORFX and a glucan endo-1,3-β-glucosidase from *Oerskovia xanthineolytica* (see S. H. Shen et al., Journal of Biological Chemistry 266:1058-1063 (1991)). This gene is unrelated to the Fα biosynthetic gene cluster.

There are several open reading frames in the 3.5 Kbp region between characterized ORFB and ORF1, which on the basis of nucleotide sequence characteristics (G+C content, potential ribosome binding sites) appear to encode proteins. BLAST analysis, however, does not reveal significant homology between the predicted amino acid sequences of these hypothetical proteins and sequences of proteins that have been deposited in public databases. Consequently, ascribing a functional role to these hypothetical proteins in the biosynthesis of Fα is not possible on the basis of their nucleotide (or predicted amino acid) sequence alone. In addition, there are a number of open reading frames in the 7.8 Kbp region between characterized ORFX and the end of the nucleotide sequence that have now been obtained. Since ORFX encodes a gene that does not appear to play a role in Fα biosynthesis, and since macrolide biosynthetic genes are typically clustered, hypothetical proteins encoded by the open reading frames beyond ORFX do not participate in Fα biosynthesis.

EXAMPLE 2

Gene Replacement, Characterization of Integrants and Excisants

A. Gene Replacement

In order to develop an *S. cyaneogriseus* strain capable of direct fermentative production of 23-keto-Fα, generating derivatives of the Fα production strain in which the module 3 ketoreductase domain had been replaced with nonfunctional variants were sought. A series of directed amino acid substitutions, each designed to disrupt ketoreductase activity while minimally affecting the rest of the polyketide synthase were designed as follows. A multiple amino acid sequence alignment was generated in which the predicted amino acid sequence of the module 3 ketoreductase domain from the *S. cyaneogriseus* Fα biosynthetic gene cluster was aligned with the predicted amino acid sequences of a large number of biologically active ketoreductase domains. These ketoreductase domain sequences were from the *S. avermitilis* avermectin biosynthetic gene cluster, the *Saccharopolyspora erythreae* erythromycin biosynthetic gene cluster, the *S. hygroscopicus* rapamycin biosynthetic gene cluster, the *S. caelestis* niddamycin biosynthetic gene cluster, and the *Amycolatopsis mediterranei* rifamycin biosynthetic gene cluster. Three ketoreductase domains known to be nonfunctional (so-called "cryptic" ketoreductase domains from module 3 of the *Saccharopolyspora erythreae* erythromycin biosynthetic gene cluster, module 4 of the *S. caelestis* niddamycin biosynthetic gene cluster, and module 3 of the *Amycolatopsis mediterranei* rifamycin biosynthetic gene cluster) were also included in the sequence alignment. This multiple amino acid sequence alignment readily supported the identification of relatively invariant amino acid sequences common to the majority of biologically active ketoreductase domains, but absent from (or altered in) nonfunctional ketoreductase domains.

Methods were also developed for gene replacement in *S. cyaneogriseus* by homologous recombination such that the desired variants of the module 3 ketoreductase domain from the Fα biosynthetic gene cluster could be replaced with the engineered variants of the module 3 ketoreductase domain, as described herein.

1. Construction of Plasmids for Site-directed Mutagenesis

Figure 3:
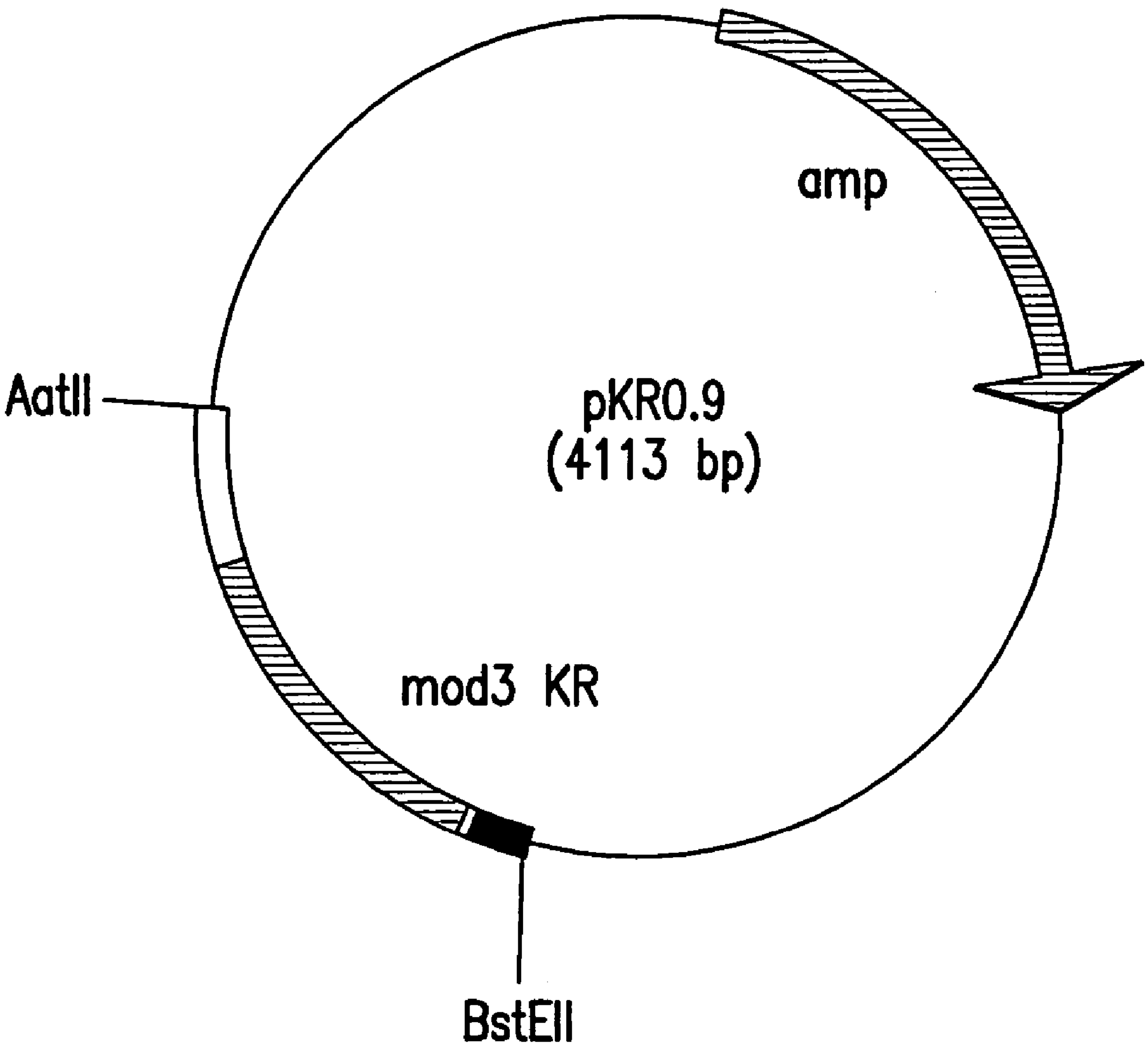
FIG. 3 shows the structure of the components of the vector designated pKR0.9, which is the 900 bp BstEII-AatII fragment of pNE57 (and contains the desired region of the Fα module 3 ketoreductase domain), in the BstEII-AatII sites of pSL301 (Invitrogen, Carlsbad, Calif.). The following abbreviations are used in the figure: mod3 KR, Fα module 3 ketoreductase domain; amp, the ampicillin resistance marker.

The QuikChange™ site-directed mutagenesis procedure is a double-stranded method based on the polymerase chain reaction that requires two mutagenic oligonucleotides, one corresponding to each strand of the double stranded region of DNA. The method is less efficient when large plasmids, particularly large plasmids containing high G+C content DNA, are used. Consequently, site-directed mutagenesis of the Fα module 3 ketoreductase domain was performed in a vector designated pKR0.9 (see FIG. 3), which is the 900 bp BstEII-AatII fragment of pNE57 (and contains the desired region of the Fα module 3 ketoreductase domain), in the BstEII-AatII sites of pSL301 (Invitrogen, Carlsbad, Calif.).

2. Site-Directed Mutagenesis

Five variants of the Fα module 3 ketoreductase domain were generated by site-directed mutagenesis using reagents, materials and procedures provided by the manufacturer of the QuikChange™ Site-Directed Mutagenesis kit (Stratagene, La Jolla, Calif.). The following amino acid substitutions were generated in pKR0.9, using the mutagenic oligonucleotides indicated below:

```
"179" GGTGTLG (SEQ ID NO:13) to GAASTLG (SEQ ID NO:14)
   5'-CTGGTGACGGGCGCTGCAAGCACTCTGGGGGCG             (SEQ ID NO:15)
   3'-GACCACTGCCCGCGACGTTCGTGAGACCCCCGC             (SEQ ID NO:16)
"204" LVSRRGM (SEQ ID NO:17) to LVAAAGM (SEQ ID NO:18)
   5'-GCGGCATCTGCTGCTGGTGGCAGCGGCAGGCATGGCCGCCGCCGGTG (SEQ ID NO:19)
   3'-CGCCGTAGACGACGACCACCGTCGCCGTCCGTACCGGCGGCGGCCAC (SEQ ID NO:20)
"260" HTAGVLD (SEQ ID NO:21) to HTPPLLD (SEQ ID NO:22)
   5'-GACCGCTGTGGTGCACACGCCACCTCTCCTGGACGACGCCACCGTG  (SEQ ID NO:23)
   3'-CTGGCGACACCACGTGTGCGGTGGAGAGGACCTGCTGCGGTGGCAC  (SEQ ID NO:24)
"283" GAKVD (SEQ ID NO:25) to GAAVD (SEQ ID NO:26)
   5'-GATGCGGTGCTCGGGGCGGCTGTGGACGGTGCCCTGCAC         (SEQ ID NO:27)
   3'-CTACGCCACGAGCCCCGCCGACACCTGCCACGGGACGTG         (SEQ ID NO:28)
"306" VLFSSAA (SEQ ID NO:29) to VLFAAAA (SEQ ID NO:30)
   5'-GTCGGCGTTCGTGCTGTTCGCAGCGGCCGCCGGGGTCCTGG       (SEQ ID NO:31)
   3'-CAGCCGCAAGCACGACAAGCGTCGCCGGCGGCCCCAGGACC       (SEQ ID NO:32)
```

The QuickChange™ mutagenesis reactions contained 125 ng of each of the mutagenic oligonucleotides, 50 ng of pKR0.9, 0.7 µl of Pfu DNA polymerase, and 2.5% DMSO in final reaction volumes of 50 µl. The reactions were subjected to 22 cycles of amplification (95° C. for 45 seconds, 63° C. for 1 minute, and 70° C. for 10 minutes), and amplified products were cloned according to detailed procedures provided by the manufacturer. After completing the site-directed mutagenesis procedure, colonies were picked and used to inoculate 2 ml LB media supplemented with 100 µg/ml carbenicillin. Plasmid DNA was purified from each of these cultures using reagents, materials and procedures included in the QIAprep® 8 Turbo Miniprep Kits, and the mutated 900 bp BstEII-AatII region of the Fα module 3 ketoreductase domain was sequenced in its entirety in order to confirm that the desired changes had been made.

3. Construction of Plasmids for Integration

Figure 5:
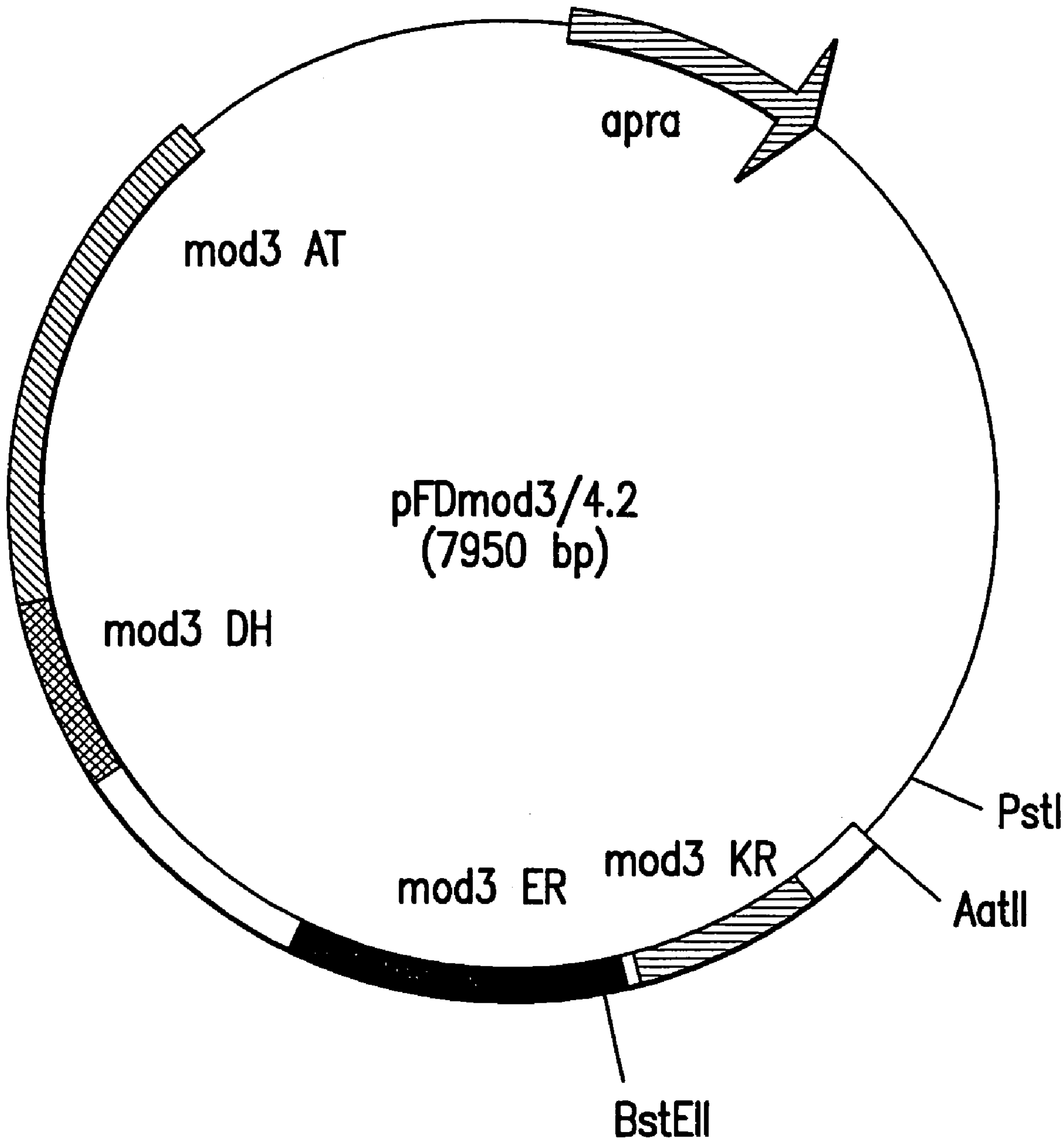
FIG. 5 shows the structure of the plasmid components of the pFDmod3/4.2 series. These plasmids are derived from the pFDmod3/4.2 series by removing approximately 1 Kbp of flanking DNA to minimize aberrant integration. The following abbreviations are used in the figure: mod3 AT, module 3 acyl transferase; mod3 DH, module 3 dehydratase; mod 3 ER, module 3 enoylreductase; mod3 KR, module 3 ketoreductase domain; apra, apramycin resistance marker.

A three-way ligation was used to combine the five site-directed mutants of the Fα module 3 ketoreductase domain with flanking DNA to facilitate homologous integration using the pKC1132 backbone. The three components included: the 4.3 Kbp NotI-BstEII fragment of pNE57 (containing the majority of the Fα module 3 adjacent to the regions mutagenized); the 1.1 Kbp BstEII-PstI fragments of six pKR0.9 constructs (containing the five site-directed mutants of the Fα module 3 ketoreductase domain, and the wild-type Fα module 3 ketoreductase domain); and the 3.6 Kbp PstI-NotI fragment of pKC1132 (containing all of the elements necessary for selection and replication of the resultant plasmid in *E. coli* and *Streptomyces*). These manipulations resulted in the generation of the pFDmod3/5.2 plasmid series. These plasmids were then used to construct versions of the plasmids for integration from which approximately 1 Kbp of flanking DNA had been removed. These plasmids were constructed by digesting each of the pFDmod3/5.2 plasmids with EcoRI. This EcoRI site is immediately adjacent to the NotI site in pKC1132 that was used to introduce the 4.3 Kbp NotI-BstEII fragment of pNE57 (containing the majority of the Fα module 3). The 3' overhang was filled in using T4 DNA polymerase under standard reaction conditions, and the linearized plasmids were digested with MscI. The digests were resolved by electrophoresis through 0.8% w/v agarose, the desired fragments were excised from the gel, and the DNA was extracted from the agarose using reagents, materials and procedures included in the QIAquick II Gel Extraction System from QIAGEN (Valencia, Calif.). Purified DNA was collected by ethanol precipitation and ligated to generate the pFDmod3/4.2 plasmid series (see FIG. 5).

Figure 4:
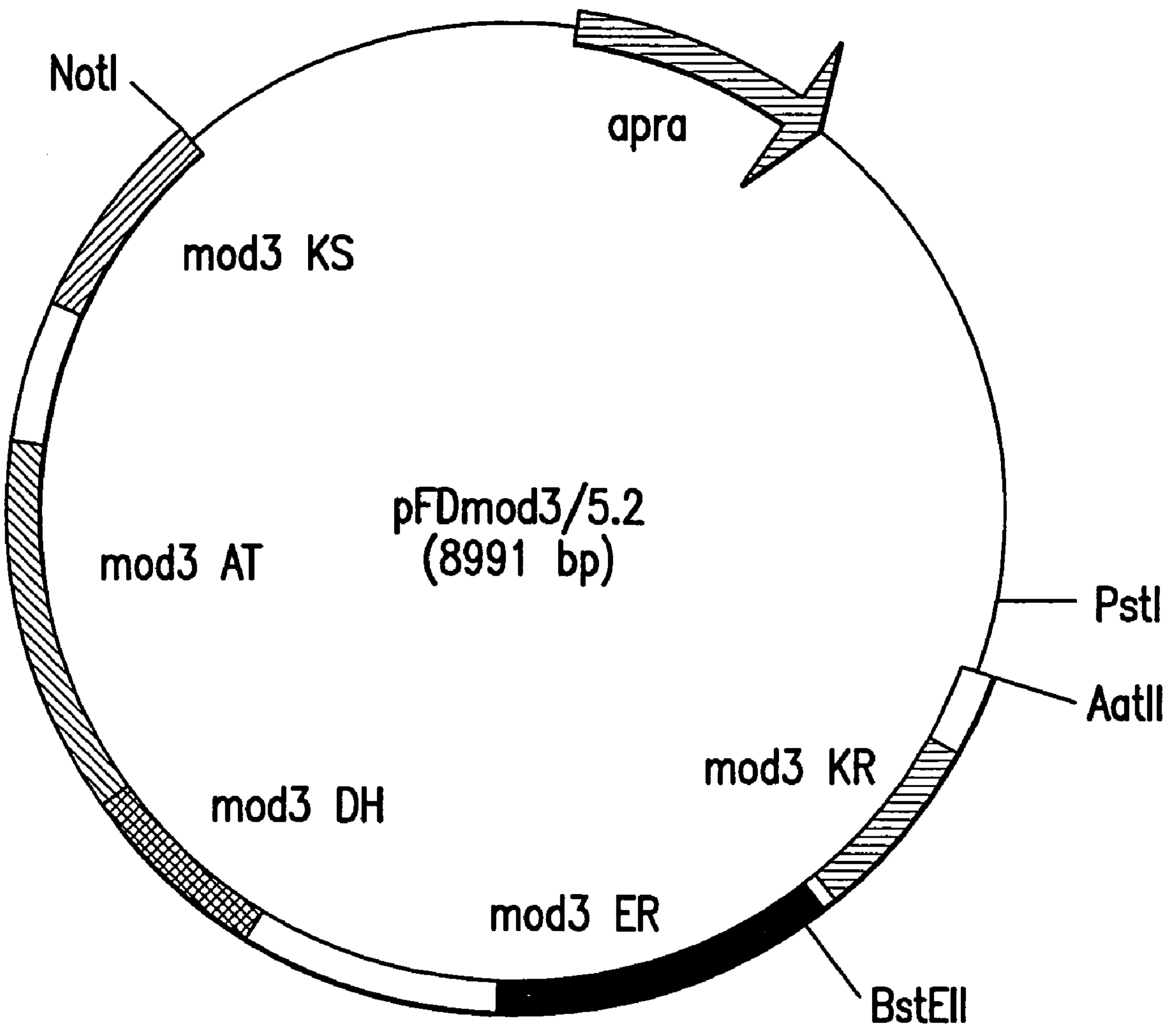
FIG. 4 shows the structure of the plasmid components of the pFDmod3/5.2 series. These plasmids are constructed to combine the site-directed mutations of the Fα module 3 ketoreductase domain with flanking DNA to facilitate homologous integration. The backbone vector is *E. coli-Streptomycin* shuttle vector pKC1132. The following abbreviations are used in the figure: mod3 KS, module 3 ketoacyl synthase domain; mod3 AT, module 3 acyl transferase; mod3 DH, module 3 dehydratase; mod 3 ER, module 3 enoylreductase; mod3 KR, module 3 ketoreductase domain; apra, apramycin resistance marker.

Plasmids of the pFDmod3/5.2 series (see FIG. 4) and the pFDmod3/4.2 series (see FIG. 5) were transformed into *E. coli* ETS12567 (pUZ8002) using methods described herein. Then, these transformed *E. coli* strains were used as the source of DNA for conjugal transfer to *S. cyaneogriseus* using methods described herein.

4. Isolation and Analysis of Genomic DNA from *S. cyaneogriseus* Transconjugants and Excisants A method modified from methods presented in D. A. Hopwood et al., *Genetic Manipulation of Streptomyces, A Laboratory Manual*, John Innes Foundation Press, Norwich, UK (1985) ("Isolation of *Streptomyces* "Total" DNA": Procedure 4) was used for the isolation of small amounts of genomic DNA from *S. cyaneogriseus* strains. Putative *S. cyaneogriseus* transconjugants and excisants were picked and used to inoculate 3 ml KB3 medium (10 g/L Bacto-tryptone, 5 g/L yeast extract, 3 g/L beef extract, 1 g/L $KH_2PO_4$, 1 g/L $K_2HPO_4$, 1.5 g/L Difco agar, pH 6.8 and 0.5 ml/L of a trace metal solution containing 30 g/L $FeSO_4$, 30 g/L $ZnSO_4.7H_2O$, 4 g/L $MnSO_4$, 4 g/L $CuCl_2.5H_2O$, 0.4 g/L $CoCl_26H_2O$). The cultures were incubated at 31° C., with shaking at 220 rpm, for 24-28 hours. The cells in 500 μl aliquots of these cultures were collected by centrifugation in a microfuge at 13,000 rpm for 5 minutes, and the supernatant was discarded. After washing the cell pellets with water, they were suspended in 450 μl of SET (0.3 M sucrose, 25 mM EDTA, 25 mM Tris, pH 8.0, containing 4 mg/ml lysozyme and 50 μg/ml RNaseA), and the suspensions were incubated at 37° C. for 2-4 hours. 250 μl of a 2% solution of SDS was added, and the samples were vortexed for 1 minute. The samples were extracted with 250 μl of phenol:$CHCl_3$ (1:1) and the phases were resolved by centrifugation in a microfuge at 13,000 rpm for 5 minutes. The aqueous layer was removed to a new tube, and after adding $1/10^{th}$ volume 3 M sodium acetate, the DNA was precipitated by adding an equal volume of isopropanol. Precipitated DNA was collected by centrifugation in a microfuge at 13,000 rpm for 5 minutes, washed with −20° C. 70% ethanol, and suspended in 100 μl of water.

For the isolation of larger amounts of genomic DNA from *S. cyaneogriseus* strains, 25 ml KB3 medium (10 g/L Bacto-tryptone, 5 g/L yeast extract, 3 g/L beef extract, 1 g/L $KH_2PO_4$, 1 g/L $K_2HPO_4$, 1.5 g/L Difco agar, pH 6.8 and 0.5 ml/L of a trace metal solution ccontaining 30 g/L $FeSO_4$, 30 g/L $ZnSO_4.7H_2O$, 4 g/L $MnSO_4$, 4 g/L $CuCl_2.5H_2O$, 00.4 g/L $CCoCl_2.6H_2O$) was inoculated with mycelial fragments of the strain of interest. The cultures were incubated at 31° C., with shaking at 220 rpm, for 24-28 hours. The cells in 3 ml aliquots of these cultures were collected by centrifugation in a microfuge at 13,000 rpm for 5 minutes, and the supernatant was discarded. After washing the cell pellets with water, genomic DNA was isolated using reagents, materials and procedures included in the DNAeasy™ system for the isolation of total (plant) DNA from QIAGEN (Valencia, Calif.).

5. Characterization of Transconjugants

Putative transconjugants were plated on CM agar (5 g/L corn steep liquor, 5 g/L Bacto-peptone, 10 g/L soluble starch, 0.5 g/L NaCl, 0.5 g/L $CaCl_2.2H_2O$, 20 g/L Bacto-agar) plates containing 100 μg/ml apramycin, 30 μg/ml nalidixic acid, 50 μg/ml cycloheximide, and 50 μg/ml nystatin A. These plates were incubated at 31° C. until the colonies were well-established. Genomic DNA was then isolated from the putative transconjugants using methods described herein, for analysis by Southern blot and nucleotide sequence analysis as follows. Aliquots of the genomic DNA preparations were digested with HindIII/StuI and with SalI. The fragments were resolved by electrophoresis through 0.8% w/v agarose, and blotted onto Nytran™ membranes (commercially available from Schleicher & Schuell BioScience, Inc. USA, Keene, N.H.) for Southern analysis according to well-established procedures similar to those described in Sambrook et al., *Molecular Cloning: A Laboratory Manual, Second Edition*, Cold Spring Harbor Laboratory Press, Cold Spring Harbor, N.Y. (1989). Typically, these Southern blots were probed with the mod3-specific probe, which was generated as described herein. The expected sizes of the fragments were:

| Strain | HindIII/StuI | SalI |
|---|---|---|
| *S. cyaneogriseus* production strain 142 | 10.8 Kbp | 4.6 Kbp |
| *S. cyaneogriseus* production strain 142/pFDmod3/5.2 transconjugants | 13.3 Kbp | 4.6 Kbp + 3.3 Kbp |
| *S. cyaneogriseus* production strain 142/pFDmod3/4.2 transconjugants | 12.3 Kbp | 4.6 Kbp + 3.3 Kbp |

The region of interest of transconjugants that appeared to be correct on the basis of the Southern analysis was amplified using standard polymerase chain reaction (PCR), and the PCR products were sequenced to confirm that the desired sequence had been obtained. Two primer sets were used to characterize the transconjugants. Each pair was comprised of one mod3-specific primer, and one primer specific for vector-derived sequences. In addition, the primer pairs were designed such that one pair would amplify products from the "right side of the cassette" and the other pair would amplify products from the "left side of the cassette." The primer pairs used were:

```
                                             (SEQ ID NO:33)
Left    (mod70F)    5'-TACTGCGCCACACGGAGCCCGAG
and
                                             (SEQ ID NO:34)
        (P6568B)    5'-TGGGTAACGCCAGGGTTTTC
                                             (SEQ ID NO:35)
Right   (PECOR1F)   5'-GGAAACAGCTATGACATGATTACG
and
                                             (SEQ ID NO:36)
        (mod3633B)  5'-TCGGAGCCGCTCCACCTGAG
```

With genomic DNA isolated from a "correct" transconjugant as a template, these PCR primers would direct the amplification of 6.4 Kbp and 5.7 Kbp products, respectively. The region of these PCR products containing the ketoreductase domain were sequenced to confirm that the desired sequence had been obtained, using the following oligonucleotide sequencing primers:

"179" Transconjugants:

```
Forward 5'-CCTGATGGACGCGGGTGCGC      (SEQ ID NO:37)
Reverse 5'-GACACCGAAACCCCTG          (SEQ ID NO:38)
```

"204" Transconjugants:

```
Forward 5'-CCTGATGGACGCGGGTGCGC      (SEQ ID NO:39)
Reverse 5'-GCCGTGTGCACCACAGCGGTCAG   (SEQ ID NO:40)
```

"260", "283", "306" Transconjugants:

```
                                     (SEQ ID NO:41)
Forward 5'-GTGTGATGTCGCCGACCGCGC-
        CCAGGTC
Reverse 5'-GCGCTGGTGGGCCAGGGCGTCC    (SEQ ID NO:42)
```

6. Excision and Characterization of Excisants

Transconjugants that had been verified by Southern analysis and by nucleotide sequence analysis of PCR products as described herein were used to inoculate 25 ml of KB3 medium (10 g/L Bacto-tryptone, 5 g/L yeast extract, 3 g/L beef extract, 1 g/L $KH_2PO_4$, 1 g/L $K_2HPO_4$, 1.5 g/L Difco agar, pH 6.8 and 0.5 ml/L of a trace metal solution containing 30 g/L $FeSO_4$, 30 g/L $ZnSO_4.7H_2O$, 4 g/L $MnSO_4$, 4 g/L $CuCl_2.5H_2O$, 0.4 g/L $CoCl_26H_2O$), and the cultures were incubated at 31° C. with shaking at 220 rpm, for 48 hours. A 500 µl aliquot of the culture was crossed into a fresh 25 ml of KB3 medium, and incubation was continued at 31° C. with shaking at 220 rpm, for an additional 48 hours. This process was continued for many such rounds, in the absence of selection, in order to allow for the excision event to occur. After rounds 3-6, serial dilutions of the cultures were prepared from $10^{-1}$ to $10^{-5}$, and 250 µl aliquots of the $10^{-3}$ to $10^{-5}$ dilutions were plated onto 140 mm diameter CM agar plates (5 g/L corn steep liquor, 5 g/L Bacto-peptone, 10 g/L soluble starch, 0.5 g/L NaCl, 0.5 g/L $CaCl_2.2H_2O$, 20 g/L Bacto-agar). These plates were incubated at 31° C. for 48-96 hours, until colonies were well-established. Individual colonies were then picked, and patched in replicate onto CM plates, and CM plates supplemented with 100 mg/ml apramycin. These plates were incubated at 31° C. for up to 5 days, at which time colonies sensitive to apramycin, but capable of growing normally in the absence of selection were identified. Genomic DNA was then isolated from these putative excisants using methods described herein. Using these genomic DNA preparations as templates, the region of interest was amplified using the polymerase chain reaction (PCR), and the PCR products were sequenced to confirm that the desired sequence had been obtained. The primer pair used for amplification was:

```
                                        (SEQ ID NO:33)
(mod70F)    5'-TACTGCGCCACACGGAGCCCGAG and
(mod3633B)  5'-TCGGAGCCGCTCCACCTGAG     (SEQ ID NO:36)
```

With genomic DNA isolated from a "correct" excisant as a template, these PCR primers would direct the amplification of a 6.6 Kbp product. The region of these PCR products containing the ketoreductase domain were sequenced herein to confirm that the desired sequence had been obtained, using the following oligonucleotide sequencing primers:

"179" Excisants:

```
Forward 5'-CCTGATGGACGCGGGTGCGC      (SEQ ID NO:37)
Reverse 5'-GACACCGAAACCCCTG          (SEQ ID NO:38)
```

"204" Excisants:

```
Forward 5'-CCTGATGGACGCGGGTGCGC      (SEQ ID NO:39)
Reverse 5'-GCCGTGTGCACCACAGCGGTCAG   (SEQ ID NO:40)
```

"260", "283", "306" Excisants:

```
                                     (SEQ ID NO:41)
Forward 5'-GTGTGATGTCGCCGACCGCGCCCAGGTC
Reverse 5'-GCGCTGGTGGGCCAGGGCGTCC    (SEQ ID NO:42)
```

B. Fermentation and Analysis of Fermentation Products

Seed flasks containing 25 ml of KB3 medium (10 g/L Bacto-tryptone, 5 g/L yeast extract, 3 g/L beef extract, 1 g/L $KH_2PO_4$, 1 g/L $K_2HPO_4$, 1.5 g/L Difco agar, pH 6.8 and 0.5 ml/L of a trace metal solution containing 30 g/L $FeSO_4$, 30 g/L $ZnSO_4.7H_2O$, 4 g/L $MnSO_4$, 4 g/L $CuCl_2.5H_2O$, 0.4 g/L $CoCl_2.6H_2O$) were inoculated with 500 µl of a suspension of *S. cyaneogriseus* mycelial fragments (either fresh or frozen) and the cultures were incubated at 31° C. with shaking at 220 rpm, for 48 hours. A 500 µl aliquot of the seed culture was crossed into production flasks containing 25 ml of SD2 production medium (85.5 g/L glucose, 0.36 g/L KCl, 0.72 g/L $MgSO_4.7H_2O$, 7.2 g/L Ca $CO_3$, 4.86 g/L $(NH_4)_2SO_4$, 0.72 g/L $K_2HPO_4$, 7.2 g/L pharmamedia, and 1.8 ml/L of a trace metal solution containing 30 g/L $FeSO_4$, 30 g/L $ZnSO_4.7H_2O$, 4 g/L $MnSO_4$, 4 g/L $CuCl_2.5H_2O$, 0.4 g/L $CoCl_2.6H_2O$) and the cultures were incubated at 31° C. for 10 days. Starting at (typically) 120 hours, and continuing through the end of the fermentation, 100 µl aliquots of the production culture were removed, and combined with 900 µl of methanol. The suspensions were vortexed for 1 minute, clarified by centrifugation in a microfuge at 13,000 rpm for 10 minutes, and 10 µl aliquots of the extract were analyzed by reversed phase HPLC.

For analysis by reversed phase HPLC, samples were subjected to chromatography on a Waters Model 625 Liquid Chromatography Station equipped with a Waters Model 996 Photodiode Array Detector, a Waters Model 717 Autosampler, and a Waters Nova-Pak $C_{18}$ column (8 mm×100 mm). The column was equilibrated in and eluted with a mobile phase containing 60% (v/v) acetonitrile and 40% (v/v) 100 mM ammonium acetate, pH 4.5 at a flow rate of 2 ml/min. The compounds of interest, Fα and 23-keto Fα (predecessor of moxidectin), were detected by monitoring their absorbance at 242 nm, and retention times were compared to those of authentic samples.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

What is claimed is:

1. A method for the preparation of a 23-oxo-LL-F28249 compound, which comprises the following steps of:

(a) mutating a module 3 ketoreductase domain of a polyketide synthase gene cluster to render said ketoreductase domain nonfunctional wherein the polyketide synthase gene cluster is responsible for the biosynthesis of an LL-F28249 compound and wherein said module 3 ketoreductase domain either has the amino acid sequence from position 3287 through position 3466, inclusive, of SEQ ID NO:6 or has a nucleotide sequence region that hybridizes at about 42° C. in a solution containing 6×SSC and 50% formamide with a nucleic acid molecule having the nucleic acid sequence from position 29,723 to position 30,262, inclusive, of SEQ ID NO:1;

(b) transforming or transfecting an antibiotic-producing wild-type or mutant *Streptomyces* strain with the mutated nucleic acid molecule to replace the original module 3 ketoreductase domain with the mutated module 3 ketoreductase domain;

(c) culturing the transformed or transfected *Streptomyces* strain in a suitable nutrient medium in a manner allowing production of the 23-oxo-LL-F28249 compound; and (d) recovering the 23-oxo-LL-F28249 compound.

2. The method according to claim 1, wherein the 23-oxo-LL-F28249 compound is 23-oxo-LL-F28249α.

3. A method for the preparation of a 23-oxo-LL-F28249 compound, which comprises the following steps of:

(a) mutating a module 3 ketoreductase domain of a polyketide synthase gene cluster to render said ketoreductase domain nonfunctional wherein the polyketide synthase gene cluster is responsible for the biosynthesis of an LL-F28249 compound and wherein said module 3 ketoreductase domain either has the amino acid sequence from position 3287 through position 3466, inclusive, of SEQ ID NO:6 or has a nucleotide sequence region that hybridizes at about 42° C. in a solution containing 6×SSC and 50% formamide with a nucleic acid molecule having the nucleic acid sequence from position 29,723 to position 30,262, inclusive, of SEQ ID NO:1

(b) transforming or transfecting an isolated prokaryotic or eukaryotic host cell with the mutated nucleic acid molecule;

(c) growing the transformed or transfected host cell under suitable nutrient conditions in a manner allowing expression of the 23-oxo-LL-F28249 compound; and (d) recovering the 23-oxo-LL-F28249 compound.

4. The method according to claim 3, wherein the 23-oxo-LL-F28249 compound is 23-oxo-LL-F28249α.

5. A method for the preparation of a 23-(O-methyloxime)-LL-F28249 compound, which comprises the following steps of:

(a) mutating a module 3 ketoreductase domain of a polyketide synthase gene cluster to render said ketoreductase domain nonfunctional wherein the polyketide synthase gene cluster is responsible for the biosynthesis of an LL-F28249 compound and wherein said module 3 ketoreductase domain either has the amino acid sequence from position 3287 through position 3466, inclusive, of SEQ ID NO:6 or has a nucleotide sequence region that hybridizes at about 42° C. in a solution containing 6×SSC and 50% formamide with a nucleic acid molecule having the nucleic acid sequence from position 29,723 to position 30,262, inclusive, of SEQ ID NO:1

(b) transforming or transfecting an antibiotic-producing wild-type or mutant *Streptomyces* strain with the mutated nucleic acid molecule to replace the original module 3 ketoreductase domain with the mutated module 3 ketoreductase domain;

(c) culturing the transformed or transfected *Streptomyces* strain in a suitable nutrient medium in a manner allowing production of a 23-oxo-LL-F28249 compound;

(d) recovering the 23-oxo-LL-F28249 compound;

(e) converting the 23-oxo-LL-F28249 compound to the 23-(O-methyloxime)-LL-F28249 compound under suitable reaction conditions; and (f) isolating the 23-(O-methyloxime)-LL-F28249 compound.

6. The method according to claim 5, wherein the 23-oxo-LL-F28249 compound is 23-oxo-LL-F28249α and the method prepares 23-(O-methyloxime)-LL-F28249α.

7. A method for the preparation of a 23-(O-methyloxime)-LL-F28249 compound, which comprises the following steps of:

(a) mutating a module 3 ketoreductase domain of a polyketide synthase gene cluster to render said ketoreductase domain nonfunctional wherein the polyketide synthase gene cluster is responsible for the biosynthesis of an LL-F28249 compound and wherein said module 3 ketoreductase domain either has the amino acid sequence from position 3287 through position 3466, inclusive, of SEQ ID NO:6 or has a nucleotide sequence region that hybridizes at about 42° C. in a solution containing 6×SSC and 50% formamide with a nucleic acid molecule having the nucleic acid sequence from position 29,723 to position 30,262, inclusive, of SEQ ID NO:1

(b) transforming or transfecting an isolated prokaryotic or eukaryotic host cell with the mutated nucleic acid molecule;

(c) growing the transformed or transfected host cell under suitable nutrient conditions in a manner allowing expression of a 23-oxo-LL-F28249 compound;

(d) recovering the 23-oxo-LL-F28249 compound;

(e) converting the 23-oxo-LL-F28249 compound to the 23-(O-methyloxime)-LL-F28249 compound under suitable reaction conditions; and (f) isolating the 23-(O-methyloxime)-LL-F28249 compound.

8. The method according to claim 7, wherein the 23-oxo-LL-F28249 compound is 23-oxo-LL-F28249and the method prepares 23-(O-methyloxime)-LL-F28249α.

* * * * *